United States Patent
Camphausen et al.

(10) Patent No.: US 10,221,232 B2
(45) Date of Patent: Mar. 5, 2019

(54) METHODS OF TREATING CANCER BY ADMINISTERING IGF-IR BINDING MOLECULES

(71) Applicant: BRISTOL-MYERS SQUIBB COMPANY, Princeton, NJ (US)

(72) Inventors: Ray Camphausen, Wayland, MA (US); David Fabrizio, South Hamilton, MA (US); Martin C. Wright, Belmont, MA (US); Patrick Gage, Bryn Mawr, PA (US); John Mendlein, Encinitas, CA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

(21) Appl. No.: 15/404,749

(22) Filed: Jan. 12, 2017

(65) Prior Publication Data

US 2017/0190761 A1    Jul. 6, 2017

Related U.S. Application Data

(63) Continuation of application No. 14/659,028, filed on Mar. 16, 2015, now abandoned, which is a continuation of application No. 13/892,418, filed on May 13, 2013, now abandoned, which is a continuation of application No. 12/312,725, filed as
(Continued)

(51) Int. Cl.
| | | |
|---|---|---|
| C07K 14/78 | (2006.01) | |
| C07K 14/47 | (2006.01) | |
| C07K 14/71 | (2006.01) | |
| A61K 38/39 | (2006.01) | |
| A61K 39/395 | (2006.01) | |
| C07K 19/00 | (2006.01) | |
| C12N 15/10 | (2006.01) | |
| C40B 30/04 | (2006.01) | |
| C40B 40/08 | (2006.01) | |
| A61K 38/18 | (2006.01) | |
| C07K 14/00 | (2006.01) | |
| C07K 14/765 | (2006.01) | |
| C07K 14/79 | (2006.01) | |
| C07K 16/00 | (2006.01) | |
| A61K 47/60 | (2017.01) | |
| A61K 47/64 | (2017.01) | |
| A61K 47/68 | (2017.01) | |
| C07K 16/22 | (2006.01) | |
| C07K 16/28 | (2006.01) | |
| A61K 39/00 | (2006.01) | |
| C40B 40/10 | (2006.01) | |

(52) U.S. Cl.
CPC ............ C07K 14/78 (2013.01); A61K 38/18 (2013.01); A61K 38/39 (2013.01); A61K 47/60 (2017.08); A61K 47/643 (2017.08); A61K 47/644 (2017.08); A61K 47/68 (2017.08); C07K 14/00 (2013.01); C07K 14/765 (2013.01); C07K 14/79 (2013.01); C07K 16/00 (2013.01); C12N 15/1062 (2013.01); C40B 30/04 (2013.01); C40B 40/08 (2013.01); *A61K 39/3955* (2013.01); *A61K 2039/505* (2013.01); *C07K 14/47* (2013.01); *C07K 14/71* (2013.01); *C07K 16/2863* (2013.01); *C07K 19/00* (2013.01); *C07K 2317/92* (2013.01); *C07K 2319/30* (2013.01); *C07K 2319/74* (2013.01); *C40B 40/10* (2013.01)

(58) Field of Classification Search
CPC ........ C07K 14/78; C07K 16/00; C07K 16/18; C07K 14/71; C07K 16/2863; C07K 2319/30; C07K 2317/92; C07K 19/00; A61K 38/00; A61K 38/16; A61K 38/39; A61K 38/17; A61K 39/3955; A61K 2039/505; C07H 21/00
See application file for complete search history.

(56) References Cited

U.S. PATENT DOCUMENTS

| | | |
|---|---|---|
| 3,773,919 A | 11/1973 | Boswell et al. |
| 4,863,457 A | 9/1989 | Lee |
| 4,997,652 A | 3/1991 | Wong |

(Continued)

FOREIGN PATENT DOCUMENTS

| | | |
|---|---|---|
| CA | 2293632 A1 | 12/1998 |
| DE | 19646372 C1 | 6/1997 |

(Continued)

OTHER PUBLICATIONS

Aoki et al. The catalytic subunit of phosphoinositide 3-kinase: requirements for oncogenicity. J Biol Chem 275(9): 6267-6275, 2000.*

(Continued)

*Primary Examiner* — Bridget E Bunner
(74) *Attorney, Agent, or Firm* — Nelson Mullins Riley & Scarborough LLP; Jane E. Remillard, Esq.; Christopher L. Frank

(57) ABSTRACT

The present invention provides innovative proteins that bind to insulin-like growth factor-I receptor (IGF-IR), as well as other important proteins. The invention also provides innovative proteins in pharmaceutical preparations and derivatives of such proteins and the uses of same in diagnostic, research and therapeutic applications. The invention further provides cells comprising such proteins, polynucleotide encoding such proteins or fragments thereof, and vectors comprising the polynucleotides encoding the innovative proteins.

10 Claims, 38 Drawing Sheets

Specification includes a Sequence Listing.

Related U.S. Application Data application No. PCT/US2007/024316 on Nov. 21, 2007, now Pat. No. 8,470,332.

(60) Provisional application No. 60/879,666, filed on Jan. 9, 2007, provisional application No. 60/860,605, filed on Nov. 22, 2006.

(56) References Cited

U.S. PATENT DOCUMENTS

| | | | |
|---|---|---|---|
| 5,164,188 A | 11/1992 | Wong | |
| 5,235,041 A | 8/1993 | Cappello et al. | |
| 5,443,505 A | 8/1995 | Wong et al. | |
| 5,501,856 A | 3/1996 | Ohtori et al. | |
| 5,514,581 A | 5/1996 | Ferrari et al. | |
| 5,516,522 A | 5/1996 | Peyman et al. | |
| 5,545,620 A | 8/1996 | Wahl et al. | |
| 5,641,648 A | 6/1997 | Ferrari et al. | |
| 5,766,242 A | 6/1998 | Wong et al. | |
| 5,770,697 A | 6/1998 | Ferrari et al. | |
| 5,792,742 A | 8/1998 | Gold et al. | |
| 5,824,072 A | 10/1998 | Wong | |
| 5,869,079 A | 2/1999 | Wong et al. | |
| 5,922,676 A | 7/1999 | Pasqualini et al. | |
| 6,018,030 A | 1/2000 | Ferrari et al. | |
| 6,207,446 B1 | 3/2001 | Szostak et al. | |
| 6,214,553 B1 | 4/2001 | Szostak et al. | |
| 6,258,558 B1 | 7/2001 | Szostak et al. | |
| 6,261,804 B1 | 7/2001 | Szostak et al. | |
| 6,281,344 B1 | 8/2001 | Szostak et al. | |
| 6,316,412 B1 | 11/2001 | Ginsberg et al. | |
| 6,342,219 B1 | 1/2002 | Thorpe et al. | |
| 6,348,333 B1 | 2/2002 | Niwa et al. | |
| 6,369,116 B1 | 4/2002 | Wong et al. | |
| 6,383,775 B1 | 5/2002 | Duff et al. | |
| 6,399,857 B1 | 6/2002 | Kloti | |
| 6,462,189 B1 | 10/2002 | Koide | |
| 6,518,018 B1 | 2/2003 | Szostak et al. | |
| 6,524,583 B1 | 2/2003 | Thorpe et al. | |
| 6,559,126 B2 | 5/2003 | Tournaire et al. | |
| 6,660,492 B1 | 12/2003 | Bode et al. | |
| 6,699,493 B2 | 3/2004 | Wong | |
| 6,818,418 B1 | 11/2004 | Lipovsek et al. | |
| 7,053,701 B2 | 5/2006 | Vice | |
| 7,115,396 B2 | 10/2006 | Lipovsek et al. | |
| 7,556,925 B2 | 7/2009 | Koide et al. | |
| 7,598,352 B2 | 10/2009 | Koide | |
| 7,847,062 B2 | 12/2010 | Chen et al. | |
| 7,858,739 B2 | 12/2010 | Chen et al. | |
| 7,858,759 B2 | 12/2010 | Brandt et al. | |
| 8,067,201 B2 | 11/2011 | Morin et al. | |
| 8,221,765 B2 | 7/2012 | Camphausen et al. | |
| 8,258,265 B2 | 9/2012 | Koide | |
| 8,263,741 B2 | 9/2012 | Koide | |
| 8,278,419 B2 | 10/2012 | Jacobs et al. | |
| 8,293,482 B2 | 10/2012 | Jacobs et al. | |
| 8,324,362 B2 | 12/2012 | Chen et al. | |
| 8,343,501 B2 | 1/2013 | Emanuel et al. | |
| 8,420,098 B2 | 4/2013 | Camphausen et al. | |
| 8,470,332 B2 | 6/2013 | Camphausen et al. | |
| 8,524,244 B2 | 9/2013 | Camphausen et al. | |
| 8,609,613 B2 | 12/2013 | Chen et al. | |
| 8,728,483 B2 | 5/2014 | Camphausen et al. | |
| 8,969,289 B2 | 3/2015 | Gosselin et al. | |
| 9,017,655 B2 | 4/2015 | Emanuel et al. | |
| 9,234,028 B2 | 1/2016 | Camphausen et al. | |
| 9,328,157 B2 | 5/2016 | Chen et al. | |
| 9,540,424 B2 | 1/2017 | Gosselin et al. | |
| 9,562,089 B2 | 2/2017 | Camphausen et al. | |
| 9,605,039 B2 | 3/2017 | Lipovsek et al. | |
| 9,771,411 B2 | 9/2017 | Emanuel et al. | |
| 9,862,758 B2 | 1/2018 | Chen et al. | |
| 2002/0019517 A1 | 2/2002 | Koide | |
| 2002/0061307 A1 | 5/2002 | Whitlow et al. | |
| 2002/0142048 A1 | 10/2002 | Sands et al. | |
| 2003/0004561 A1 | 1/2003 | Bigus et al. | |
| 2003/0104520 A1 | 6/2003 | Ellington et al. | |
| 2003/0170753 A1 | 9/2003 | Koide | |
| 2003/0186385 A1 | 10/2003 | Koide | |
| 2005/0244469 A1 | 11/2005 | Whitcup et al. | |
| 2005/0255548 A1 | 11/2005 | Lipovsek et al. | |
| 2005/0281861 A1 | 12/2005 | Hughes et al. | |
| 2006/0122162 A1 | 6/2006 | Cutler | |
| 2006/0182783 A1 | 8/2006 | Hughes et al. | |
| 2006/0210604 A1 | 9/2006 | Dadey et al. | |
| 2006/0246059 A1 | 11/2006 | Lipovsek et al. | |
| 2006/0246549 A1 | 11/2006 | Kurz et al. | |
| 2007/0059120 A1 | 3/2007 | Vigliotti et al. | |
| 2007/0059336 A1 | 3/2007 | Hughes et al. | |
| 2007/0071575 A1 | 3/2007 | Rudduck et al. | |
| 2007/0071675 A1 | 3/2007 | Wu et al. | |
| 2007/0072933 A1 | 3/2007 | Peyman | |
| 2007/0082365 A1 | 4/2007 | Lipovsek et al. | |
| 2007/0088014 A1 | 4/2007 | Edelman et al. | |
| 2007/0099879 A1 | 5/2007 | Sheibani et al. | |
| 2007/0160533 A1 | 7/2007 | Chen et al. | |
| 2007/0203089 A1 | 8/2007 | Rodrigues et al. | |
| 2008/0015339 A1 | 1/2008 | Lipovsek et al. | |
| 2008/0063651 A1 | 3/2008 | Lipovsek et al. | |
| 2008/0108798 A1 | 5/2008 | Lipovsek et al. | |
| 2008/0139791 A1 | 6/2008 | Lipovsek et al. | |
| 2008/0193445 A1 | 8/2008 | Goetsch et al. | |
| 2008/0220049 A1 | 9/2008 | Chen et al. | |
| 2008/0268051 A1 | 10/2008 | Hughes et al. | |
| 2009/0176654 A1 | 7/2009 | Cappuccilli et al. | |
| 2009/0299040 A1 | 12/2009 | Camphausen et al. | |
| 2010/0121033 A1 | 5/2010 | Camphausen et al. | |
| 2010/0144599 A1 | 6/2010 | Mendlein et al. | |
| 2010/0144601 A1 | 6/2010 | Jacobs et al. | |
| 2010/0152063 A1 | 6/2010 | Cappuccilli et al. | |
| 2010/0210511 A1 | 8/2010 | Carvajal | |
| 2010/0273216 A1 | 10/2010 | Morin et al. | |
| 2010/0285000 A1 | 11/2010 | Mamluk | |
| 2010/0298541 A1 | 11/2010 | Wu et al. | |
| 2010/0310549 A1 | 12/2010 | Chen et al. | |
| 2010/0322930 A1 | 12/2010 | Kolbinger et al. | |
| 2011/0021746 A1 | 1/2011 | Cappuccilli et al. | |
| 2011/0034384 A1 | 2/2011 | Carvajal | |
| 2011/0038866 A1 | 2/2011 | Hastewell et al. | |
| 2011/0123545 A1 | 5/2011 | Marsh et al. | |
| 2011/0124527 A1 | 5/2011 | Cappuccilli et al. | |
| 2011/0274623 A1 | 11/2011 | Jacobs | |
| 2011/0275535 A1 | 11/2011 | Loew | |
| 2012/0208704 A1 | 8/2012 | Loew et al. | |
| 2012/0270797 A1 | 10/2012 | Wittrup et al. | |
| 2013/0079243 A1 | 3/2013 | Diem et al. | |
| 2013/0079280 A1 | 3/2013 | Baca et al. | |
| 2013/0096019 A1 | 4/2013 | Jacobs et al. | |
| 2013/0096058 A1 | 4/2013 | Baca et al. | |
| 2013/0184212 A1 | 7/2013 | Camphausen et al. | |
| 2013/0310317 A1 | 11/2013 | Camphausen et al. | |
| 2014/0179896 A1 | 6/2014 | Chen et al. | |
| 2014/0349929 A1 | 11/2014 | Camphausen et al. | |
| 2015/0152147 A1 | 6/2015 | Gosselin et al. | |
| 2015/0252097 A1 | 9/2015 | Camphausen et al. | |
| 2015/0259398 A1 | 9/2015 | Emanuel et al. | |
| 2016/0152688 A1 | 6/2016 | Camphausen et al. | |
| 2016/0297869 A1 | 10/2016 | Chen et al. | |
| 2017/0145464 A1 | 5/2017 | Gosselin et al. | |
| 2017/0166627 A1 | 6/2017 | Camphausen et al. | |
| 2017/0275342 A1 | 9/2017 | Lipovsek et al. | |
| 2017/0334958 A1 | 11/2017 | Lipovsek et al. | |
| 2018/0037631 A1 | 2/2018 | Emanuel et al. | |
| 2018/0162926 A1 | 6/2018 | Chen et al. | |

FOREIGN PATENT DOCUMENTS

| | | | |
|---|---|---|---|
| EP | 0430539 | A2 | 6/1991 |
| EP | 0488401 | A1 | 6/1992 |
| EP | 0654256 | A1 | 5/1995 |
| EP | 0962527 | A1 | 12/1999 |
| EP | 0985039 | B1 | 3/2000 |
| EP | 1477561 | B1 | 11/2004 |
| EP | 1266025 | B1 | 11/2006 |

(56) References Cited

FOREIGN PATENT DOCUMENTS

| | | |
|---|---|---|
| EP | 1137941 B1 | 8/2009 |
| EP | 2141243 A2 | 1/2010 |
| EP | 2385067 A1 | 11/2011 |
| EP | 2439212 A1 | 4/2012 |
| EP | 2379718 B1 | 3/2013 |
| JP | 4-108827 | 4/1992 |
| JP | 2001-500531 | 1/2001 |
| JP | 2007-516707 | 6/2007 |
| WO | 92/02536 A1 | 2/1992 |
| WO | 93/03172 A1 | 2/1993 |
| WO | 95/11922 A1 | 5/1995 |
| WO | 95/13765 A1 | 5/1995 |
| WO | 96/22391 A1 | 7/1996 |
| WO | 98/12226 A1 | 3/1998 |
| WO | 98/31700 A1 | 7/1998 |
| WO | 98/56915 A2 | 12/1998 |
| WO | 99/51773 A1 | 10/1999 |
| WO | 2000/34784 A1 | 6/2000 |
| WO | 2000/34787 A1 | 6/2000 |
| WO | 2001/07657 A1 | 2/2001 |
| WO | 2001/64942 A1 | 9/2001 |
| WO | 2002/04523 A2 | 1/2002 |
| WO | 2002/32925 A2 | 4/2002 |
| WO | 2002/081497 A2 | 10/2002 |
| WO | 2002/088171 A2 | 11/2002 |
| WO | 2003/022858 A2 | 3/2003 |
| WO | 03/062830 A2 | 7/2003 |
| WO | 2003/072082 A1 | 9/2003 |
| WO | 2003/075840 A2 | 9/2003 |
| WO | 2003/104418 A2 | 12/2003 |
| WO | 2005/016970 A2 | 2/2005 |
| WO | 2005/056764 A2 | 6/2005 |
| WO | 2006/020258 A2 | 2/2006 |
| WO | 2006/091209 A2 | 8/2006 |
| WO | 2007/012614 A2 | 2/2007 |
| WO | 2007/044688 A1 | 4/2007 |
| WO | 2007/062188 A2 | 5/2007 |
| WO | 2007/092537 A2 | 8/2007 |
| WO | 2007/096076 A2 | 8/2007 |
| WO | 2007/121894 A2 | 11/2007 |
| WO | 2008/031098 A1 | 3/2008 |
| WO | 2008/048970 A2 | 4/2008 |
| WO | 2008/066752 A2 | 6/2008 |
| WO | 2008/097497 A2 | 8/2008 |
| WO | 2008/108986 A2 | 9/2008 |
| WO | 2008/153745 A2 | 12/2008 |
| WO | 2009/023184 A2 | 2/2009 |
| WO | 2009/025806 A2 | 2/2009 |
| WO | 2009/058379 A2 | 5/2009 |
| WO | 2009/073115 A1 | 6/2009 |
| WO | 2009/083804 A2 | 7/2009 |
| WO | 2009/086116 A2 | 7/2009 |
| WO | 2009/102421 A2 | 8/2009 |
| WO | 2009/133208 A1 | 11/2009 |
| WO | 2009/142773 A2 | 11/2009 |
| WO | 2010/051274 A2 | 5/2010 |
| WO | 2010/051310 A2 | 5/2010 |
| WO | 2010/060095 A1 | 5/2010 |
| WO | 2010/069913 A1 | 6/2010 |
| WO | 2010/093627 A2 | 8/2010 |
| WO | 2010/093771 A1 | 8/2010 |
| WO | 2011/020033 A2 | 2/2011 |
| WO | 2011/035202 A2 | 3/2011 |
| WO | 2011/051333 A1 | 5/2011 |
| WO | 2011/051466 A1 | 5/2011 |
| WO | 2011/092233 A1 | 8/2011 |
| WO | 2011/100700 A2 | 8/2011 |
| WO | 2011/103105 A1 | 8/2011 |
| WO | 2011/130324 A1 | 10/2011 |
| WO | 2011/130328 A1 | 10/2011 |
| WO | 2011/130354 A1 | 10/2011 |
| WO | 2011/137319 A2 | 11/2011 |
| WO | 2011/140086 A2 | 11/2011 |
| WO | 2011/150133 A2 | 12/2011 |
| WO | 2012/016245 A2 | 2/2012 |
| WO | 2012/088006 A1 | 6/2012 |
| WO | 2012/142515 A2 | 10/2012 |
| WO | 2012/158678 A1 | 11/2012 |
| WO | 2012/158739 A1 | 11/2012 |
| WO | 2013/049275 A1 | 4/2013 |

OTHER PUBLICATIONS

Chen et al. IGF-1R as an anti-cancer target-trials and tribulations. Chin J Cancer 32(5): 242-252, 2013.*
Haluska et al. HER receptor signaling confers resistance to the insulin-like growth factor-I receptor inhibitor, BMA-536924. Mol Cancer Ther 7(9): 2589-2598, 2008.*
Kang et al. Phosphatidylinositol 3-kinase mutations identified in human cancer are oncogenic. Proc Natl Acad Sci USA 102(3): 802-807, 2005.*
Luo et al. Targeting the P13K-Akt pathway in human cancer: rationale and promise. Cancer Cell 257-262, 2003.*
Garcia-Echeverrfa et al. In vivo antitumor activity of NVP-AEW541-a novel, potent, and selective inhibitor of the IGF-IR kinase. Cancer Cell 5: 231-239, 2004.*
Dunn et al. A dominant negative mutant of the insulin-like growth factor-I receptor inhibits the adhesion, invasion, and metastasis of breast cancer. Cancer Res 58: 3353-3361, 1998.*
Cohen et al. Combination therapy enhances the inhibition of tumor growth with the fully human anti-type 1 insulin-like growth factor receptor monoclonal antibody CP-751,871. Clin Cancer Res 11: 2063-2073, 2005.*
Resnicoff et al. Growth inhibition of human melanoma cells in nude mice by antisense strategies to the Type 1 insulin-like growth factor receptor. Cancer Res 54: 4848-4850, 1994.*
Lee et al. Antitumor effects of an adenovirus expressing antisense insulin-like growth factor I receptor on human lung cancer cell lines. Cancer Res 56: 3038-3041, 1996.*
Wang et al. Activation of the IGF-IR system contributes to malignant growth of human and mouse medulloblastomas. Oncogene 20: 3857-3868, 2001.*
Scotlandi et al. Expression of an IGF-I receptor dominant negative mutant induces apoptosis, inhibits tumorigenesis and enhances chemosensitivity in Ewing's sarcoma cells. Int J Cancer 101: 11-16, 2002.*
Wang et al. Inhibition of insulin-like growth factor-I receptor (IGF-IR) signaling and tumor cell growth by a fully human neutralizing anti-IGF-IR antibody. Mol Cancer Ther 4(8): 1214-1221, 2005.*
Burtrum et al. A fully human monoclonal antibody to the insulin-like growth factor I receptor blocks ligand-dependent signaling and inhibits human tumor growth in vivo. Cancer Res 63: 8912-8921, 2003.*
Maloney et al. An anti-insulin-like growth factor I receptor antibody that is a potenti inhibitor of cancer cell proliferation. Cancer Res 63: 5073-5083, 2003.*
Samani et al. The role of the IGF system in cancer growth and metastasis: overview and recent insights. Endocrine Rev 28(1): 20-47, 2007.*
Leahy, Daniel J. et al., "2.0 A Crystal Structure of a Four-Domain Segment of Human Fibronectin Encompassing the RGD Loop and Synergy Region," Cell, vol. 84:155-164 (1996).
Leahy, Daniel J. et al., "Structure of a Fibronectin Type III Domain from Tenascin Phased by MAD Analysis of the Selenomethionyl Protein," Science, vol. 258:987-991 (1992).
Lee, Grace et al., "Strong Inhibition of Fibrogen Binding to Platelet Receptor Alpha2b beta 3 by RGD Sequences installed into the Presentation Scaffold," Prot. Eng., vol. 6:745-754 (1993).
Lewin, B. Genes IV, Oxford: Oxford University Press, 1990; pp. 118-120.
Lipovsek, D., "Adnectins: engineered target-binding protein therapeutics," Protein Engineering, Design & Selection, vol. 24(1-2):3-9 (2011).

(56) References Cited

OTHER PUBLICATIONS

Lipovsek, Dasa et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," J. Mol. Biol., vol. 368:1024-1041 (2007).

Lipovsek, Dasa et al., "In-vitro protein evolution by ribosome display and mRNA display," Journal of Immunological Methods, vol. 290:51-67 (2004).

Litvinovich, Sergei V. et al., "Interactions Between Type III Domains in the 110 kDa Cell-binding Fragments of Fibronectin," J. Mol. Biol., vol. 248:611-626 (1995).

Liu, Zhihong et al., "Fine mapping of the antigen-antibody interaction of scFv215, a recombinant antibody inhibiting RNA polymerase II from *Drosophila melanogaster*," Journal of Molecular Recognition, vol. 12:103-111 (1999).

Lombardo, A. et al., "Conformational flexibility and crystallization of tandemly linked type III modules of human fibronectin," Protein Science, vol. 5:1934-1938 (1996).

Lu, Dan et al., "Tailoring in Vitro Selection for a Picomolar Affinity Human Antibody Directed against Vascular Endothelial Growth Factor Receptor 2 for Enhanced Neutralizing Activity," The Journal of Biological Chemistry, vol. 278(44):43496-43507 (2003).

Lu, Dan et al., Simultaneous Blockade of Both the Epidermal Growth Factor Receptor and the Insulin-like Growth Factor Receptor Signaling Pathways in Cancer Cells with a Fully Human Recombinant Bispecific Antibody, The Journal of Biological Chemistry, vol. 279(4):2856-2865 (2004).

Lyden, David et al., "Impaired recruitment of bone-marrow-derived endothelial and hematopoietic precursor cells blocks tumor angiogenesis and growth," Nature Medicine, vol. 7(11):1194-1201 (2001).

Maeda, Hiroshi et al., "SMANCS and polymer-conjugated macromolecular drugs: advantages in cancer chemotherapy," Advanced Drug Delivery Reviews, vol. 46:169-185 (2001).

Main, Alison L. et al., "The Three-Dimensional Structure of the Tenth Type III Module of Fibronectin: An Insight into RGD-Mediated Interactions," Cell, vol. 71:671-678 (1992).

Mamluk, Roni et al., "Anti-tumor effect of CT-322 as an adnectin inhibitor of vascular endothelial growth factor receptor-2," mAbs, vol. 2(2):199-208 (2010).

Mao, Yong et al., "Fibronectin fibrillogenesis, a cell-mediated matrix assembly process," Matrix Biology, vol. 24:389-399 (2005).

Markland, William et al., "Iterative Optimization of High-Affinity Protease Inhibitors Using Phage Display. 2. Plasma Kallikrein and Thrombin," Biochemistry, vol. 35:8058-8067 (1996).

Maruyama, Kazuo et al., "Oligo-capping: a simple method to replace the cap structure of eukaryotic mRNAs with bligonbonucleotides," Gene, vol. 138:171-174 (1994).

Matsushima, Ayako et al., "Modification of *E. coli* Asparaginase with 2.4-Bis(O-Methoxypolyethylene Glycol)-6-Chloro-S-Triazine(Activated PEG2); Disapperance of Binding Ability Towards Anti-serum and Retention of Enzymic Activity," Chemistry Letters, pp. 773-776 (1980).

Mattheakis, Larry C. et al., "An in vitro polysome display system for identifying ligands from very large peptide libraries," Proc. Natl. Acad. Sci. USA, vol. 91:9022-9026 (1994).

McCleod, D. Scott et al., "Localization of VEGF Receptor-2 (KDR/Flk-1) and Effects of Blocking It in Oxygen-Induced Retinopathy," Investigative Ophthalmology & Visual Science, vol. 43(2):474-482 (2002).

McConnell, Stephen J. et al., "Tendamistat as a Scaffold for Conformationally Constrained Phage Peptide Libraries," J. Mol. Biol., vol. 250:460-470 (1995).

McPherson, Michael et al., "Drug Receptor Identification from Multiple Tissues Using Cellular-Derived mRNA Display Libraries," Chemistry & Biology, vol. 9:691-698 (2002).

Meinke, A. et al., "Cellulose-Binding Polypeptides from Cellulomonas fimi: Endoglucanase D (CenD), a Family A beta-1,4-Glucanase," Journal of Bacteriology, vol. 175(7):1910-1918 (1993).

Meissner, Markus et al., "Suppression of VEGFR2 Expression in Human Endothelial Cells by Dimethylfumarate Treatment: Evidence for Anti-Angiogenic Action," Journal of Investigative Dermatology, vol. 131:1356-1364 (2011).

Meyer, Rosana D. et al., "Comparative Structure-Function Analysis of VEGFR-1 and VEGFR-2, What Have We Learned from Chimeric Systems,?" Ann. N.Y. Acad. Sci., vol. 995:200-207 (2003).

Muller, Christoph W. et al., "Structure of the NF-kappaB p50 homodimer bound to DNA," Nature, vol. 373:311-317 (1995).

Muyldermans, Serge, "Single domain camel antibodies: current status," Reviews in Molecular Biotechnology, vol. 74:277-302 (2001).

Nemoto, Naoto et al., "In vitro virus: Bonding of mRNA bearing puromycin at the 3'-terminal end to the C-terminal end of its encoded protein on the ribosome in vitro," FEBS Letters, vol. 414:405-408 (1997).

Ng, Eugene W.M. et al., "Targeting angiogenesis, the underlying disorder in neovascular age-related macular degeneration," Can. J. Ophthalmol., vol. 40:352-368 (2005).

Ngo, J. Thomas et al., "Computational Complexity Protein Structure Prediction, and the Levinthal Paradox," The Protein Folding Problem and Tertiary Structure Prediction, Birkhauser, Boston, MA, K. Merz (Ed.), pp. 433-440 and 191-495 (1994).

Niemeyer, Christof M. et al., "Oligonucleotide-directed self-assembly of proteins: semisynthetic DNA—streptavidin cybrid molecules as connectors for the generation of macroscopic arrays and the construction of supramolecular hioconjugates," Nucleic Acids Research, vol. 22(25):5530-5539 (1994).

Nilsen, Timothy W., "Trans-Splicing in Protozoa and Helminths," Infections Agents and Disease, vol. 1:212-218 (1992).

Nord, Karin et al., "A combinatorial library of an alpha-helical bacterial receptor domain," Prot. Eng., vol. 8:601-608 (1995).

Nord, Karin et al., "Binding proteins selected from combinatorial libraries of an alpha-helical bacterial receptor lomain," Nature Biotechnology, vol. 15:772-777 (1997).

Notice of Opposition to European Patent No. 1137941 (Application No. 99 967 261.1), 29 pages, dated May 11, 2010.

Nygren, Per-Ake et al., "Scaffolds for engineering novel binding sites in proteins," Current Opinion in Structural Biology, vol. 7:463-469 (1997).

Parker, M.H. et al., "Antibody mimics based on human fibronectin type three domain engineered for thermostability and high-affinity binding to vascular endothelial growth factor receptor two," Protein Engineering, Design & Selection, vol. 18(9):435-444 (2005).

Partial European Search Report for Application No. 01981621.4, 5 pages, dated Feb. 25, 2005.

Patel, Neela et al., "A Selective and Oral Small Molecule Inhibitor of Vascular Epithelial Growth Factor (VEGFR)-2 and VEGFR-1 Inhibits Neovascularization and Vascular Permeability," The Journal of Pharmacology and Experimental Therapeutics, vol. 306(3):838-845 (2003).

Phillips, Anthony J., "The challenge of gene therapy and DNA delivery," Journal of Pharmacy and Pharmacology, vol. 53:1169-1174 (2001).

Plaxco, Kevin W. et al., "A Comparison of the Folding Kinetics and Thermodynamics of Two Homologous Fibronectin Type III Modules," J. Mol. Biol., vol. 270:763-770 (1997).

Plaxco, Kevin W. et al., "Rapid refolding of a proline-rich all-beta-sheet fibronectin type III module," Proc. Natl. Acad. Sci. USA, vol. 93:10703-10706 (1996).

Posey, J. et al., "A Phase I Trial of an Anti-Kdr (VEGFR2) Chimeric Antibody in Patients with Liver Metastases in Colorectal Cancer (CRC)," Slides from presentation at 2002 American Society of Clinical Oncology (ASCO) Annual Meeting, 20 pages, (2002).

Potts, Jennifer R. et al., "Fibronectin structure and assembly," Current Biology, vol. 6:648-655 (1994).

Potts, Jennifer R. et al., "Structure and Function of Fibronectin Modules," Matrix Biology, vol. 15:313-320 (1996).

Proescholdt, Martin A. et al., "Vascular Endothelial Growth Factor Is Expressed in Multiple Sclerosis Plaques and Can Induce Inflammatory Lesions in Experimental Allergic Encephalomyelitis Rats," Journal of Neuropathology and Experimental Neurology, vol. 61(10):914-925 (2002).

(56) References Cited

OTHER PUBLICATIONS

Richards, Julie et al., "Engineered Fibronectin Type III Domain with a RGDWXE Sequence Binds with Enhanced Affinity and Specificity to Human alphavbeta3 Integrin," J. Mol. Biol., vol. 326:1475-1488 (2003).
Roberts, Richard W. et al., "RNA-peptide fusions for the in vitro selection of peptides and proteins," Proc. Natl. Acad. Sci. USA, vol. 94:12297-12302 (1997).
Roberts, Richard W., "Totally in vitro protein selection using mRNA-protein fusions and ribosome display," Current Opinion in Chemical Biology, vol. 3:268-273 (1999).
Rottgen, Peter et al., "A human pancreatic secretory trypsin inhibitor presenting a hyperveriable highly constrained epitope via monovalent phagemid display," Gene, vol. 164:243-250 (1995).
Rudikoff, Stuart et al., "Single amino acid substitution altering antigen-binding specificity," Proc. Natl. Acad. Sci. USA, vol. 79:1979-1983 (1982).
Sambrook et al. Molecular Cloning A Laboratory Manual, 2nd edition, Cold Spring Harbor, N.Y., 1989, pp. 2.43-2.84.
Schildbach, Joel F. et al., "Contribution of a single heavy chain residue to specificity of an anti-digoxin monoclonal antibody," Protein Science, vol. 3:737-749 (1994).
Schildbach, Joel F. et al., "Heavy Chain Position 50 Is a Determination of Affinity and Specificity for the Anti-digoxin Antibody 26-10," The Journal of Biological Chemistry, vol. 268(29):21739-21747 (1993).
Scott, Jamie K. et al., "Searching for Peptide Ligands with an Epitope Library," Science, vol. 249:386-390 (1990).
Shibata, K. et al., "An attempt to substitute the cell binding domain of human fibronectin in lambda phage J protein: Computer design and expression," Biochimie, vol. 75:459-465 (1993).
Shibuya, Masabumi, "Vascular endothelial growth factor receptor-2: Its unique signaling and specific ligand, VEGF-E," Cancer Sci., vol. 94(9):751-756 (2003).
Shima, David T. et al., "The Mouse Gene for Vascular Endothelial Growth Factor," The Journal of Biological chemistry, vol. 271(7):3877-3883 (1996).
Skolnick, Jeffrey et al., "From genes to protein structure and function: novel applications of computational approaches in the genomic era," TibTech, vol. 18:34-39 (2000).
Smith, George P. et al., "Phage Display," Chem. Rev., vol. 97:391-410 (1997).
Smith, Temple F. et al., "The challenges of genome sequence annotation of 'The devil is in the details,'" Nature Biotechnology, vol. 15:1222-1223 (1997).
Supplementary European Search Report for Application No. 01913159.8, 3 pages, dated Dec. 21, 2004.
Supplementary European Search Report for Application No. 99967261.1, 3 pages, dated Mar. 6, 2002.
Takahashi, Satoru, "Vascular Endothelial Growth Factor (VEGF), VEGF Receptors and Their Inhibitors for Antiangiogenic Tumor Therapy," Biol. Pharm. Bull. vol. 34(12):1785-1788 (2011).
Tang, Lisa et al., "Pharmacokinetic Aspects of Biotechnology Products," Journal of Pharmaceutical Sciences, vol. 93 (9):2184-2204 (2004).
Tischer, Edmund et al., "The Human Gene for Vascular Endothelial Growth Factor," The Journal of Biological Chemistry, vol. 266(18):11947-11954 (1991).
Tokuriki, Nobuhiko et al., "Stability effects of mutations and protein evolvability," Current Opinion in Structural Biology, vol. 19:596-604 (2009).
Tramontano, Anna et al., "The Making of the Minibody: an Engineered beta-Protein for the Display of Conformationally Constrained Peptides," Journal of Molecular Recognition, vol. 7:9-24 (1994).
Trinh, Ryan et al., "Optimization of codon pair use within the (GGGGS)3 linker sequence results in enhanced protein expression," Molecular Immunology, vol. 40:717-722 (2004).

Verheul, H.M.W. et al., "Targeting Vascular Endothelial Growth Factor Blockade: Ascites and Pleural Effusion Formation," The Oncologist, vol. 5(Suppl. 1):45-50 (2000).
Vuento, Math et al., "Purification of Fibronectin from Human Plasma by Affinity Chromatography under Non-Denaturing Conditions," Biochem. J., vol. 183:331-337 (1979).
Wang, Cheng-I et al., "Isolation of a High Affinity Inhibitor of Urokinase-type Plasminogen Activator by Phage Display of Ecotin," The Journal of Biological Chemistry, vol. 270(20):12250-12256 (1995).
Watanabe, H. et al., "Anti-vascular endothelial growth factor receptor-2 (Flk-1/KDR) antibody suppresses contact hypersensitivity," Experimental Dermatology, vol. 13:671-681 (2004).
Watanabe, Takeshi et al., "Gene Cloning of Chitinase A1 from Bacillus circulans WL-12 Revealed Its Evolutionary Relationship to Serratia Chitinase and to the Type III Homology Units of Fibronectin," The Journal of Biological Chemistry, vol. 265:15659-15665 (1990).
Wells, James A., "Additivity of Mutational Effects in Proteins," Biochemistry, vol. 29(37):8509-8517 (1990).
Williams, Alan F. et al., "The Immunoglobulin Superfamily—Domains for Cell Surface Recognition," Ann. Rev. Immunol., vol. 6:381-405 (1988).
Williams, Michael J. et al., "Solution Structures of Modular Proteins by Nuclear Magnetic Resonance," Methods in Enzymology, vol. 245:451-469 (1994).
Wilson, David S. et al., "The use of mRNA display to select high-affinity protein-binding peptides," PNAS, vol. 98 (7):3750-3755 (2001).
Written Opinion for Application No. PCT/US01/06414, 5 pages, dated Feb. 7, 2002.
Xiang, Jim et al., "Study of B72.3 combining sites by molecular modeling and site-directed mutagenesis," Protein Engineering, vol. 13(5):339-344 (2000).
Xu, Lihui et al., "Directed Evolution of High-Affinity Antibody Mimics Using mRNA Display," Chemistry & Biology, vol. 9:933-942 (2002).
Yang, Karen et al., "Tailoring structure-function and pharmacokinetic properties of single-chain Fv proteins by site-specific PEGylation," Protein Engineering, vol. 16(10):761-770 (2003).
Yoshiji, H. et al., "Vascular endothelial growth factor and receptor interaction is a prerequisite for murine hepatic fibrogenesis," Gut, vol. 52:1347-1354 (2003).
Zdanov, Alexander et al., Structure of a single-chain antibody variable domain (Fv) fragment complexed with a carbohydrate antigen at 1.7-A resolution, Proc. Natl. Acad. Sci. USA, vol. 91:6423-6427 (1994).
Zhou, Tianhong et al., "Development of a multi-drug delivery implant for intraocular management of proliferative vitreoretinopathy," Journal of Controlled Release, vol. 55:281-295 (1998).
Zhu, Z. et al., "Inhibition of human leukemia in an animal model with human antibodies directed against vascular endothelial growth factor receptor 2. Correlation between antibody affinity and biological activity," Leukemia, vol. 17:604-611 (2003).
Ackermann, Maximilian et al., "Anti-VEGFR2 and anti-IGF-1R-Adnectins inhibit Ewing's sarcoma A673-xenograft growth and normalize tumor vascular architecture," Angiogenesis, vol. 15:685-695 (2012).
Apte, Aaron N. et al., "Anchor-Ligated cDNA Libraries: A Technique for Generating a cDNA Library for the Immediate Cloning of the 5' Ends of mRNAs," BioTechniques, vol. 15(5):890-893 (1993).
Bae, Dong-Goo et al., "Arginine-rich Anti-vascular Endothelial Growth Factor Peptides Inhibit Tumor Growth and Metastasis by Blocking Angiogenesis," The Journal of Biological Chemistry, vol. 275(18):13588-13596 (2000).
Baggio, Rick et al., "Identification of epitope-like consensus motifs using mRNA display," Journal of Molecular Recognition, vol. 15:126-134 (2002).
Baron, Martin et al., "H NMR Assignment and Secondary Structure of the Cell Adhesion Type III Module of Fibronectin," Biochemistry, vol. 31:2068-2073 (1992).
Baron, Martin et al., "Protein modules," TIBS, vol. 16:13-17 (1991).

(56) References Cited

OTHER PUBLICATIONS

Batori, Vincent et al., "Exploring the potential of the monobody scaffold: effects of loop elongation on the stability of a fibronectin type III domain," Protein Engineering, vol. 15(12):1015-1020 (2002).
Bianchi, Elisabetta et al., "High Level Expression and Rational Mutagenesis of a Designed Protein, the Minibody," J. Mol. Biol., vol. 236:649-659 (1994).
Boder, Eric T. et al., "Directed evolution of antibody fragments with monovalent femtomolar antigen-binding affinity," PNAS, vol. 97(20):10701-10705 (2000).
Boder, Eric T. et al., "Yeast surface display for screening combinatorial polypeptide libraries," Nature Biotechnology, vol. 15:553-557 (1997).
Boldicke, Thomas et al., "Anti-VEGFR-2 scFvs for Cell Isolation. Single-Chain Antibodies Recognizing the Human Vascular Endothelial Growth Factor Receptor-2 (VEGFR-2/flk-1) on the Surface of Primary Endothelial Cells and Preselected CD34+ Cells from Cord Blood," Stem Cells, vol. 19:24-36 (2001).
Bork, P. et al., "The Immunoglobulin Fold, Structural Classification, Sequence Patterns and Common Core," J. Mol. . Biol., vol. 242:309-320 (1994).
Bork, Peer et al., "Go hunting in sequence databases but watch out for the traps," TIG, vol. 12(10):425-427 (1996).
Bork, Peer et al., "Proposed acquisition of an animal protein domain by bacteria," Proc. Natl. Acad. Sci. USA, vol. 89:8990-8994 (1992).
Bork, Peer, "Powers and Pitfalls in Sequence Analysis: The 70% Hurdle," Genome Research, vol. 10:398-400 (2000).
Brenchley, P.E.C. et al., "Angiogenesis in inflammatory joint disease: a target for therapeutic intervention," Clin. Exp. Immunol., vol. 121:426-429 (2000).
Brenner, Steven E., "Errors in genome annotation," TIG, vol. 15(4):132-133 (1999).
Brock, Kenny V. et al., "Nucleotide sequencing of 5' and 3' termini of bovine viral diarrhea virus by RNA ligation and PCR," Journal of Virological Methods, vol. 38:39-46 (1992).
Brown, McKay et al., "Tolerance to Single, but Not Multiple, Amino Acid Replacements in Antibody VH CDR2," The Journal of Immunology, vol. 156:3285-3291 (1996).
Bruzik, James P. et al., "Spliced leader RNAs from lower eukaryotes are trans-spliced in mammalian cells," Nature, vol. 360(6405):692-695 (1992).
Caliceti, Paolo et al., "Pharmacokinetic and biodistribution properties of poly(ethylene glycol)-protein conjugates," Advanced Drug Delivery Reviews, vol. 55:1261-1277 (2003).
Campbell, Iain D. et al., "Building proteins with fibronectin type III modules, Fibronectin type III modules are versatile components of many proteins. Recent structures of module pairs show how these modules are joined together," Structure, vol. 2:333-337 (1994).
Carvalho, Jozelio Freire et al., "Vascular Endothelial Growth Factor (VEGF) in Autoimmune Diseases," Journal of Clinical Immunology, vol. 27(3):246-256 (2007).
Chinese Office Action for Application No. 201180036862.4, 5 pages, dated Mar. 20, 2014.
Choy, E.H.S. et al., "Efficacy of a novel PEGylated humanized anti-TNF fragment (CDP870) in patients with rheumatoid arthritis: a phase II double-blinded, randomized, dose-escalating trial," Rheumatology, vol. 41:1133-1137 (2002).
Clackson, Tim et al., "In vitro selection from protein and peptide libraries," TibTech, vol. 12(5):173-184 (1994).
Clackson, Tim et al., "Making antibody fragments using phage display libraries," Nature, vol. 352:624-628 (1991).
Claffey, Kevin P. et al., "Vascular Endothelial Growth Factor, Regulation by Cell Differentiation and Activated Second Messenger Pathways," The Journal of Biological Chemistry, vol. 267(23):16317-16323 (1992).
Clarke, Jane et al., "Folding and Stability of a Fibronectin Type III Domain of Human Tenascin," J. Mol. Biol., vol. 270:771-778 (1997).
Connelly, Roberta et al., "Mitogenic properties of a bispecific single-chain Fv-Ig fusion generated from CD2-specific mAb to distinct epitopes," International Immunology, vol. 10(12):1863-1872 (1998).
Copie, Valerie et al., "Solution Structure and Dynamics of Linked Cell Attachment Modules of Mouse Fibronectin Containing the RGD and Synergy Regions: Comparison wtih the Human Fibronectin Crystal Structure," J. Mol. Biol., vol. 277:663-682 (1998).
Cota, Ernesto et al., "Two Proteins with the Same Structure Respond very Differently to Mutation: The Role of Plasticity in Protein Stability," J. Mol. Biol., vol. 302:713-725 (2000).
Cujec, Thomas P. et al., "Selection of v-Abl Tyrosine Kinase Substrate Sequences from Randomized Peptide and Cellular Proteomic Libraries Using mRNA Display," Chemistry & Biology, vol. 9:253-264 (2002).
Devlin, James J. et al., "Random Peptide Libraries: A Source of Specific Protein Binding Molecules," Science, vol. 249:404-406 (1990).
DGENE Search Results, 33 pages (2005).
Dickinson, Craig D. et al., "Crystal Structure of the Tenth Type III Cell Adhesion Module of Human Fibronectin," J. Mol. Biol., vol. 236:1079-1092 (1994).
Dickinson, Craig D. et al., "Crystals of the Cell-binding Module of Fibronectin Obtained from a Series of Recombinant Fragments Differing in Length," J. Mol. Biol., vol. 238:123-127 (1994).
Doerks, Tobias et al., "Protein annotation: detective work for function prediction," TIG, vol. 14(6):248-250 (1998).
Duan, Jinzhu et al., "Fibronectin Type III Domain Based Monobody with High Affinity," Biochemistry, vol. 46:12656-12664 (2007).
Ely, Kathryn R. et al., "Common molecular scaffold for two unrelated RGD molecules," Protein Engineering, vol. 8 (8):823-827 (1995).
Emanuel, Stuart L. et al., "A fibronectin scaffold approach to bispecific inhibitors of epidermal growth factor receptor and insulin-like growth factor-I receptor," MAbs, vol. 3(1):38-48 (2011).
Emanuel, Stuart L. et al., "Adnectins as a platform for multi-specific targeted biologics: A novel bispecific inhibitor of EGFR and IGF-IR growth factor receptors," Cancer Research, vol. 70(8 Suppl. 1), Abstract 2586, 1 page, AACR 101st Annual Meeting (2010).
Emanuel, Stuart L. et al., "Functional activity of a bispecific Adnectin inhibitor to EGFR and IGFR," 2009 AACR Annual Meeting, 1 page, Abstract No. 2813 (2009).
Emanuel, Stuart L. et al., "Functional activity of a bispecific Adnectin inhibitor to EGFR and IGFR," 2009 AACR Annual Meeting, Session Title: IGF-IR and PI3K Pathways, Abstract No. 2813, 2 pages (2009).
European Office Action for Application No. 06013825.2, 9 pages, dated Sep. 17, 2008.
European Office Action for Application No. 09167669.2, 7 pages, dated Dec. 28, 2009.
European Search Report for Application No. 13191581.1, 9 pages, dated Apr. 8, 2014.
European Search Report for Application No. 14168988.5, 7 pages, dated Oct. 7, 2014.
Extended European Search Report, EP 16187428.4-1402, dated Feb. 21, 2017, 7 pages.
Fenton, Bruce et al., "Pathophysiological effects of antibodies to IGF-1R and Vegfr-2 plus fractionated radiation in DU145 prostate carcinoma xenografts," Radiation Research Society 2005 Annual Meeting, Abstract No. PP109, 1 page (2005).
Ferguson, Kimberly C. et al., "The SL1 trans-spliced leader RNA performs an essential embryonic function in Caenorhabditis elegans that can also be supplied by SL2 RNA," Genes & Development, vol. 10:1543-1556 (1996).
GenBank Accession No. AAC48614, MacLeod, J.N. et al., "Fibronectin mRNA splice variant in articular cartilage lacks bases encoding the V, III-15, and I-10 protein segments," J. Biol. Chem., vol. 271(31):18954-18960 (1996), 2 pages, (1996).
GenBank Accession No. CAA26536, Komblihtt, A.R. et al., "Primary structure of human fibronectin: differential splicing may generate at least 10 polypeptides froma single gene," EMBO J., vol. 4(7):1755-1759 (1985), 7 pages, (1996).

(56) References Cited

OTHER PUBLICATIONS

GenBank Accession No. P07589, Skorstengaard, K. et al., "Complete primary structure of bovine plasma fibronectin," Eur. J. Biochem., vol. 161(2):441-453 (1986), 9 pages, (1997).
GenBank Accession No. X02761, Kornblihtt, A.R. et al., "Primary structure of human fibronectin: differential splicing may generate at least 10 polypeptides from a single gene," EMBO J., vol. 4(7):1755-1759 (1985), 4 pages, (1996).
Ghosh, Gourisankar et al., "Structure of NF-kappaB p50 homodimer bound to a kappaB site," Nature, vol. 373:303-310 (1995).
Gill, Davinder S. et al., "Biopharmaceutical drug discovery using novel protein scaffolds," Current Opinion in Biotechnology, vol. 17:653-658 (2006).
Giusti, Angela M. et al., "Somatic diversification of S107 from an antiphosphocholine to an anti-DNA autoantibody is due to a single base change in its heavy chain variable region," Proc. Natl. Acad. Sci. USA, vol. 84:2926-2930 (1987).
Goedert, M. et al., "Cloning and sequencing of the cDNA encoding an isoform of microtubule-associated protein tau containing four tandem repeats: differential expression of tau protein mRNAs in human brain," The EMBO Journal, vol. 8(2):393-399 (1989).
Grant, Richard P. et al., "Structural Requirements for Biological Activity of the Ninth and Tenth FIII Domains of Human Fibronectin," The Journal of Biological Chemistry, vol. 272(10):6159-6166 (1997).
Hamers-Casterman, C. et al., "Naturally occurring antibodies devoid of light chains," Nature, vol. 363:446-448 (1993).
Hammond, Philip W. et al., "In Vitro Selection and Characterization of Bcl-XL-binding Proteins from a Mix of Tissue-specific mRNA Display Libraries," The Journal of Biological Chemistry, vol. 276(24):20898-20906 (2001).
Harpaz, Yahouda et al., "Many of the IMmunoglobulin Superfamily Domains in Cell Adhesion Molecules and Surface Receptors Belong to a New Structural Set Which is Close to That Containing Variable Domains," J. Mol. Biol., vol. 238:528-539 (1994).
Hey, Thomas et al., "Artificial, non-antibody binding proteins for pharmaceutical and industrial applications," Trends in Biotechnology, vol. 23(10):514-522 (2005).
Hocking, Denise C. et al., "A Novel Role for the Integrin-binding III-10 Module in Fibronectin Matrix Assembly," The Journal of Cell Biology, vol. 133(2):431-444 (1996).
Hocking, Denise C. et al., "Activation of Distinct alpha5beta1-mediated Signaling Pathways by Fibronectin's Cell Adhesion and Matrix Assembly Domains," The Journal of Cell Biology, vol. 141(1):241-253 (1998).
Huang, Fei et al., "The Mechanisms of Differential Sensitivity to an Insulin-like Growth Factor-1 Receptor Inhibitor (BMS-536924) and Rationale for Combining With EGFR/HER2 Inhibitors," Cancer Res., vol. 69(1) pp. 161-170 (2009).
Huang, Hu et al., "Blockade of VEGFR1 and 2 Suppresses Pathological Angiogenesis and Vascular Leakage in the Eye," PLoS One, vol. 6(6):e21411, 14 pages, doi:10.1371/journal.pone.0021411 (2011).
Husimi, Y. et al., "Role of the Virus-type Strategy in Encoded Molecular Evolution," Progress in Biophysics and Molecular Biology, vol. 65(Suppl. 1):64 (1996).
Hynes, Richard O. et al., "Integrins: Versability, Modulation, and Signaling in Cell Adhesion," Cell, vol. 69:11-25 (1992).
International Preliminary Examination Report for Application No. PCT/US01/06414, 6 pages, dated Aug. 27, 2002.
International Preliminary Examination Report for Application No. PCT/US01/32233, 5 pages, dated Dec. 10, 2002.
International Preliminary Examination Report for Application No. PCT/US99/29317, 4 pages, dated Aug. 14, 2000.
International Preliminary Report on Patentability and Written Opinion for Application No. PCT/US2009/003192, 12 pages, dated Nov. 12, 2010.
International Preliminary Report on Patentability and Written Opinion for Application No. PCT/US2011/034998, 10 pages, dated Nov. 6, 2012.
International Preliminary Report on Patentability for Applicaiton No. PCT/US2004/040885, 6 pages, dated Jun. 7, 2006.
International Preliminary Report on Patentability for Application No. PCT/US2011/038013, 9 pages, dated Nov. 27, 2012.
International Search Report for Application No. PCT/US01/06414, 5 pages, dated Aug. 7, 2001.
International Search Report for Application No. PCT/US01/32233, 3 pages, dated Jun. 12, 2003.
International Search Report for Application No. PCT/US04/40885, 3 pages, dated Feb. 21, 2006.
International Search Report for Application No. PCT/US2009/003192, 8 pages, dated Jun. 1, 2010.
International Search Report for Application No. PCT/US2011/034998, 5 pages, dated Jul. 17, 2012.
International Search Report for Application No. PCTUS2011/038013, 7 pages, dated Jan. 25, 2012.
International Search Report for Application No. PCT/US99/29317, 2 pages, dated Apr. 6, 2000.
Jain, Rakesh K. et al., "Dissecting Tumour Pathophysiology Using Intravital Microscopy," Nature, vol. 2:266-276 (2002).
Jakob, W. et al., "The chick embryo chorioallantoic membrane as a bioassay for angiogenesis factors: Reactions induced by carrier materials," Exp. Path. Bd., vol. 15:241-249 (1978).
Jaye et al. "Isolation probe deduced from of a human anti-haemophilic factor IX cDNA clone using a unique 52-base synthetic nucleotide probe deduced from the amino acid sequence of bovine factor IX," Nucl Acids Res 11 (8): 2325-2355, 1983.
Jung, Gyoo Yeol et al., "A Functional Protein Chip for Pathway Optimization and in Vitro Metabolic Engineering," Science, vol. 304:428-431 (2004).
Keefe, Anthony D. et al., "Functional proteins from a random-sequence library," Nature, vol. 410:715-718 (2001).
King, Catherine A. et al., "DNA vaccines with single-chain Fv fused to fragment C of tetanus toxin induce protective immunity against lymphoma and myeloma," Nature Medicine, vol. 4(11):1281-1286 (1998).
Kohler, G. et al., "Continuous cultures of fused cells secreting antibody of predefined specificity," Nature, vol. 256:495-497 (1975).
Koide, Akiko et al., "Monobodies. Antibody Mimics Based on the Scaffold of the Fibronectin Type III Domain," Methods in Molecular Biology, vol. 352: Protein Engineering Protocols, K.M. ARndt (Ed.), Humana Press, Totowa, NJ, Chapter 6, pp. 95-109 (2007).
Koide, Akiko et al., "Stabilization of a Fibronectin Type III Domain by the Removal of Unfavorable Electrostatic Interactions on the Protein Surface," Biochemistry, vol. 40:10326-10333 (2001).
Koide, Akiko et al., "The Fibronectin Type III Domain as a Scaffold for Novel Binding Proteins," J. Mol. Biol., vol. 284:1141-1151 (1998).
Koide, Shohei et al., "Directed Evolution of Fibronectin Type III Domain to Novel Ligand Binding Proteins," FASEB J., vol. 11(9 Suppl.), Poster No. M40, p. A837, (1997).
Koide, Shohei et al., "Directed Evolution of Fibronectin Type III Domain to Novel Ligand Binding Proteins," The Faseb Journal, vol. 11(9):A1155, Poster No. 1739 (1997).
Korean Office Action for Application No. 10-2009-7012553, 9 pages, dated Feb. 28, 2014.
Ku, Jung et al., "Alternate protein frameworks for molecular recognition," Proc. Natl. Acad. Sci. USA, vol. 92:6552-6556 (1995).
Kurz, Markus et al., "Psoralen photo-crosslinked mRNA-puromycin conjugates: a novel template for the rapid and facile preparation of mRNA-protein fusions," Nucleic Acids Research, vol. 28(18):e83, 5 pages (2000).
Kussie, Paul H. et al., "A Single Engineered Amino Acid Substitution Changes Antibody Fine Specificity," Journal of Immunology, vol. 152:146-152 (1994).

* cited by examiner

Individual loops are amplified and
recombined into a master library

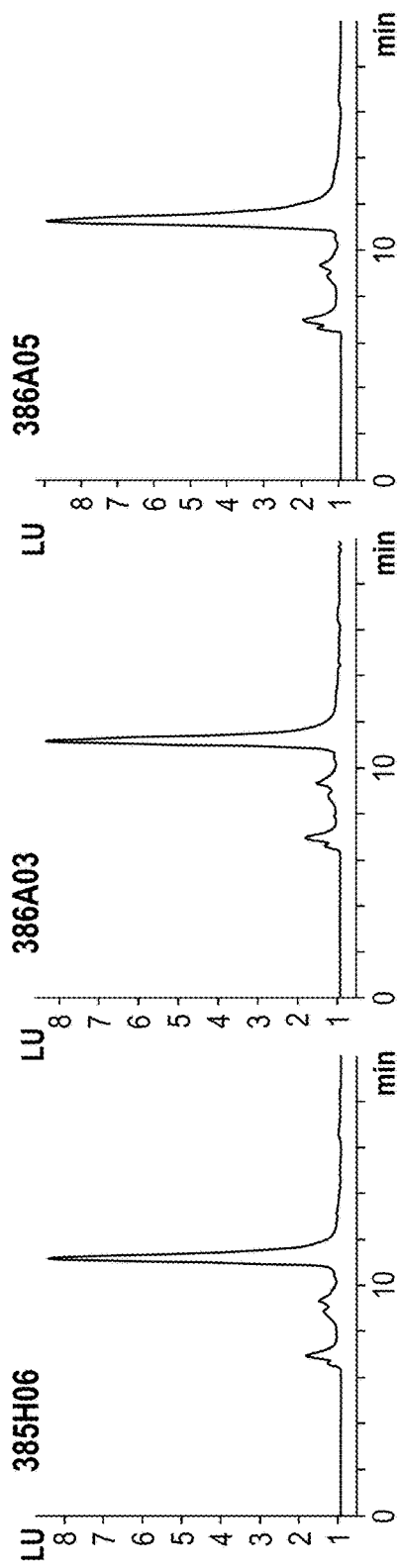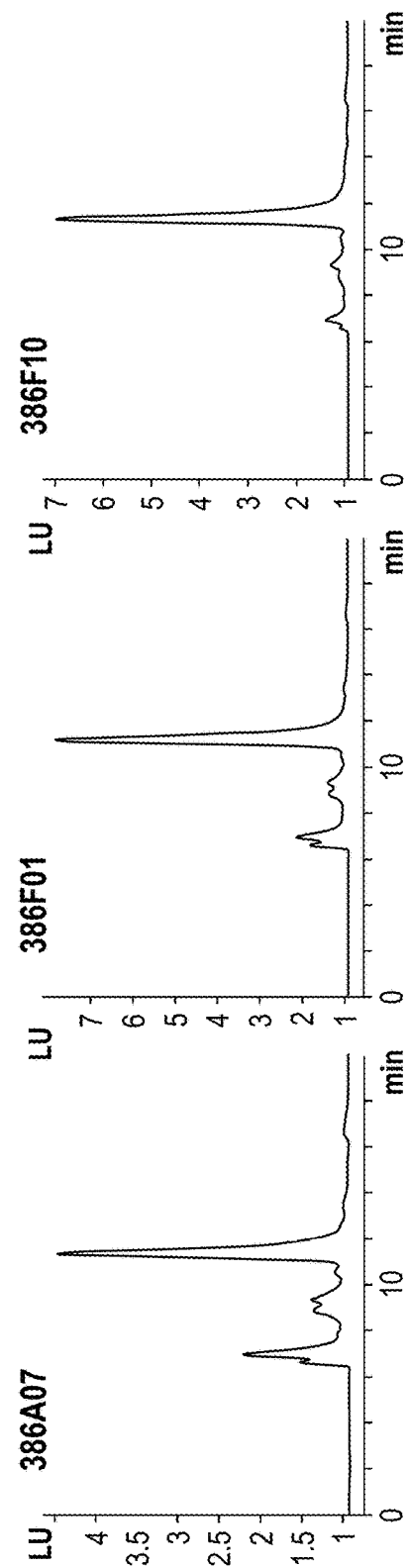
Fig. 15G  Fig. 15H  Fig. 15I
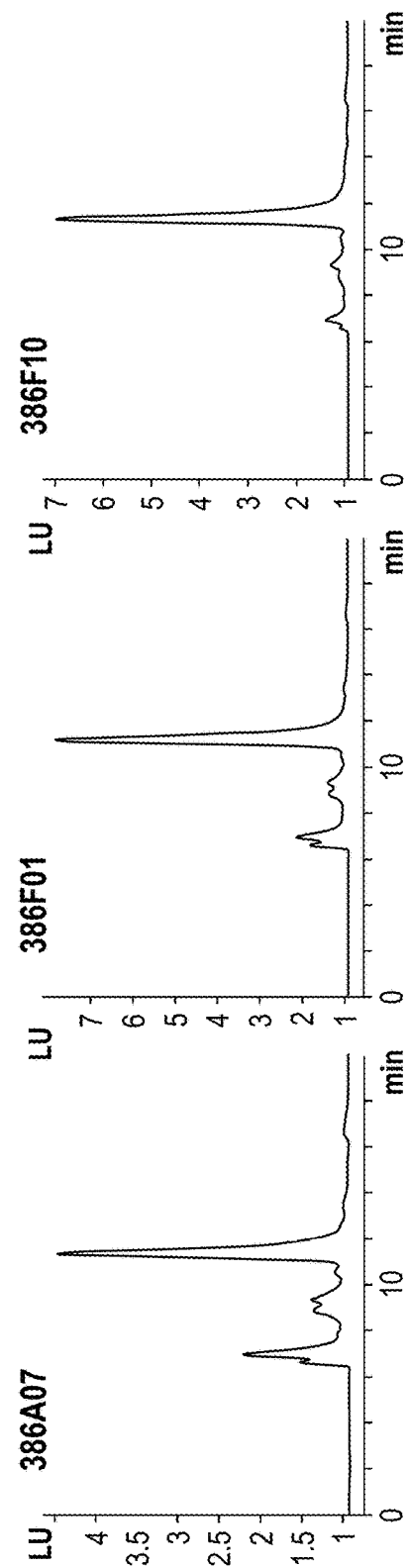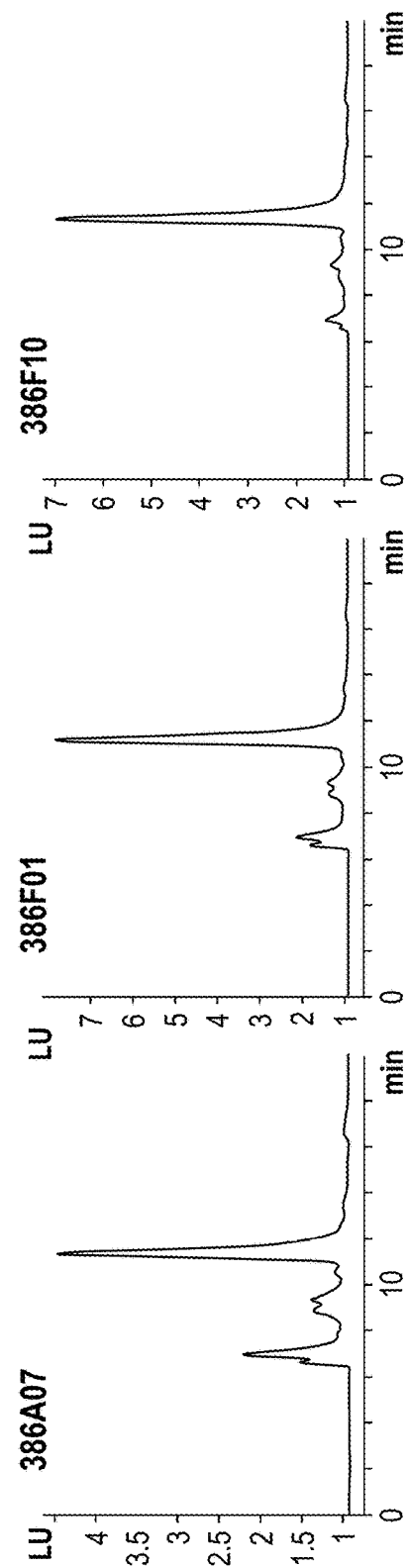
Fig. 15J  Fig. 15K  Fig. 15L

1: 385A08
2: 385A08-PEG20-385A08
3: 385A08-PEG40

SEQUENCE LISTING

<160> NUMBER OF SEQ ID NOS: 248

<210> SEQ ID NO 1
<211> LENGTH: 94
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr
                85                  90

<210> SEQ ID NO 2
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Val Ser Asp Val Pro Arg Asp Leu Glu Val Val Ala Ala Thr Pro Thr
 1               5                  10                  15

Ser Leu Leu Ile Ser Trp Arg Ala Arg Gln Asn Leu Ser Arg Tyr Tyr
                20                  25                  30

Arg Ile Thr Tyr Gly Glu Thr Gly Gly Asn Ser Pro Val Gln Glu Phe
            35                  40                  45

Thr Val Pro Val Leu Pro Asn Thr Ala Thr Ile Ser Gly Leu Lys Pro
 50                  55                  60

Gly Val Asp Tyr Thr Ile Thr Val Tyr Ala Val Thr Gly Val Pro
 65                  70                  75                  80

Phe Tyr Asp Met Leu Ile Gly Leu Leu Tyr Pro Ile Ser Ile Asn Tyr
                85                  90                  95

Arg Thr

<210> SEQ ID NO 3
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Val Ser Asp Val Pro Arg Asp Leu Glu Val Val Ala Ala Thr Pro Thr
 1               5                  10                  15

Ser Leu Leu Ile Ser Trp Leu Pro Pro Gly Phe Val Ile Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser Arg Leu Thr Thr Ala Thr Ile Ser Gly Leu Lys Pro
 50                  55                  60

Gly Val Asp Tyr Thr Ile Thr Val Tyr Ala Val Thr Ser Ser Asn Gly
 65                  70                  75                  80

Phe Tyr Ser Lys Ile Leu Ser Leu Trp Trp Pro Ile Ser Ile Asn Tyr
                85                  90                  95

Arg Thr

<210> SEQ ID NO 4
<211> LENGTH: 96
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 4

Val Ser Asp Val Pro Arg Asp Leu Glu Val Val Ala Ala Thr Pro Thr
1               5                   10                  15

Ser Leu Leu Ile Ser Trp Gly Pro His Val Leu Gly Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Glu Arg Thr Ala Thr Ile Ser Gly Leu Lys Pro
    50                  55                  60

Gly Val Asp Tyr Thr Ile Thr Val Tyr Ala Val Thr Leu Arg Thr Gly
65                  70                  75                  80

Leu Pro Thr Leu His Ser Pro Gly Pro Ile Ser Ile Asn Tyr Arg Thr
                85                  90                  95

<210> SEQ ID NO 5
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Val Ser Asp Val Pro Arg Asp Leu Glu Val Val Ala Ala Thr Pro Thr
1               5                   10                  15

Ser Leu Leu Ile Ser Trp Ile Phe Ile Pro Ser Thr Trp Arg Tyr Tyr
            20                  25                  30

Arg Ile Thr Tyr Gly Glu Thr Gly Gly Asn Ser Pro Val Gln Glu Phe
        35                  40                  45

Thr Val Pro Thr Met Asp His Thr Ala Thr Ile Ser Gly Leu Lys Pro
    50                  55                  60

Gly Val Asp Tyr Thr Ile Thr Val Tyr Ala Val Thr Leu Asp His Arg
65                  70                  75                  80

Ser Leu Trp Pro Ile Ser Ile Asn Tyr Arg Thr
                85                  90

<210> SEQ ID NO 6
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Val Ser Asp Val Pro Arg Asp Leu Glu Val Val Ala Ala Thr Pro Thr
1               5                   10                  15

Ser Leu Leu Ile Ser Trp Pro Thr His Tyr Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Tyr His Asp His Thr Ala Thr Ile Ser Gly Leu Lys Pro
    50                  55                  60

Gly Val Asp Tyr Thr Ile Thr Val Tyr Ala Val Thr Asp Tyr Lys Met
65                  70                  75                  80
```

```
Lys Pro Arg Asn Tyr Gly Pro Ile Ser Ile Asn Tyr Arg Thr
                85                  90

<210> SEQ ID NO 7
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Val Ser Asp Val Pro Arg Asp Leu Glu Val Val Ala Ala Thr Pro Thr
1               5                   10                  15

Ser Leu Leu Ile Ser Trp Ser Tyr Glu Ser Tyr Lys Tyr Arg Tyr Tyr
                20                  25                  30

Arg Ile Thr Tyr Gly Glu Thr Gly Gly Asn Ser Pro Val Gln Glu Phe
            35                  40                  45

Thr Val Pro Ala Tyr Tyr Pro Thr Ala Thr Ile Ser Gly Leu Lys Pro
        50                  55                  60

Gly Val Asp Tyr Thr Ile Thr Val Tyr Ala Val Thr Glu Lys Gly His
65                  70                  75                  80

Tyr Arg Tyr Ile Tyr Ala Pro Ile Ser Ile Asn Tyr Arg Thr
                85                  90

<210> SEQ ID NO 8
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Val Ser Asp Val Pro Arg Asp Leu Glu Val Val Ala Ala Thr Pro Thr
1               5                   10                  15

Ser Leu Leu Ile Ser Trp Gly Ser His Leu Lys Val Lys Arg Tyr Tyr
                20                  25                  30

Arg Ile Thr Tyr Gly Glu Thr Gly Gly Asn Ser Pro Val Gln Glu Phe
            35                  40                  45

Thr Val Pro Phe Thr Ser Arg Thr Ala Thr Ile Ser Gly Leu Lys Pro
        50                  55                  60

Gly Val Asp Tyr Thr Ile Thr Val Tyr Ala Val Thr Lys Phe Arg Asn
65                  70                  75                  80

Tyr Arg Pro Ile Ser Ile Asn Tyr Arg Thr
                85                  90

<210> SEQ ID NO 9
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Val Ser Asp Val Pro Arg Asp Leu Glu Val Val Ala Ala Thr Pro Thr
1               5                   10                  15

Ser Leu Leu Ile Ser Trp Ala Pro Tyr Val Arg Val Ala Arg Tyr Tyr
                20                  25                  30

Arg Ile Thr Tyr Gly Glu Thr Gly Gly Asn Ser Pro Val Gln Glu Phe
```

```
                 35                  40                  45

Thr Val Pro Thr Leu Ser Arg Thr Ala Thr Ile Ser Gly Leu Lys Pro
     50                  55                  60

Gly Val Asp Tyr Thr Ile Thr Val Tyr Ala Val Thr Arg Thr Arg Asn
 65                  70                  75                  80

Tyr Gly Pro Ile Ser Ile Asn Tyr Arg Thr
                 85                  90

<210> SEQ ID NO 10
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Val Ser Asp Val Pro Arg Asp Leu Glu Val Val Ala Ala Thr Pro Thr
 1               5                  10                  15

Ser Leu Leu Ile Ser Trp Gly Ser His Leu Lys Val Lys Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Tyr Thr Ser Arg Thr Ala Thr Ile Ser Gly Leu Lys Pro
     50                  55                  60

Gly Val Asp Tyr Thr Ile Thr Val Tyr Ala Val Thr Lys Ser Gln His
 65                  70                  75                  80

Ser Arg Pro Ile Ser Ile Asn Tyr Arg Thr
                 85                  90

<210> SEQ ID NO 11
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Val Ser Asp Val Pro Arg Asp Leu Glu Val Val Ala Ala Thr Pro Thr
 1               5                  10                  15

Ser Leu Leu Ile Ser Trp Ser Val Glu Ala Met Asp Gly Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Glu Glu Pro Gly Thr Ala Thr Ile Ser Gly Leu Lys Pro
     50                  55                  60

Gly Val Asp Tyr Thr Ile Thr Val Tyr Ala Val Thr Thr Lys Tyr Tyr
 65                  70                  75                  80

Tyr Leu Val Ile Glu Pro Pro Ile Ser Ile Asn Tyr Arg Thr
                 85                  90

<210> SEQ ID NO 12
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

```
Val Ser Asp Val Pro Arg Asp Leu Glu Val Val Ala Ala Thr Pro Thr
1               5                   10                  15

Ser Leu Leu Ile Ser Trp Asp Pro His Asn Gln Asp Pro Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Ala Tyr Ser Thr Ala Thr Ile Ser Gly Leu Lys Pro
    50                  55                  60

Gly Val Asp Tyr Thr Ile Thr Val Tyr Ala Val Thr Asp Lys Glu His
65                  70                  75                  80

His Gln Tyr Leu Ile Asn Pro Ile Ser Ile Asn Tyr Arg Thr
                85                  90
```

<210> SEQ ID NO 13
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Val Ser Asp Val Pro Arg Asp Leu Glu Val Val Ala Ala Thr Pro Thr
1               5                   10                  15

Ser Leu Leu Ile Ser Trp Ile Gly Leu Asp Gly Leu Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Glu Lys Gln Thr Ala Thr Ile Ser Gly Leu Lys Pro
    50                  55                  60

Gly Val Asp Tyr Thr Ile Thr Val Tyr Ala Val Thr Thr Asp Thr Gly
65                  70                  75                  80

Phe Ile Ala Arg Leu Met Ser Leu Ile Tyr Pro Ile Ser Ile Asn Tyr
                85                  90                  95

Arg Thr
```

<210> SEQ ID NO 14
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Val Ser Asp Val Pro Arg Asp Leu Glu Val Val Ala Ala Thr Pro Thr
1               5                   10                  15

Ser Leu Leu Ile Ser Trp Ile Tyr Val Leu His His Ile Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Gln His His Thr Ala Thr Ile Ser Gly Leu Lys Pro
    50                  55                  60

Gly Val Asp Tyr Thr Ile Thr Val Tyr Ala Val Thr Glu Thr Arg Pro
65                  70                  75                  80

Tyr Arg Tyr Leu Met Tyr Pro Ile Ser Ile Asn Tyr Arg Thr
                85                  90
```

<210> SEQ ID NO 15
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Val Ser Asp Val Pro Arg Asp Leu Glu Val Val Ala Ala Thr Pro Thr
1               5                   10                  15

Ser Leu Leu Ile Ser Trp Pro Pro Tyr Leu Arg Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Ala Arg Thr Ala Thr Ile Ser Gly Leu Lys Pro
    50                  55                  60

Gly Val Asp Tyr Thr Ile Thr Val Tyr Ala Val Thr Pro Ser Asn Ile
65                  70                  75                  80

Ile Gly Arg His Tyr Gly Pro Ile Ser Ile Asn Tyr Arg Thr
                85                  90

<210> SEQ ID NO 16
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Val Ser Asp Val Pro Arg Asp Leu Glu Val Val Ala Ala Thr Pro Thr
1               5                   10                  15

Ser Leu Leu Ile Ser Trp Gly Thr His Val Lys Val Pro Arg Tyr Tyr
            20                  25                  30

Arg Ile Thr Tyr Gly Glu Thr Gly Gly Asn Ser Pro Val Gln Glu Phe
        35                  40                  45

Thr Val Pro Tyr Ser Asp His Thr Ala Thr Ile Ser Gly Leu Lys Pro
    50                  55                  60

Gly Val Asp Tyr Thr Ile Thr Val Tyr Ala Val Thr Asp Tyr Asp Tyr
65                  70                  75                  80

Lys Pro Ile Ser Ile Asn Tyr Arg Thr
                85

<210> SEQ ID NO 17
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Val Ser Asp Val Pro Arg Asp Leu Glu Val Val Ala Ala Thr Pro Thr
1               5                   10                  15

Ser Leu Leu Ile Ser Trp Ser Pro Tyr Leu Arg Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Ala Arg Thr Ala Thr Ile Ser Gly Leu Lys Pro

Gly Val Asp Tyr Thr Ile Thr Val Tyr Ala Val Thr Pro Ser Asn Ile
65                  70                  75                  80

Ile Gly Arg His Tyr Gly Pro Ile Ser Ile Asn Tyr Arg Thr
                85                  90

<210> SEQ ID NO 18
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Val Ser Asp Val Pro Arg Asp Leu Glu Val Val Ala Ala Thr Pro Thr
1               5                   10                  15

Ser Leu Leu Ile Ser Trp Glu Val Arg Tyr Tyr Pro Tyr Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser Lys Tyr Ser Thr Ala Thr Ile Ser Gly Leu Lys Pro
        50                  55                  60

Gly Val Asp Tyr Thr Ile Thr Val Tyr Ala Val Thr Asp Tyr Lys Met
65                  70                  75                  80

Lys Pro Arg Asn Tyr Gly Pro Ile Ser Ile Asn Tyr Arg Thr
                85                  90

<210> SEQ ID NO 19
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Val Ser Asp Val Pro Arg Asp Leu Glu Val Val Ala Ala Thr Pro Thr
1               5                   10                  15

Ser Leu Leu Ile Ser Trp Thr Thr His Phe Thr Val Ser Arg Tyr Tyr
                20                  25                  30

Arg Ile Thr Tyr Gly Glu Thr Gly Gly Asn Ser Pro Val Gln Glu Phe
            35                  40                  45

Thr Val Pro Glu Val His Tyr Thr Ala Thr Ile Ser Gly Leu Lys Pro
        50                  55                  60

Gly Val Asp Tyr Thr Ile Thr Val Tyr Ala Val Thr His Arg Arg Arg
65                  70                  75                  80

Arg Arg Tyr His Pro Ile Ser Ile Asn Tyr Arg Thr
                85                  90

<210> SEQ ID NO 20
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Val Ser Asp Val Pro Arg Asp Leu Glu Val Val Ala Ala Thr Pro Thr
1               5                   10                  15

Ser Leu Leu Ile Ser Trp Asp His Asp Met Pro Gly Gly Arg Tyr Tyr
            20                  25                  30

Arg Ile Thr Tyr Gly Glu Thr Gly Asn Ser Pro Val Gln Glu Phe
            35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Tyr Ser Tyr Leu
65                  70                  75                  80

Tyr Gln Tyr Asn His Ala Pro Ile Ser Ile Asn Tyr Arg Thr
                85                  90

<210> SEQ ID NO 21
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Val Ser Asp Val Pro Arg Asp Leu Glu Val Val Ala Ala Thr Pro Thr
1               5                   10                  15

Ser Leu Leu Ile Ser Trp Tyr Asn Asp Pro Arg Arg Asn Arg Tyr Tyr
            20                  25                  30

Arg Ile Thr Tyr Gly Glu Thr Gly Gly Asn Ser Pro Val Gln Glu Phe
            35                  40                  45

Thr Val Pro Ala Tyr Tyr Pro Thr Ala Thr Ile Ser Gly Leu Lys Pro
    50                  55                  60

Gly Val Asp Tyr Thr Ile Thr Val Tyr Ala Val Thr Gln Thr Asn Met
65                  70                  75                  80

His Tyr Leu Met His Tyr Pro Ile Ser Ile Asn Tyr Arg Thr
                85                  90

<210> SEQ ID NO 22
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Val Ser Asp Val Pro Arg Asp Leu Glu Val Val Ala Ala Thr Pro Thr
1               5                   10                  15

Ser Leu Leu Ile Ser Trp Gly Ser Lys Leu Leu Val Gln Arg Tyr Tyr
            20                  25                  30

Arg Ile Thr Tyr Gly Glu Thr Gly Gly Asn Ser Pro Val Gln Glu Phe
            35                  40                  45

Thr Val Pro Arg Leu Ala Lys Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90

<210> SEQ ID NO 23
<211> LENGTH: 94
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 23

Val Ser Asp Val Pro Arg Asp Leu Glu Val Val Ala Ala Thr Pro Thr
1               5                   10                  15

Ser Leu Leu Ile Ser Trp Ile Tyr Arg Ser Tyr Lys Arg Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser Asn Tyr Pro Thr Ala Thr Ile Ser Gly Leu Lys Pro
50                  55                  60

Gly Val Asp Tyr Thr Ile Thr Val Tyr Ala Val Thr Gln Gln Tyr Ser
65                  70                  75                  80

Ser Pro Thr Tyr Ser His Pro Ile Ser Ile Asn Tyr Arg Thr
                85                  90

<210> SEQ ID NO 24
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Val Ser Asp Val Pro Arg Asp Leu Glu Val Val Ala Ala Thr Pro Thr
1               5                   10                  15

Ser Leu Leu Ile Ser Trp Ser Pro Tyr Leu Arg Val Ala Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser Ala Ala Arg Thr Ala Thr Ile Ser Gly Leu Lys Pro
50                  55                  60

Gly Val Asp Tyr Thr Ile Thr Val Tyr Ala Val Thr Ala Ser Leu Ile
65                  70                  75                  80

Ile Gly Arg His Tyr Gly Pro Ile Ser Ile Asn Tyr Arg Thr
                85                  90

<210> SEQ ID NO 25
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Val Ser Asp Val Pro Arg Asp Leu Glu Val Val Ala Ala Thr Pro Thr
1               5                   10                  15

Ser Leu Leu Ile Ser Trp Asn His Thr Leu Lys Val Gln Arg Tyr Tyr
                20                  25                  30

Arg Ile Thr Tyr Gly Glu Thr Gly Gly Asn Ser Pro Val Gln Glu Phe
            35                  40                  45

Thr Val Pro Tyr Thr His Ser Thr Ala Thr Ile Ser Gly Leu Lys Pro
50                  55                  60

Gly Val Asp Tyr Thr Ile Thr Val Tyr Ala Val Thr Glu Arg Glu Ser
65                  70                  75                  80
```

Tyr Arg Tyr Met His Ile Pro Ile Ser Ile Asn Tyr Arg Thr
                85                  90

<210> SEQ ID NO 26
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Val Ser Asp Val Pro Arg Asp Leu Glu Val Val Ala Ala Thr Pro Thr
1               5                   10                  15

Ser Leu Leu Ile Ser Trp Ser Asp Thr Leu Arg Val Lys Arg Tyr Tyr
                20                  25                  30

Arg Ile Thr Tyr Gly Glu Thr Gly Gly Asn Ser Pro Val Gln Glu Phe
                35                  40                  45

Thr Val Pro Tyr His Ser Gln Thr Ala Thr Ile Ser Gly Leu Lys Pro
                50                  55                  60

Gly Val Asp Tyr Thr Ile Thr Val Tyr Ala Val Thr Pro Ser Met Met
65                  70                  75                  80

Asn Tyr Arg Asn Tyr Gly Pro Ile Ser Ile Asn Tyr Arg Thr
                85                  90

<210> SEQ ID NO 27
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Val Ser Asp Val Pro Arg Asp Leu Glu Val Val Ala Ala Thr Pro Thr
1               5                   10                  15

Ser Leu Leu Ile Ser Trp Asp Asn Ser Phe Val Val Gln Arg Tyr Tyr
                20                  25                  30

Arg Ile Thr Tyr Gly Glu Thr Gly Gly Asn Ser Pro Val Gln Glu Phe
                35                  40                  45

Thr Val Pro Arg Tyr Ala Arg Thr Ala Thr Ile Ser Gly Leu Lys Pro
                50                  55                  60

Gly Val Asp Tyr Thr Ile Thr Val Tyr Ala Val Thr Ala Leu Asn Pro
65                  70                  75                  80

Arg Ala Tyr Arg Pro Ile Ser Ile Asn Tyr Arg Thr
                85                  90

<210> SEQ ID NO 28
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Val Ser Asp Val Pro Arg Asp Leu Glu Val Val Ala Ala Thr Pro Thr
1               5                   10                  15

Ser Leu Leu Ile Ser Trp Ser Ser Arg Leu Ile Val Arg Arg Tyr Tyr
                20                  25                  30

Arg Ile Thr Tyr Gly Glu Thr Gly Gly Asn Ser Pro Val Gln Glu Phe

```
                35                  40                  45

Thr Val Pro Trp Gly Asn Arg Thr Ala Thr Ile Ser Gly Leu Lys Pro
         50                  55                  60

Gly Val Asp Tyr Thr Ile Thr Val Tyr Ala Val Thr Lys Met Arg Asp
 65                  70                  75                  80

Tyr Arg Pro Ile Ser Ile Asn Tyr Arg Thr
                 85                  90

<210> SEQ ID NO 29
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Val Ser Asp Val Pro Arg Asp Leu Glu Val Val Ala Ala Thr Pro Thr
 1               5                  10                  15

Ser Leu Leu Ile Ser Trp Ser Ser Arg Leu Ile Val Arg Arg Tyr Tyr
                 20                  25                  30

Arg Ile Thr Tyr Gly Glu Thr Gly Gly Asn Ser Pro Val Gln Glu Phe
             35                  40                  45

Thr Val Pro Trp Gly Asn Arg Thr Ala Thr Ile Ser Gly Leu Lys Pro
         50                  55                  60

Gly Val Asp Tyr Thr Ile Thr Val Tyr Ala Val Thr His Thr Arg Pro
 65                  70                  75                  80

Arg Asn Tyr Gln Pro Ile Ser Ile Asn Tyr Arg Thr
                 85                  90

<210> SEQ ID NO 30
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Val Ser Asp Val Pro Arg Asp Leu Glu Val Val Ala Ala Thr Pro Thr
 1               5                  10                  15

Ser Leu Leu Ile Ser Trp Gly Thr Arg Leu Arg Val Ser Arg Tyr Tyr
                 20                  25                  30

Arg Ile Thr Tyr Gly Glu Thr Gly Gly Asn Ser Pro Val Gln Glu Phe
             35                  40                  45

Thr Val Pro Arg Ser Val Glu Thr Ala Thr Ile Ser Gly Leu Lys Pro
         50                  55                  60

Gly Val Asp Tyr Thr Ile Thr Val Tyr Ala Val Thr Leu Asn Ser Leu
 65                  70                  75                  80

Arg Arg Tyr Gly Pro Ile Ser Ile Asn Tyr Arg Thr
                 85                  90

<210> SEQ ID NO 31
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31
```

-continued

Val Ser Asp Val Pro Arg Asp Leu Glu Val Ala Ala Thr Pro Thr
1               5                   10                  15

Ser Leu Leu Ile Ser Trp Glu Tyr Asp Arg Pro Ala Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Gln Thr Asn Met
65                  70                  75                  80

His Tyr Leu Met His Tyr Pro Ile Ser Ile Asn Tyr Arg Thr
                85                  90

<210> SEQ ID NO 32
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Val Ser Asp Val Pro Arg Asp Leu Glu Val Ala Ala Thr Pro Thr
1               5                   10                  15

Ser Leu Leu Ile Ser Trp Ser Thr His Phe Thr Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Val Asn Tyr Thr Ala Thr Ile Ser Gly Leu Lys Pro
    50                  55                  60

Gly Val Asp Tyr Thr Ile Thr Val Tyr Ala Val Thr Arg Thr Arg Asn
65                  70                  75                  80

Tyr Gly Pro Ile Ser Ile Asn Tyr Arg Thr
                85                  90

<210> SEQ ID NO 33
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Val Ser Asp Val Pro Arg Asp Leu Glu Val Ala Ala Thr Pro Thr
1               5                   10                  15

Ser Leu Leu Ile Ser Trp Asp Lys His Ala Tyr Tyr Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Glu Asn His Leu Thr Ala Thr Ile Ser Gly Leu Lys Pro
    50                  55                  60

Gly Val Asp Tyr Thr Ile Thr Val Tyr Ala Val Thr Asp Arg Thr His
65                  70                  75                  80

Ser Arg Ile Tyr His Arg Pro Ile Ser Ile Asn Tyr Arg Thr
                85                  90

<210> SEQ ID NO 34

<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Val Ser Asp Val Pro Arg Asp Leu Glu Val Val Ala Ala Thr Pro Thr
1               5                   10                  15

Ser Leu Leu Ile Ser Trp Pro Asn Asn Thr Ser Arg Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Ser Tyr Pro Thr Ala Thr Ile Ser Gly Leu Lys Pro
    50                  55                  60

Gly Val Asp Tyr Thr Ile Thr Val Tyr Ala Val Thr Glu Arg Val Ala
65                  70                  75                  80

Tyr Arg Tyr Met His Lys Pro Ile Ser Ile Asn Tyr Arg Thr
                85                  90

<210> SEQ ID NO 35
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Val Ser Asp Val Pro Arg Asp Leu Glu Val Val Ala Ala Thr Pro Thr
1               5                   10                  15

Ser Leu Leu Ile Ser Trp Ser His Arg Leu Arg Val Lys Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser His Tyr Gln Thr Ala Thr Ile Ser Gly Leu Lys Pro
    50                  55                  60

Gly Val Asp Tyr Thr Ile Thr Val Tyr Ala Val Thr Glu Lys Thr Ser
65                  70                  75                  80

Tyr Arg Ile Met His Ser Pro Ile Ser Ile Asn Tyr Arg Thr
                85                  90

<210> SEQ ID NO 36
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Val Ser Asp Val Pro Arg Asp Leu Glu Val Val Ala Ala Thr Pro Thr
1               5                   10                  15

Ser Leu Leu Ile Ser Trp Glu Tyr Asp Gly Thr Ala Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Tyr Ser Tyr Leu
65                  70                  75                  80

Tyr Gln Tyr Asn His Ala Pro Ile Ser Ile Asn Tyr Arg Thr
                85                  90

<210> SEQ ID NO 37
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Val Ser Asp Val Pro Arg Asp Leu Glu Val Val Ala Ala Thr Pro Thr
1               5                   10                  15

Ser Leu Leu Ile Ser Trp Ser His Arg Leu Arg Val Lys Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser His Tyr Gln Thr Ala Thr Ile Ser Gly Leu Lys Pro
        50                  55                  60

Gly Val Asp Tyr Thr Ile Thr Val Tyr Ala Val Thr Pro Ala Val Tyr
65                  70                  75                  80

Tyr Ser Tyr Asn Tyr Gly Pro Ile Ser Ile Asn Tyr Arg Thr
                85                  90

<210> SEQ ID NO 38
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Val Ser Asp Val Pro Arg Asp Leu Glu Val Val Ala Ala Thr Pro Thr
1               5                   10                  15

Ser Leu Leu Ile Ser Trp Asn His Thr Leu Lys Val Gln Arg Tyr Tyr
                20                  25                  30

Arg Ile Thr Tyr Gly Glu Thr Gly Gly Asn Ser Pro Val Gln Glu Phe
            35                  40                  45

Thr Val Pro Tyr Thr His Ser Thr Ala Thr Ile Ser Gly Leu Lys Pro
        50                  55                  60

Gly Val Asp Tyr Thr Ile Thr Val Tyr Ala Val Thr Asn Tyr Lys Gly
65                  70                  75                  80

Pro Arg Gly Tyr Gly Pro Ile Ser Ile Asn Tyr Arg Thr
                85                  90

<210> SEQ ID NO 39
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Val Ser Asp Val Pro Arg Asp Leu Glu Val Val Ala Ala Thr Pro Thr
1               5                   10                  15

Ser Leu Leu Ile Ser Trp Ser Asp Val Phe Pro Ala Tyr Arg Tyr Tyr

```
                    20                  25                  30

Arg Ile Thr Tyr Gly Glu Thr Gly Asn Ser Pro Val Gln Glu Phe
            35                  40                  45

Thr Val Pro Ala His Ser Pro Thr Ala Thr Ile Ser Gly Leu Lys Pro
        50                  55                  60

Gly Val Asp Tyr Thr Ile Thr Val Tyr Ala Val Thr Pro Ser Met Met
65                  70                  75                  80

Asn Tyr Arg Asn Tyr Gly Pro Ile Ser Ile Asn Tyr Arg Thr
                85                  90
```

<210> SEQ ID NO 40
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Val Ser Asp Val Pro Arg Asp Leu Glu Val Val Ala Ala Thr Pro Thr
1               5                   10                  15

Ser Leu Leu Ile Ser Trp Asp Asn Asn Phe Leu Val Gln Arg Tyr Tyr
                20                  25                  30

Arg Ile Thr Tyr Gly Glu Thr Gly Gly Asn Ser Pro Val Gln Glu Phe
            35                  40                  45

Thr Val Pro Arg Tyr Ala His Thr Ala Thr Ile Ser Gly Leu Lys Pro
        50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90
```

<210> SEQ ID NO 41
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Val Ser Asp Val Pro Arg Asp Leu Glu Val Val Ala Ala Thr Pro Thr
1               5                   10                  15

Ser Leu Leu Ile Ser Trp Pro Phe Gln Ala Val Ser Asn Arg Tyr Tyr
                20                  25                  30

Arg Ile Thr Tyr Gly Glu Thr Gly Gly Asn Ser Pro Val Gln Glu Phe
            35                  40                  45

Thr Val Pro Ala Tyr Pro Asn Thr Ala Thr Ile Ser Gly Leu Lys Pro
        50                  55                  60

Gly Val Asp Tyr Thr Ile Thr Val Tyr Ala Val Thr Tyr Met Ser Gly
65                  70                  75                  80

His Arg Leu Leu His Ala Pro Ile Ser Ile Asn Tyr Arg Thr
                85                  90
```

<210> SEQ ID NO 42
<211> LENGTH: 94
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Val Ser Asp Val Pro Arg Asp Leu Glu Val Val Ala Ala Thr Pro Thr
1               5                   10                  15

Ser Leu Leu Ile Ser Trp Tyr Pro Ser Leu Ile Leu Glu Arg Tyr Tyr
            20                  25                  30

Arg Ile Thr Tyr Gly Glu Thr Gly Gly Asn Ser Pro Val Gln Glu Phe
        35                  40                  45

Thr Val Pro Asp Leu Arg Leu Thr Ala Thr Ile Ser Gly Leu Lys Pro
    50                  55                  60

Gly Val Asp Tyr Thr Ile Thr Val Tyr Ala Val Thr Asp Lys Lys Ser
65                  70                  75                  80

Tyr Arg Tyr Tyr His Ala Pro Ile Ser Ile Asn Tyr Arg Thr
                85                  90

<210> SEQ ID NO 43
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Val Ser Asp Val Pro Arg Asp Leu Glu Val Val Ala Ala Thr Pro Thr
1               5                   10                  15

Ser Leu Leu Ile Ser Trp Tyr Asn Asp Pro Arg Arg Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Tyr Tyr Pro Thr Ala Thr Ile Ser Gly Leu Lys Pro
    50                  55                  60

Gly Val Asp Tyr Thr Ile Thr Val Tyr Ala Val Thr Ile Lys Gly Ile
65                  70                  75                  80

Tyr Gln Tyr Thr Tyr His Pro Ile Ser Ile Asn Tyr Arg Thr
                85                  90

<210> SEQ ID NO 44
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Val Ser Asp Val Pro Arg Asp Leu Glu Val Val Ala Ala Thr Pro Thr
1               5                   10                  15

Ser Leu Leu Ile Ser Trp Tyr Asn Asp Pro Arg Arg Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Tyr Ser Tyr Leu
65                  70                  75                  80

Tyr Gln Tyr Asn His Ala Pro Ile Ser Ile Asn Tyr Arg Thr
                85                  90

<210> SEQ ID NO 45
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Val Ser Asp Val Pro Arg Asp Leu Glu Val Val Ala Ala Thr Pro Thr
1               5                   10                  15

Ser Leu Leu Ile Ser Trp Gln Tyr Asn Thr Ser Arg Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Ser Tyr Pro Thr Ala Thr Ile Ser Gly Leu Lys Pro
    50                  55                  60

Gly Val Asp Tyr Thr Ile Thr Val Tyr Ala Val Thr Glu Arg Val Ala
65                  70                  75                  80

Tyr Arg Tyr Met His Lys Pro Ile Ser Ile Asn Tyr Arg Thr
                85                  90

<210> SEQ ID NO 46
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Val Ser Asp Val Pro Arg Asp Leu Glu Val Val Ala Ala Thr Pro Thr
1               5                   10                  15

Ser Leu Leu Ile Ser Trp Pro Val His Arg Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Gly Gln Phe Thr Ala Thr Ile Ser Gly Leu Lys Pro
    50                  55                  60

Gly Val Asp Tyr Thr Ile Thr Val Tyr Ala Val Thr Leu Gly Lys Phe
65                  70                  75                  80

Arg Ser Tyr Leu Pro Ile Ser Ile Asn Tyr Arg Thr
                85                  90

<210> SEQ ID NO 47
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Val Ser Asp Val Pro Arg Asp Leu Glu Val Val Ala Ala Thr Pro Thr
1               5                   10                  15

Ser Leu Leu Ile Ser Trp Ser Tyr Asn Met Lys Pro His Arg Tyr Tyr
            20                  25                  30

Arg Ile Thr Tyr Gly Glu Thr Gly Gly Asn Ser Pro Val Gln Glu Phe
        35                  40                  45

```
Thr Val Pro Ser Ser Tyr Pro Thr Ala Thr Ile Ser Gly Leu Lys Pro
         50                  55                  60

Gly Val Asp Tyr Thr Ile Thr Val Tyr Ala Val Thr Asp Arg Tyr Met
 65                  70                  75                  80

Tyr Arg Met Leu His Lys Pro Ile Ser Ile Asn Tyr Arg Thr
                 85                  90
```

<210> SEQ ID NO 48
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Val Ser Asp Val Pro Arg Asp Leu Glu Val Val Ala Ala Thr Pro Thr
 1               5                  10                  15

Ser Leu Leu Ile Ser Trp Gly Thr Arg Leu Arg Val Ser Arg Tyr Tyr
                 20                  25                  30

Arg Ile Thr Tyr Gly Glu Thr Gly Gly Asn Ser Pro Val Gln Glu Phe
             35                  40                  45

Thr Val Pro Arg Ser Val Glu Thr Ala Thr Ile Ser Gly Leu Lys Pro
         50                  55                  60

Gly Val Asp Tyr Thr Ile Thr Val Tyr Ala Val Thr Leu Asn Ser Leu
 65                  70                  75                  80

Arg Arg Tyr Gly Pro Ile Ser Ile Asn Tyr Arg Thr
                 85                  90
```

<210> SEQ ID NO 49
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Val Ser Asp Val Pro Arg Asp Leu Glu Val Val Ala Ala Thr Pro Thr
 1               5                  10                  15

Ser Leu Leu Ile Ser Trp Gly Thr Val Arg Arg Val Ala Arg Tyr Tyr
                 20                  25                  30

Arg Ile Thr Tyr Gly Glu Thr Gly Gly Asn Ser Pro Val Gln Glu Phe
             35                  40                  45

Thr Val Pro Ala Leu Gly Thr Thr Ala Thr Ile Ser Gly Leu Lys Pro
         50                  55                  60

Gly Val Asp Tyr Thr Ile Thr Val Tyr Ala Val Thr Arg Thr Arg Asn
 65                  70                  75                  80

Tyr Gly Pro Ile Ser Ile Asn Tyr Arg Thr
                 85                  90
```

<210> SEQ ID NO 50
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Val Ser Asp Val Pro Arg Asp Leu Glu Val Val Ala Ala Thr Pro Thr
```

```
                1               5                   10                  15
            Ser Leu Leu Ile Ser Trp Tyr Leu Asp Thr Thr Arg Asp Arg Tyr Tyr
                            20                  25                  30

Arg Ile Thr Tyr Gly Glu Thr Gly Gly Asn Ser Pro Val Gln Glu Phe
                            35                  40                  45

Thr Val Pro Pro Tyr Pro Met Thr Ala Thr Ile Ser Gly Leu Lys Pro
                        50                  55                  60

Gly Val Asp Tyr Thr Ile Thr Val Tyr Ala Val Thr Glu Ser Ile Gln
            65                  70                  75                  80

Tyr Arg Arg Ile His Arg Pro Ile Ser Ile Asn Tyr Arg Thr
                                85                  90
```

<210> SEQ ID NO 51
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
            Val Ser Asp Val Pro Arg Asp Leu Glu Val Val Ala Ala Thr Pro Thr
            1               5                   10                  15

Ser Leu Leu Ile Ser Trp Ala Pro Tyr Val Arg Val Ala Arg Tyr Tyr
                            20                  25                  30

Arg Ile Thr Tyr Gly Glu Thr Gly Gly Asn Ser Pro Val Gln Glu Phe
                            35                  40                  45

Thr Val Pro Thr Leu Ser Arg Thr Ala Thr Ile Ser Gly Leu Lys Pro
                        50                  55                  60

Gly Val Asp Tyr Thr Ile Thr Val Tyr Ala Val Thr Arg Thr Arg Asn
            65                  70                  75                  80

Tyr Gly Pro Ile Ser Ile Asn Tyr Arg Thr
                                85                  90
```

<210> SEQ ID NO 52
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
            Val Ser Asp Val Pro Arg Asp Leu Glu Val Val Ala Ala Thr Pro Thr
            1               5                   10                  15

Ser Leu Leu Ile Ser Trp Tyr Ser Glu His Asp Tyr Tyr Arg Tyr Tyr
                            20                  25                  30

Arg Ile Thr Tyr Gly Glu Thr Gly Gly Asn Ser Pro Val Gln Glu Phe
                            35                  40                  45

Thr Val Pro His Asn Tyr Pro Thr Ala Thr Ile Ser Gly Leu Lys Pro
                        50                  55                  60

Gly Val Asp Tyr Thr Ile Thr Val Tyr Ala Val Thr Asp His Gly Gln
            65                  70                  75                  80

Tyr Arg Lys Met His Ser Pro Ile Ser Ile Asn Tyr Arg Thr
                                85                  90
```

<210> SEQ ID NO 53
<211> LENGTH: 94
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 53

Val Ser Asp Val Pro Arg Asp Leu Glu Val Val Ala Ala Thr Pro Thr
1               5                   10                  15

Ser Leu Leu Ile Ser Trp Val Gln Glu Phe Thr Val Pro Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Tyr Tyr Pro Thr Ala Thr Ile Ser Gly Leu Lys Pro
    50                  55                  60

Gly Val Asp Tyr Thr Ile Thr Val Tyr Ala Val Thr Gln Thr Asn Met
65                  70                  75                  80

His Tyr Leu Met His Tyr Pro Ile Ser Ile Asn Tyr Arg Thr
                85                  90

<210> SEQ ID NO 54
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Val Ser Asp Val Pro Arg Asp Leu Glu Val Val Ala Ala Thr Pro Thr
1               5                   10                  15

Ser Leu Leu Ile Ser Trp Gly Arg Val Ser Lys His Arg Arg Tyr Tyr
            20                  25                  30

Arg Ile Thr Tyr Gly Glu Thr Gly Gly Asn Ser Pro Val Gln Glu Phe
        35                  40                  45

Thr Val Pro Val Pro Gly Thr Thr Ala Thr Ile Ser Gly Leu Lys Pro
    50                  55                  60

Gly Val Asp Tyr Thr Ile Thr Val Tyr Ala Val Thr Arg Glu Ala Pro
65                  70                  75                  80

Thr Gly Ile Arg Pro Ile Ser Ile Asn Tyr Arg Thr
                85                  90

<210> SEQ ID NO 55
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Val Ser Asp Val Pro Arg Asp Leu Glu Val Val Ala Ala Thr Pro Thr
1               5                   10                  15

Ser Leu Leu Ile Ser Trp Lys Lys Tyr Tyr His Met Asp Arg Tyr Tyr
            20                  25                  30

Arg Ile Thr Tyr Gly Glu Thr Gly Gly Asn Ser Pro Val Gln Glu Phe
        35                  40                  45

Thr Val Pro Asp Ala Tyr Ser Thr Ala Thr Ile Ser Gly Leu Lys Pro
    50                  55                  60

Gly Val Asp Tyr Thr Ile Thr Val Tyr Ala Val Thr Tyr Asp Gly Ile
65                  70                  75                  80

```
Pro Ile Ser Ile Asn Tyr Arg Thr
                85

<210> SEQ ID NO 56
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Val Ser Asp Val Pro Arg Asp Leu Glu Val Val Ala Ala Thr Pro Thr
1               5                   10                  15

Ser Leu Leu Ile Ser Trp Val Asn Asp Pro Gln Arg Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Tyr Tyr Pro Thr Ala Thr Ile Ser Gly Leu Lys Pro
    50                  55                  60

Gly Val Asp Tyr Thr Ile Thr Val Tyr Ala Val Thr Tyr Ser His Ile
65                  70                  75                  80

Lys Tyr Leu Tyr His Lys Pro Ile Ser Ile Asn Tyr Arg Thr
                85                  90

<210> SEQ ID NO 57
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Val Ser Asp Val Pro Arg Asp Leu Glu Val Val Ala Ala Thr Pro Thr
1               5                   10                  15

Ser Leu Leu Ile Ser Trp Glu Tyr Asp Arg Val Lys Lys Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Tyr Tyr Pro Thr Ala Thr Ile Ser Gly Leu Lys Pro
    50                  55                  60

Gly Val Asp Tyr Thr Ile Thr Val Tyr Ala Val Thr Glu His Ser His
65                  70                  75                  80

Val Arg Arg Met His Val Pro Ile Ser Ile Asn Tyr Arg Thr
                85                  90

<210> SEQ ID NO 58
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Val Ser Asp Val Pro Arg Asp Leu Glu Val Val Ala Ala Thr Pro Thr
1               5                   10                  15

Ser Leu Leu Ile Ser Trp Ala Ser Gln Val Leu Gly His Arg Tyr Tyr
            20                  25                  30
```

```
Arg Ile Thr Tyr Gly Glu Thr Gly Gly Asn Ser Pro Val Gln Glu Phe
            35                  40                  45

Thr Val Pro Ala Leu Pro Asn Thr Ala Thr Ile Ser Gly Leu Lys Pro
 50                  55                  60

Gly Val Asp Tyr Thr Ile Thr Val Tyr Ala Val Thr Lys Met Arg Asp
 65                  70                  75                  80

Tyr Arg Pro Ile Ser Ile Asn Tyr Arg Thr
                85                  90

<210> SEQ ID NO 59
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Val Ser Asp Val Pro Arg Asp Leu Glu Val Val Ala Ala Thr Pro Thr
 1               5                  10                  15

Ser Leu Leu Ile Ser Trp Gly Leu Asp Asp Tyr Tyr Gly Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Tyr Pro Thr Ala Thr Ile Ser Gly Leu Lys Pro
 50                  55                  60

Gly Val Asp Tyr Thr Ile Thr Val Tyr Ala Val Thr Asp Arg Lys His
 65                  70                  75                  80

Tyr Met Tyr Tyr His His Pro Ile Ser Ile Asn Tyr Arg Thr
                85                  90

<210> SEQ ID NO 60
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Val Ser Asp Val Pro Arg Asp Leu Glu Val Val Ala Ala Thr Pro Thr
 1               5                  10                  15

Ser Leu Leu Ile Ser Trp Lys Tyr Tyr Gly Ser Arg Asp Arg Tyr Tyr
                20                  25                  30

Arg Ile Thr Tyr Gly Glu Thr Gly Gly Asn Ser Pro Val Gln Glu Phe
            35                  40                  45

Thr Val Pro Glu Ser Tyr Pro Thr Ala Thr Ile Ser Gly Leu Lys Pro
 50                  55                  60

Gly Val Asp Tyr Thr Ile Thr Val Tyr Ala Val Thr Asp Ser Arg Leu
 65                  70                  75                  80

Tyr Arg Tyr Tyr His Ala Pro Ile Ser Ile Asn Tyr Arg Thr
                85                  90

<210> SEQ ID NO 61
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 61

Val Ser Asp Val Pro Arg Asp Leu Glu Val Val Ala Ala Thr Pro Thr
1               5                   10                  15

Ser Leu Leu Ile Ser Trp Ser Arg Ala Val Arg Val Arg Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Asn Met Phe Thr Ala Thr Ile Ser Gly Leu Lys Pro
    50                  55                  60

Gly Val Asp Tyr Thr Ile Thr Val Tyr Ala Val Thr Ile Pro His Tyr
65                  70                  75                  80

Arg Asn Tyr Lys Pro Ile Ser Ile Asn Tyr Arg Thr
                85                  90

<210> SEQ ID NO 62
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Val Ser Asp Val Pro Arg Asp Leu Glu Val Val Ala Ala Thr Pro Thr
1               5                   10                  15

Ser Leu Leu Ile Ser Trp Ser Tyr Val Tyr Ala Pro Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala His Tyr Pro Thr Ala Thr Ile Ser Gly Leu Lys Pro
    50                  55                  60

Gly Val Asp Tyr Thr Ile Thr Val Tyr Ala Val Thr Glu Lys Thr Ser
65                  70                  75                  80

Tyr Arg Ile Met His Ser Pro Ile Ser Ile Asn Tyr Arg Thr
                85                  90

<210> SEQ ID NO 63
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Val Ser Asp Val Pro Arg Asp Leu Glu Val Val Ala Ala Thr Pro Thr
1               5                   10                  15

Ser Leu Leu Ile Ser Trp Tyr Tyr Met Pro His Arg Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Ser Tyr Pro Thr Ala Thr Ile Ser Gly Leu Lys Pro
    50                  55                  60

Gly Val Asp Tyr Thr Ile Thr Val Tyr Ala Val Thr Asp Gln Asn Tyr
65                  70                  75                  80

Tyr Arg Tyr Tyr His Lys Pro Ile Ser Ile Asn Tyr Arg Thr
                85                  90

-continued

```
<210> SEQ ID NO 64
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Val Ser Asp Val Pro Arg Asp Leu Glu Val Val Ala Ala Thr Pro Thr
1               5                   10                  15

Ser Leu Leu Ile Ser Trp Thr Tyr Asp Ala His Lys Arg Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Glu Lys Gly Ser
65                  70                  75                  80

Leu Lys Ile Leu His Tyr Pro Ile Ser Ile Asn Tyr Arg Thr
                85                  90

<210> SEQ ID NO 65
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Val Ser Asp Val Pro Arg Asp Leu Glu Val Val Ala Ala Thr Pro Thr
1               5                   10                  15

Ser Leu Leu Ile Ser Trp Ala Pro Tyr Val Arg Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Thr Leu Ser Arg Thr Ala Thr Ile Ser Gly Leu Lys Pro
    50                  55                  60

Gly Val Asp Tyr Thr Ile Thr Val Tyr Ala Val Thr Ser Pro Ser Leu
65                  70                  75                  80

Arg Asp Tyr Arg Pro Ile Ser Ile Asn Tyr Arg Thr
                85                  90

<210> SEQ ID NO 66
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Val Ser Asp Val Pro Arg Asp Leu Glu Val Val Ala Ala Thr Pro Thr
1               5                   10                  15

Ser Leu Leu Ile Ser Trp Tyr Pro Glu Tyr Val Arg Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Ser Tyr Pro Thr Ala Thr Ile Ser Gly Leu Lys Pro
    50                  55                  60
```

Gly Val Asp Tyr Thr Ile Thr Val Tyr Ala Val Thr Thr Lys Gly Val
65                  70                  75                  80

His Tyr Leu Tyr His Ser Pro Ile Ser Ile Asn Tyr Arg Thr
                85                  90

<210> SEQ ID NO 67
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Val Ser Asp Val Pro Arg Asp Leu Glu Val Val Ala Ala Thr Pro Thr
1               5                   10                  15

Ser Leu Leu Ile Ser Trp Pro Asp Ile Pro Ile Val Ala Arg Tyr Tyr
                20                  25                  30

Arg Ile Thr Tyr Gly Glu Thr Gly Gly Asn Ser Pro Val Gln Glu Phe
                35                  40                  45

Thr Val Pro Val Gly Thr Thr Ala Thr Ile Ser Gly Leu Lys Pro
            50                  55                  60

Gly Val Asp Tyr Thr Ile Thr Val Tyr Ala Val Thr Ser Ser Met Leu
65                  70                  75                  80

Tyr Ile Gln Ile Glu Pro Pro Ile Ser Ile Asn Tyr Arg Thr
                85                  90

<210> SEQ ID NO 68
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Val Ser Asp Val Pro Arg Asp Leu Glu Val Val Ala Ala Thr Pro Thr
1               5                   10                  15

Ser Leu Leu Ile Ser Trp Ala His Ser Gly Tyr Ser Tyr Arg Tyr Tyr
                20                  25                  30

Arg Ile Thr Tyr Gly Glu Thr Gly Gly Asn Ser Pro Val Gln Glu Phe
                35                  40                  45

Thr Val Pro Glu Ser Tyr Pro Thr Ala Thr Ile Ser Gly Leu Lys Pro
            50                  55                  60

Gly Val Asp Tyr Thr Ile Thr Val Tyr Ala Val Thr Asp Lys Asn Thr
65                  70                  75                  80

Tyr Arg Tyr Tyr His Lys Pro Ile Ser Ile Asn Tyr Arg Thr
                85                  90

<210> SEQ ID NO 69
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Val Ser Asp Val Pro Arg Asp Leu Glu Val Val Ala Ala Thr Pro Thr
1               5                   10                  15

-continued

```
Ser Leu Leu Ile Ser Trp Asp His Ser Gly Ser Ser Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Glu Ser Tyr Pro Thr Ala Thr Ile Ser Gly Leu Lys Pro
    50                  55                  60

Gly Val Asp Tyr Thr Ile Thr Val Tyr Ala Val Thr Asp Lys Asn Thr
65                  70                  75                  80

Tyr Arg Tyr Tyr His Lys Pro Ile Ser Ile Asn Tyr Arg Thr
                85                  90
```

<210> SEQ ID NO 70
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Val Ser Asp Val Pro Arg Asp Leu Glu Val Val Ala Ala Thr Pro Thr
1               5                   10                  15

Ser Leu Leu Ile Ser Trp His Val Thr Ser Asp Arg Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Thr Tyr Pro Thr Ala Thr Ile Ser Gly Leu Lys Pro
    50                  55                  60

Gly Val Asp Tyr Thr Ile Thr Val Tyr Ala Val Thr Ile Tyr Lys Gly
65                  70                  75                  80

His Gln Ile Gln Tyr Thr Pro Ile Ser Ile Asn Tyr Arg Thr
                85                  90
```

<210> SEQ ID NO 71
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Val Ser Asp Val Pro Arg Asp Leu Glu Val Val Ala Ala Thr Pro Thr
1               5                   10                  15

Ser Leu Leu Ile Ser Trp Ile Pro Tyr Ser Gly Pro Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala His Tyr Pro Thr Ala Thr Ile Ser Gly Leu Lys Pro
    50                  55                  60

Gly Val Asp Tyr Thr Ile Thr Val Tyr Ala Val Thr Gln Ser Val Ile
65                  70                  75                  80

Val Tyr Lys Gln Ala Ala Pro Ile Ser Ile Asn Tyr Arg Thr
                85                  90
```

<210> SEQ ID NO 72
<211> LENGTH: 94
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 72

Val Ser Asp Val Pro Arg Asp Leu Glu Val Val Ala Ala Thr Pro Thr
1               5                   10                  15

Ser Leu Leu Ile Ser Trp Ser Tyr Asp Gln Ser Arg Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Met Tyr Pro Thr Ala Thr Ile Ser Gly Leu Lys Pro
    50                  55                  60

Gly Val Asp Tyr Thr Ile Thr Val Tyr Ala Val Thr Asp Lys Asn Thr
65                  70                  75                  80

Tyr Arg Tyr Tyr His Lys Pro Ile Ser Ile Asn Tyr Arg Thr
                85                  90

<210> SEQ ID NO 73
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Val Ser Asp Val Pro Arg Asp Leu Glu Val Val Ala Ala Thr Pro Thr
1               5                   10                  15

Ser Leu Leu Ile Ser Trp Gly Glu Pro Leu Glu Asp Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Asp His Ser Gln Thr Ala Thr Ile Ser Gly Leu Lys Pro
    50                  55                  60

Gly Val Asp Tyr Thr Ile Thr Val Tyr Ala Val Thr Ala Gly Ser Trp
65                  70                  75                  80

Leu Arg Ile Trp Pro Ile Ser Ile Asn Tyr Arg Thr
                85                  90

<210> SEQ ID NO 74
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Val Ser Asp Val Pro Arg Asp Leu Glu Val Val Ala Ala Thr Pro Thr
1               5                   10                  15

Ser Leu Leu Ile Ser Trp Pro Lys Arg Pro Met Asn Met Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Ala Tyr Thr Ala Thr Ile Ser Gly Leu Lys Pro
    50                  55                  60

Gly Val Asp Tyr Thr Ile Thr Val Tyr Ala Val Thr Tyr Leu Tyr Ala
65                  70                  75                  80

Thr Tyr Val Met His Gln Pro Ile Ser Ile Asn Tyr Arg Thr

<210> SEQ ID NO 75
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Val Ser Asp Val Pro Arg Asp Leu Glu Val Val Ala Ala Thr Pro Thr
1               5                   10                  15

Ser Leu Leu Ile Ser Trp Ser Tyr Asp Gln Ser Arg Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Met Tyr Pro Thr Ala Thr Ile Ser Gly Leu Lys Pro
    50                  55                  60

Gly Val Asp Tyr Thr Ile Thr Val Tyr Ala Val Thr Glu Arg Asp Arg
65                  70                  75                  80

Tyr Ser Tyr Met His His Pro Ile Ser Ile Asn Tyr Arg Thr
                85                  90

<210> SEQ ID NO 76
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Val Ser Asp Val Pro Arg Asp Leu Glu Val Val Ala Ala Thr Pro Thr
1               5                   10                  15

Ser Leu Leu Ile Ser Trp Pro Phe Gln Ala Val Ser Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Phe Pro Asn Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90

<210> SEQ ID NO 77
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Val Ser Asp Val Pro Arg Asp Leu Glu Val Val Ala Ala Thr Pro Thr
1               5                   10                  15

Ser Leu Leu Ile Ser Trp Tyr His Asp Met His Arg Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Tyr Tyr Pro Thr Ala Thr Ile Ser Gly Leu Lys Pro
            50                  55                  60

Gly Val Asp Tyr Thr Ile Thr Val Tyr Ala Val Thr Lys Gly Ser Gly
 65                  70                  75                  80

Tyr Gln Val Met His Thr Pro Ile Ser Ile Asn Tyr Arg Thr
                85                  90

<210> SEQ ID NO 78
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Val Ser Asp Val Pro Arg Asp Leu Glu Val Val Ala Ala Thr Pro Thr
 1               5                  10                  15

Ser Leu Leu Ile Ser Trp Ala Tyr Tyr Met Gly Gly Tyr Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Tyr Pro Thr Ala Thr Ile Ser Gly Leu Lys Pro
            50                  55                  60

Gly Val Asp Tyr Thr Ile Thr Val Tyr Ala Val Thr Asp Arg Lys His
 65                  70                  75                  80

Tyr Met Tyr Tyr His His Pro Ile Ser Ile Asn Tyr Arg Thr
                85                  90

<210> SEQ ID NO 79
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Val Ser Asp Val Pro Arg Asp Leu Glu Val Val Ala Ala Thr Pro Thr
 1               5                  10                  15

Ser Leu Leu Ile Ser Trp Tyr Tyr Met Pro His Arg Asn Arg Tyr Tyr
                20                  25                  30

Arg Ile Thr Tyr Gly Glu Thr Gly Gly Asn Ser Pro Val Gln Glu Phe
                35                  40                  45

Thr Val Pro Ser Thr Tyr Pro Thr Ala Thr Ile Ser Gly Leu Lys Pro
            50                  55                  60

Gly Val Asp Tyr Thr Ile Thr Val Tyr Ala Val Thr Asn His His Val
 65                  70                  75                  80

His Arg Leu Met His Ile Pro Ile Ser Ile Asn Tyr Arg Thr
                85                  90

<210> SEQ ID NO 80
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Val Ser Asp Val Pro Arg Asp Leu Glu Val Ala Ala Thr Pro Thr
1               5                   10                  15

Ser Leu Leu Ile Ser Trp His Glu Asp Pro Ser Thr Tyr Arg Tyr Tyr
            20                  25                  30

Arg Ile Thr Tyr Gly Glu Thr Gly Asn Ser Pro Val Gln Glu Phe
            35                  40                  45

Thr Val Pro Ser Tyr Tyr Pro Thr Ala Thr Ile Ser Gly Leu Lys Pro
        50                  55                  60

Gly Val Asp Tyr Thr Ile Thr Val Tyr Ala Val Thr Asp Tyr His Glu
65                  70                  75                  80

Leu Val Tyr Met His His Pro Ile Ser Ile Asn Tyr Arg Thr
                85                  90

<210> SEQ ID NO 81
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Val Ser Asp Val Pro Arg Asp Leu Glu Val Ala Ala Thr Pro Thr
1               5                   10                  15

Ser Leu Leu Ile Ser Trp Asp Glu Ile Glu Phe Pro Val Arg Tyr Tyr
            20                  25                  30

Arg Ile Thr Tyr Gly Glu Thr Gly Asn Ser Pro Val Gln Glu Phe
            35                  40                  45

Thr Val Pro Gly Pro Arg Gly Thr Ala Thr Ile Ser Gly Leu Lys Pro
        50                  55                  60

Gly Val Asp Tyr Thr Ile Thr Val Tyr Ala Val Thr Met His Tyr Tyr
65                  70                  75                  80

Leu Arg Val Trp Pro Ile Ser Ile Asn Tyr Arg Thr
                85                  90

<210> SEQ ID NO 82
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Val Ser Asp Val Pro Arg Asp Leu Glu Val Ala Ala Thr Pro Thr
1               5                   10                  15

Ser Leu Leu Ile Ser Trp Ser Thr His Phe Thr Val Ser Arg Tyr Tyr
            20                  25                  30

Arg Ile Thr Tyr Gly Glu Thr Gly Asn Ser Pro Val Gln Glu Phe
            35                  40                  45

Thr Val Pro Lys Val Asn Tyr Thr Ala Thr Ile Ser Gly Leu Lys Pro
        50                  55                  60

Gly Val Asp Tyr Thr Ile Thr Val Tyr Ala Val Thr His Ser Arg Pro
65                  70                  75                  80

Arg His Tyr His Pro Ile Ser Ile Asn Tyr Arg Thr
                85                  90

<210> SEQ ID NO 83
<211> LENGTH: 94

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Val Ser Asp Val Pro Arg Asp Leu Glu Val Val Ala Ala Thr Pro Thr
1               5                   10                  15

Ser Leu Leu Ile Ser Trp Gly Lys His Ile Arg Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro His Asn Ser Val Thr Ala Thr Ile Ser Gly Leu Lys Pro
    50                  55                  60

Gly Val Asp Tyr Thr Ile Thr Val Tyr Ala Val Thr Val Ala Tyr Asn
65                  70                  75                  80

Tyr Leu Arg Asp Tyr Lys Pro Ile Ser Ile Asn Tyr Arg Thr
                85                  90

<210> SEQ ID NO 84
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Val Ser Asp Val Pro Arg Asp Leu Glu Val Val Ala Ala Thr Pro Thr
1               5                   10                  15

Ser Leu Leu Ile Ser Trp His Ser Asn Leu Leu Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Ala Val Thr Ala Thr Ile Ser Gly Leu Lys Pro
    50                  55                  60

Gly Val Asp Tyr Thr Ile Thr Val Tyr Ala Val Thr Pro Gly His Leu
65                  70                  75                  80

Arg Lys Tyr Gly Pro Ile Ser Ile Asn Tyr Arg Thr
                85                  90

<210> SEQ ID NO 85
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Val Ser Asp Val Pro Arg Asp Leu Glu Val Val Ala Ala Thr Pro Thr
1               5                   10                  15

Ser Leu Leu Ile Ser Trp Asp Tyr Asp Arg Ser Lys Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Ser Tyr Pro Thr Ala Thr Ile Ser Gly Leu Lys Pro
    50                  55                  60

Gly Val Asp Tyr Thr Ile Thr Val Tyr Ala Val Thr Gln Lys Asp Ile

```
                65                  70                  75                  80
Tyr Tyr Tyr Ile Tyr Tyr Pro Ile Ser Ile Asn Tyr Arg Thr
                85                  90

<210> SEQ ID NO 86
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Val Ser Asp Val Pro Arg Asp Leu Glu Val Val Ala Ala Thr Pro Thr
1               5                   10                  15

Ser Leu Leu Ile Ser Trp Gly Asp Glu Leu Val Ala Ala Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser Phe Asn Asp Thr Ala Thr Ile Ser Gly Leu Lys Pro
        50                  55                  60

Gly Val Asp Tyr Thr Ile Thr Val Tyr Ala Val Thr His Leu Leu Gly
65                  70                  75                  80

Thr Leu Trp Leu Ile Pro Pro Ile Ser Ile Asn Tyr Arg Thr
                85                  90

<210> SEQ ID NO 87
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Val Ser Asp Val Pro Arg Asp Leu Glu Val Val Ala Ala Thr Pro Thr
1               5                   10                  15

Ser Leu Leu Ile Ser Trp Ser Leu Tyr Leu Arg Val Lys Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser Asn Ala Met Thr Ala Thr Ile Ser Gly Leu Lys Pro
        50                  55                  60

Gly Val Asp Tyr Thr Ile Thr Val Tyr Ala Val Thr Ser Pro Ser Leu
65                  70                  75                  80

Arg Gly Tyr Gly Pro Ile Ser Ile Asn Tyr Arg Thr
                85                  90

<210> SEQ ID NO 88
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Val Ser Asp Val Pro Arg Asp Leu Glu Val Val Ala Ala Thr Pro Thr
1               5                   10                  15

Ser Leu Leu Ile Ser Trp Ala Tyr Asp Met His Arg Lys Arg Tyr Tyr
                20                  25                  30
```

```
Arg Ile Thr Tyr Gly Glu Thr Gly Asn Ser Pro Val Gln Glu Phe
            35                  40                  45

Thr Val Pro Ser Ser Tyr Pro Thr Ala Thr Ile Ser Gly Leu Lys Pro
 50                  55                  60

Gly Val Asp Tyr Thr Ile Thr Val Tyr Ala Val Thr Ser Lys Tyr Ser
 65                  70                  75                  80

Gly His Tyr Val His Asn Pro Ile Ser Ile Asn Tyr Arg Thr
                 85                  90

<210> SEQ ID NO 89
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Val Ser Asp Val Pro Arg Asp Leu Glu Val Val Ala Ala Thr Pro Thr
  1               5                  10                  15

Ser Leu Leu Ile Ser Trp Leu Asp Leu Ser Leu Lys Met Arg Tyr Tyr
             20                  25                  30

Arg Ile Thr Tyr Gly Glu Thr Gly Asn Ser Pro Val Gln Glu Phe
            35                  40                  45

Thr Val Pro Ser His His Gln Thr Ala Thr Ile Ser Gly Leu Lys Pro
 50                  55                  60

Gly Val Asp Tyr Thr Ile Thr Val Tyr Ala Val Thr Glu Tyr Ala Ala
 65                  70                  75                  80

Tyr Arg Met Met His Ile Pro Ile Ser Ile Asn Tyr Arg Thr
                 85                  90

<210> SEQ ID NO 90
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Val Ser Asp Val Pro Arg Asp Leu Glu Val Val Ala Ala Thr Pro Thr
  1               5                  10                  15

Ser Leu Leu Ile Ser Trp Gly Leu Ile Leu Gly Arg Asp Arg Tyr Tyr
             20                  25                  30

Arg Ile Thr Tyr Gly Glu Thr Gly Asn Ser Pro Val Gln Glu Phe
            35                  40                  45

Thr Val Pro Ala Phe Pro Phe Thr Ala Thr Ile Ser Gly Leu Lys Pro
 50                  55                  60

Gly Val Asp Tyr Thr Ile Thr Val Tyr Ala Val Thr Tyr Arg Gly Phe
 65                  70                  75                  80

Asp Thr Phe Phe Pro Asn Pro Ile Ser Ile Asn Tyr Arg Thr
                 85                  90

<210> SEQ ID NO 91
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 91

Val Ser Asp Val Pro Arg Asp Leu Glu Val Val Ala Ala Thr Pro Thr
1               5                   10                  15

Ser Leu Leu Ile Ser Trp Leu Pro Ser Pro Ala Ile Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Asp Pro Leu Ser Thr Ala Thr Ile Ser Gly Leu Lys Pro
    50                  55                  60

Gly Val Asp Tyr Thr Ile Thr Val Tyr Ala Val Thr Tyr Arg Tyr Ser
65                  70                  75                  80

Thr Trp Pro Ile Ser Ile Asn Tyr Arg Thr
                85                  90

<210> SEQ ID NO 92
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Val Ser Asp Val Pro Arg Asp Leu Glu Val Val Ala Ala Thr Pro Thr
1               5                   10                  15

Ser Leu Leu Ile Ser Trp Val Tyr Glu Asn Asn Arg Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Tyr Tyr Pro Thr Ala Thr Ile Ser Gly Leu Lys Pro
    50                  55                  60

Gly Val Asp Tyr Thr Ile Thr Val Tyr Ala Val Thr Gln Gln Ser Gln
65                  70                  75                  80

His Ala Tyr Tyr His Leu Pro Ile Ser Ile Asn Tyr Arg Thr
                85                  90

<210> SEQ ID NO 93
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Val Ser Asp Val Pro Arg Asp Leu Glu Val Val Ala Ala Thr Pro Thr
1               5                   10                  15

Ser Leu Leu Ile Ser Trp Val Glu Phe His Lys Pro Asp Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Glu Gln Gly Thr Ala Thr Ile Ser Gly Leu Lys Pro
    50                  55                  60

Gly Val Asp Tyr Thr Ile Thr Val Tyr Ala Val Thr Glu Tyr Ala Ala
65                  70                  75                  80

Tyr Arg Met Met His Ile Pro Ile Ser Ile Asn Tyr Arg Thr
                85                  90
```

-continued

<210> SEQ ID NO 94
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Val Ser Asp Val Pro Arg Asp Leu Glu Val Val Ala Ala Thr Pro Thr
1               5                   10                  15

Ser Leu Leu Ile Ser Trp Asp Glu Ile Glu Phe Pro Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Pro Arg Gly Thr Ala Thr Ile Ser Gly Leu Lys Pro
    50                  55                  60

Gly Val Asp Tyr Thr Ile Thr Val Tyr Ala Val Thr Met His Tyr Tyr
65                  70                  75                  80

Leu Arg Val Trp Pro Ile Ser Ile Asn Tyr Arg Thr
                85                  90

<210> SEQ ID NO 95
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Val Ser Asp Val Pro Arg Asp Leu Glu Val Val Ala Ala Thr Pro Thr
1               5                   10                  15

Ser Leu Leu Ile Ser Trp Ser Tyr Asn Met Lys Pro Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Asp Arg Tyr Met
65                  70                  75                  80

Tyr Arg Met Leu His Lys Pro Ile Ser Ile Asn Tyr Arg Thr
                85                  90

<210> SEQ ID NO 96
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Val Ser Asp Val Pro Arg Asp Leu Glu Val Val Ala Ala Thr Pro Thr
1               5                   10                  15

Ser Leu Leu Ile Ser Trp Tyr Tyr Glu His Ile Arg Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro

```
Gly Val Asp Tyr Thr Ile Thr Val Tyr Ala Val Thr Gly Tyr Gly Gln
 65                  70                  75                  80

Tyr Tyr Tyr Tyr His Ser Pro Ile Ser Ile Asn Tyr Arg Thr
                 85                  90
```

<210> SEQ ID NO 97
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Val Ser Asp Val Pro Arg Asp Leu Glu Val Val Ala Ala Thr Pro Thr
  1               5                  10                  15

Ser Leu Leu Ile Ser Trp Tyr Asn Asp Pro Arg Arg Asn Arg Tyr Tyr
                 20                  25                  30

Arg Ile Thr Tyr Gly Glu Thr Gly Gly Asn Ser Pro Val Gln Glu Phe
             35                  40                  45

Thr Val Pro Ala Tyr Tyr Pro Thr Ala Thr Ile Ser Gly Leu Lys Pro
         50                  55                  60

Gly Val Asp Tyr Thr Ile Thr Val Tyr Ala Val Thr Tyr Arg Tyr Ser
 65                  70                  75                  80

Tyr Gln Tyr Gln His Ala Pro Ile Ser Ile Asn Tyr Arg Thr
                 85                  90
```

<210> SEQ ID NO 98
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Val Ser Asp Val Pro Arg Asp Leu Glu Val Val Ala Ala Thr Pro Thr
  1               5                  10                  15

Ser Leu Leu Ile Ser Trp Tyr Tyr Asp Asp His Ala Gln Arg Tyr Tyr
                 20                  25                  30

Arg Ile Thr Tyr Gly Glu Thr Gly Gly Asn Ser Pro Val Gln Glu Phe
             35                  40                  45

Thr Val Pro Ser Thr Tyr Pro Thr Ala Thr Ile Ser Gly Leu Lys Pro
         50                  55                  60

Gly Val Asp Tyr Thr Ile Thr Val Tyr Ala Val Thr Val Arg Gly Val
 65                  70                  75                  80

Tyr Tyr Tyr Tyr Tyr Gln Pro Ile Ser Ile Asn Tyr Arg Thr
                 85                  90
```

<210> SEQ ID NO 99
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Val Ser Asp Val Pro Arg Asp Leu Glu Val Val Ala Ala Thr Pro Thr
  1               5                  10                  15
```

Ser Leu Leu Ile Ser Trp Ile Pro Thr Ser Lys Asn Gly Arg Tyr Tyr
            20                  25                  30

Arg Ile Thr Tyr Gly Glu Thr Gly Gly Asn Ser Pro Val Gln Glu Phe
            35                  40                  45

Thr Val Pro Ser Tyr Tyr Pro Thr Ala Thr Ile Ser Gly Leu Lys Pro
        50                  55                  60

Gly Val Asp Tyr Thr Ile Thr Val Tyr Ala Val Thr Glu Val Gln His
65                  70                  75                  80

Tyr Arg Tyr Leu His Ala Pro Ile Ser Ile Asn Tyr Arg Thr
                85                  90

<210> SEQ ID NO 100
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Val Ser Asp Val Pro Arg Asp Leu Glu Val Val Ala Ala Thr Pro Thr
1               5                   10                  15

Ser Leu Leu Ile Ser Trp Pro Thr His Tyr Lys Val Ala Arg Tyr Tyr
            20                  25                  30

Arg Ile Thr Tyr Gly Glu Thr Gly Gly Asn Ser Pro Val Gln Glu Phe
            35                  40                  45

Thr Val Pro Ala Tyr Tyr Pro Thr Ala Thr Ile Ser Gly Leu Lys Pro
        50                  55                  60

Gly Val Asp Tyr Thr Ile Thr Val Tyr Ala Val Thr Glu His Ser His
65                  70                  75                  80

Val Arg Arg Met His Val Pro Ile Ser Ile Asn Tyr Arg Thr
                85                  90

<210> SEQ ID NO 101
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Val Ser Asp Val Pro Arg Asp Leu Glu Val Val Ala Ala Thr Pro Thr
1               5                   10                  15

Ser Leu Leu Ile Ser Trp Leu Met Lys Leu Tyr Leu Glu Arg Tyr Tyr
            20                  25                  30

Arg Ile Thr Tyr Gly Glu Thr Gly Gly Asn Ser Pro Val Gln Glu Phe
            35                  40                  45

Thr Val Pro Pro Ser Tyr Ile Thr Ala Thr Ile Ser Gly Leu Lys Pro
        50                  55                  60

Gly Val Asp Tyr Thr Ile Thr Val Tyr Ala Val Thr Tyr His Glu Ser
65                  70                  75                  80

Gln Glu Gly Ala Gly His Pro Ile Ser Ile Asn Tyr Arg Thr
                85                  90

<210> SEQ ID NO 102
<211> LENGTH: 94
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 102

Val Ser Asp Val Pro Arg Asp Leu Glu Val Val Ala Ala Thr Pro Thr
1               5                   10                  15

Ser Leu Leu Ile Ser Trp Glu Tyr Val Glu Tyr Thr His Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Val His Tyr Thr Ala Thr Ile Ser Gly Leu Lys Pro
    50                  55                  60

Gly Val Asp Tyr Thr Ile Thr Val Tyr Ala Val Thr Tyr Met Asp Thr
65                  70                  75                  80

Ser Met Tyr Val Ser Ser Pro Ile Ser Ile Asn Tyr Arg Thr
                85                  90

<210> SEQ ID NO 103
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Val Ser Asp Val Pro Arg Asp Leu Glu Val Val Ala Ala Thr Pro Thr
1               5                   10                  15

Ser Leu Leu Ile Ser Trp Lys Tyr Asp Ser Tyr Ser Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Tyr Gln Ser Ile
65                  70                  75                  80

Tyr Tyr Tyr Met His Ser Pro Ile Ser Ile Asn Tyr Arg Thr
                85                  90

<210> SEQ ID NO 104
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Val Ser Asp Val Pro Arg Asp Leu Glu Val Val Ala Ala Thr Pro Thr
1               5                   10                  15

Ser Leu Leu Ile Ser Trp Glu Tyr Asp Gly Pro Ala Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Gln Thr Asn Met
65                  70                  75                  80
```

His Tyr Leu Met His Tyr Pro Ile Ser Ile Asn Tyr Arg Thr
                85                  90

<210> SEQ ID NO 105
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Val Ser Asp Val Pro Arg Asp Leu Glu Val Val Ala Ala Thr Pro Thr
1               5                   10                  15

Ser Leu Leu Ile Ser Trp Asp Tyr Asp Arg Ser Lys Tyr Arg Tyr Tyr
                20                  25                  30

Arg Ile Thr Tyr Gly Glu Thr Gly Gly Asn Ser Pro Val Gln Glu Phe
            35                  40                  45

Thr Val Pro Ala Ser Tyr Pro Thr Ala Thr Ile Ser Gly Leu Lys Pro
        50                  55                  60

Gly Val Asp Tyr Thr Ile Thr Val Tyr Ala Val Thr Gln Lys Asp Ile
65                  70                  75                  80

Tyr Tyr Tyr Ile Tyr Asn Pro Ile Ser Ile Asn Tyr Arg Thr
                85                  90

<210> SEQ ID NO 106
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Val Ser Asp Val Pro Arg Asp Leu Glu Val Val Ala Ala Thr Pro Thr
1               5                   10                  15

Ser Leu Leu Ile Ser Trp Tyr Tyr Met Pro His Arg Asn Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser Thr Tyr Pro Thr Ala Thr Ile Ser Gly Leu Lys Pro
        50                  55                  60

Gly Val Asp Tyr Thr Ile Thr Val Tyr Ala Val Thr Asn His His Val
65                  70                  75                  80

His Arg Leu Met His Ile Pro Ile Ser Ile Asn Tyr Arg Thr
                85                  90

<210> SEQ ID NO 107
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Val Ser Asp Val Pro Arg Asp Leu Glu Val Val Ala Ala Thr Pro Thr
1               5                   10                  15

Ser Leu Leu Ile Ser Trp Ser Ser His Leu Pro Tyr Asp Arg Tyr Tyr
                20                  25                  30

Arg Ile Thr Tyr Gly Glu Thr Gly Gly Asn Ser Pro Val Gln Glu Phe

```
                35                  40                  45

Thr Val Pro Lys Tyr Lys Thr Ala Thr Ile Ser Gly Leu Lys Pro Gly
 50                  55                  60

Val Asp Tyr Thr Ile Thr Val Tyr Ala Val Thr Lys Gly Val His
 65                  70                  75                  80

Tyr Leu Phe His Ser Pro Ile Ser Ile Asn Tyr Arg Thr
                 85                  90

<210> SEQ ID NO 108
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Val Ser Asp Val Pro Arg Asp Leu Glu Val Val Ala Ala Thr Pro Thr
 1               5                  10                  15

Ser Leu Leu Ile Ser Trp Gln Tyr Asp Arg Ser Ser Tyr Arg Tyr Tyr
                20                  25                  30

Arg Ile Thr Tyr Gly Glu Thr Gly Gly Asn Ser Pro Val Gln Glu Phe
                35                  40                  45

Thr Val Pro Ala Ser Tyr Pro Thr Ala Thr Ile Ser Gly Leu Lys Pro
 50                  55                  60

Gly Val Asp Tyr Thr Ile Thr Val Tyr Ala Val Thr Arg Val Gly Thr
 65                  70                  75                  80

Tyr Gln Tyr Tyr Tyr Leu Pro Ile Ser Ile Asn Tyr Arg Thr
                 85                  90

<210> SEQ ID NO 109
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Val Ser Asp Val Pro Arg Asp Leu Glu Val Val Ala Ala Thr Pro Thr
 1               5                  10                  15

Ser Leu Leu Ile Ser Trp Tyr Thr Pro Tyr Lys Tyr Ser Arg Tyr Tyr
                20                  25                  30

Arg Ile Thr Tyr Gly Glu Thr Gly Gly Asn Ser Pro Val Gln Glu Phe
                35                  40                  45

Thr Val Pro Ser His Ser Thr Ala Thr Ile Ser Gly Leu Lys Pro Gly
 50                  55                  60

Val Asp Tyr Thr Ile Thr Val Tyr Ala Val Thr Val Gly Asn Met Tyr
 65                  70                  75                  80

Leu Ser Ile Val Pro Pro Ile Ser Ile Asn Tyr Arg Thr
                 85                  90

<210> SEQ ID NO 110
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110
```

```
Val Ser Asp Val Pro Arg Asp Leu Glu Val Val Ala Ala Thr Pro Thr
1               5                   10                  15

Ser Leu Leu Ile Ser Trp Ser Asp Ser Leu Lys Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Gln Tyr His Thr Ala Thr Ile Ser Gly Leu Lys Pro
    50                  55                  60

Gly Val Asp Tyr Thr Ile Thr Val Tyr Ala Val Thr Pro Ser Asn Ile
65                  70                  75                  80

Ile Gly Arg His Tyr Gly Pro Ile Ser Ile Asn Tyr Arg Thr
                85                  90
```

<210> SEQ ID NO 111
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90
```

<210> SEQ ID NO 112
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Val Ser Asp Val Pro Arg Asp Leu Glu Val Val Ala Ala Thr Pro Thr
1               5                   10                  15

Ser Leu Leu Ile Ser Trp Ser Thr Ala Leu Lys Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys His Ser His Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90
```

<210> SEQ ID NO 113

```
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Val Ser Asp Val Pro Arg Asp Leu Glu Val Val Ala Ala Thr Pro Thr
1               5                   10                  15

Ser Leu Leu Ile Ser Trp Pro Thr His Tyr Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys His Thr Tyr Thr Ala Thr Ile Ser Gly Leu Lys Pro
    50                  55                  60

Gly Val Asp Tyr Thr Ile Thr Val Tyr Ala Val Thr Thr Lys Gly
65                  70                  75                  80

Leu Arg His Tyr Gly Pro Ile Ser Ile Asn Tyr Arg Thr
                85                  90

<210> SEQ ID NO 114
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Val Ser Asp Val Pro Arg Asp Leu Glu Val Val Ala Ala Thr Pro Thr
1               5                   10                  15

Ser Leu Leu Ile Ser Trp Ser Asp Lys Leu Lys Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys His Asp Arg Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90

<210> SEQ ID NO 115
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Val Ser Asp Val Pro Arg Asp Leu Glu Val Val Ala Ala Thr Pro Thr
1               5                   10                  15

Ser Leu Leu Ile Ser Trp Ser Lys Arg Leu Gln Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Tyr Asn Tyr Lys Thr Ala Thr Ile Ser Gly Leu Lys Pro
    50                  55                  60
```

```
Gly Val Asp Tyr Thr Ile Thr Val Tyr Ala Val Thr Pro Ser Asn Ile
 65                  70                  75                  80

Ile Gly Arg His Tyr Gly Pro Ile Ser Ile Asn Tyr Arg Thr
                 85                  90
```

<210> SEQ ID NO 116
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Val Ser Asp Val Pro Arg Asp Leu Glu Val Val Ala Ala Thr Pro Thr
  1               5                  10                  15

Ser Leu Leu Ile Ser Trp Ser Asn Arg Leu Val Val Lys Arg Tyr Tyr
                 20                  25                  30

Arg Ile Thr Tyr Gly Glu Thr Gly Gly Asn Ser Pro Val Gln Glu Phe
                 35                  40                  45

Thr Val Pro His Gln Met Lys Thr Ala Thr Ile Ser Gly Leu Lys Pro
         50                  55                  60

Gly Val Asp Tyr Thr Ile Thr Val Tyr Ala Val Thr Pro Gly Gly Tyr
 65                  70                  75                  80

Ser Gly Arg Asn Tyr Gly Pro Ile Ser Ile Asn Tyr Arg Thr
                 85                  90
```

<210> SEQ ID NO 117
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Val Ser Asp Val Pro Arg Asp Leu Glu Val Val Ala Ala Thr Pro Thr
  1               5                  10                  15

Ser Leu Leu Ile Ser Trp Ser Glu Asn Leu Arg Val Gln Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Ser Ser Val His Thr Ala Thr Ile Ser Gly Leu Lys Pro
         50                  55                  60

Gly Val Asp Tyr Thr Ile Thr Val Tyr Ala Val Thr Lys Met Arg Asp
 65                  70                  75                  80

Tyr Arg Pro Ile Ser Ile Asn Tyr Arg Thr
                 85                  90
```

<210> SEQ ID NO 118
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Val Ser Asp Val Pro Arg Asp Leu Glu Val Val Ala Ala Thr Pro Thr
  1               5                  10                  15

Ser Leu Leu Ile Ser Trp Ser Ser Asn Leu Val Val Lys Arg Tyr Tyr
```

```
                20                  25                  30

Arg Ile Thr Tyr Gly Glu Thr Gly Asn Ser Pro Val Gln Glu Phe
            35                  40                  45

Thr Val Pro Lys Asp Pro Ser Thr Ala Thr Ile Ser Gly Leu Lys Pro
        50                  55                  60

Gly Val Asp Tyr Thr Ile Thr Val Tyr Ala Val Thr Asp Tyr Glu Met
65                  70                  75                  80

Lys Pro Arg Asn Tyr Gly Pro Ile Ser Ile Asn Tyr Arg Thr
                85                  90

<210> SEQ ID NO 119
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Val Ser Asp Val Pro Arg Asp Leu Glu Val Val Ala Ala Thr Pro Thr
1               5                   10                  15

Ser Leu Leu Ile Ser Trp Pro Thr His Tyr Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys His Glu Ser Thr Ala Thr Ile Ser Gly Leu Lys Pro
    50                  55                  60

Gly Val Asp Tyr Thr Ile Thr Val Tyr Ala Val Thr Leu Asn Val Ala
65                  70                  75                  80

Tyr Ser Arg Glu Val Arg Pro Ile Ser Ile Asn Tyr Arg Thr
                85                  90

<210> SEQ ID NO 120
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Val Ser Asp Val Pro Arg Asp Leu Glu Val Val Ala Ala Thr Pro Thr
1               5                   10                  15

Ser Leu Leu Ile Ser Trp Pro Asp His Val Lys Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Gln His Ser Arg Thr Ala Thr Ile Ser Gly Leu Lys Pro
    50                  55                  60

Gly Val Asp Tyr Thr Ile Thr Val Tyr Ala Val Thr Tyr Thr Gly Tyr
65                  70                  75                  80

Gly Thr Glu Arg Asn Tyr Gln Pro Ile Ser Ile Asn Tyr Arg Thr
                85                  90                  95

<210> SEQ ID NO 121
<211> LENGTH: 94
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 121

Val Ser Asp Val Pro Arg Asp Leu Glu Val Val Ala Ala Thr Pro Thr
1               5                   10                  15

Ser Leu Leu Ile Ser Trp Gly Ser His Leu Arg Val Ser Arg Tyr Tyr
            20                  25                  30

Arg Ile Thr Tyr Gly Glu Thr Gly Asn Ser Pro Val Gln Glu Phe
        35                  40                  45

Thr Val Pro Tyr Asp Ser His Thr Ala Thr Ile Ser Gly Leu Lys Pro
    50                  55                  60

Gly Val Asp Tyr Thr Ile Thr Val Tyr Ala Val Thr Gln Gly Pro Asn
65                  70                  75                  80

Arg Gly Arg Asn Tyr Gln Pro Ile Ser Ile Asn Tyr Arg Thr
                85                  90

<210> SEQ ID NO 122
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Val Ser Asp Val Pro Arg Asp Leu Glu Val Val Ala Ala Thr Pro Thr
1               5                   10                  15

Ser Leu Leu Ile Ser Trp Gly Lys His Leu Val Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Arg Gly His Tyr Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90

<210> SEQ ID NO 123
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Val Ser Asp Val Pro Arg Asp Leu Glu Val Val Ala Ala Thr Pro Thr
1               5                   10                  15

Ser Leu Leu Ile Ser Trp Thr Thr Asn Leu Gln Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Ala Asn Thr Ala Thr Ile Ser Gly Leu Lys Pro
    50                  55                  60

Gly Val Asp Tyr Thr Ile Thr Val Tyr Ala Val Thr Val Ser Lys Gly
65                  70                  75                  80

Asn Arg Ser Tyr Gly Pro Ile Ser Ile Asn Tyr Arg Thr
                85                  90

<210> SEQ ID NO 124
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Val Ser Asp Val Pro Arg Asp Leu Glu Val Val Ala Ala Thr Pro Thr
1               5                   10                  15

Ser Leu Leu Ile Ser Trp Ala Glu His Leu Gln Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Arg Gly Val Tyr Thr Ala Thr Ile Ser Gly Leu Lys Pro
    50                  55                  60

Gly Val Asp Tyr Thr Ile Thr Val Tyr Ala Val Thr Pro Ser Asn Ile
65                  70                  75                  80

Ile Gly Arg His Tyr Gly Pro Ile Ser Ile Asn Tyr Arg Thr
                85                  90

<210> SEQ ID NO 125
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Val Ser Asp Val Pro Arg Asp Leu Glu Val Val Ala Ala Thr Pro Thr
1               5                   10                  15

Ser Leu Leu Ile Ser Trp Pro Gln His Leu Arg Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Arg Gly Ser Asp Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90

<210> SEQ ID NO 126
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

-continued

Thr Val Pro Leu Gln Pro Pro Thr Ala Thr Ile Ser Gly Leu Lys Pro
    50                  55                  60

Gly Val Asp Tyr Thr Ile Thr Val Tyr Ala Val Thr Glu Gly Pro Asn
65                  70                  75                  80

Glu Arg Ser Leu Phe Ile Pro Ile Ser Ile Asn Tyr Arg Thr
                85                  90

<210> SEQ ID NO 127
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Val
    50                  55                  60

Tyr Ala Val Thr Glu Gly Pro Asn Glu Arg Ser Leu Phe Ile Pro Ile
65                  70                  75                  80

Ser Ile Asn Tyr Arg Thr
                85

<210> SEQ ID NO 128
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gly Glu Val Val Ala Ala Thr Pro Thr Ser Leu Leu Ile Ser Trp Arg
1               5                   10                  15

His Pro His Phe Pro Thr Arg Tyr Tyr Arg Ile Thr Tyr Gly Glu Thr
                20                  25                  30

Gly Gly Asn Ser Pro Val Gln Glu Phe Thr Val Pro Leu Gln Pro Pro
            35                  40                  45

Thr Ala Thr Ile Ser Gly Leu Lys Pro Gly Val Asp Tyr Thr Ile Thr
    50                  55                  60

Val Tyr Ala Val Thr Asp Gly Arg Asn Gly Arg Leu Leu Ser Ile Pro
65                  70                  75                  80

Ile Ser Ile Asn Tyr Arg Thr Glu Ile Asp Lys Pro Cys Gln
                85                  90

<210> SEQ ID NO 129
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Val Ala Ala Thr Pro Thr Ser Leu Leu Ile Ser Trp Arg His

```
                1               5                   10                  15
Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Val
        50                  55                  60

Tyr Ala Val Thr Asp Gly Arg Asn Gly Arg Leu Leu Ser Ile Pro Ile
65                  70                  75                  80

Ser Ile Asn Tyr Arg Thr
                85
```

<210> SEQ ID NO 130
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Met Gly Leu Tyr Gly His Glu Leu Leu Thr Pro Ile
65                  70                  75                  80

Ser Ile Asn Tyr Arg Thr
                85
```

<210> SEQ ID NO 131
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Asp Gly Glu Asn Gly Gln Phe Leu Leu Val Pro Ile
65                  70                  75                  80

Ser Ile Asn Tyr Arg Thr
                85
```

<210> SEQ ID NO 132
<211> LENGTH: 86
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 132

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Met Gly Pro Asn Asp Asn Glu Leu Leu Thr Pro Ile
65                  70                  75                  80

Ser Ile Asn Tyr Arg Thr
                85

<210> SEQ ID NO 133
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Ala Gly Trp Asp Asp His Glu Leu Phe Ile Pro Ile
65                  70                  75                  80

Ser Ile Asn Tyr Arg Thr
                85

<210> SEQ ID NO 134
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Ser Gly His Asn Asp His Met Leu Met Ile Pro Ile
65                  70                  75                  80
```

Ser Ile Asn Tyr Arg Thr
                85

<210> SEQ ID NO 135
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Ala Gly Tyr Asn Asp Gln Ile Leu Met Thr Pro Ile
65                  70                  75                  80

Ser Ile Asn Tyr Arg Thr
                85

<210> SEQ ID NO 136
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Phe Gly Leu Tyr Gly Lys Glu Leu Leu Ile Pro Ile
65                  70                  75                  80

Ser Ile Asn Tyr Arg Thr
                85

<210> SEQ ID NO 137
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Thr Gly Pro Asn Asp Arg Leu Leu Phe Val Pro Ile
 65                  70                  75                  80

Ser Ile Asn Tyr Arg Thr
                 85

<210> SEQ ID NO 138
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Asp Val Tyr Asn Asp His Glu Ile Lys Thr Pro Ile
 65                  70                  75                  80

Ser Ile Asn Tyr Arg Thr
                 85

<210> SEQ ID NO 139
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Asp Gly Lys Asp Gly Arg Val Leu Leu Thr Pro Ile
 65                  70                  75                  80

Ser Ile Asn Tyr Arg Thr
                 85

<210> SEQ ID NO 140
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Glu Val His His Asp Arg Glu Ile Lys Thr Pro Ile
65                  70                  75                  80

Ser Ile Asn Tyr Arg Thr
                85

<210> SEQ ID NO 141
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Gln Ala Pro Asn Asp Arg Val Leu Tyr Thr Pro Ile
65                  70                  75                  80

Ser Ile Asn Tyr Arg Thr
                85

<210> SEQ ID NO 142
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Arg Glu Asn Asp His Glu Leu Leu Ile Pro Ile
65                  70                  75                  80

Ser Ile Asn Tyr Arg Thr
                85

```
<210> SEQ ID NO 143
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Thr His Asn Gly His Pro Leu Met Thr Pro Ile
65                  70                  75                  80

Ser Ile Asn Tyr Arg Thr
                85

<210> SEQ ID NO 144
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Ala Leu Lys Gly His Glu Leu Leu Thr Pro Ile
65                  70                  75                  80

Ser Ile Asn Tyr Arg Thr
                85

<210> SEQ ID NO 145
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60
```

```
Gly Val Asp Tyr Thr Ile Thr Gly Tyr Ala Val Thr Val Ala Gln Asn
65                  70                  75                  80

Asp His Glu Leu Ile Thr Pro Ile Ser Ile Asn Tyr Arg Thr
                85                  90

<210> SEQ ID NO 146
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Val Ser Asp Val Pro Arg Asp Leu Gln Glu Val Val Ala Ala Thr Pro
1               5                   10                  15

Thr Ser Leu Leu Ile Ser Trp Arg His Pro His Phe Pro Thr Arg Tyr
                20                  25                  30

Tyr Arg Ile Thr Tyr Gly Glu Thr Gly Gly Asn Ser Pro Val Gln Glu
            35                  40                  45

Phe Thr Val Pro Leu Gln Pro Pro Ala Ala Thr Ile Ser Gly Leu Lys
        50                  55                  60

Pro Gly Val Asp Tyr Thr Ile Thr Gly Tyr Ala Val Thr Met Ala Gln
65                  70                  75                  80

Ser Gly His Glu Leu Phe Thr Pro Ile Ser Ile Asn Tyr Arg Thr
                85                  90                  95

<210> SEQ ID NO 147
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Gly Arg Val Leu Met Thr Pro Ile
65                  70                  75                  80

Ser Ile Asn Tyr Arg Thr
                85

<210> SEQ ID NO 148
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Val Val Ala Ala Thr Pro Thr Ser Leu Leu Ile Ser Trp Arg His
1               5                   10                  15
```

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
50                  55                  60

Tyr Ala Val Thr Val Glu Arg Asn Gly Arg His Leu Met Thr Pro Ile
65                  70                  75                  80

Ser Ile Asn Tyr Arg Thr
                85

<210> SEQ ID NO 149
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
50                  55                  60

Tyr Ala Val Thr Leu Glu Arg Asn Gly Arg Glu Leu Met Thr Pro Ile
65                  70                  75                  80

Ser Ile Asn Tyr Arg Thr
                85

<210> SEQ ID NO 150
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
50                  55                  60

Tyr Ala Val Thr Glu Glu Arg Asn Gly Arg Thr Leu Arg Thr Pro Ile
65                  70                  75                  80

Ser Ile Asn Tyr Arg Thr
                85

<210> SEQ ID NO 151
<211> LENGTH: 86
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 151

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Asp Arg Val Leu Phe Thr Pro Ile
65                  70                  75                  80

Ser Ile Asn Tyr Arg Thr
                85

<210> SEQ ID NO 152
<211> LENGTH: 86
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 152

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Arg Glu Leu Met Thr Pro Ile
65                  70                  75                  80

Ser Ile Asn Tyr Arg Thr
                85

<210> SEQ ID NO 153
<211> LENGTH: 86
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 153

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Glu Arg Asn Gly Arg Glu Leu Met Val Pro Ile
65                  70                  75                  80

Ser Ile Asn Tyr Arg Thr

<210> SEQ ID NO 154
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Gly Arg Asn Asp Arg Lys Leu Met Val Pro Ile
65                  70                  75                  80

Ser Ile Asn Tyr Arg Thr
                85

<210> SEQ ID NO 155
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Gly Gln Asn Gly Arg Leu Leu Asn Val Pro Ile
65                  70                  75                  80

Ser Ile Asn Tyr Arg Thr
                85

<210> SEQ ID NO 156
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Val Val Ala Ala Thr Pro Thr Ser Leu Leu Ile Ser Trp Arg His
1               5                   10                  15

His Pro His Phe Pro Thr Arg Tyr Tyr Arg Ile Thr Tyr Gly Glu Thr
            20                  25                  30

Gly Gly Asn Ser Pro Val Gln Glu Phe Thr Val Pro Leu Gln Pro Pro
        35                  40                  45

```
Thr Ala Thr Ile Ser Gly Leu Lys Pro Gly Val Asp Tyr Thr Ile Thr
            50                  55                  60

Gly Tyr Ala Val Thr Val His Trp Asn Gly Arg Glu Leu Met Thr Pro
 65                  70                  75                  80

Ile Ser Ile Asn Tyr Arg Thr
                85

<210> SEQ ID NO 157
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Glu Glu Trp Asn Gly Arg Val Leu Met Thr Pro Ile
 65                  70                  75                  80

Ser Ile Asn Tyr Arg Thr
                85

<210> SEQ ID NO 158
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Val Glu Arg Asn Gly His Thr Leu Met Thr Pro Ile
 65                  70                  75                  80

Ser Ile Asn Tyr Arg Thr
                85

<210> SEQ ID NO 159
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159
```

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Asn Gly Arg Gln Leu Met Thr Pro Ile
65                  70                  75                  80

Ser Ile Asn Tyr Arg Thr
                85

<210> SEQ ID NO 160
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Glu Arg Asn Gly Gln Val Leu Phe Thr Pro Ile
65                  70                  75                  80

Ser Ile Asn Tyr Arg Thr
                85

<210> SEQ ID NO 161
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Gly Gln Val Leu Tyr Thr Pro Ile
65                  70                  75                  80

Ser Ile Asn Tyr Arg Thr
                85

<210> SEQ ID NO 162
<211> LENGTH: 86

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Trp Gly Tyr Lys Asp His Glu Leu Leu Ile Pro Ile
65                  70                  75                  80

Ser Ile Asn Tyr Arg Thr
                85

<210> SEQ ID NO 163
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Gly Arg Asn Asp Arg Glu Leu Leu Thr Pro Ile
65                  70                  75                  80

Ser Ile Asn Tyr Arg Thr
                85

<210> SEQ ID NO 164
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Gly Pro Asn Asp Arg Leu Leu Asn Ile Pro Ile
```

Ser Ile Asn Tyr Arg Thr
            85

<210> SEQ ID NO 165
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Phe Ala Arg Asp Gly His Glu Ile Leu Thr Pro Ile
65                  70                  75                  80

Ser Ile Asn Tyr Arg Thr
            85

<210> SEQ ID NO 166
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Glu Gln Asn Gly Arg Glu Leu Met Thr Pro Ile
65                  70                  75                  80

Ser Ile Asn Tyr Arg Thr
            85

<210> SEQ ID NO 167
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Val Glu Glu Asn Gly Arg Val Leu Asn Thr Pro Ile
 65                  70                  75                  80

Ser Ile Asn Tyr Arg Thr
                85

<210> SEQ ID NO 168
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Leu Glu Pro Asn Gly Arg Tyr Leu Met Val Pro Ile
 65                  70                  75                  80

Ser Ile Asn Tyr Arg Thr
                85

<210> SEQ ID NO 169
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
 50                  55                  60

Tyr Ala Val Thr Glu Gly Arg Asn Gly Arg Glu Leu Phe Ile Pro Ile
 65                  70                  75                  80

Ser Ile Asn Tyr Arg Thr
                85

<210> SEQ ID NO 170
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Trp Glu Arg Asn
65                  70                  75                  80

Gly Arg Glu Leu Phe Thr Pro Ile Ser Ile Asn Tyr Arg Thr
                85                  90

<210> SEQ ID NO 171
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Lys Glu Arg Asn
65                  70                  75                  80

Gly Arg Glu Leu Phe Thr Pro Ile Ser Ile Asn Tyr Arg Thr
                85                  90

<210> SEQ ID NO 172
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Thr Glu Arg Thr
65                  70                  75                  80

Gly Arg Glu Leu Phe Thr Pro Ile Ser Ile Asn Tyr Arg Thr
                85                  90

<210> SEQ ID NO 173
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Lys Glu Arg Ser
65                  70                  75                  80

Gly Arg Glu Leu Phe Thr Pro Ile Ser Ile Asn Tyr Arg Thr
                85                  90

<210> SEQ ID NO 174
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Leu Glu Arg Asp
65                  70                  75                  80

Gly Arg Glu Leu Phe Thr Pro Ile Ser Ile Asn Tyr Arg Thr
                85                  90

<210> SEQ ID NO 175
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Leu Ala Thr Ile Ser Gly Leu Lys Pro

```
                    50                  55                  60
Gly Val Asp Tyr Thr Ile Thr Gly Val Tyr Ala Val Thr Lys Glu Arg
 65                  70                  75                  80

Asn Gly Arg Glu Leu Phe Thr Pro Ile Ser Ile Asn Tyr Arg Thr
                 85                  90                  95
```

<210> SEQ ID NO 176
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

```
Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
                35                  40                  45

Thr Val Pro Leu Gln Pro Thr Thr Ala Thr Ile Ser Gly Leu Lys Pro
            50                  55                  60

Gly Val Asp Tyr Thr Ile Thr Gly Tyr Ala Val Thr Trp Glu Arg Asn
 65                  70                  75                  80

Gly Arg Glu Leu Phe Thr Pro Ile Ser Ile Asn Tyr Arg Thr
                 85                  90
```

<210> SEQ ID NO 177
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
                35                  40                  45

Thr Val Pro Leu Gln Pro Thr Val Ala Thr Ile Ser Gly Leu Lys Pro
            50                  55                  60

Gly Val Asp Tyr Thr Ile Thr Gly Tyr Ala Val Thr Leu Glu Arg Asn
 65                  70                  75                  80

Asp Arg Glu Leu Phe Thr Pro Ile Ser Ile Asn Tyr Arg Thr
                 85                  90
```

<210> SEQ ID NO 178
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

```
Met Gly Glu Val Val Ala Ala Thr Pro Thr Ser Leu Leu Ile Ser Trp
 1               5                  10                  15
```

Arg His Pro His Phe Pro Thr Arg Tyr Tyr Arg Ile Thr Tyr Gly Glu
            20                  25                  30

Thr Gly Gly Asn Ser Pro Val Gln Glu Phe Thr Val Pro Leu Gln Pro
        35                  40                  45

Pro Thr Ala Thr Ile Ser Gly Leu Lys Pro Gly Val Asp Tyr Thr Ile
50                  55                  60

Thr Val Tyr Ala Val Thr Asp Gly Arg Asn Gly Arg Leu Leu Ser Ile
65                  70                  75                  80

Pro Ile Ser Ile Asn Tyr Arg Thr Glu Ile Asp Lys Pro Ser Gln
                85                  90                  95

<210> SEQ ID NO 179
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Met Gly Glu Val Val Ala Ala Thr Pro Thr Ser Leu Leu Ile Ser Trp
1               5                   10                  15

Arg His Pro His Phe Pro Thr Arg Tyr Tyr Arg Ile Thr Tyr Gly Glu
            20                  25                  30

Thr Gly Gly Asn Ser Pro Val Gln Glu Phe Thr Val Pro Leu Gln Pro
        35                  40                  45

Pro Thr Ala Thr Ile Ser Gly Leu Lys Pro Gly Val Asp Tyr Thr Ile
50                  55                  60

Thr Val Tyr Ala Val Thr Asp Gly Arg Asn Gly Arg Leu Leu Ser Ile
65                  70                  75                  80

Pro Ile Ser Ile Asn Tyr Arg Thr Glu Ile Asp Lys Pro Cys Gln
                85                  90                  95

<210> SEQ ID NO 180
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Met Val Ser Asp Val Pro Arg Asp Leu Glu Val Val Ala Ala Thr Pro
1               5                   10                  15

Thr Ser Leu Leu Ile Ser Trp Arg His Pro His Phe Pro Thr Arg Tyr
            20                  25                  30

Tyr Arg Ile Thr Tyr Gly Glu Thr Gly Gly Asn Ser Pro Val Gln Glu
        35                  40                  45

Phe Thr Val Pro Leu Gln Pro Pro Thr Ala Thr Ile Ser Gly Leu Lys
50                  55                  60

Pro Gly Val Asp Tyr Thr Ile Thr Val Tyr Ala Val Thr Asp Gly Arg
65                  70                  75                  80

Asn Gly Arg Leu Leu Ser Ile Pro Ile Ser Ile Asn Tyr Arg Thr Glu
                85                  90                  95

Ile Asp Lys Pro Ser Gln
            100

<210> SEQ ID NO 181

<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Gly Glu Val Val Ala Ala Thr Pro Thr Ser Leu Leu Ile Ser Trp
1               5                   10                  15

Arg His Pro His Phe Pro Thr Arg Tyr Tyr Arg Ile Thr Tyr Gly Glu
            20                  25                  30

Thr Gly Gly Asn Ser Pro Val Gln Glu Phe Thr Val Pro Leu Gln Pro
        35                  40                  45

Pro Thr Ala Thr Ile Ser Gly Leu Lys Pro Gly Val Asp Tyr Thr Ile
    50                  55                  60

Thr Val Tyr Ala Val Thr Asp Gly Trp Asn Gly Arg Leu Leu Ser Ile
65                  70                  75                  80

Pro Ile Ser Ile Asn Tyr Arg Thr
                85

<210> SEQ ID NO 182
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Met Gly Glu Val Val Ala Ala Thr Pro Thr Ser Leu Leu Ile Ser Trp
1               5                   10                  15

Arg His Pro His Phe Pro Thr Arg Tyr Tyr Arg Ile Thr Tyr Gly Glu
            20                  25                  30

Thr Gly Gly Asn Ser Pro Val Gln Glu Phe Thr Val Pro Leu Gln Pro
        35                  40                  45

Pro Thr Ala Thr Ile Ser Gly Leu Lys Pro Gly Val Asp Tyr Thr Ile
    50                  55                  60

Thr Val Tyr Ala Val Thr Glu Gly Pro Asn Glu Arg Ser Leu Phe Ile
65                  70                  75                  80

Pro Ile Ser Ile Asn Tyr Arg Thr
                85

<210> SEQ ID NO 183
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Met Val Ser Asp Val Pro Arg Asp Leu Glu Val Val Ala Ala Thr Pro
1               5                   10                  15

Thr Ser Leu Leu Ile Ser Trp Arg His Pro His Phe Pro Thr Arg Tyr
            20                  25                  30

Tyr Arg Ile Thr Tyr Gly Glu Thr Gly Gly Asn Ser Pro Val Gln Glu
        35                  40                  45

Phe Thr Val Pro Leu Gln Pro Pro Thr Ala Thr Ile Ser Gly Leu Lys
    50                  55                  60

```
Pro Gly Val Asp Tyr Thr Ile Thr Val Tyr Ala Val Thr Glu Gly Pro
 65                  70                  75                  80

Asn Glu Arg Ser Leu Phe Ile Pro Ile Ser Ile Asn Tyr Arg Thr
                 85                  90                  95

<210> SEQ ID NO 184
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Val Ser Asp Val Pro Arg Asp Leu Glu Val Val Ala Ala Thr Pro Thr
  1               5                  10                  15

Ser Leu Leu Ile Ser Trp Ser Ala Arg Leu Lys Val Ala Arg Tyr Tyr
                 20                  25                  30

Arg Ile Thr Tyr Gly Glu Thr Gly Gly Asn Ser Pro Val Gln Glu Phe
             35                  40                  45

Thr Val Pro Lys Asn Val Tyr Thr Ala Thr Ile Ser Gly Leu Lys Pro
         50                  55                  60

Gly Val Asp Tyr Thr Ile Thr Val Tyr Ala Val Thr Arg Phe Arg Asp
 65                  70                  75                  80

Tyr Gln Pro Ile Ser Ile Asn Tyr Arg Thr
                 85                  90

<210> SEQ ID NO 185
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Val Ser Asp Val Pro Arg Asp Leu Glu Val Val Ala Ala Thr Pro Thr
  1               5                  10                  15

Ser Leu Leu Ile Ser Trp Ser Ala Arg Leu Lys Val Ala Arg Tyr Tyr
                 20                  25                  30

Arg Ile Thr Tyr Gly Glu Thr Gly Gly Asn Ser Pro Val Gln Glu Phe
             35                  40                  45

Thr Val Pro Lys Asn Val Tyr Thr Ala Thr Ile Ser Gly Leu Lys Pro
         50                  55                  60

Gly Val Asp Tyr Thr Ile Thr Val Tyr Ala Val Thr Arg Ile Arg Asp
 65                  70                  75                  80

Tyr Gly Pro Ile Ser Ile Asn Tyr Arg Thr
                 85                  90

<210> SEQ ID NO 186
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Val Ser Asp Val Pro Arg Asp Leu Glu Val Val Ala Ala Thr Pro Thr
  1               5                  10                  15

Ser Leu Leu Ile Ser Trp Ser Ala Arg Leu Lys Val Ala Arg Tyr Tyr
```

```
                    20                  25                  30

Arg Ile Thr Tyr Gly Glu Thr Gly Gly Asn Ser Pro Val Gln Glu Phe
                35                  40                  45

Thr Val Pro Lys Asn Val Tyr Thr Ala Thr Ile Ser Gly Leu Lys Pro
            50                  55                  60

Gly Val Asp Tyr Thr Ile Thr Val Tyr Ala Val Ala Tyr Arg Asp
65                  70                  75                  80

Tyr Gln Pro Ile Ser Ile Asn Tyr Arg Thr
                85                  90

<210> SEQ ID NO 187
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
                20                  25                  30

Arg Ile Thr Tyr Gly Glu Thr Gly Gly Asn Ser Pro Val Gln Glu Phe
                35                  40                  45

Thr Val Pro Lys Asn Val Tyr Thr Ala Thr Ile Ser Gly Leu Lys Pro
            50                  55                  60

Gly Val Asp Tyr Thr Ile Thr Val Tyr Ala Val Thr Arg Glu Arg Asp
65                  70                  75                  80

Tyr Arg Pro Ile Ser Ile Asn Tyr Arg Thr
                85                  90

<210> SEQ ID NO 188
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
                20                  25                  30

Arg Ile Thr Tyr Gly Glu Thr Gly Gly Asn Ser Pro Val Gln Glu Phe
                35                  40                  45

Thr Val Pro Lys Asn Val Tyr Thr Ala Thr Ile Ser Gly Leu Lys Pro
            50                  55                  60

Gly Val Asp Tyr Thr Ile Thr Val Tyr Ala Val Thr Ala Val Arg Asp
65                  70                  75                  80

Tyr Arg Pro Ile Ser Ile Asn Tyr Arg Thr
                85                  90

<210> SEQ ID NO 189
<211> LENGTH: 90
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 189

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Glu Leu Arg Asn
65                  70                  75                  80

Tyr Gly Pro Ile Ser Ile Asn Tyr Arg Thr
                85                  90

<210> SEQ ID NO 190
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Ser Leu Arg Asp
65                  70                  75                  80

Tyr Ala Pro Ile Ser Ile Asn Tyr Arg Thr
                85                  90

<210> SEQ ID NO 191
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Gln Leu Arg Asp
65                  70                  75                  80

Tyr Ser Pro Ile Ser Ile Asn Tyr Arg Thr
                85                  90

<210> SEQ ID NO 192
<211> LENGTH: 90
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 192

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Asn Leu Arg Asp
65                  70                  75                  80

Tyr Gly Pro Ile Ser Ile Asn Tyr Arg Thr
                85                  90

<210> SEQ ID NO 193
<211> LENGTH: 90
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 193

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Glu Arg Arg Asp
65                  70                  75                  80

Tyr Arg Pro Ile Ser Ile Asn Tyr Arg Thr
                85                  90

<210> SEQ ID NO 194
<211> LENGTH: 90
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 194

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
            50                  55                  60

Gly Val Asp Tyr Thr Ile Thr Val Tyr Ala Val Thr Leu Val Arg Asn
65                  70                  75                  80

Tyr Gly Pro Ile Ser Ile Asn Tyr Arg Thr
                85                  90

<210> SEQ ID NO 195
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Ile Arg Asp
65                  70                  75                  80

Tyr Arg Pro Ile Ser Ile Asn Tyr Arg Thr
                85                  90

<210> SEQ ID NO 196
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Leu Leu Arg Asp
65                  70                  75                  80

Tyr Gly Pro Ile Ser Ile Asn Tyr Arg Thr
                85                  90

<210> SEQ ID NO 197
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Val Ser Asp Val Pro Arg Asp Leu Glu Val Val Ala Ala Thr Pro Thr

```
                1               5                   10                  15
Ser Leu Leu Ile Ser Trp Ser Ala Arg Leu Lys Val Ala Arg Tyr Tyr
                20                  25                  30

Arg Ile Thr Tyr Gly Glu Thr Gly Gly Asn Ser Pro Val Gln Glu Phe
            35                  40                  45

Thr Val Pro Lys Asn Val Tyr Thr Ala Thr Ile Ser Gly Leu Lys Pro
        50                  55                  60

Gly Val Asp Tyr Thr Ile Thr Val Tyr Ala Val Thr Leu Thr Arg Asp
65                  70                  75                  80

Tyr Lys Pro Ile Ser Ile Asn Tyr Arg Thr
                85                  90

<210> SEQ ID NO 198
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
                20                  25                  30

Arg Ile Thr Tyr Gly Glu Thr Gly Gly Asn Ser Pro Val Gln Glu Phe
            35                  40                  45

Thr Val Pro Lys Asn Val Tyr Thr Ala Thr Ile Ser Gly Leu Lys Pro
        50                  55                  60

Gly Val Asp Tyr Thr Ile Thr Val Tyr Ala Val Thr Val Val Arg Asp
65                  70                  75                  80

Tyr Arg Pro Ile Ser Ile Asn Tyr Arg Thr
                85                  90

<210> SEQ ID NO 199
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
                20                  25                  30

Arg Ile Thr Tyr Gly Glu Thr Gly Gly Asn Ser Pro Val Gln Glu Phe
            35                  40                  45

Thr Val Pro Lys Asn Val Tyr Thr Ala Thr Ile Ser Gly Leu Lys Pro
        50                  55                  60

Gly Val Asp Tyr Thr Ile Thr Val Tyr Ala Val Thr Ser Tyr Arg Asp
65                  70                  75                  80

Tyr Trp Pro Ile Ser Ile Asn Tyr Arg Thr
                85                  90

<210> SEQ ID NO 200
<211> LENGTH: 90
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 200

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Met Ser Arg Asp
65                  70                  75                  80

Tyr Gly Pro Ile Ser Ile Asn Tyr Arg Thr
                85                  90

<210> SEQ ID NO 201
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Ser Leu Arg Asp
65                  70                  75                  80

Tyr Gly Pro Ile Ser Ile Asn Tyr Arg Thr
                85                  90

<210> SEQ ID NO 202
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Gly Val Arg Asn
65                  70                  75                  80

Tyr Gly Pro Ile Ser Ile Asn Tyr Arg Thr
            85                  90

<210> SEQ ID NO 203
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gly Val Ser Asp Val Pro Arg Asp Leu Glu Val Val Ala Ala Thr Pro
1               5                   10                  15

Thr Ser Leu Leu Ile Ser Trp Ser Ala Arg Leu Lys Val Ala Arg Tyr
            20                  25                  30

Tyr Arg Ile Thr Tyr Gly Glu Thr Gly Gly Asn Ser Pro Val Gln Glu
        35                  40                  45

Phe Thr Val Pro Lys Asn Val Tyr Thr Ala Thr Ile Ser Gly Leu Lys
    50                  55                  60

Pro Gly Val Asp Tyr Thr Ile Thr Val Tyr Ala Val Thr Arg Phe Arg
65                  70                  75                  80

Asp Tyr Gln Pro Ile Ser Ile Asn Tyr Arg Thr Glu Ile Asp Lys Pro
                85                  90                  95

Cys Gln

<210> SEQ ID NO 204
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
taatacgact cactataggg acaattacta tttacaatta caatg                45

<210> SEQ ID NO 205
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gggacaatta ctatttacaa ttacaatggt ttctgatgtg ccgcgcgacc tggaagtggt     60
tgctgccacc cccaccagcc tgctgatcag ctgg                                 94

<210> SEQ ID NO 206
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, g, t, unknown, or other
<220> FEATURE:
<221> NAME/KEY: modified_base
<222> LOCATION: (22)..(23)
<223> OTHER INFORMATION: a, c, g, t, unknown, or other

```
<220> FEATURE:
<221> NAME/KEY: modified_base
<222> LOCATION: (25)..(26)
<223> OTHER INFORMATION: a, c, g, t, unknown, or other
<220> FEATURE:
<221> NAME/KEY: modified_base
<222> LOCATION: (28)..(29)
<223> OTHER INFORMATION: a, c, g, t, unknown, or other
<220> FEATURE:
<221> NAME/KEY: modified_base
<222> LOCATION: (31)..(32)
<223> OTHER INFORMATION: a, c, g, t, unknown, or other
<220> FEATURE:
<221> NAME/KEY: modified_base
<222> LOCATION: (34)..(35)
<223> OTHER INFORMATION: a, c, g, t, unknown, or other
<220> FEATURE:
<221> NAME/KEY: modified_base
<222> LOCATION: (37)..(38)
<223> OTHER INFORMATION: a, c, g, t, unknown, or other

<400> SEQUENCE: 206
agcctgctga tcagctggnn snnsnnsnns nnsnnsnnsc gatattaccg catcact      57

<210> SEQ ID NO 207
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
aggcacagtg aactcctgga cagggctatt gcctcctgtt tcgccgtaag tgatgcggta    60
atatcg                                                              66

<210> SEQ ID NO 208
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, g, t, unknown, or other
<220> FEATURE:
<221> NAME/KEY: modified_base
<222> LOCATION: (22)..(23)
<223> OTHER INFORMATION: a, c, g, t, unknown, or other
<220> FEATURE:
<221> NAME/KEY: modified_base
<222> LOCATION: (25)..(26)
<223> OTHER INFORMATION: a, c, g, t, unknown, or other
<220> FEATURE:
<221> NAME/KEY: modified_base
<222> LOCATION: (28)..(29)
<223> OTHER INFORMATION: a, c, g, t, unknown, or other

<400> SEQUENCE: 208
caggagttca ctgtgcctnn snnsnnsnns acagctacca tcagcggc                48

<210> SEQ ID NO 209
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
```
agtgacagca tacacagtga tggtataatc aacgccaggt ttaaggccgc tgatggtagc    60
tgt                                                                  63

<210> SEQ ID NO 210
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, g, t, unknown, or other
<220> FEATURE:
<221> NAME/KEY: modified_base
<222> LOCATION: (22)..(23)
<223> OTHER INFORMATION: a, c, g, t, unknown, or other
<220> FEATURE:
<221> NAME/KEY: modified_base
<222> LOCATION: (25)..(26)
<223> OTHER INFORMATION: a, c, g, t, unknown, or other
<220> FEATURE:
<221> NAME/KEY: modified_base
<222> LOCATION: (28)..(29)
<223> OTHER INFORMATION: a, c, g, t, unknown, or other
<220> FEATURE:
<221> NAME/KEY: modified_base
<222> LOCATION: (31)..(32)
<223> OTHER INFORMATION: a, c, g, t, unknown, or other
<220> FEATURE:
<221> NAME/KEY: modified_base
<222> LOCATION: (34)..(35)
<223> OTHER INFORMATION: a, c, g, t, unknown, or other

<400> SEQUENCE: 210
actgtgtatg ctgtcactnn snnsnnsnns nnsnnsccaa tttccattaa ttac          54

<210> SEQ ID NO 211
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, g, t, unknown, or other
<220> FEATURE:
<221> NAME/KEY: modified_base
<222> LOCATION: (22)..(23)
<223> OTHER INFORMATION: a, c, g, t, unknown, or other
<220> FEATURE:
<221> NAME/KEY: modified_base
<222> LOCATION: (25)..(26)
<223> OTHER INFORMATION: a, c, g, t, unknown, or other
<220> FEATURE:
<221> NAME/KEY: modified_base
<222> LOCATION: (28)..(29)
<223> OTHER INFORMATION: a, c, g, t, unknown, or other
<220> FEATURE:
<221> NAME/KEY: modified_base
<222> LOCATION: (31)..(32)
<223> OTHER INFORMATION: a, c, g, t, unknown, or other
<220> FEATURE:
<221> NAME/KEY: modified_base
<222> LOCATION: (34)..(35)
<223> OTHER INFORMATION: a, c, g, t, unknown, or other
<220> FEATURE:
<221> NAME/KEY: modified_base
<222> LOCATION: (37)..(38)
<223> OTHER INFORMATION: a, c, g, t, unknown, or other
<220> FEATURE:

```
<221> NAME/KEY: modified_base
<222> LOCATION: (40)..(41)
<223> OTHER INFORMATION: a, c, g, t, unknown, or other

<400> SEQUENCE: 211
actgtgtatg ctgtcactnn snnsnnsnns nnsnnsnnsn nsccaatttc cattaattac    60

<210> SEQ ID NO 212
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, g, t, unknown, or other
<220> FEATURE:
<221> NAME/KEY: modified_base
<222> LOCATION: (22)..(23)
<223> OTHER INFORMATION: a, c, g, t, unknown, or other
<220> FEATURE:
<221> NAME/KEY: modified_base
<222> LOCATION: (25)..(26)
<223> OTHER INFORMATION: a, c, g, t, unknown, or other
<220> FEATURE:
<221> NAME/KEY: modified_base
<222> LOCATION: (28)..(29)
<223> OTHER INFORMATION: a, c, g, t, unknown, or other
<220> FEATURE:
<221> NAME/KEY: modified_base
<222> LOCATION: (31)..(32)
<223> OTHER INFORMATION: a, c, g, t, unknown, or other
<220> FEATURE:
<221> NAME/KEY: modified_base
<222> LOCATION: (34)..(35)
<223> OTHER INFORMATION: a, c, g, t, unknown, or other
<220> FEATURE:
<221> NAME/KEY: modified_base
<222> LOCATION: (37)..(38)
<223> OTHER INFORMATION: a, c, g, t, unknown, or other
<220> FEATURE:
<221> NAME/KEY: modified_base
<222> LOCATION: (40)..(41)
<223> OTHER INFORMATION: a, c, g, t, unknown, or other
<220> FEATURE:
<221> NAME/KEY: modified_base
<222> LOCATION: (43)..(44)
<223> OTHER INFORMATION: a, c, g, t, unknown, or other
<220> FEATURE:
<221> NAME/KEY: modified_base
<222> LOCATION: (46)..(47)
<223> OTHER INFORMATION: a, c, g, t, unknown, or other

<400> SEQUENCE: 212
actgtgtatg ctgtcactnn snnsnnsnns nnsnnsnnsn nsnnsnnscc aatttccatt    60
aattac                                                               66

<210> SEQ ID NO 213
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, g, t, unknown, or other
<220> FEATURE:
<221> NAME/KEY: modified_base
<222> LOCATION: (22)..(23)
<223> OTHER INFORMATION: a, c, g, t, unknown, or other
```

<220> FEATURE:
<221> NAME/KEY: modified_base
<222> LOCATION: (25)..(26)
<223> OTHER INFORMATION: a, c, g, t, unknown, or other
<220> FEATURE:
<221> NAME/KEY: modified_base
<222> LOCATION: (28)..(29)
<223> OTHER INFORMATION: a, c, g, t, unknown, or other
<220> FEATURE:
<221> NAME/KEY: modified_base
<222> LOCATION: (31)..(32)
<223> OTHER INFORMATION: a, c, g, t, unknown, or other
<220> FEATURE:
<221> NAME/KEY: modified_base
<222> LOCATION: (34)..(35)
<223> OTHER INFORMATION: a, c, g, t, unknown, or other
<220> FEATURE:
<221> NAME/KEY: modified_base
<222> LOCATION: (37)..(38)
<223> OTHER INFORMATION: a, c, g, t, unknown, or other
<220> FEATURE:
<221> NAME/KEY: modified_base
<222> LOCATION: (40)..(41)
<223> OTHER INFORMATION: a, c, g, t, unknown, or other
<220> FEATURE:
<221> NAME/KEY: modified_base
<222> LOCATION: (43)..(44)
<223> OTHER INFORMATION: a, c, g, t, unknown, or other
<220> FEATURE:
<221> NAME/KEY: modified_base
<222> LOCATION: (46)..(47)
<223> OTHER INFORMATION: a, c, g, t, unknown, or other
<220> FEATURE:
<221> NAME/KEY: modified_base
<222> LOCATION: (49)..(50)
<223> OTHER INFORMATION: a, c, g, t, unknown, or other
<220> FEATURE:
<221> NAME/KEY: modified_base
<222> LOCATION: (52)..(53)
<223> OTHER INFORMATION: a, c, g, t, unknown, or other

<400> SEQUENCE: 213
actgtgtatg ctgtcactnn snnsnnsnns nnsnnsnnsn nsnnsnnsnn snnsccaatt    60
tccattaatt ac                                                      72

<210> SEQ ID NO 214
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, g, t, unknown, or other
<220> FEATURE:
<221> NAME/KEY: modified_base
<222> LOCATION: (22)..(23)
<223> OTHER INFORMATION: a, c, g, t, unknown, or other
<220> FEATURE:
<221> NAME/KEY: modified_base
<222> LOCATION: (25)..(26)
<223> OTHER INFORMATION: a, c, g, t, unknown, or other
<220> FEATURE:
<221> NAME/KEY: modified_base
<222> LOCATION: (28)..(29)
<223> OTHER INFORMATION: a, c, g, t, unknown, or other
<220> FEATURE:
<221> NAME/KEY: modified_base
<222> LOCATION: (31)..(32)
<223> OTHER INFORMATION: a, c, g, t, unknown, or other
<220> FEATURE:
<221> NAME/KEY: modified_base
<222> LOCATION: (34)..(35)
<223> OTHER INFORMATION: a, c, g, t, unknown, or other

```
<220> FEATURE:
<221> NAME/KEY: modified_base
<222> LOCATION: (37)..(38)
<223> OTHER INFORMATION: a, c, g, t, unknown, or other
<220> FEATURE:
<221> NAME/KEY: modified_base
<222> LOCATION: (40)..(41)
<223> OTHER INFORMATION: a, c, g, t, unknown, or other
<220> FEATURE:
<221> NAME/KEY: modified_base
<222> LOCATION: (43)..(44)
<223> OTHER INFORMATION: a, c, g, t, unknown, or other
<220> FEATURE:
<221> NAME/KEY: modified_base
<222> LOCATION: (46)..(47)
<223> OTHER INFORMATION: a, c, g, t, unknown, or other
<220> FEATURE:
<221> NAME/KEY: modified_base
<222> LOCATION: (49)..(50)
<223> OTHER INFORMATION: a, c, g, t, unknown, or other
<220> FEATURE:
<221> NAME/KEY: modified_base
<222> LOCATION: (52)..(53)
<223> OTHER INFORMATION: a, c, g, t, unknown, or other
<220> FEATURE:
<221> NAME/KEY: modified_base
<222> LOCATION: (55)..(56)
<223> OTHER INFORMATION: a, c, g, t, unknown, or other
<220> FEATURE:
<221> NAME/KEY: modified_base
<222> LOCATION: (58)..(59)
<223> OTHER INFORMATION: a, c, g, t, unknown, or other

<400> SEQUENCE: 214
actgtgtatg ctgtcactnn snnsnnsnns nnsnnsnnsn nsnnsnnsnn snnsnnsnns     60
ccaatttcca ttaattac                                                  78

<210> SEQ ID NO 215
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
ttaaatagcg gatgccttgt cgtcgtcgtc cttgtagtct gtgcggtaat taatggaaat     60
tgg                                                                  63

<210> SEQ ID NO 216
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tttttttttt tttttttttt aaatagcgga tgccttgtcg tcgtcgtcct tgta           54

<210> SEQ ID NO 217
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
agcctgctga tcagctggtc cccgtacctg cgcgtcgccc gatattaccg catcact        57
```

<210> SEQ ID NO 218
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
caggagttca ctgtgccttc ctccgcccgc acagctacca tcagcggc                    48

<210> SEQ ID NO 219
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
actgtgtatg ctgtcactcc gtccaacatc atcggccgtc actatggccc aatttccatt      60
aattac                                                                  66

<210> SEQ ID NO 220
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
agcctgctga tcagctgg                                                     18

<210> SEQ ID NO 221
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
caggagttca ctgtgcct                                                     18

<210> SEQ ID NO 222
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
actgtgtatg ctgtcact                                                     18

<210> SEQ ID NO 223
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223

-continued agcctgctga tcagctggtc tgcgcgtctg aaagttgcgc gatattaccg catcact        57

<210> SEQ ID NO 224
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
caggagttca ctgtgcctaa aaacgtttac acagctacca tcagcggc                  48

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Glu Ile Asp Lys Pro Cys Gln
1               5

<210> SEQ ID NO 226
<211> LENGTH: 98
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 226

Gly Val Ser Asp Val Pro Arg Asp Leu Glu Val Val Ala Ala Thr Pro
1               5                   10                  15

Thr Ser Leu Leu Ile Ser Trp Ser Ala Arg Leu Lys Val Ala Arg Tyr
            20                  25                  30

Tyr Arg Ile Thr Tyr Gly Glu Thr Gly Gly Asn Ser Pro Val Gln Glu
        35                  40                  45

Phe Thr Val Pro Lys Asn Val Tyr Thr Ala Thr Ile Ser Gly Leu Lys
    50                  55                  60

Pro Gly Val Asp Tyr Thr Ile Thr Val Tyr Ala Val Thr Arg Phe Arg
65                  70                  75                  80

Asp Tyr Gln Pro Ile Ser Ile Asn Tyr Arg Thr Glu Ile Asp Lys Pro
                85                  90                  95

Ser Gln

<210> SEQ ID NO 227
<211> LENGTH: 95
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 227

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Glu Thr Gly Gly Asn Ser Pro Val Gln Glu
        35                  40                  45

```
Phe Thr Val Pro Gly Ser Lys Ser Thr Ala Thr Ile Ser Gly Leu Lys
 50                  55                  60

Pro Gly Val Asp Tyr Thr Ile Thr Gly Tyr Ala Val Thr Gly Ser Gly
 65                  70                  75                  80

Glu Ser Pro Ala Ser Ser Lys Pro Ile Ser Ile Asn Tyr Arg Thr
                 85                  90                  95
```

<210> SEQ ID NO 228
<211> LENGTH: 707
<212> TYPE: PRT
<213> ORGANISM: Artificial Sequence
<220> FEATURE:
<223> OTHER INFORMATION: Description of Artificial Sequence: Synthetic construct

<400> SEQUENCE: 228

```
Met Lys Trp Val Thr Phe Ile Ser Leu Leu Phe Leu Phe Ser Ser Ala
 1               5                  10                  15

Tyr Ser Arg Gly Val Phe Arg Arg Asp Ala His Lys Ser Glu Val Ala
                 20                  25                  30

His Arg Phe Lys Asp Leu Gly Glu Glu Asn Phe Lys Ala Leu Val Leu
             35                  40                  45

Ile Ala Phe Ala Gln Tyr Leu Gln Gln Cys Pro Phe Glu Asp His Val
 50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
```

```
            305                 310                 315                 320
        Glu Met Pro Ala Asp Leu Pro Ser Leu Ala Ala Asp Phe Val Glu Ser
                        325                 330                 335
        Lys Asp Val Cys Lys Asn Tyr Ala Glu Ala Lys Asp Val Phe Leu Gly
                        340                 345                 350
        Met Phe Leu Tyr Glu Tyr Ala Arg Arg His Pro Asp Tyr Ser Val Val
                        355                 360                 365
        Leu Leu Leu Arg Leu Ala Lys Thr Tyr Glu Thr Thr Leu Glu Lys Cys
                        370                 375                 380
        Cys Ala Ala Ala Asp Pro His Glu Cys Tyr Ala Lys Val Phe Asp Glu
        385                 390                 395                 400
        Phe Lys Pro Leu Val Glu Glu Pro Gln Asn Leu Ile Lys Gln Asn Cys
                        405                 410                 415
        Glu Leu Phe Glu Gln Leu Gly Glu Tyr Lys Phe Gln Asn Ala Leu Leu
                        420                 425                 430
        Val Arg Tyr Thr Lys Lys Val Pro Gln Val Ser Thr Pro Thr Leu Val
                        435                 440                 445
        Glu Val Ser Arg Asn Leu Gly Lys Val Gly Ser Lys Cys Cys Lys His
                        450                 455                 460
        Pro Glu Ala Lys Arg Met Pro Cys Ala Glu Asp Tyr Leu Ser Val Val
        465                 470                 475                 480
        Leu Asn Gln Leu Cys Val Leu His Glu Lys Thr Pro Val Ser Asp Arg
                        485                 490                 495
        Val Thr Lys Cys Cys Thr Glu Ser Leu Val Asn Arg Arg Pro Cys Phe
                        500                 505                 510
        Ser Ala Leu Glu Val Asp Glu Thr Tyr Val Pro Lys Glu Phe Asn Ala
                        515                 520                 525
        Glu Thr Phe Thr Phe His Ala Asp Ile Cys Thr Leu Ser Glu Lys Glu
                        530                 535                 540
        Arg Gln Ile Lys Lys Gln Thr Ala Leu Val Glu Leu Val Lys His Lys
        545                 550                 555                 560
        Pro Lys Ala Thr Lys Glu Gln Leu Lys Ala Val Met Asp Asp Phe Ala
                        565                 570                 575
        Ala Phe Val Glu Lys Cys Cys Lys Ala Asp Asp Lys Glu Thr Cys Phe
                        580                 585                 590
        Ala Glu Glu Gly Lys Lys Leu Val Ala Ala Ser Gln Ala Ala Leu Gly
                        595                 600                 605
        Leu Pro Ser Thr Ser Thr Ser Thr Gly Val Ser Asp Val Pro Arg Asp
                        610                 615                 620
        Leu Glu Val Val Ala Ala Thr Pro Thr Ser Leu Leu Ile Ser Trp Ser
        625                 630                 635                 640
        Ala Arg Leu Lys Val Ala Arg Tyr Tyr Arg Ile Thr Tyr Gly Glu Thr
                        645                 650                 655
        Gly Gly Asn Ser Pro Val Gln Glu Phe Thr Val Pro Lys Asn Val Tyr
                        660                 665                 670
        Thr Ala Thr Ile Ser Gly Leu Lys Pro Gly Val Asp Tyr Thr Ile Thr
                        675                 680                 685
        Val Tyr Ala Val Thr Arg Phe Arg Asp Tyr Gln Pro Ile Ser Ile Asn
                        690                 695                 700
        Tyr Arg Thr
        705

<210> SEQ ID NO 229
```

<211> LENGTH: 682
<212> TYPE: PRT
<213> ORGANISM: Artificial Sequence
<220> FEATURE:
<223> OTHER INFORMATION: Description of Artificial Sequence: Synthetic construct

<400> SEQUENCE: 229

```
Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Pro Ser Thr Ser
                85                  90                  95

Thr Ser Thr Ala His Lys Ser Glu Val Ala His Arg Phe Lys Asp Leu
            100                 105                 110

Gly Glu Glu Asn Phe Lys Ala Leu Val Leu Ile Ala Phe Ala Gln Tyr
        115                 120                 125

Leu Gln Gln Cys Pro Phe Glu Asp His Val Lys Leu Val Asn Glu Val
130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
        195                 200                 205

Asn Leu Pro Arg Leu Val Arg Pro Glu Val Asp Val Met Cys Thr Ala
210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
                245                 250                 255

Lys Arg Tyr Lys Ala Ala Phe Thr Glu Cys Cys Gln Ala Ala Asp Lys
            260                 265                 270

Ala Ala Cys Leu Leu Pro Lys Leu Asp Glu Leu Arg Asp Glu Gly Lys
        275                 280                 285

Ala Ser Ser Ala Lys Gln Arg Leu Lys Cys Ala Ser Leu Gln Lys Phe
290                 295                 300

Gly Glu Arg Ala Phe Lys Ala Trp Ala Val Ala Arg Leu Ser Gln Arg
305                 310                 315                 320

Phe Pro Lys Ala Glu Phe Ala Glu Val Ser Lys Leu Val Thr Asp Leu
                325                 330                 335

Thr Lys Val His Thr Glu Cys Cys His Gly Asp Leu Leu Glu Cys Ala
            340                 345                 350

Asp Asp Arg Ala Asp Leu Ala Lys Tyr Ile Cys Glu Asn Gln Asp Ser
        355                 360                 365

Ile Ser Ser Lys Leu Lys Glu Cys Cys Glu Lys Pro Leu Leu Glu Lys
```

```
            370                 375                 380
Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
                405                 410                 415

Tyr Ala Glu Ala Lys Asp Val Phe Leu Gly Met Phe Leu Tyr Glu Tyr
                420                 425                 430

Ala Arg Arg His Pro Asp Tyr Ser Val Val Leu Leu Leu Arg Leu Ala
                435                 440                 445

Lys Thr Tyr Glu Thr Thr Leu Glu Lys Cys Cys Ala Ala Ala Asp Pro
450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
                485                 490                 495

Gly Glu Tyr Lys Phe Gln Asn Ala Leu Leu Val Arg Tyr Thr Lys Lys
                500                 505                 510

Val Pro Gln Val Ser Thr Pro Thr Leu Val Glu Val Ser Arg Asn Leu
                515                 520                 525

Gly Lys Val Gly Ser Lys Cys Cys Lys His Pro Glu Ala Lys Arg Met
530                 535                 540

Pro Cys Ala Glu Asp Tyr Leu Ser Val Val Leu Asn Gln Leu Cys Val
545                 550                 555                 560

Leu His Glu Lys Thr Pro Val Ser Asp Arg Val Thr Lys Cys Cys Thr
                565                 570                 575

Glu Ser Leu Val Asn Arg Arg Pro Cys Phe Ser Ala Leu Glu Val Asp
                580                 585                 590

Glu Thr Tyr Val Pro Lys Glu Phe Asn Ala Glu Thr Phe Thr Phe His
                595                 600                 605

Ala Asp Ile Cys Thr Leu Ser Glu Lys Glu Arg Gln Ile Lys Lys Gln
610                 615                 620

Thr Ala Leu Val Glu Leu Val Lys His Lys Pro Lys Ala Thr Lys Glu
625                 630                 635                 640

Gln Leu Lys Ala Val Met Asp Asp Phe Ala Ala Phe Val Glu Lys Cys
                645                 650                 655

Cys Lys Ala Asp Asp Lys Glu Thr Cys Phe Ala Glu Glu Gly Lys Lys
                660                 665                 670

Leu Val Ala Ala Ser Gln Ala Ala Leu Gly
                675                 680

<210> SEQ ID NO 230
<211> LENGTH: 707
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 230

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
                35                  40                  45
```

-continued

```
Ile Ala Phe Ala Gln Tyr Leu Gln Gln Cys Pro Phe Glu Asp His Val
 50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
                115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
```

```
            465                 470                 475                 480
Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
                530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu Glu Ile Asp Lys Pro Ser Gln Gly Val Ser Asp Val Pro Arg Asp
                610                 615                 620

Leu Glu Val Val Ala Ala Thr Pro Thr Ser Leu Leu Ile Ser Trp Ser
625                 630                 635                 640

Ala Arg Leu Lys Val Ala Arg Tyr Tyr Arg Ile Thr Tyr Gly Glu Thr
                645                 650                 655

Gly Gly Asn Ser Pro Val Gln Glu Phe Thr Val Pro Lys Asn Val Tyr
                660                 665                 670

Thr Ala Thr Ile Ser Gly Leu Lys Pro Gly Val Asp Tyr Thr Ile Thr
                675                 680                 685

Val Tyr Ala Val Thr Arg Phe Arg Asp Tyr Gln Pro Ile Ser Ile Asn
                690                 695                 700

Tyr Arg Thr
705

<210> SEQ ID NO 231
<211> LENGTH: 710
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 231

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
                100                 105                 110
```

```
Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
```

```
                    530                 535                 540
Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                    565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu Gly Ser Gly Ser Gly Ser Gly Ser Gly Ser Gly Val Ser Asp Val
                610                 615                 620

Pro Arg Asp Leu Glu Val Val Ala Ala Thr Pro Thr Ser Leu Leu Ile
625                 630                 635                 640

Ser Trp Ser Ala Arg Leu Lys Val Ala Arg Tyr Tyr Arg Ile Thr Tyr
                    645                 650                 655

Gly Glu Thr Gly Gly Asn Ser Pro Val Gln Glu Phe Thr Val Pro Lys
                660                 665                 670

Asn Val Tyr Thr Ala Thr Ile Ser Gly Leu Lys Pro Gly Val Asp Tyr
                675                 680                 685

Thr Ile Thr Val Tyr Ala Val Thr Arg Phe Arg Asp Tyr Gln Pro Ile
                690                 695                 700

Ser Ile Asn Tyr Arg Thr
705                 710

<210> SEQ ID NO 232
<211> LENGTH: 720
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 232

Met Lys Trp Val Thr Phe Ile Ser Leu Leu Phe Leu Phe Ser Ser Ala
1                   5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175
```

```
Glu Leu Leu Phe Phe Ala Lys Arg Tyr Lys Ala Ala Phe Thr Glu Cys
                180                 185                 190
Cys Gln Ala Ala Asp Lys Ala Ala Cys Leu Leu Pro Lys Leu Asp Glu
            195                 200                 205
Leu Arg Asp Glu Gly Lys Ala Ser Ser Ala Lys Gln Arg Leu Lys Cys
        210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
            260                 265                 270
Asp Leu Leu Glu Cys Ala Asp Asp Arg Ala Asp Leu Ala Lys Tyr Ile
        275                 280                 285
Cys Glu Asn Gln Asp Ser Ile Ser Ser Lys Leu Lys Glu Cys Cys Glu
    290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
            340                 345                 350
Met Phe Leu Tyr Glu Tyr Ala Arg Arg His Pro Asp Tyr Ser Val Val
        355                 360                 365
Leu Leu Leu Arg Leu Ala Lys Thr Tyr Glu Thr Thr Leu Glu Lys Cys
        370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
            420                 425                 430
Val Arg Tyr Thr Lys Lys Val Pro Gln Val Ser Thr Pro Thr Leu Val
        435                 440                 445
Glu Val Ser Arg Asn Leu Gly Lys Val Gly Ser Lys Cys Cys Lys His
    450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
            500                 505                 510
Ser Ala Leu Glu Val Asp Glu Thr Tyr Val Pro Lys Glu Phe Asn Ala
        515                 520                 525
Glu Thr Phe Thr Phe His Ala Asp Ile Cys Thr Leu Ser Glu Lys Glu
    530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
            580                 585                 590
Ala Glu Glu Gly Lys Lys Leu Val Ala Ala Ser Gln Ala Ala Leu Gly
```

```
              595                 600                 605
Leu Gly Ser Gly Ser Gly Ser Gly Ser Gly Ser Gly
    610                 615                 620

Ser Gly Ser Gly Ser Gly Val Ser Asp Val Pro Arg Asp Leu Glu Val
625                 630                 635                 640

Val Ala Ala Thr Pro Thr Ser Leu Leu Ile Ser Trp Ser Ala Arg Leu
                645                 650                 655

Lys Val Ala Arg Tyr Tyr Arg Ile Thr Tyr Gly Glu Thr Gly Gly Asn
            660                 665                 670

Ser Pro Val Gln Glu Phe Thr Val Pro Lys Asn Val Tyr Thr Ala Thr
        675                 680                 685

Ile Ser Gly Leu Lys Pro Gly Val Asp Tyr Thr Ile Thr Val Tyr Ala
    690                 695                 700

Val Thr Arg Phe Arg Asp Tyr Gln Pro Ile Ser Ile Asn Tyr Arg Thr
705                 710                 715                 720

<210> SEQ ID NO 233
<211> LENGTH: 682
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 233

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Pro Ser Gln Ala His Lys Ser Glu Val Ala His Arg Phe Lys Asp Leu
            100                 105                 110

Gly Glu Glu Asn Phe Lys Ala Leu Val Leu Ile Ala Phe Ala Gln Tyr
        115                 120                 125

Leu Gln Gln Cys Pro Phe Glu Asp His Val Lys Leu Val Asn Glu Val
    130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
        195                 200                 205

Asn Leu Pro Arg Leu Val Arg Pro Glu Val Asp Val Met Cys Thr Ala
    210                 215                 220

Phe His Asp Asn Glu Glu Thr Phe Leu Lys Lys Tyr Leu Tyr Glu Ile
225                 230                 235                 240
```

-continued

```
Ala Arg Arg His Pro Tyr Phe Tyr Ala Pro Glu Leu Leu Phe Phe Ala
                245                 250                 255
Lys Arg Tyr Lys Ala Ala Phe Thr Glu Cys Cys Gln Ala Ala Asp Lys
            260                 265                 270
Ala Ala Cys Leu Leu Pro Lys Leu Asp Glu Leu Arg Asp Glu Gly Lys
        275                 280                 285
Ala Ser Ser Ala Lys Gln Arg Leu Lys Cys Ala Ser Leu Gln Lys Phe
    290                 295                 300
Gly Glu Arg Ala Phe Lys Ala Trp Ala Val Ala Arg Leu Ser Gln Arg
305                 310                 315                 320
Phe Pro Lys Ala Glu Phe Ala Glu Val Ser Lys Leu Val Thr Asp Leu
                325                 330                 335
Thr Lys Val His Thr Glu Cys Cys His Gly Asp Leu Leu Glu Cys Ala
            340                 345                 350
Asp Asp Arg Ala Asp Leu Ala Lys Tyr Ile Cys Glu Asn Gln Asp Ser
        355                 360                 365
Ile Ser Ser Lys Leu Lys Glu Cys Cys Glu Lys Pro Leu Leu Glu Lys
    370                 375                 380
Ser His Cys Ile Ala Glu Val Glu Asn Asp Glu Met Pro Ala Asp Leu
385                 390                 395                 400
Pro Ser Leu Ala Ala Asp Phe Val Glu Ser Lys Asp Val Cys Lys Asn
                405                 410                 415
Tyr Ala Glu Ala Lys Asp Val Phe Leu Gly Met Phe Leu Tyr Glu Tyr
            420                 425                 430
Ala Arg Arg His Pro Asp Tyr Ser Val Val Leu Leu Leu Arg Leu Ala
        435                 440                 445
Lys Thr Tyr Glu Thr Thr Leu Glu Lys Cys Cys Ala Ala Ala Asp Pro
    450                 455                 460
His Glu Cys Tyr Ala Lys Val Phe Asp Glu Phe Lys Pro Leu Val Glu
465                 470                 475                 480
Glu Pro Gln Asn Leu Ile Lys Gln Asn Cys Glu Leu Phe Glu Gln Leu
                485                 490                 495
Gly Glu Tyr Lys Phe Gln Asn Ala Leu Leu Val Arg Tyr Thr Lys Lys
            500                 505                 510
Val Pro Gln Val Ser Thr Pro Thr Leu Val Glu Val Ser Arg Asn Leu
        515                 520                 525
Gly Lys Val Gly Ser Lys Cys Cys Lys His Pro Glu Ala Lys Arg Met
    530                 535                 540
Pro Cys Ala Glu Asp Tyr Leu Ser Val Val Leu Asn Gln Leu Cys Val
545                 550                 555                 560
Leu His Glu Lys Thr Pro Val Ser Asp Arg Val Thr Lys Cys Cys Thr
                565                 570                 575
Glu Ser Leu Val Asn Arg Arg Pro Cys Phe Ser Ala Leu Glu Val Asp
            580                 585                 590
Glu Thr Tyr Val Pro Lys Glu Phe Asn Ala Glu Thr Phe Thr Phe His
        595                 600                 605
Ala Asp Ile Cys Thr Leu Ser Glu Lys Glu Arg Gln Ile Lys Lys Gln
    610                 615                 620
Thr Ala Leu Val Glu Leu Val Lys His Lys Pro Lys Ala Thr Lys Glu
625                 630                 635                 640
Gln Leu Lys Ala Val Met Asp Asp Phe Ala Ala Phe Val Glu Lys Cys
                645                 650                 655
Cys Lys Ala Asp Asp Lys Glu Thr Cys Phe Ala Glu Glu Gly Lys Lys
```

Leu Val Ala Ala Ser Gln Ala Ala Leu Gly
       675                 680

<210> SEQ ID NO 234
<211> LENGTH: 685
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 234

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Gly Ser Gly Ser
                85                  90                  95

Gly Ser Gly Ser Gly Ser Ala His Lys Ser Glu Val Ala His Arg Phe
            100                 105                 110

Lys Asp Leu Gly Glu Glu Asn Phe Lys Ala Leu Val Leu Ile Ala Phe
        115                 120                 125

Ala Gln Tyr Leu Gln Gln Cys Pro Phe Glu Asp His Val Lys Leu Val
    130                 135                 140

Asn Glu Val Thr Glu Phe Ala Lys Thr Cys Val Ala Asp Glu Ser Ala
145                 150                 155                 160

Glu Asn Cys Asp Lys Ser Leu His Thr Leu Phe Gly Asp Lys Leu Cys
                165                 170                 175

Thr Val Ala Thr Leu Arg Glu Thr Tyr Gly Glu Met Ala Asp Cys Cys
            180                 185                 190

Ala Lys Gln Glu Pro Glu Arg Asn Glu Cys Phe Leu Gln His Lys Asp
        195                 200                 205

Asp Asn Pro Asn Leu Pro Arg Leu Val Arg Pro Glu Val Asp Val Met
    210                 215                 220

Cys Thr Ala Phe His Asp Asn Glu Glu Thr Phe Leu Lys Lys Tyr Leu
225                 230                 235                 240

Tyr Glu Ile Ala Arg Arg His Pro Tyr Phe Tyr Ala Pro Glu Leu Leu
                245                 250                 255

Phe Phe Ala Lys Arg Tyr Lys Ala Ala Phe Thr Glu Cys Cys Gln Ala
            260                 265                 270

Ala Asp Lys Ala Ala Cys Leu Leu Pro Lys Leu Asp Glu Leu Arg Asp
        275                 280                 285

Glu Gly Lys Ala Ser Ser Ala Lys Gln Arg Leu Lys Cys Ala Ser Leu
    290                 295                 300

Gln Lys Phe Gly Glu Arg Ala Phe Lys Ala Trp Ala Val Ala Arg Leu
305                 310                 315                 320

Ser Gln Arg Phe Pro Lys Ala Glu Phe Ala Glu Val Ser Lys Leu Val
                325                 330                 335

```
Thr Asp Leu Thr Lys Val His Thr Glu Cys Cys His Gly Asp Leu Leu
            340                 345                 350

Glu Cys Ala Asp Arg Ala Asp Leu Ala Lys Tyr Ile Cys Glu Asn
        355                 360                 365

Gln Asp Ser Ile Ser Ser Lys Leu Lys Glu Cys Cys Glu Lys Pro Leu
    370                 375                 380

Leu Glu Lys Ser His Cys Ile Ala Glu Val Glu Asn Asp Glu Met Pro
385                 390                 395                 400

Ala Asp Leu Pro Ser Leu Ala Ala Asp Phe Val Glu Ser Lys Asp Val
                405                 410                 415

Cys Lys Asn Tyr Ala Glu Ala Lys Asp Val Phe Leu Gly Met Phe Leu
        420                 425                 430

Tyr Glu Tyr Ala Arg Arg His Pro Asp Tyr Ser Val Val Leu Leu Leu
    435                 440                 445

Arg Leu Ala Lys Thr Tyr Glu Thr Thr Leu Glu Lys Cys Cys Ala Ala
450                 455                 460

Ala Asp Pro His Glu Cys Tyr Ala Lys Val Phe Asp Glu Phe Lys Pro
465                 470                 475                 480

Leu Val Glu Glu Pro Gln Asn Leu Ile Lys Gln Asn Cys Glu Leu Phe
                485                 490                 495

Glu Gln Leu Gly Glu Tyr Lys Phe Gln Asn Ala Leu Leu Val Arg Tyr
            500                 505                 510

Thr Lys Lys Val Pro Gln Val Ser Thr Pro Thr Leu Val Glu Val Ser
        515                 520                 525

Arg Asn Leu Gly Lys Val Gly Ser Lys Cys Cys Lys His Pro Glu Ala
    530                 535                 540

Lys Arg Met Pro Cys Ala Glu Asp Tyr Leu Ser Val Val Leu Asn Gln
545                 550                 555                 560

Leu Cys Val Leu His Glu Lys Thr Pro Val Ser Asp Arg Val Thr Lys
                565                 570                 575

Cys Cys Thr Glu Ser Leu Val Asn Arg Arg Pro Cys Phe Ser Ala Leu
            580                 585                 590

Glu Val Asp Glu Thr Tyr Val Pro Lys Glu Phe Asn Ala Glu Thr Phe
        595                 600                 605

Thr Phe His Ala Asp Ile Cys Thr Leu Ser Glu Lys Glu Arg Gln Ile
    610                 615                 620

Lys Lys Gln Thr Ala Leu Val Glu Leu Val Lys His Lys Pro Lys Ala
625                 630                 635                 640

Thr Lys Glu Gln Leu Lys Ala Val Met Asp Asp Phe Ala Ala Phe Val
                645                 650                 655

Glu Lys Cys Cys Lys Ala Asp Asp Lys Glu Thr Cys Phe Ala Glu Glu
            660                 665                 670

Gly Lys Lys Leu Val Ala Ala Ser Gln Ala Ala Leu Gly
        675                 680                 685

<210> SEQ ID NO 235
<211> LENGTH: 695
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 235

Met Gly Val Ser Asp Val Pro Arg Asp Leu Glu Val Val Ala Ala Thr
1               5                   10                  15
```

```
Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Gly Ser Gly Ser
                 85                  90                  95

Gly Ser Gly Ser Gly Ser Gly Ser Gly Ser Gly Ser Gly Ser Gly Ser
            100                 105                 110

Ala His Lys Ser Glu Val Ala His Arg Phe Lys Asp Leu Gly Glu Glu
            115                 120                 125

Asn Phe Lys Ala Leu Val Leu Ile Ala Phe Ala Gln Tyr Leu Gln Gln
130                 135                 140

Cys Pro Phe Glu Asp His Val Lys Leu Val Asn Glu Val Thr Glu Phe
145                 150                 155                 160

Ala Lys Thr Cys Val Ala Asp Glu Ser Ala Glu Asn Cys Asp Lys Ser
                165                 170                 175

Leu His Thr Leu Phe Gly Asp Lys Leu Cys Thr Val Ala Thr Leu Arg
            180                 185                 190

Glu Thr Tyr Gly Glu Met Ala Asp Cys Cys Ala Lys Gln Glu Pro Glu
            195                 200                 205

Arg Asn Glu Cys Phe Leu Gln His Lys Asp Asp Asn Pro Asn Leu Pro
210                 215                 220

Arg Leu Val Arg Pro Glu Val Asp Val Met Cys Thr Ala Phe His Asp
225                 230                 235                 240

Asn Glu Glu Thr Phe Leu Lys Lys Tyr Leu Tyr Glu Ile Ala Arg Arg
                245                 250                 255

His Pro Tyr Phe Tyr Ala Pro Glu Leu Leu Phe Phe Ala Lys Arg Tyr
            260                 265                 270

Lys Ala Ala Phe Thr Glu Cys Cys Gln Ala Ala Asp Lys Ala Ala Cys
            275                 280                 285

Leu Leu Pro Lys Leu Asp Glu Leu Arg Asp Glu Gly Lys Ala Ser Ser
290                 295                 300

Ala Lys Gln Arg Leu Lys Cys Ala Ser Leu Gln Lys Phe Gly Glu Arg
305                 310                 315                 320

Ala Phe Lys Ala Trp Ala Val Ala Arg Leu Ser Gln Arg Phe Pro Lys
                325                 330                 335

Ala Glu Phe Ala Glu Val Ser Lys Leu Val Thr Asp Leu Thr Lys Val
            340                 345                 350

His Thr Glu Cys Cys His Gly Asp Leu Leu Glu Cys Ala Asp Asp Arg
            355                 360                 365

Ala Asp Leu Ala Lys Tyr Ile Cys Glu Asn Gln Asp Ser Ile Ser Ser
370                 375                 380

Lys Leu Lys Glu Cys Cys Glu Lys Pro Leu Leu Glu Lys Ser His Cys
385                 390                 395                 400

Ile Ala Glu Val Glu Asn Asp Glu Met Pro Ala Asp Leu Pro Ser Leu
                405                 410                 415

Ala Ala Asp Phe Val Glu Ser Lys Asp Val Cys Lys Asn Tyr Ala Glu
            420                 425                 430
```

-continued

```
Ala Lys Asp Val Phe Leu Gly Met Phe Leu Tyr Glu Tyr Ala Arg Arg
            435                 440                 445

His Pro Asp Tyr Ser Val Val Leu Leu Leu Arg Leu Ala Lys Thr Tyr
        450                 455                 460

Glu Thr Thr Leu Glu Lys Cys Cys Ala Ala Ala Asp Pro His Glu Cys
465                 470                 475                 480

Tyr Ala Lys Val Phe Asp Glu Phe Lys Pro Leu Val Glu Glu Pro Gln
                485                 490                 495

Asn Leu Ile Lys Gln Asn Cys Glu Leu Phe Glu Gln Leu Gly Glu Tyr
            500                 505                 510

Lys Phe Gln Asn Ala Leu Leu Val Arg Tyr Thr Lys Lys Val Pro Gln
        515                 520                 525

Val Ser Thr Pro Thr Leu Val Glu Val Ser Arg Asn Leu Gly Lys Val
530                 535                 540

Gly Ser Lys Cys Cys Lys His Pro Glu Ala Lys Arg Met Pro Cys Ala
545                 550                 555                 560

Glu Asp Tyr Leu Ser Val Val Leu Asn Gln Leu Cys Val Leu His Glu
                565                 570                 575

Lys Thr Pro Val Ser Asp Arg Val Thr Lys Cys Cys Thr Glu Ser Leu
            580                 585                 590

Val Asn Arg Arg Pro Cys Phe Ser Ala Leu Glu Val Asp Glu Thr Tyr
        595                 600                 605

Val Pro Lys Glu Phe Asn Ala Glu Thr Phe Thr Phe His Ala Asp Ile
610                 615                 620

Cys Thr Leu Ser Glu Lys Glu Arg Gln Ile Lys Lys Gln Thr Ala Leu
625                 630                 635                 640

Val Glu Leu Val Lys His Lys Pro Lys Ala Thr Lys Glu Gln Leu Lys
                645                 650                 655

Ala Val Met Asp Asp Phe Ala Ala Phe Val Glu Lys Cys Cys Lys Ala
            660                 665                 670

Asp Asp Lys Glu Thr Cys Phe Ala Glu Glu Gly Lys Lys Leu Val Ala
        675                 680                 685

Ala Ser Gln Ala Ala Leu Gly
    690                 695

<210> SEQ ID NO 236
<211> LENGTH: 796
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 236

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95
```

```
Lys Pro Val Val Ala Glu Phe Tyr Gly Ser Lys Glu Asp Pro Gln Thr
            100                 105                 110
Phe Tyr Tyr Ala Val Ala Val Val Lys Lys Asp Ser Gly Phe Gln Met
            115                 120                 125
Asn Gln Leu Arg Gly Lys Ser Cys His Thr Gly Leu Gly Arg Ser
    130                 135                 140
Ala Gly Trp Asn Ile Pro Ile Gly Leu Leu Tyr Cys Asp Leu Pro Glu
145                 150                 155                 160
Pro Arg Lys Pro Leu Glu Lys Ala Val Ala Asn Phe Phe Ser Gly Ser
                165                 170                 175
Cys Ala Pro Cys Ala Asp Gly Thr Asp Phe Pro Gln Leu Cys Gln Leu
            180                 185                 190
Cys Pro Gly Cys Gly Cys Ser Thr Leu Asn Gln Tyr Phe Gly Tyr Ser
            195                 200                 205
Gly Ala Phe Lys Cys Leu Lys Asp Gly Ala Gly Asp Val Ala Phe Val
    210                 215                 220
Lys His Ser Thr Ile Phe Glu Asn Leu Ala Asn Lys Ala Asp Arg Asp
225                 230                 235                 240
Gln Tyr Glu Leu Leu Cys Leu Asp Asn Thr Arg Lys Pro Val Asp Glu
                245                 250                 255
Tyr Lys Asp Cys His Leu Ala Gln Val Pro Ser His Thr Val Val Ala
            260                 265                 270
Arg Ser Met Gly Gly Lys Glu Asp Leu Ile Trp Glu Leu Leu Asn Gln
            275                 280                 285
Ala Gln Glu His Phe Gly Lys Asp Lys Ser Lys Glu Phe Gln Leu Phe
    290                 295                 300
Ser Ser Pro His Gly Lys Asp Leu Leu Phe Lys Asp Ser Ala His Gly
305                 310                 315                 320
Phe Leu Lys Val Pro Pro Arg Met Asp Ala Lys Met Tyr Leu Gly Tyr
                325                 330                 335
Glu Tyr Val Thr Ala Ile Arg Asn Leu Arg Glu Gly Thr Cys Pro Glu
            340                 345                 350
Ala Pro Thr Asp Glu Cys Lys Pro Val Lys Trp Cys Ala Leu Ser His
            355                 360                 365
His Glu Arg Leu Lys Cys Asp Glu Trp Ser Val Asn Ser Val Gly Lys
    370                 375                 380
Ile Glu Cys Val Ser Ala Glu Thr Thr Glu Asp Cys Ile Ala Lys Ile
385                 390                 395                 400
Met Asn Gly Glu Ala Asp Ala Met Ser Leu Asp Gly Gly Phe Val Tyr
                405                 410                 415
Ile Ala Gly Lys Cys Gly Leu Val Pro Val Leu Ala Glu Asn Tyr Asn
            420                 425                 430
Lys Ser Asp Asn Cys Glu Asp Thr Pro Glu Ala Gly Tyr Phe Ala Val
            435                 440                 445
Ala Val Val Lys Lys Ser Ala Ser Asp Leu Thr Trp Asp Asn Leu Lys
    450                 455                 460
Gly Lys Lys Ser Cys His Thr Ala Val Gly Arg Thr Ala Gly Trp Asn
465                 470                 475                 480
Ile Pro Met Gly Leu Leu Tyr Asn Lys Ile Asn His Cys Arg Phe Asp
                485                 490                 495
Glu Phe Phe Ser Glu Gly Cys Ala Pro Gly Ser Lys Lys Asp Ser Ser
            500                 505                 510
```

Leu Cys Lys Leu Cys Met Gly Ser Gly Leu Asn Leu Cys Glu Pro Asn
            515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
        595                 600                 605

Arg Lys Asp Lys Glu Ala Cys Val His Lys Ile Leu Arg Gln Gln Gln
    610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
        675                 680                 685

Leu Leu Glu Ala Cys Thr Phe Arg Arg Pro Ser Thr Ser Thr Ser
    690                 695                 700

Thr Gly Val Ser Asp Val Pro Arg Asp Leu Glu Val Val Ala Ala Thr
705                 710                 715                 720

Pro Thr Ser Leu Leu Ile Ser Trp Ser Ala Arg Leu Lys Val Ala Arg
                725                 730                 735

Tyr Tyr Arg Ile Thr Tyr Gly Glu Thr Gly Gly Asn Ser Pro Val Gln
            740                 745                 750

Glu Phe Thr Val Pro Lys Asn Val Tyr Thr Ala Thr Ile Ser Gly Leu
        755                 760                 765

Lys Pro Gly Val Asp Tyr Thr Ile Thr Val Tyr Ala Val Thr Arg Phe
    770                 775                 780

Arg Asp Tyr Gln Pro Ile Ser Ile Asn Tyr Arg Thr
785                 790                 795

<210> SEQ ID NO 237
<211> LENGTH: 778
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 237

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

```
Arg Asp Tyr Gln Pro Ile Ser Ile Asn Tyr Arg Thr Pro Ser Thr Ser
                85                  90                  95

Thr Ser Thr Val Pro Asp Lys Thr Val Arg Trp Cys Ala Val Ser Glu
            100                 105                 110

His Glu Ala Thr Lys Cys Gln Ser Phe Arg Asp His Met Lys Ser Val
            115                 120                 125

Ile Pro Ser Asp Gly Pro Ser Val Ala Cys Val Lys Lys Ala Ser Tyr
        130                 135                 140

Leu Asp Cys Ile Arg Ala Ile Ala Ala Asn Glu Ala Asp Ala Val Thr
145                 150                 155                 160

Leu Asp Ala Gly Leu Val Tyr Asp Ala Tyr Leu Ala Pro Asn Asn Leu
                165                 170                 175

Lys Pro Val Val Ala Glu Phe Tyr Gly Ser Lys Glu Asp Pro Gln Thr
            180                 185                 190

Phe Tyr Tyr Ala Val Ala Val Val Lys Lys Asp Ser Gly Phe Gln Met
            195                 200                 205

Asn Gln Leu Arg Gly Lys Lys Ser Cys His Thr Gly Leu Gly Arg Ser
        210                 215                 220

Ala Gly Trp Asn Ile Pro Ile Gly Leu Leu Tyr Cys Asp Leu Pro Glu
225                 230                 235                 240

Pro Arg Lys Pro Leu Glu Lys Ala Val Ala Asn Phe Phe Ser Gly Ser
                245                 250                 255

Cys Ala Pro Cys Ala Asp Gly Thr Asp Phe Pro Gln Leu Cys Gln Leu
            260                 265                 270

Cys Pro Gly Cys Gly Cys Ser Thr Leu Asn Gln Tyr Phe Gly Tyr Ser
            275                 280                 285

Gly Ala Phe Lys Cys Leu Lys Asp Gly Ala Gly Asp Val Ala Phe Val
        290                 295                 300

Lys His Ser Thr Ile Phe Glu Asn Leu Ala Asn Lys Ala Asp Arg Asp
305                 310                 315                 320

Gln Tyr Glu Leu Leu Cys Leu Asp Asn Thr Arg Lys Pro Val Asp Glu
                325                 330                 335

Tyr Lys Asp Cys His Leu Ala Gln Val Pro Ser His Thr Val Val Ala
            340                 345                 350

Arg Ser Met Gly Gly Lys Glu Asp Leu Ile Trp Glu Leu Leu Asn Gln
            355                 360                 365

Ala Gln Glu His Phe Gly Lys Asp Lys Ser Lys Glu Phe Gln Leu Phe
        370                 375                 380

Ser Ser Pro His Gly Lys Asp Leu Leu Phe Lys Asp Ser Ala His Gly
385                 390                 395                 400

Phe Leu Lys Val Pro Pro Arg Met Asp Ala Lys Met Tyr Leu Gly Tyr
                405                 410                 415

Glu Tyr Val Thr Ala Ile Arg Asn Leu Arg Glu Gly Thr Cys Pro Glu
            420                 425                 430

Ala Pro Thr Asp Glu Cys Lys Pro Val Lys Trp Cys Ala Leu Ser His
            435                 440                 445

His Glu Arg Leu Lys Cys Asp Glu Trp Ser Val Asn Ser Val Gly Lys
        450                 455                 460

Ile Glu Cys Val Ser Ala Glu Thr Thr Glu Asp Cys Ile Ala Lys Ile
465                 470                 475                 480

Met Asn Gly Glu Ala Asp Ala Met Ser Leu Asp Gly Gly Phe Val Tyr
                485                 490                 495
```

```
Ile Ala Gly Lys Cys Gly Leu Val Pro Val Leu Ala Glu Asn Tyr Asn
            500                 505                 510

Lys Ser Asp Asn Cys Glu Asp Thr Pro Glu Ala Gly Tyr Phe Ala Val
        515                 520                 525

Ala Val Val Lys Lys Ser Ala Ser Asp Leu Thr Trp Asp Asn Leu Lys
    530                 535                 540

Gly Lys Lys Ser Cys His Thr Ala Val Gly Arg Thr Ala Gly Trp Asn
545                 550                 555                 560

Ile Pro Met Gly Leu Leu Tyr Asn Lys Ile Asn His Cys Arg Phe Asp
            565                 570                 575

Glu Phe Phe Ser Glu Gly Cys Ala Pro Gly Ser Lys Lys Asp Ser Ser
        580                 585                 590

Leu Cys Lys Leu Cys Met Gly Ser Gly Leu Asn Leu Cys Glu Pro Asn
    595                 600                 605

Asn Lys Glu Gly Tyr Tyr Gly Tyr Thr Gly Ala Phe Arg Cys Leu Val
610                 615                 620

Glu Lys Gly Asp Val Ala Phe Val Lys His Gln Thr Val Pro Gln Asn
625                 630                 635                 640

Thr Gly Gly Lys Asn Pro Asp Pro Trp Ala Lys Asn Leu Asn Glu Lys
            645                 650                 655

Asp Tyr Glu Leu Leu Cys Leu Asp Gly Thr Arg Lys Pro Val Glu Glu
        660                 665                 670

Tyr Ala Asn Cys His Leu Ala Arg Ala Pro Asn His Ala Val Val Thr
    675                 680                 685

Arg Lys Asp Lys Glu Ala Cys Val His Lys Ile Leu Arg Gln Gln Gln
690                 695                 700

His Leu Phe Gly Ser Asn Val Thr Asp Cys Ser Gly Asn Phe Cys Leu
705                 710                 715                 720

Phe Arg Ser Glu Thr Lys Asp Leu Leu Phe Arg Asp Asp Thr Val Cys
            725                 730                 735

Leu Ala Lys Leu His Asp Arg Asn Thr Tyr Glu Lys Tyr Leu Gly Glu
        740                 745                 750

Glu Tyr Val Lys Ala Val Gly Asn Leu Arg Lys Cys Ser Thr Ser Ser
    755                 760                 765

Leu Leu Glu Ala Cys Thr Phe Arg Arg Pro
770                 775

<210> SEQ ID NO 238
<211> LENGTH: 796
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 238

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80
```

```
Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
                100                 105                 110

Phe Tyr Tyr Ala Val Ala Val Val Lys Lys Asp Ser Gly Phe Gln Met
                115                 120                 125

Asn Gln Leu Arg Gly Lys Lys Ser Cys His Thr Gly Leu Gly Arg Ser
            130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
                180                 185                 190

Cys Pro Gly Cys Gly Cys Ser Thr Leu Asn Gln Tyr Phe Gly Tyr Ser
                195                 200                 205

Gly Ala Phe Lys Cys Leu Lys Asp Gly Ala Gly Asp Val Ala Phe Val
                210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
                260                 265                 270

Arg Ser Met Gly Gly Lys Glu Asp Leu Ile Trp Glu Leu Leu Asn Gln
                275                 280                 285

Ala Gln Glu His Phe Gly Lys Asp Lys Ser Lys Glu Phe Gln Leu Phe
                290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
                340                 345                 350

Ala Pro Thr Asp Glu Cys Lys Pro Val Lys Trp Cys Ala Leu Ser His
                355                 360                 365

His Glu Arg Leu Lys Cys Asp Glu Trp Ser Val Asn Ser Val Gly Lys
                370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
                420                 425                 430

Lys Ser Asp Asn Cys Glu Asp Thr Pro Glu Ala Gly Tyr Phe Ala Val
                435                 440                 445

Ala Val Val Lys Lys Ser Ala Ser Asp Leu Thr Trp Asp Asn Leu Lys
450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495
```

Glu Phe Phe Ser Glu Gly Cys Ala Pro Gly Ser Lys Lys Asp Ser Ser
                500                 505                 510

Leu Cys Lys Leu Cys Met Gly Ser Gly Leu Asn Leu Cys Glu Pro Asn
            515                 520                 525

Asn Lys Glu Gly Tyr Tyr Gly Tyr Thr Gly Ala Phe Arg Cys Leu Val
        530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
        595                 600                 605

Arg Lys Asp Lys Glu Ala Cys Val His Lys Ile Leu Arg Gln Gln Gln
610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
        675                 680                 685

Leu Leu Glu Ala Cys Thr Phe Arg Arg Pro Glu Ile Asp Lys Pro Ser
690                 695                 700

Gln Gly Val Ser Asp Val Pro Arg Asp Leu Glu Val Val Ala Ala Thr
705                 710                 715                 720

Pro Thr Ser Leu Leu Ile Ser Trp Ser Ala Arg Leu Lys Val Ala Arg
                725                 730                 735

Tyr Tyr Arg Ile Thr Tyr Gly Glu Thr Gly Gly Asn Ser Pro Val Gln
            740                 745                 750

Glu Phe Thr Val Pro Lys Asn Val Tyr Thr Ala Thr Ile Ser Gly Leu
        755                 760                 765

Lys Pro Gly Val Asp Tyr Thr Ile Thr Val Tyr Ala Val Thr Arg Phe
770                 775                 780

Arg Asp Tyr Gln Pro Ile Ser Ile Asn Tyr Arg Thr
785                 790                 795

<210> SEQ ID NO 239
<211> LENGTH: 799
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 239

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

```
Leu Asp Cys Ile Arg Ala Ile Ala Ala Asn Glu Ala Asp Ala Val Thr
 65                  70                  75                  80

Leu Asp Ala Gly Leu Val Tyr Asp Ala Tyr Leu Ala Pro Asn Asn Leu
                 85                  90                  95

Lys Pro Val Val Ala Glu Phe Tyr Gly Ser Lys Glu Asp Pro Gln Thr
                100                 105                 110

Phe Tyr Tyr Ala Val Ala Val Val Lys Lys Asp Ser Gly Phe Gln Met
            115                 120                 125

Asn Gln Leu Arg Gly Lys Lys Ser Cys His Thr Gly Leu Gly Arg Ser
130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
            195                 200                 205

Gly Ala Phe Lys Cys Leu Lys Asp Gly Ala Gly Asp Val Ala Phe Val
210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
            275                 280                 285

Ala Gln Glu His Phe Gly Lys Asp Lys Ser Lys Glu Phe Gln Leu Phe
            290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
            355                 360                 365

His Glu Arg Leu Lys Cys Asp Glu Trp Ser Val Asn Ser Val Gly Lys
            370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Val
            435                 440                 445

Ala Val Val Lys Lys Ser Ala Ser Asp Leu Thr Trp Asp Asn Leu Lys
            450                 455                 460

Gly Lys Lys Ser Cys His Thr Ala Val Gly Arg Thr Ala Gly Trp Asn
465                 470                 475                 480
```

```
Ile Pro Met Gly Leu Leu Tyr Asn Lys Ile Asn His Cys Arg Phe Asp
            485                 490                 495

Glu Phe Phe Ser Glu Gly Cys Ala Pro Gly Ser Lys Lys Asp Ser Ser
        500                 505                 510

Leu Cys Lys Leu Cys Met Gly Ser Gly Leu Asn Leu Cys Glu Pro Asn
        515                 520                 525

Asn Lys Glu Gly Tyr Tyr Gly Tyr Thr Gly Ala Phe Arg Cys Leu Val
        530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
                595                 600                 605

Arg Lys Asp Lys Glu Ala Cys Val His Lys Ile Leu Arg Gln Gln Gln
            610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
                675                 680                 685

Leu Leu Glu Ala Cys Thr Phe Arg Arg Pro Gly Ser Gly Ser Gly Ser
            690                 695                 700

Gly Ser Gly Ser Gly Val Ser Asp Val Pro Arg Asp Leu Glu Val Val
705                 710                 715                 720

Ala Ala Thr Pro Thr Ser Leu Leu Ile Ser Trp Ser Ala Arg Leu Lys
                725                 730                 735

Val Ala Arg Tyr Tyr Arg Ile Thr Tyr Gly Glu Thr Gly Gly Asn Ser
                740                 745                 750

Pro Val Gln Glu Phe Thr Val Pro Lys Asn Val Tyr Thr Ala Thr Ile
            755                 760                 765

Ser Gly Leu Lys Pro Gly Val Asp Tyr Thr Ile Thr Val Tyr Ala Val
            770                 775                 780

Thr Arg Phe Arg Asp Tyr Gln Pro Ile Ser Ile Asn Tyr Arg Thr
785                 790                 795

<210> SEQ ID NO 240
<211> LENGTH: 809
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 240

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45
```

```
Ile Pro Ser Asp Gly Pro Ser Val Ala Cys Val Lys Ala Ser Tyr
 50                  55                  60

Leu Asp Cys Ile Arg Ala Ile Ala Ala Asn Glu Ala Asp Ala Val Thr
 65                  70                  75                  80

Leu Asp Ala Gly Leu Val Tyr Asp Ala Tyr Leu Ala Pro Asn Asn Leu
                 85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
        355                 360                 365

His Glu Arg Leu Lys Cys Asp Glu Trp Ser Val Asn Ser Val Gly Lys
    370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Val
        435                 440                 445

Ala Val Val Lys Lys Ser Ala Ser Asp Leu Thr Trp Asp Asn Leu Lys
450                 455                 460
```

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
            485                 490                 495

Glu Phe Phe Ser Glu Gly Cys Ala Pro Gly Ser Lys Lys Asp Ser Ser
                500                 505                 510

Leu Cys Lys Leu Cys Met Gly Ser Gly Leu Asn Leu Cys Glu Pro Asn
        515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
            565                 570                 575

Asp Tyr Glu Leu Leu Cys Leu Asp Gly Thr Arg Lys Pro Val Glu Glu
                580                 585                 590

Tyr Ala Asn Cys His Leu Ala Arg Ala Pro Asn His Ala Val Val Thr
        595                 600                 605

Arg Lys Asp Lys Glu Ala Cys Val His Lys Ile Leu Arg Gln Gln Gln
    610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
            645                 650                 655

Leu Ala Lys Leu His Asp Arg Asn Thr Tyr Glu Lys Tyr Leu Gly Glu
                660                 665                 670

Glu Tyr Val Lys Ala Val Gly Asn Leu Arg Lys Cys Ser Thr Ser Ser
        675                 680                 685

Leu Leu Glu Ala Cys Thr Phe Arg Arg Pro Gly Ser Gly Ser Gly Ser
    690                 695                 700

Gly Ser Gly Ser Gly Ser Gly Ser Gly Ser Gly Ser Gly Ser Gly Val
705                 710                 715                 720

Ser Asp Val Pro Arg Asp Leu Glu Val Val Ala Ala Thr Pro Thr Ser
            725                 730                 735

Leu Leu Ile Ser Trp Ser Ala Arg Leu Lys Val Ala Arg Tyr Tyr Arg
                740                 745                 750

Ile Thr Tyr Gly Glu Thr Gly Gly Asn Ser Pro Val Gln Glu Phe Thr
        755                 760                 765

Val Pro Lys Asn Val Tyr Thr Ala Thr Ile Ser Gly Leu Lys Pro Gly
    770                 775                 780

Val Asp Tyr Thr Ile Thr Val Tyr Ala Val Thr Arg Phe Arg Asp Tyr
785                 790                 795                 800

Gln Pro Ile Ser Ile Asn Tyr Arg Thr
            805

<210> SEQ ID NO 241
<211> LENGTH: 778
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 241

Met Gly Val Ser Asp Val Pro Arg Asp Leu Glu Val Val Ala Ala Thr
1               5                   10                  15

```
Pro Thr Ser Leu Leu Ile Ser Trp Ser Ala Arg Leu Lys Val Ala Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Ile Asp Lys
                 85                  90                  95

Pro Ser Gln Val Pro Asp Lys Thr Val Arg Trp Cys Ala Val Ser Glu
                100                 105                 110

His Glu Ala Thr Lys Cys Gln Ser Phe Arg Asp His Met Lys Ser Val
                115                 120                 125

Ile Pro Ser Asp Gly Pro Ser Val Ala Cys Val Lys Lys Ala Ser Tyr
130                 135                 140

Leu Asp Cys Ile Arg Ala Ile Ala Ala Asn Glu Ala Asp Ala Val Thr
145                 150                 155                 160

Leu Asp Ala Gly Leu Val Tyr Asp Ala Tyr Leu Ala Pro Asn Asn Leu
                165                 170                 175

Lys Pro Val Val Ala Glu Phe Tyr Gly Ser Lys Glu Asp Pro Gln Thr
                180                 185                 190

Phe Tyr Tyr Ala Val Ala Val Val Lys Lys Asp Ser Gly Phe Gln Met
            195                 200                 205

Asn Gln Leu Arg Gly Lys Lys Ser Cys His Thr Gly Leu Gly Arg Ser
            210                 215                 220

Ala Gly Trp Asn Ile Pro Ile Gly Leu Leu Tyr Cys Asp Leu Pro Glu
225                 230                 235                 240

Pro Arg Lys Pro Leu Glu Lys Ala Val Ala Asn Phe Phe Ser Gly Ser
                245                 250                 255

Cys Ala Pro Cys Ala Asp Gly Thr Asp Phe Pro Gln Leu Cys Gln Leu
                260                 265                 270

Cys Pro Gly Cys Gly Cys Ser Thr Leu Asn Gln Tyr Phe Gly Tyr Ser
                275                 280                 285

Gly Ala Phe Lys Cys Leu Lys Asp Gly Ala Gly Asp Val Ala Phe Val
                290                 295                 300

Lys His Ser Thr Ile Phe Glu Asn Leu Ala Asn Lys Ala Asp Arg Asp
305                 310                 315                 320

Gln Tyr Glu Leu Leu Cys Leu Asp Asn Thr Arg Lys Pro Val Asp Glu
                325                 330                 335

Tyr Lys Asp Cys His Leu Ala Gln Val Pro Ser His Thr Val Val Ala
                340                 345                 350

Arg Ser Met Gly Gly Lys Glu Asp Leu Ile Trp Glu Leu Leu Asn Gln
                355                 360                 365

Ala Gln Glu His Phe Gly Lys Asp Lys Ser Lys Glu Phe Gln Leu Phe
                370                 375                 380

Ser Ser Pro His Gly Lys Asp Leu Leu Phe Lys Asp Ser Ala His Gly
385                 390                 395                 400

Phe Leu Lys Val Pro Pro Arg Met Asp Ala Lys Met Tyr Leu Gly Tyr
                405                 410                 415

Glu Tyr Val Thr Ala Ile Arg Asn Leu Arg Glu Gly Thr Cys Pro Glu
                420                 425                 430
```

Ala Pro Thr Asp Glu Cys Lys Pro Val Lys Trp Cys Ala Leu Ser His
             435                 440                 445

His Glu Arg Leu Lys Cys Asp Glu Trp Ser Val Asn Ser Val Gly Lys
    450                 455                 460

Ile Glu Cys Val Ser Ala Glu Thr Thr Glu Asp Cys Ile Ala Lys Ile
465                 470                 475                 480

Met Asn Gly Glu Ala Asp Ala Met Ser Leu Asp Gly Phe Val Tyr
                485                 490                 495

Ile Ala Gly Lys Cys Gly Leu Val Pro Val Leu Ala Glu Asn Tyr Asn
                500                 505                 510

Lys Ser Asp Asn Cys Glu Asp Thr Pro Glu Ala Gly Tyr Phe Ala Val
            515                 520                 525

Ala Val Val Lys Lys Ser Ala Ser Asp Leu Thr Trp Asp Asn Leu Lys
530                 535                 540

Gly Lys Lys Ser Cys His Thr Ala Val Gly Arg Thr Ala Gly Trp Asn
545                 550                 555                 560

Ile Pro Met Gly Leu Leu Tyr Asn Lys Ile Asn His Cys Arg Phe Asp
                565                 570                 575

Glu Phe Phe Ser Glu Gly Cys Ala Pro Gly Ser Lys Lys Asp Ser Ser
                580                 585                 590

Leu Cys Lys Leu Cys Met Gly Ser Gly Leu Asn Leu Cys Glu Pro Asn
    595                 600                 605

Asn Lys Glu Gly Tyr Tyr Gly Tyr Thr Gly Ala Phe Arg Cys Leu Val
            610                 615                 620

Glu Lys Gly Asp Val Ala Phe Val Lys His Gln Thr Val Pro Gln Asn
625                 630                 635                 640

Thr Gly Gly Lys Asn Pro Asp Pro Trp Ala Lys Asn Leu Asn Glu Lys
                645                 650                 655

Asp Tyr Glu Leu Leu Cys Leu Asp Gly Thr Arg Lys Pro Val Glu Glu
                660                 665                 670

Tyr Ala Asn Cys His Leu Ala Arg Ala Pro Asn His Ala Val Val Thr
            675                 680                 685

Arg Lys Asp Lys Glu Ala Cys Val His Lys Ile Leu Arg Gln Gln Gln
690                 695                 700

His Leu Phe Gly Ser Asn Val Thr Asp Cys Ser Gly Asn Phe Cys Leu
705                 710                 715                 720

Phe Arg Ser Glu Thr Lys Asp Leu Leu Phe Arg Asp Asp Thr Val Cys
                725                 730                 735

Leu Ala Lys Leu His Asp Arg Asn Thr Tyr Glu Lys Tyr Leu Gly Glu
            740                 745                 750

Glu Tyr Val Lys Ala Val Gly Asn Leu Arg Lys Cys Ser Thr Ser Ser
            755                 760                 765

Leu Leu Glu Ala Cys Thr Phe Arg Arg Pro
770                 775

<210> SEQ ID NO 242
<211> LENGTH: 781
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 242

Met Gly Val Ser Asp Val Pro Arg Asp Leu Glu Val Val Ala Ala Thr
1               5                   10                  15

```
Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Gly Ser Gly Ser
                85                  90                  95

Gly Ser Gly Ser Gly Ser Val Pro Asp Lys Thr Val Arg Trp Cys Ala
            100                 105                 110

Val Ser Glu His Glu Ala Thr Lys Cys Gln Ser Phe Arg Asp His Met
        115                 120                 125

Lys Ser Val Ile Pro Ser Asp Gly Pro Ser Val Ala Cys Val Lys Lys
130                 135                 140

Ala Ser Tyr Leu Asp Cys Ile Arg Ala Ile Ala Ala Asn Glu Ala Asp
145                 150                 155                 160

Ala Val Thr Leu Asp Ala Gly Leu Val Tyr Asp Ala Tyr Leu Ala Pro
                165                 170                 175

Asn Asn Leu Lys Pro Val Val Ala Glu Phe Tyr Gly Ser Lys Glu Asp
            180                 185                 190

Pro Gln Thr Phe Tyr Tyr Ala Val Ala Val Val Lys Lys Asp Ser Gly
        195                 200                 205

Phe Gln Met Asn Gln Leu Arg Gly Lys Lys Ser Cys His Thr Gly Leu
210                 215                 220

Gly Arg Ser Ala Gly Trp Asn Ile Pro Ile Gly Leu Leu Tyr Cys Asp
225                 230                 235                 240

Leu Pro Glu Pro Arg Lys Pro Leu Glu Lys Ala Val Ala Asn Phe Phe
                245                 250                 255

Ser Gly Ser Cys Ala Pro Cys Ala Asp Gly Thr Asp Phe Pro Gln Leu
            260                 265                 270

Cys Gln Leu Cys Pro Gly Cys Gly Cys Ser Thr Leu Asn Gln Tyr Phe
        275                 280                 285

Gly Tyr Ser Gly Ala Phe Lys Cys Leu Lys Asp Gly Ala Gly Asp Val
290                 295                 300

Ala Phe Val Lys His Ser Thr Ile Phe Glu Asn Leu Ala Asn Lys Ala
305                 310                 315                 320

Asp Arg Asp Gln Tyr Glu Leu Leu Cys Leu Asp Asn Thr Arg Lys Pro
                325                 330                 335

Val Asp Glu Tyr Lys Asp Cys His Leu Ala Gln Val Pro Ser His Thr
            340                 345                 350

Val Val Ala Arg Ser Met Gly Gly Lys Glu Asp Leu Ile Trp Glu Leu
        355                 360                 365

Leu Asn Gln Ala Gln Glu His Phe Gly Lys Asp Lys Ser Lys Glu Phe
370                 375                 380

Gln Leu Phe Ser Ser Pro His Gly Lys Asp Leu Leu Phe Lys Asp Ser
385                 390                 395                 400

Ala His Gly Phe Leu Lys Val Pro Pro Arg Met Asp Ala Lys Met Tyr
                405                 410                 415

Leu Gly Tyr Glu Tyr Val Thr Ala Ile Arg Asn Leu Arg Glu Gly Thr
            420                 425                 430
```

Cys Pro Glu Ala Pro Thr Asp Glu Cys Lys Pro Val Lys Trp Cys Ala
            435                 440                 445

Leu Ser His His Glu Arg Leu Lys Cys Asp Glu Trp Ser Val Asn Ser
450                 455                 460

Val Gly Lys Ile Glu Cys Val Ser Ala Glu Thr Thr Glu Asp Cys Ile
465                 470                 475                 480

Ala Lys Ile Met Asn Gly Ala Asp Ala Met Ser Leu Asp Gly Gly
                485                 490                 495

Phe Val Tyr Ile Ala Gly Lys Cys Gly Leu Val Pro Val Leu Ala Glu
                500                 505                 510

Asn Tyr Asn Lys Ser Asp Asn Cys Glu Asp Thr Pro Glu Ala Gly Tyr
            515                 520                 525

Phe Ala Val Ala Val Lys Lys Ser Ala Ser Asp Leu Thr Trp Asp
            530                 535                 540

Asn Leu Lys Gly Lys Lys Ser Cys His Thr Ala Val Gly Arg Thr Ala
545                 550                 555                 560

Gly Trp Asn Ile Pro Met Gly Leu Leu Tyr Asn Lys Ile Asn His Cys
                565                 570                 575

Arg Phe Asp Glu Phe Ser Glu Gly Cys Ala Pro Gly Ser Lys Lys
            580                 585                 590

Asp Ser Ser Leu Cys Lys Leu Cys Met Gly Ser Gly Leu Asn Leu Cys
            595                 600                 605

Glu Pro Asn Asn Lys Glu Gly Tyr Tyr Gly Tyr Thr Gly Ala Phe Arg
            610                 615                 620

Cys Leu Val Glu Lys Gly Asp Val Ala Phe Val Lys His Gln Thr Val
625                 630                 635                 640

Pro Gln Asn Thr Gly Gly Lys Asn Pro Asp Pro Trp Ala Lys Asn Leu
                645                 650                 655

Asn Glu Lys Asp Tyr Glu Leu Leu Cys Leu Asp Gly Thr Arg Lys Pro
            660                 665                 670

Val Glu Glu Tyr Ala Asn Cys His Leu Ala Arg Ala Pro Asn His Ala
            675                 680                 685

Val Val Thr Arg Lys Asp Lys Glu Ala Cys Val His Lys Ile Leu Arg
690                 695                 700

Gln Gln Gln His Leu Phe Gly Ser Asn Val Thr Asp Cys Ser Gly Asn
705                 710                 715                 720

Phe Cys Leu Phe Arg Ser Glu Thr Lys Asp Leu Leu Phe Arg Asp Asp
                725                 730                 735

Thr Val Cys Leu Ala Lys Leu His Asp Arg Asn Thr Tyr Glu Lys Tyr
            740                 745                 750

Leu Gly Glu Glu Tyr Val Lys Ala Val Gly Asn Leu Arg Lys Cys Ser
            755                 760                 765

Thr Ser Ser Leu Leu Glu Ala Cys Thr Phe Arg Arg Pro
770                 775                 780

<210> SEQ ID NO 243
<211> LENGTH: 791
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 243

Met Gly Val Ser Asp Val Pro Arg Asp Leu Glu Val Val Ala Ala Thr
1               5                   10                  15

```
Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Gly Ser Gly Ser
                85                  90                  95

Gly Ser Gly Ser Gly Ser Gly Ser Gly Ser Gly Ser Gly Ser Gly Ser
            100                 105                 110

Val Pro Asp Lys Thr Val Arg Trp Cys Ala Val Ser Glu His Glu Ala
            115                 120                 125

Thr Lys Cys Gln Ser Phe Arg Asp His Met Lys Ser Val Ile Pro Ser
            130                 135                 140

Asp Gly Pro Ser Val Ala Cys Val Lys Lys Ala Ser Tyr Leu Asp Cys
145                 150                 155                 160

Ile Arg Ala Ile Ala Ala Asn Glu Ala Asp Ala Val Thr Leu Asp Ala
                165                 170                 175

Gly Leu Val Tyr Asp Ala Tyr Leu Ala Pro Asn Asn Leu Lys Pro Val
            180                 185                 190

Val Ala Glu Phe Tyr Gly Ser Lys Glu Asp Pro Gln Thr Phe Tyr Tyr
            195                 200                 205

Ala Val Ala Val Val Lys Lys Asp Ser Gly Phe Gln Met Asn Gln Leu
            210                 215                 220

Arg Gly Lys Lys Ser Cys His Thr Gly Leu Gly Arg Ser Ala Gly Trp
225                 230                 235                 240

Asn Ile Pro Ile Gly Leu Leu Tyr Cys Asp Leu Pro Glu Pro Arg Lys
                245                 250                 255

Pro Leu Glu Lys Ala Val Ala Asn Phe Phe Ser Gly Ser Cys Ala Pro
            260                 265                 270

Cys Ala Asp Gly Thr Asp Phe Pro Gln Leu Cys Gln Leu Cys Pro Gly
            275                 280                 285

Cys Gly Cys Ser Thr Leu Asn Gln Tyr Phe Gly Tyr Ser Gly Ala Phe
            290                 295                 300

Lys Cys Leu Lys Asp Gly Ala Gly Asp Val Ala Phe Val Lys His Ser
305                 310                 315                 320

Thr Ile Phe Glu Asn Leu Ala Asn Lys Ala Asp Arg Asp Gln Tyr Glu
                325                 330                 335

Leu Leu Cys Leu Asp Asn Thr Arg Lys Pro Val Asp Glu Tyr Lys Asp
            340                 345                 350

Cys His Leu Ala Gln Val Pro Ser His Thr Val Val Ala Arg Ser Met
            355                 360                 365

Gly Gly Lys Glu Asp Leu Ile Trp Glu Leu Leu Asn Gln Ala Gln Glu
            370                 375                 380

His Phe Gly Lys Asp Lys Ser Lys Glu Phe Gln Leu Phe Ser Ser Pro
385                 390                 395                 400

His Gly Lys Asp Leu Leu Phe Lys Asp Ser Ala His Gly Phe Leu Lys
                405                 410                 415

Val Pro Pro Arg Met Asp Ala Lys Met Tyr Leu Gly Tyr Glu Tyr Val
            420                 425                 430
```

Thr Ala Ile Arg Asn Leu Arg Glu Gly Thr Cys Pro Glu Ala Pro Thr
            435                 440                 445

Asp Glu Cys Lys Pro Val Lys Trp Cys Ala Leu Ser His His Glu Arg
450                 455                 460

Leu Lys Cys Asp Glu Trp Ser Val Asn Ser Val Gly Lys Ile Glu Cys
465                 470                 475                 480

Val Ser Ala Glu Thr Thr Glu Asp Cys Ile Ala Lys Ile Met Asn Gly
                485                 490                 495

Glu Ala Asp Ala Met Ser Leu Asp Gly Gly Phe Val Tyr Ile Ala Gly
            500                 505                 510

Lys Cys Gly Leu Val Pro Val Leu Ala Glu Asn Tyr Asn Lys Ser Asp
        515                 520                 525

Asn Cys Glu Asp Thr Pro Glu Ala Gly Tyr Phe Ala Val Ala Val Val
    530                 535                 540

Lys Lys Ser Ala Ser Asp Leu Thr Trp Asp Asn Leu Lys Gly Lys Lys
545                 550                 555                 560

Ser Cys His Thr Ala Val Gly Arg Thr Ala Gly Trp Asn Ile Pro Met
                565                 570                 575

Gly Leu Leu Tyr Asn Lys Ile Asn His Cys Arg Phe Asp Glu Phe Phe
            580                 585                 590

Ser Glu Gly Cys Ala Pro Gly Ser Lys Lys Asp Ser Ser Leu Cys Lys
        595                 600                 605

Leu Cys Met Gly Ser Gly Leu Asn Leu Cys Glu Pro Asn Asn Lys Glu
    610                 615                 620

Gly Tyr Tyr Gly Tyr Thr Gly Ala Phe Arg Cys Leu Val Glu Lys Gly
625                 630                 635                 640

Asp Val Ala Phe Val Lys His Gln Thr Val Pro Gln Asn Thr Gly Gly
                645                 650                 655

Lys Asn Pro Asp Pro Trp Ala Lys Asn Leu Asn Glu Lys Asp Tyr Glu
            660                 665                 670

Leu Leu Cys Leu Asp Gly Thr Arg Lys Pro Val Glu Glu Tyr Ala Asn
        675                 680                 685

Cys His Leu Ala Arg Ala Pro Asn His Ala Val Val Thr Arg Lys Asp
    690                 695                 700

Lys Glu Ala Cys Val His Lys Ile Leu Arg Gln Gln Gln His Leu Phe
705                 710                 715                 720

Gly Ser Asn Val Thr Asp Cys Ser Gly Asn Phe Cys Leu Phe Arg Ser
                725                 730                 735

Glu Thr Lys Asp Leu Leu Phe Arg Asp Asp Thr Val Cys Leu Ala Lys
            740                 745                 750

Leu His Asp Arg Asn Thr Tyr Glu Lys Tyr Leu Gly Glu Glu Tyr Val
        755                 760                 765

Lys Ala Val Gly Asn Leu Arg Lys Cys Ser Thr Ser Ser Leu Leu Glu
    770                 775                 780

Ala Cys Thr Phe Arg Arg Pro
785                 790

<210> SEQ ID NO 244
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

```
Pro Ser Thr Ser Thr Ser Thr
1               5

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Glu Ile Asp Lys Pro Ser Gln
1               5

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Ser Gly Ser Gly Ser Gly Ser Gly Ser
1               5                   10

<210> SEQ ID NO 247
<211> LENGTH: 423
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 247

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Gly Val Ser Asp Val Pro Arg
                85                  90                  95

Asp Leu Glu Val Val Ala Ala Thr Pro Thr Ser Leu Leu Ile Ser Trp
            100                 105                 110

Ser Ala Arg Leu Lys Val Ala Arg Tyr Tyr Arg Ile Thr Tyr Gly Glu
        115                 120                 125

Thr Gly Gly Asn Ser Pro Val Gln Glu Phe Thr Val Pro Lys Asn Val
    130                 135                 140

Tyr Thr Ala Thr Ile Ser Gly Leu Lys Pro Gly Val Asp Tyr Thr Ile
145                 150                 155                 160

Thr Val Tyr Ala Val Thr Arg Phe Arg Asp Tyr Gln Pro Ile Ser Ile
                165                 170                 175

Asn Tyr Arg Thr Glu Ile Asp Lys Pro Ser Gln Asp Pro Gly Ser Glu
            180                 185                 190
```

```
Pro Lys Ser Cys Asp Lys Thr His Thr Cys Pro Pro Cys Pro Ala Pro
        195                 200                 205

Glu Leu Leu Gly Gly Ser Ser Val Phe Leu Phe Pro Pro Lys Pro Lys
    210                 215                 220

Asp Thr Leu Met Ile Ser Arg Thr Pro Glu Val Thr Cys Val Val Val
225                 230                 235                 240

Asp Val Ser His Glu Asp Pro Glu Val Lys Phe Asn Trp Tyr Val Asp
                245                 250                 255

Gly Val Glu Val His Asn Ala Lys Thr Lys Pro Arg Glu Glu Gln Tyr
                260                 265                 270

Asn Ser Thr Tyr Arg Val Val Ser Val Leu Thr Val Leu His Gln Asp
        275                 280                 285

Trp Leu Asn Gly Lys Glu Tyr Lys Cys Lys Val Ser Asn Lys Ala Leu
    290                 295                 300

Pro Ala Pro Ile Glu Lys Thr Ile Ser Lys Ala Lys Gly Gln Pro Arg
305                 310                 315                 320

Glu Pro Gln Val Tyr Thr Leu Pro Pro Ser Arg Asp Glu Leu Thr Lys
                325                 330                 335

Asn Gln Val Ser Leu Thr Cys Leu Val Lys Gly Phe Tyr Pro Ser Asp
                340                 345                 350

Ile Ala Val Glu Trp Glu Ser Asn Gly Gln Pro Glu Asn Asn Tyr Lys
                355                 360                 365

Thr Thr Pro Pro Val Leu Asp Ser Asp Gly Ser Phe Phe Leu Tyr Ser
        370                 375                 380

Lys Leu Thr Val Asp Lys Ser Arg Trp Gln Gln Gly Asn Val Phe Ser
385                 390                 395                 400

Cys Ser Val Met His Glu Ala Leu His Asn His Tyr Thr Gln Lys Ser
                405                 410                 415

Leu Ser Leu Ser Pro Gly Lys
                420

<210> SEQ ID NO 248
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uagcggaugc                                                              10
```

METHODS OF TREATING CANCER BY ADMINISTERING IGF-IR BINDING MOLECULES

RELATED APPLICATIONS

This application is a continuation of U.S. patent application Ser. No. 14/659,028, filed Mar. 16, 2015, abandoned, which is a continuation of U.S. patent application Ser. No. 13/892,418, filed May 13, 2013, abandoned which is a continuation of U.S. patent application Ser. No. 12/312,725, filed Jan. 20, 2010 (now U.S. Pat. No. 8,470,332), which is a 35 U.S.C. 371 national stage filing of International Application No. PCT/US2007/024316, filed Nov. 21, 2007, which claims the benefit of U.S. Provisional Patent Application Nos. 60/879,666, filed Jan. 9, 2007 and 60/860,605, filed Nov. 22, 2006. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Jan. 12, 2017, is named MXI_519USCN3_Sequence_Listing.txt and is 311,368 bytes in size.

FIELD OF THE INVENTION

The present invention relates to innovative proteins that bind to insulin-like growth factor-I receptor (IGF-IR), as well as other important proteins. The invention also relates to innovative proteins in pharmaceutical preparations and derivatives of such proteins and the uses of same in diagnostic, research and therapeutic applications. The invention further relates to cells comprising such proteins, polynucleotide encoding such proteins or fragments thereof, and to vectors comprising the polynucleotides encoding the innovative proteins.

INTRODUCTION

Insulin-like growth factor-I receptor (IGF-IR) is a transmembrane heterotetrameric protein, which has two extracellular alpha chains and two membrane-spanning beta chains in a disulfide-linked beta-alpha-alpha-beta. configuration. The binding of the ligands, such as insulin-like growth-factor-I (IGF-I) and insulin-like growth factor-II (IGF-II), by the extracellular domain of IGF-IR receptor activates it and in many instances its intracellular tyrosine kinase domain resulting in autophosphorylation of the receptor and substrate phosphorylation.

IGF-IR is homologous to the insulin receptor, having a high sequence similarity of 84% in the beta chain tyrosine kinase domain and a low sequence similarity of 48% in the alpha chain extracellular cysteine rich domain (Ulrich, A. et al., 1986, EMBO, 5, 2503-2512; Fujita-Yamaguchi, Y. et al., 1986, J. Biol. Chem., 261, 16727-16731; LeRoith, D. et al., 1995, Endocrine Reviews, 16, 143-163). The IGF-IR and ligands (IGF-I and IGF-II) play important roles in numerous physiological processes including growth and development during embryogenesis, metabolism, cellular proliferation and cell differentiation in adults (LeRoith, D., 2000, Endocrinology, 141, 1287-1288; LeRoith, D., 1997, New England J. Med., 336, 633-640).

IGF-I and IGF-II ligands function both as endocrine hormones in the blood, where they are predominantly present in complexes with IGF-binding proteins, and as paracrine and autocrine growth factors that are produced locally (Humbel, R. E., 1990, Eur. J. Biochem., 190, 445-462; Cohick, W. S. and Clemmons, D. R., 1993, Annu. Rev. Physiol. 55, 131-153).

In vivo, serum levels of IGF-I are dependent upon the presence of pituitary growth hormone (GH). Although the liver is a major site of GH dependent IGF-I synthesis, a large number of extrahepatic tissues also produce IGF-I (Daughaday and Rotwein, Endocrine Rev. 10:68-91 (1989). A variety of neoplastic tissues may also produce IGF-I (Werner and LeRoith, Adv. Cancer Res. 68:183-223 (1996). Thus IGF-I may act as a regulator of normal and abnormal cellular proliferation via autocrine or paracrine, as well as endocrine mechanisms. IGF-I and IGF-II bind to IGF binding proteins (IGFBPs) in vivo. Upon binding to IGFs the IGFBPs either transport IGFs through the circulation or they may protect IGFs from proteolytic cleavage and inactivation. The availability of free IGF for interaction with the IGF-IR is modulated by the IGFBPs. For a review of IGFBPs and IGF-I, see Grimberg et al., J. Cell. Physiol. 183: 1-9, 2000.

At a molecular level IGF-IR has been implicated in promoting growth, transformation and survival of tumor cells (Baserga, R. et al., 1997, Biochem. Biophys. Acta, 1332, F105-F126; Blakesley, V. A. et al., 1997, Journal of Endocrinology, 152, 339-344; Kaleko, M., Rutter, W. J., and Miller, A. D. 1990, Mol. Cell. Biol., 10, 464-473). Several types of tumors are known to express higher than normal levels of IGF-IR, including breast cancer, colon cancer, ovarian carcinoma, synovial sarcoma and pancreatic cancer. See Khandwala, H. M. et al., 2000, Endocrine Reviews, 21, 215-244; Werner, H. and LeRoith, D., 1996, Adv. Cancer Res., 68, 183-223; Happerfield, L. C. et al., 1997, J. Pathol., 183, 412-417; Frier, S. et al., 1999, Gut, 44, 704-708; van Dam, P. A. et al., 1994, J. Clin. Pathol., 47, 914-919; Xie, Y. et al., 1999, Cancer Res., 59, 3588-3591; Bergmann, U. et al., 1995, Cancer Res., 55, 2007-2011.

In vitro, IGF-I and IGF-II have been shown to be potent mitogens for several human tumor cell lines such as lung cancer, breast cancer, colon cancer, osteosarcoma and cervical cancer (Ankrapp, D. P. and Bevan, D. R., 1993, Cancer Res., 53, 3399-3404; Cullen, K. J., 1990, Cancer Res., 50, 48-53; Hermanto, U. et al., 2000, Cell Growth & Differentiation, 11, 655-664; Guo, Y. S. et al., 1995, J. Am. Coll. Surg., 181, 145-154; Kappel, C. C. et al., 1994, Cancer Res., 54, 2803-2807; Steller, M. A. et al., 1996, Cancer Res., 56, 1761-1765). Several of these tumors and tumor cell lines also express high levels of IGF-I or IGF-II, which may stimulate their growth in an autocrine or paracrine manner (Quinn, K. A. et al., 1996, J. Biol. Chem., 271, 11477-11483).

Epidemiological studies have shown a correlation of elevated plasma level of IGF-I (and lower level of IGF-binding protein-3) with increased risk for prostate cancer, colon cancer, lung cancer and breast cancer (Chan, J. M. et al., 1998, Science, 279, 563-566; Wolk, A. et al., 1998, J. Natl. Cancer Inst., 90, 911-915; Ma, J. et al., 1999, J. Natl. Cancer Inst., 91, 620-625; Yu, H. et al., 1999, J. Natl. Cancer Inst., 91, 151-156; Hankinson, S. E. et al., 1998, Lancet, 351, 1393-1396). Strategies to lower the IGF-I level in plasma or to inhibit the function of IGF-IR have been suggested for cancer prevention (Wu, Y. et al., 2002, Cancer Res., 62, 1030-1035; Grimberg, A and Cohen P., 2000, J. Cell. Physiol., 183, 1-9).

IGF-IR can protect tumor cells from apoptosis caused by growth factor deprivation, anchorage independence or cytotoxic drug treatment (Navarro, M. and Baserga, R., 2001, Endocrinology, 142, 1073-1081; Baserga, R. et al., 1997, Biochem. Biophys. Acta, 1332, F105-F126). Domains of IGF-IR that are critical for its mitogenic, transforming and anti-apoptotic activities have been identified by mutational analysis. For example, the tyrosine 1251 residue of IGF-IR has been identified as critical for anti-apoptotic and transformation activities but not for its mitogenic activity (O'Connor, R. et al., 1997, Mol. Cell. Biol., 17, 427-435; Miura, M. et al., 1995, J. Biol. Chem., 270, 22639-22644).

Difficulty of Making a Therapeutic Based on IGF-IR Antagonism or Inhibition

While IGF-IR has attractive biology as a therapeutic target, attempts to make antagonists or other types of inhibitors have been slow, largely due to one or more of the following factors depending on the therapeutic paradigm: difficulty or inability to antagonize the target without agonism; difficulty or inability to make selective antagonists or inhibitors due to undesired cross reactivity with other tyrosine kinase targets or receptors, such as the insulin receptor; difficulty in effective administration due to short half life of the potential therapeutic; difficulty in effective administration due to low solubility of the potential therapeutic; and difficulty in effective administration due to aggregation of the potential therapeutic. Therapeutics of the invention traverse one or more of these difficulties.

Tumor cells expressing an antisense to the IGF-IR mRNA undergo massive apoptosis when injected into animals in biodiffusion chambers. This observation makes the IGF-IR an attractive therapeutic target, based upon the hypothesis that tumor cells are more susceptible than normal cells to apoptosis by inhibition of IGF-IR (Resnicoff, M. et al., 1995, Cancer Res., 55, 2463-2469; Baserga, R., 1995, Cancer Res., 55, 249-252). However, both antisense and siRNA therapeutic strategies suffer from administration challenges and potential cost of goods obstacles.

Another strategy to inhibit the function of IGF-IR in tumor cells has been to use anti-IGF-IR antibodies that bind to the extracellular domain of IGF-IR and which may inhibit activation. Several attempts have been reported to develop mouse monoclonal antibodies against IGF-IR, of which two inhibitory antibodies—IR3 and 1H7—are available and their use has been reported in several IGF-IR studies.

The IR3 antibody was developed using a partially purified placental preparation of insulin receptor to immunize mice, which yielded an antibody, IR1, that was selective for binding insulin receptor, and two antibodies, IR2 and IR3, that showed preferential immunoprecipitation of IGF-IR (somatomedin-C receptor) but also weak immunoprecipitation of insulin receptor (Kull, F. C. et al., 1983, J. Biol. Chem., 258, 6561-6566).

Exemplary Deficiencies of Antibodies

In some cases, antibodies activate IGF-IR. This has been shown a number of times in the literature. In addition, antibodies that are shown to "inhibit" may not have been carefully characterized and may actually activate IGF-IR under certain conditions, such as lower antibody concentrations. In a tumor where there is a likely diffusion gradient of antibody, activation of IGF-IR could occur with antibodies at lower concentrations of antibody in the tumor.

The 1H7 antibody was developed by immunizing mice with purified placental preparation of IGF-IR, which yielded an inhibitory antibody 1H7 in addition to three stimulatory antibodies (Li, S.-L. et al., 1993, Biochem. Biophys. Res. Commun., 196, 92-98; Xiong, L. et al., 1992, Proc. Natl. Acad. Sci. USA, 89, 5356-5360).

In another report, a panel of mouse monoclonal antibodies specific for human IGF-IR was obtained by immunization of mice with transfected 3T3 cells expressing high levels of IGF-IR, which were categorized into seven groups by binding competition studies and by their inhibition or stimulation of IGF-I binding to transfected 3T3 cells (Soos, M. A. et al., 1992, J. Biol. Chem., 267, 12955-12963).

Although IR3 antibody is the most commonly used inhibitory antibody for IGF-IR studies in vitro, it suffers from the drawback that it exhibits agonistic activity in transfected 3T3 and CHO cells expressing human IGF-IR (Kato, H. et al., 1993, J. Biol. Chem., 268, 2655-2661; Steele-Perkins, G. and Roth, R. A., 1990, Biochem. Biophys. Res. Commun., 171, 1244-1251). Similarly, among the panel of antibodies developed by Soos et al., the most inhibitory antibodies 24-57 and 24-60 also showed agonistic activities in the transfected 3T3 cells (Soos, M. A. et al., 1992, J. Biol. Chem., 267, 12955-12963). Although, IR3 antibody has been reported to inhibit the binding of IGF-I (but not IGF-II) to expressed receptors in intact cells and after solubilization, it has been shown to inhibit the ability of both IGF-I and IGF-II to stimulate DNA synthesis in cells in vitro (Steele-Perkins, G. and Roth, R. A., 1990, Biochem. Biophys. Res. Commun., 171, 1244-1251). The binding epitope of IR3 antibody has been inferred from chimeric insulin-IGF-IR constructs to be the 223-274 region of IGF-IR (Gustafson, T. A. and Rutter, W. J., 1990, J. Biol. Chem., 265, 18663-18667; Soos, M. A. et al., 1992, J. Biol. Chem., 267, 12955-12963).

The MCF-7 human breast cancer cell line is typically used as a model cell line to demonstrate the growth response of IGF-I and IGF-II in vitro (Dufourny, B. et al., 1997, J. Biol. Chem., 272, 31163-31171). In MCF-7 cells, the IR3 antibody incompletely blocks the stimulatory effect of exogenously added IGF-I and IGF-II in serum-free conditions by approximately 80%. Also, the IR3 antibody does not significantly inhibit (less than 25%) the growth of MCF-7 cells in 10% serum (Cullen, K. J. et al., 1990, Cancer Res., 50, 48-53). This weak inhibition of serum-stimulated growth of MCF-7 cells by IR3 antibody in vitro may be related to the results of an in vivo study in which IR3 antibody treatment did not significantly inhibit the growth of a MCF-7 xenograft in nude mice (Arteaga, C. L. et al., 1989, J. Clin. Invest., 84, 1418-1423).

Because of the weak agonistic activities of the IR3 and other reported antibodies, and their inability to significantly inhibit the growth of tumor cells such as MCF-7 cells in the more physiological condition of serum-stimulation (instead of stimulation by exogenously added IGF-I or IGF-II in serum-free condition), there is a need for new anti-IGF-IR modulators that could inhibit the serum-stimulated growth of tumor cells without significant agonistic activity by themselves. Although, in some instances, agonist activity will be desired, usually for applications outside of oncology or mis-controlled or undesired tissue expansion, proliferation, or growth.

Although anti-IGF-IR antibodies have been reported present in certain patients with autoimmune diseases, none of these antibodies has been purified and none has been shown to be suitable for inhibiting IGF-I activity for diagnostic or clinical procedures. See, e.g., Thompson et al., Pediat. Res. 32: 455 459, 1988; Tappy et al., Diabetes 37: 1708-1714, 1988; Weightman et al., Autoimmunity 16:251-257, 1993; Drexhage et al., Nether. J. of Med. 45:285-293, 1994. Additionally, monoclonal antibodies against the IGF-1R have been reported with can stimulate cell proliferation (Xiong et al., Proc. Natl. Acad. Sci. USA 89:5356-5360, 1992).

Additionally, it has been historically difficult to make antibodies and other therapeutics due to specificity, agonism, aggregation and solubility, as well as bi-specific therapeutics that include IGF-IR as a target, particularly with using antibodies.

Exemplary Deficiencies of Small Molecule Inhibitors

Small molecule chemistry programs have largely not been successful in creating a therapeutic to IGF-IR. The drug-gability of this target by proteins and small molecules has been difficult for a number of reasons including the ability to obtain selective chemistry for IGF-IR while not inhibiting or binding to related tyrosine kinases or receptors, such as the insulin receptor. In addition, the small molecules are often of low solubility making bioavailability, administration or formulation challenging.

Apoptosis and IGF-IR

One of many aspects of the invention is for a polypeptide of the invention to selectively bind to IGF-IR to trigger apoptosis in the cells of a desired tissue, such as a tumor. IGF-IR biology, including activation, contributes to the regulation of apoptosis. It can slow or prevent apoptosis. Suppression of the apoptotic program by a variety of genetic lesions may contribute to the development and progression of malignancies.

Current potential therapeutic strategies, although capable of inducing apoptosis in vitro or for inhibiting in vitro cell proliferation associated with increased IGF-I, increased IGF-II, and/or increased IGF-IR receptor levels include suppressing IGF-I levels or IGF-II levels or preventing the binding of IGF-I to the IGF-IR, remain unsuitable for better therapeutics. For example, the long acting somatostatin analogue octreotide has been employed to reduce IGF synthesis and/or secretion. Soluble IGF-IR has been used to induce apoptosis in tumor cells in vivo and inhibit tumorigenesis in an experimental animal system (D'Ambrosio et al., Cancer Res. 56: 4013-20, 1996). In addition, IGF-IR antisense oligonucleotides, peptide analogues of IGF-I, and antibodies to IGF-IR have been used to decrease IGF-I or IGF-IR expression (see supra). However, none of these agents has been suitable for longer-term administration to human patients. In addition, although IGF-I has been administered to patients for treatment of short stature, osteoporosis, decreased muscle mass, neuropathy or diabetes, the binding of IGF-I to IGFBPs has often made treatment with IGF-I difficult or ineffective. In view of the roles that IGF-I, IGF-II and IGF-IR have in disorders, including cancer and proliferative disorders, such as when IGF-I or IGF-II and/or IGF-IR are over-expressed, and the deficiencies of other therapeutic approaches (e.g., small molecules, siRNA, antisense and antibodies), it would be desirable to generate therapeutics, such as polypeptides of the invention, to the IGF-IR pathway (or various isoforms or mutants of the receptor or its ligands) that could selectively modulate, inhibit or block IGF-IR.

In addition, it would be desirable for such a polypeptide to be expressed in a cost effective manner, possess desirable biophysical properties (e.g., Tm, substantially monomeric, or well folded), small size to penetrate tissues and proper half life or in vivo exposure time in blood over the binding affinity for IGF-IR or other targets.

SUMMARY OF THE INVENTION

One aspect of the invention relates to novel polypeptides that bind IGF-IR with high affinity. In some embodiments, the polypeptides bind IGF-IR with a disassociation constant of about 1 µM or less, about 10 nM or less, or about 1 nM or less. In some embodiments, the polypeptides bind to the insulin receptor with a disassociation constant of about 1 µM or more. In some embodiments, the polypeptide of the invention inhibits the binding of IGF-I or IGF-II to IGF-IR and does not activate human IGF-IR at sub IC50 concentrations in a cell-based assay with an IC50 of less than about 1 nM or about 100 pM. In some embodiments, the polypeptide of the invention induces apoptosis in a cell based assay in a cell line dependent on IGF-IR activation. In some embodiments, IGF-IR binders block IGF-IR activities such as control of apoptosis, phosphorylation or dimerization.

It will be often desirable, particularly in in vivo applications, that proteins of the invention targeting IGF-IR either as a mono-specific therapeutic or multi-specific (including bi-specific or tri-specific) therapeutics are selective over IGF-IR compared to the insulin receptor. Such selectivity is preferably at least about 100 times, at least about 1000 times, at least about 10,000 times and at least about 100,000 times. In addition, it my be desirable, particularly for proteins with high affinity to IGF-IR to not detectably bind the insulin receptor at a defined concentration or lower of therapeutic or protein, such concentrations are about 100 nM, about 1 uM, or about 10 uM. Selectivity relationships of proteins that bind to IGF-IR over the insulin receptor may also be expressed by comparing Kd, IC50, and Ki's either as measured or calculated depending on the assay; or as a ratio of the same biochemical or biological parameters (e.g., Kd, IC50, and Ki's). Such ratios preferably include ratios of insulin receptor binding or other measurement to IGF-IR binding or other measurement of about 100, about 1,000, about 10,000 or about 100,000. Other proteins of the invention that bind to other targets, particularly tyrosine kinase receptors, preferably are selective for the desired target (e.g., EGFR or Her2) compared to the insulin receptor using the selectivity guidance provided herein.

In some embodiments, the polypeptide comprises a fibronectin-based scaffold protein. In some embodiments, the polypeptide comprising a tenth fibronectin type III ($^{10}$Fn3) domain, wherein the $^{10}$Fn3 domain (i) comprises a loop, AB; a loop, BC; a loop, CD; a loop, DE; a loop EF; and a loop FG; (ii) has at least one loop selected from loop BC, DE, and FG with an altered amino acid sequence relative to the sequence of the corresponding loop of the human $^{10}$Fn3 domain, and (iii) binds human IGF-IR with a disassociation constant of about 1 µM or less. In some embodiments, at least 1, 2, 3, 4, 5, 6, 7, 8, 9, or 10 amino acids in at least one loop selected from loop BC, DE, and FG are substituted with an amino acid that differs from the wild-type sequence. In some embodiments, at least 1, 2, 3, 4, 5, 6, 7, 8, 9, or 10 amino acids are deleted or added to at least one loop selected from loop BC, DE, and FG. In some embodiments, loop BC and loop FG have an altered amino acid sequence relative to the sequence of the corresponding loop of the human $^{10}$Fn3 domain. In some embodiments, the polypeptide comprises the amino acid sequence of any of one of SEQ ID NOS: 2-125, 184-203, or 226. Substantially monovalent binding to IGF-IR via fibronectin based scaffolds is helpful in reducing IGF-IR activation in this and other embodiments of the invention.

In some embodiments, the polypeptides of the invention further comprise one or more pharmacokinetic (PK) moieties. PK moieties improve one or more pharmacokinetic properties of the polypeptides, e.g., bioavailability, serum half-life, in vivo stability, and drug distribution. In some embodiments, the PK moiety is selected from: a polyoxyalkylene moiety, a human serum albumin binding protein, sialic acid, human serum albumin, transferrin, and Fc or an Fc fragment. In some embodiments, the PK moiety is polyethylene glycol (PEG). In some embodiments, the PEG moiety is covalently linked to the polypeptide of the invention via a Cys or Lys amino acid. In some embodiments, a polypeptide of the invention is linked by at least one peptide bond to a second protein that binds human serum albumin (HSA) with a binding affinity of about 300 nM or less.

In some embodiments, the polypeptides of the invention further comprise a second domain that binds to a human protein. In some embodiments the human protein is selected from EGFR, folate receptor, Her2, Her3, c-kit, c-Met, FGFR1, FGFR2, PDGFR, VEGFR1, VEGFR2, VEGF3, Tie2, Ang1, Ang2, FGF (fibroblast growth factor), EGF (epidermal growth factor), HGF (hepatocyte growth factor), VEGF-A (vascular endothelial growth factor-A), VEGF-C, and VEGF-D. In some embodiments the human protein is IGF-IR. In some embodiments, the human protein is a tyrosine receptor. In some embodiments, the second domain binds to a human protein with a disassociation constant of about 1 µM or less, about 10 nM or less, or about 1 nM or less. In some embodiments, the second domain binds to VEGFR2 with a disassociation constant of about 1 µM or less, about 10 nM or less, or about 1 nM or less and binds to VEGFR1 with a disassociation constant of about 1 µM, 10 µM, or 10 µM, or more.

In some embodiments, the polypeptide comprises a first and second protein, wherein either or both proteins are a single chain antibody and the first and second proteins are linked via a PEG moiety. In some embodiments, the first protein binds IGF-IR.

In some embodiments, the second domain is selected from: an antibody moiety of less than about 50 kDa; a derivative of lipocalin; a derivative of tetranectin; an avimer; a derivative of ankyrin, and a second tenth fibronectin type III ($^{10}$Fn3) domain, wherein the second $^{10}$Fn3 domain comprises a loop, AB; a loop, BC; a loop, CD; a loop, DE; and a loop FG; and has at least one loop selected from loop BC, DE, and FG with a randomized amino acid sequence relative to the sequence of the corresponding loop of the human $^{10}$Fn3 domain, and binds a human protein, which is not bound by the human $^{10}$Fn3 domain, with a disassociation constant of about 10 nM or less. In some embodiments the second domain is a $^{10}$Fn3 domain and comprises the amino acid sequence of any of one of SEQ ID NOS: 2-203, or 226. In some embodiments, the polypeptide of the invention and the second domain are operably linked via at least one disulfide bond, a peptide bond, a polypeptide, a polymeric sugar, or a polyethylene glycol (PEG) moiety. In some embodiments, the PEG is between about 0.5 kDa and about 100 kDa.

In some embodiments of the invention, polypeptides of the invention comprise a first and second protein linked via a polypeptide, wherein the first or second protein or polypeptide linker has a protease site that is cleavable by a protease in the blood or target tissue. Such embodiments can be used to release two or more therapeutic proteins for better delivery or therapeutic properties or more efficient production compared to separately producing such proteins.

In some embodiments, a first and second protein are linked using a biocompatible polymer such as a polymeric sugar. Such polymeric sugar can include an enzymatic cleavage site that is cleavable by an enzyme in the blood or target tissue. Such embodiments can be used to release two or more therapeutic proteins for better delivery or therapeutic properties or more efficient production compared to separately producing such proteins.

Another aspect of the invention is the operable linkage of one or more proteins of the invention, or other proteins described herein to make a protein therapeutic of the invention, via a polymer to create multi-functional proteins. For instance the polymer could be a polypeptide, polymeric sugar, carbon based polymer (e.g., aliphatic chain) or PEG. An additional aspect of the invention includes linking a protein of the invention that binds IGF-IR as described herein with PEG to another protein, such as: a Fab, a single chain Ab, domain antibodies, camel antibodies and their derivatives (particularly entities less than about 50 kDa), antibody moiety (e.g., less than about 50 kDa), an Adtein (e.g., a protein between 5 and 40 kDa the binds a target with a desired specificity while having one or more of pharmaceutical or biochemical properties described herein, particularly those related to tyrosine kinase receptors), a fibronectin based scaffold protein (e.g., an Adnectin™), or antibody alternatives, such as Avimers, microbodies, Trans-Bodies™, Affibodies™, Affilins™, or trinectins (e.g., tetranectins) and other derivatives of proteins like lipocalin, or ankyrin (DARPin). In some embodiments, the first and second linked proteins collectively have 1 or 0 disulfide bonds. This may be desirable to improve protein production in cell based systems. Preferably, said first protein is substantially a single domain that has substantially monovalent binding to IGF-IR. This may be desirable to improve protein production in cell based systems. Preferably, said first protein binds human IGF-IR with an binding affinity of about 100 pM or less and has at least two structural loops that participate in the binding of said first protein to human IGF-IR. Preferably, said second protein is a fibronectin based scaffold protein linked by at least one peptide bond to said first protein. In some embodiments, said first protein and second protein are linked by at least one disulfide bond. Though this can be accomplished in cells in may be desired to perform this linkage in vitro without cells. The polypeptide of the invention may include a first protein that binds human IGF-IR with an binding affinity of about 300 pM or less and has at least two structural loops that participate in the binding of said first protein to human IGF-IR. Preferably, said first protein binds human IGF-IR with an binding affinity of about 1 nM or less and binds human insulin receptor with a binding affinity of about 1 uM or greater. Preferably, the polypeptide of the invention further comprises a PEG moiety operably linked either said first protein or said second protein. Preferably, said second protein binds a human tyrosine kinase receptor up-regulated in a human cancer, wherein said second protein binds the human tyrosine kinase receptor with an binding affinity of about 10 nM or less and binds human insulin receptor with a binding affinity of about 1 uM or greater.

In some embodiments, the polypeptide of the invention may comprise a first protein and said second protein that collectively have at least 6 disulfide bonds or, in another aspect, collectively have at least 8 disulfide bonds. Preferably, said first protein and said second protein are a single polypeptide expressed from a microbe. Preferably, said first protein binds human IGF-IR with a binding affinity of about 100 pM or less and has at least two structural loops that participate in the binding of said first protein to human IGF-IR. In some embodiments, at least one of said first protein and said second protein is an antibody moiety. Preferably, such antibody moiety is less than about 50 kDa or, in another aspect, is less than about 40 kDa. In some embodiments, the antibody moiety is a single chain antibody moiety. The protein therapeutic includes an embodiment wherein said second protein binds one of the following human proteins: EGFR, folate receptor, Her2, Her3, c-kit, c-Met, FGFRI, FGFR2, PDGFR, VEGFR1, VEGFR2, VEGF3, and Tie2; and ligands: Ang1, Ang2, FGF, EGF, HGF, stem cell factor (SCF), VEGF-A, VEGF-C, and VEGF-D. In some embodiments, the first protein and/or the second protein are a derivative of lipocalin. In some embodiments, least one of said first protein and said second protein is a derivative of a tetranectin. In some embodiments, at least one of said first protein moiety and said second protein moiety is a derivative of an avimer.

PEG may be used in many aspects of the invention and different sizes may be used as described herein for the desired therapeutic or other in vivo effect, such as imaging. Larger PEGs are preferred to increase half life in the body, blood, non-blood extracellular fluids or tissues. For in vivo cellular activity, PEGs of the range of about 10 to 60 kDa are preferred, as well as PEGs less than about 100 kDa and more preferably less than about 60 kDa, though sizes greater than about 100 kDa can be used as well. For in vivo imaging application, smaller PEGs, generally less than about 20 kDa, may be used that do not increase half life as much as larger PEGs so as to permit quicker distribution and less half life.

In some embodiments, polypeptides of the invention comprise a first protein and second protein operably linked to PEG through a single Cys or Lys. In some embodiments, at least the first or second protein has no more than a single Cys or Lys. In some embodiments, the single Cys or Lys is located in said first or second protein in a non-wildtype location in the amino acid sequence.

In some embodiments, the polypeptide of the invention comprises a first and second protein, wherein said first protein inhibits cell proliferation, has a Tm of at least 55° C., and a non-wildtype Cys or Lys in region of its amino acid sequence that does not substantially interfere with binding to human IGF-IR. In some embodiments, the first protein and second protein are a single polypeptide expressed from a microbe. In some embodiments, the first protein binds human IGF-IR with a binding affinity of about 50 pM or less and has at least two structural loops that participate in the binding of said first protein to human IGF-IR. In some embodiments, the polypeptide of the invention has a half life in in vivo of at least one day with IV administration. In some embodiments, the polypeptide of the invention has an exposure level at a concentration of at least about 10 times the binding affinity of said first protein to human IGF-IR for over 24 hours in a rodent after administration. In some embodiments, the polypeptide of the invention has an exposure level at a concentration of at least about 100 times the binding affinity of said first protein to human IGF-IR for over 24 hours in a rodent after subcutaneous administration. In some embodiments, the first or second protein is a fibronectin based scaffold protein.

A variety of affinities of the polypeptides of the invention to IGF-IR, other human proteins, or PK moieties can be can be used depending on diagnostic, therapeutic, in vitro or in vivo application. For instance, affinities with a disassociation constant similar or less than about 1 uM, about 100 nM, about 10 nM, about 1 nM, about 100 pM, about 10 pM, about 1 pM or about 100 fM are preferred, particularly for IGF-IR. In vivo testing of proteins of the invention with different affinity to the desired target aids in selecting the desired affinity for in vivo applications. In vitro testing depending on the presence of other proteins and amounts of IGF-IR may generally use proteins of the invention of different affinity compared to in vivo applications. Often less affinity or weaker binding can be used in in vitro.

In some embodiments, the polypeptide is an $^{10}$Fn3 domain selected by the method comprising the steps of a) producing a population of candidate RNA molecules, each comprising a candidate tenth fibronectin type III ($^{10}$Fn3) domain sequence which differs from human $^{10}$Fn3 domain coding sequence, said RNA molecules each comprising a translation initiation sequence and a start codon operably linked to said candidate $^{10}$Fn3 domain coding sequence and each being operably linked to a nucleic acid-puromycin linker at the 3' end; b) in vitro translating said candidate $^{10}$Fn3 domain coding sequences to produce a population of candidate RNA-$^{10}$Fn3 fusions; c) contacting said population of candidate RNA-Fn3 fusions with IGF-IR; and d) selecting an RNA-$^{10}$Fn3 fusion, the protein portion of which has a binding affinity or specificity for IGF-IR that is altered relative to the binding affinity or specificity of said human $^{10}$Fn3 for IGF-IR.

One aspect of the invention relates to polypeptides comprising fibronectin-based scaffold proteins that bind to a hu methods for the treatment of a subject having a cancer man target. In some embodiments, the polypeptides further comprise PK moieties as described herein. The PK moiety may be linked to the fibronectin-based scaffold protein by any suitable linker, such as those described herein.

An aspect of the invention provides for a polypeptide of the invention capable of inhibiting the growth of a cancer cell by greater than about 80% in the presence of a growth stimulant such as, for example, serum, insulin-like growth factor-I and insulin-like growth factor-II.

A further aspect of the invention provides for pharmaceutically acceptable compositions comprising the polypeptides of the invention, wherein the composition is essentially endotoxin free. Preferably, the composition is substantially free of microbial contamination making it suitable for in vivo administration. The composition may be formulated, for example, for IV, IP or subcutaneous administration.

A further aspect of the invention provides for a cell, comprising a polynucleotide encoding one or more polypeptides of the invention. Vectors containing polynucleotides for such proteins are included as well. Sequences are preferably optimized to maximize expression in the cell type used. Preferably, expression is in *E. coli*. Proteins of then invention can also be expressed, for example, in eukaryotic microbes, including yeast (e.g., pichia or cervaisea) or blue green algae. Yeast cells can be engineered to produce desired glycosylations on any of the proteins described herein. The cells of the invention can be a mammalian cell. In one aspect, the mammalian cell can be engineered to produce desired glycosylations on any of the proteins described herein. In one aspect, the cell expresses a fibronectin based scaffold protein. In one aspect, the polynucleotides encoding fibronectin based scaffold proteins are codon optimized for expression in the selected cell type.

An aspect of the invention provides by administering a novel polypeptide of the present invention, either alone or in combination with other cytotoxic or therapeutic agents. The cancer can be one or more of, for example, breast cancer, colon cancer, ovarian carcinoma, osteosarcoma, cervical cancer, prostate cancer, lung cancer, synovial carcinoma, pancreatic cancer, or other cancer yet to be determined in which IGF-IR levels are elevated, up-regulated, mutated or altered in physiology compared to non-oncogenic cells.

Another aspect of the invention provides methods for the treatment of a subject having a cancer by administering a polypeptide of the invention, either alone or in combination with other cytotoxic or therapeutic agents. In particular, preferred cytotoxic and therapeutic agents include docetaxel, paclitaxel, doxorubicin, epirubicin, cyclophosphamide, trastuzumab, capecitabine, tamoxifen, toremifene, letrozole, anastrozole, fulvestrant, exemestane, goserelin, oxaliplatin, carboplatin, cisplatin, dexamethasone, antide, bevacizumab, 5-fluorouracil, leucovorin, levamisole, irinotecan, etoposide, topotecan, gemcitabine, vinorelbine, estramustine, mitoxantrone, abarelix, zoledronate, streptozocin, rituximab, idarubicin, busulfan, chlorambucil, fludarabine, imatinib, cytarabine, ibritumomab, tositumomab, interferon alpha-2b, melphalam, bortezomib, altretamine, asparaginase, gefitinib, erlonitib, anti-EGF receptor antibody (e.g., cetuximab or panitumumab), ixabepilone, and an epothilone or derivative thereof. More preferably, the therapeutic agent is a platinum agent (such as carboplatin, oxaliplatin, cisplatin), a taxane (such as paclitaxel, docetaxel), gemcitabine, or camptothecin.

In addition, it may be preferred to combine a polypeptide of the invention with a second therapeutic protein as a single molecule or perhaps as a single molecule with a third therapeutic protein. Such a therapeutic entity comprises a protein of the invention linked by PEG or other polymer (e.g., Cys-Cys disulfide or polypeptide) to one or more therapeutic proteins. Such therapeutic proteins include antibody derivatives (e.g., Fabs, camel antibodies and their derivatives, domain antibodies (e.g., less than about 50 kDa in size) and single chains (preferably less than about 50 kDa in size)), Adnectins™ and proteins preferably in the range of ~5 to ~40 kDa.

Targets of proteins of the invention include, particularly human versions, although in some instances model species such as mouse, rat, monkey and dog: IGF-IR, FGFR1, FGFR2, FGFR3, FGFR4, c-Kit, human p185 receptor-like tyrosine kinase (HER2 or Her2), Her3, c-Met, folate receptor, PDGFR, VEGFR1, VEGFR2, VEGFR3, human vascular endothelial growth factor (VEGF) A, VEGF C, VEGF D, human CD20, human CD18, human CD11a, human apoptosis receptor-2 (Apo-2), human .alpha.4.beta.7 integrin, human GPIIb-IIIa integrin, stem cell factor (SCF), human epidermal growth factor receptor (EGFR), and human CD3. In addition, aspects of the invention include multifunctional proteins that bind a first target and at least one other target. Preferably, such proteins are linked by the PEG related inventions described herein, although in many embodiments such proteins may be linked by polypeptides or other polymeric linkers or non-polymeric linkers.

Stably linked proteins of the invention may be of use for therapeutic treatment of cancer. Multispecific proteins of the invention have the advantage of modulating, blocking or inhibiting more than one therapeutic target when directed to 2, 3, 4 or more therapeutic targets or epitopes.

It is anticipated that any type of tumor and any type of tumor antigen may be targeted with the corresponding biology of the therapeutic. The cancer can be one or more of, for example, breast cancer, colon cancer, ovarian carcinoma, osteosarcoma, cervical cancer, prostate cancer, lung cancer, synovial carcinoma, pancreatic cancer, melanoma, multiple myeloma, neuroblastoma, and rhabdomyosarcoma, or other cancer yet to be determined in which IGF-IR levels are elevated, up-regulated, mutated or altered in physiology compared to non-oncogenic cells.

Other exemplary types of tumors that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer.

Additionally, tumor-associated targets may be targeted by polypeptides of the invention. In some embodiments antigen targeting will help localize the therapeutic in terms of tissue distribution or increased local concentration affect either in the tissue or desired cell type. Alternatively, it may provide an additional mechanism of action to combat cancer along with one of the targets described herein for which a therapeutic is made. Such antigens or targets include, but are not limited to, carbonic anhydrase IX, A3, antigen specific for A33 antibody, BrE3-antigen, CD1, CD1a, CD3, CD5, CD15, CD16, CD19, CD20, CD21, CD22, CD23, CD25, CD30, CD45, CD74, CD79a, CD80, HLA-DR, NCA 95, NCA90, HCG and its subunits, CEA (CEACAM-5), CEACAM-6, CSAp, EGFR, EGP-1, EGP-2, Ep-CAM, Ba 733, HER2/neu, hypoxia inducible factor (HIF), KC4-antigen, KS-1-antigen, KS1-4, Le-Y, macrophage inhibition factor (MIF), MAGE, MUC1, MUC2, MUC3, MUC4, PAM-4-antigen, PSA, PSMA, RS5, S100, TAG-72, p53, tenascin, IL-6, IL-8, insulin growth factor-I (IGF-I), insulin growth factor-II (IGF-II), Tn antigen, Thomson-Friedenreich antigens, tumor necrosis antigens, placenta growth factor (P1GF), 17-1A-antigen, an angiogenesis marker (e.g., ED-B fibronectin), an oncogene marker, an oncogene product, and other tumor-associated antigens. Recent reports on tumor associated antigens include Mizukami et al., (2005, Nature Med. 11:992-97); Hatfield et al., (2005, Curr. Cancer Drug Targets 5:229-48); Vallbohmer et al. (2005, J. Clin. Oncol. 23:3536-44); and Ren et al. (2005, Ann. Surg. 242:55-63), each incorporated herein by reference.

In other embodiments, an anti-angiogenic agent may form a portion of a therapeutic and may be operably linked to a protein of the invention. Exemplary anti-angiogenic agents of use include angiostatin, baculostatin, canstatin, maspin, anti-VEGF antibodies or peptides, anti-placental growth factor antibodies or peptides, anti-Flk-1 antibodies, anti-Flt-1 antibodies or peptides, laminin peptides, fibronectin peptides, plasminogen activator inhibitors, tissue metalloproteinase inhibitors, interferons, interleukin 12, IP-10, Gro-.beta., thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline.

Another aspect of the invention provides kits comprising one or more of the elements described herein, and instructions for the use of those elements. In a preferred embodiment, a kit of the present invention includes a protein of the invention, alone or with a second therapeutic agent. The instructions for this preferred embodiment include instructions for inhibiting the growth of a cancer cell using a protein of the invention, alone or with a second therapeutic agent, and/or instructions for a method of treating a patient having a cancer using the same.

Another aspect of the invention provides a protein based composition of matter, comprising a first protein that specifically binds human IGF-IR; wherein said first protein is between about 4 kD and about 40 kD in MW, has less than about 30 percent amino acid identity to human IGF I or IGF II and is substantially free of microbial contamination making it suitable for in vivo administration. In some embodiments, the composition of matter further comprises a PK moiety, such as PEG or a protein that binds human serum albumin. In some embodiments, the first protein has a disassociation constant of about 1 nM or less for human IGF-IR. In some embodiments, the composition of matter blocks the binding of IGF-I or IGF-II to IGF-IR.

Another aspect of the invention provides a protein based composition of matter, comprising a first protein that binds human IGF-IR with a binding affinity of about 10 nM or less and binds human insulin receptor with a binding affinity of about 1 uM or greater; wherein said first protein is substantially a single domain that has substantially monovalent binding with respect to human IGF-IR, and is substantially free of microbial contamination making it suitable for in vivo administration. In some embodiments, the composition of matter further comprises a second protein linked by a peptide bond to said first protein, wherein said second protein binds human IGF-IR with a binding affinity of about 10 nM or less and binds human insulin receptor with a binding affinity of about 1 uM or greater. In some embodiments, the composition of matter further comprises a second protein linked by at least one peptide bond to said first protein, wherein said second protein binds human serum albumin with a binding affinity of about 300 nM or less. In some embodiments, the composition of matter further comprises a second protein linked by PEG to said first protein, wherein said second protein binds human IGF-IR with a binding affinity of about 10 nM or less and binds human insulin receptor with a binding affinity of about 1 uM or greater. In some embodiments, the first or second protein comprises a fibronectin-based scaffold protein.

Another aspect of the invention provides a PEG based composition of matter, comprising a first PEG linked to a first protein that binds human IGF-IR with a binding affinity of about 100 nM and a second protein that binds a human protein; wherein said PEG is between about 0.5 kD and about 100 kD, and said composition of matter is substantially free of free PEG and is substantially free of microbial contamination making it suitable for in vivo administration. In some embodiments, the second protein binds at least one human tyrosine receptor or at least one human tyrosine receptor ligand with an binding affinity of about 1 nM or less and binds human insulin receptor with a binding affinity of about 1 uM or greater. In some embodiments, one or both proteins is a fibronectin-based scaffold protein.

Another aspect of the invention provides a protein based composition of matter, comprising a first protein that binds human IGF-IR operably linked to a second protein that binds a human protein; wherein said first protein binds human IGF-IR with a binding affinity of about 10 nM or less and binds human insulin receptor with a binding affinity of about 1 uM or greater, and is substantially free of microbial contamination making it suitable for in vivo administration. In some embodiments, the protein based composition of matter, further comprising a PEG moiety operably linked either said first protein or said second protein. In some embodiments, the second protein binds a human tyrosine kinase receptor up-regulated in a human cancer, wherein said second protein binds the human tyrosine kinase receptor with an binding affinity of about 10 nM or less and binds human insulin receptor with a binding affinity of about 1 uM or greater.

Another aspect of the invention provides a protein therapeutic, comprising a first protein moiety that binds human IGF-IR operably linked to a second protein moiety that binds a human therapeutic target; wherein said first protein binds human IGF-IR with a binding affinity of about 10 nM or less and binds human insulin receptor with a binding affinity of about 1 uM or greater, and is substantially free of microbial contamination making it suitable for in vivo administration; and further wherein said second protein binds the human therapeutic target with a binding affinity of about 10 nM or less and binds human insulin receptor with a binding affinity of about 1 uM or greater, and is substantially free of microbial contamination making it suitable for in vivo administration. In some embodiments, the first protein and second protein are a single polypeptide expressed from a microbe.

Another aspect of the invention provides a protein therapeutic, comprising a first protein moiety that binds human IGF-IR operably linked to a PEG that is operable linked to a second protein moiety that binds a human therapeutic target; wherein said first protein moiety binds human IGF-IR with a binding affinity of about 10 nM or less and binds human insulin receptor with a binding affinity of about 1 uM or greater, and is substantially free of microbial contamination making it suitable for in vivo administration; and further wherein said second protein moiety binds the human therapeutic target with a binding affinity of about 10 nM or less and binds human insulin receptor with a binding affinity of about 1 uM or greater, and is substantially free of microbial contamination making it suitable for in vivo administration. In some embodiments, the first protein moiety and second protein moiety collectively have at least 6 disulfide bonds.

Another aspect of the invention provides a protein therapeutic, comprising a first protein moiety that binds human IGF-IR operably linked to a PEG that is operable linked to a second protein moiety that binds a human therapeutic target; wherein said first protein moiety binds human IGF-IR with a binding affinity of about 10 nM or less and binds human insulin receptor with a binding affinity of about 1 uM or greater and binding with respect to human IGF-IR is substantially monovalent, and is substantially free of microbial contamination making it suitable for in vivo administration; and further wherein said second protein moiety binds the human therapeutic target with a binding affinity of about 10 nM or less and binds human insulin receptor with a binding affinity of about 1 uM or greater and binding with respect to human IGF-IR, and is substantially free of microbial contamination making it suitable for in vivo administration.

Another aspect of the invention provides a protein therapeutic, comprising a first protein moiety that binds human IGF-IR operably linked to a biocompatible polymer that is operable linked to a second protein moiety that binds a human therapeutic target; wherein said first protein moiety binds human IGF-IR with a binding affinity of about 10 nM or less and binds human insulin receptor with a binding affinity of about 1 uM or greater, and is substantially free of microbial contamination making it suitable for in vivo administration; further wherein said second protein moiety binds the human therapeutic target with a binding affinity of about 10 nM or less and binds human insulin receptor with a binding affinity of about 1 uM or greater, and is substantially free of microbial contamination making it suitable for in vivo administration; and further wherein said first protein moiety and second protein moiety have affinities for their respective targets that are optimized to minimize non-therapeutic affects and to maximize therapeutic benefit of binding to more than one therapeutic target. In some embodiments, the polypeptide has a protease site that is cleavable by a protease in the blood or target tissue.

Another aspect of the invention provides a protein therapeutic, comprising a first protein that binds human IGF-IR operably linked to a PEG that is operable linked to a second protein that binds a human protein; wherein said first protein binds human IGF-IR with a binding affinity of about 10 nM or less and binds human insulin receptor with a binding affinity of about 1 uM or greater and is antagonist of human IGF-IR, and is substantially free of microbial contamination making it suitable for in vivo administration; and further wherein said second protein binds the human therapeutic target with a binding affinity of about 10 nM or less and binds human insulin receptor with a binding affinity of about 1 uM or greater, and is substantially free of microbial contamination making it suitable for in vivo administration. In some embodiments, the first protein inhibits cell proliferation, has a Tm of at least 55 C, and non-wildtype cys or lys in region of its amino acid sequence that does not substantially interfere with binding to human IGF-IR. In some embodiments, the protein therapeutic has a half life in in vivo of at least one day with IV administration. In some embodiments, the protein therapeutic has an exposure level at a concentration of at least about 10 times the binding affinity of said first protein to human IGF-IR for over 24 hours in a rodent after administration. In some embodiments, the first and/or second protein is a fibronectin based scaffold.

Another aspect of the invention provides a cell, comprising a polynucleotide encoding one or more protein described herein. In some embodiments, the cell is a yeast engineered to produce desired glycosylations on any of the proteins described herein. In some embodiments, the cell is blue green algae. In some embodiments, the cell is a mammalian cell engineered to produce desired glycosylations on any of the proteins described herein. In some embodiments, the protein is a fibronectin based scaffold and optionally has a polynucleotide codon optimized for expression in a cell.

BRIEF DESCRIPTION OF THE FIGURES

FIG. 5A shows results from 3 libraries obtained by randomization of one loop each from clone 218C04. Libraries of a trillion mRNA/cDNA-protein fusions were bound to 100 nM biotinylated IGF-IR in solution and captured on streptavidin-coated magnetic beads. The cDNA was eluted, amplified by PCR, and used to generate new libraries of mRNA/cDNA-protein fusions. The processes of library construction and affinity selection were repeated until the percentage bound to IGF-IR exceeded 1%, as measured by quantitative PCR. At this point, the optimized loops were amplified and recombined to make a single library containing all three optimized loops (FIG. 5B). mRNA/cDNA-protein fusions from this library were captured on IGF-IR-coated beads followed by 3 rounds of PROfusion with 1 nM biotinylated IGF-IR. In each case, binding percentage was measured by quantitative PCR (FIG. 5C).

FIGS. 15A-15R show SECs for clones 385A08 (FIG. 15A), 385B04 (FIG. 15B), 385D05 (FIG. 15C), 385E01 (FIG. 15D), 385E04 (FIG. 15E), 385F08 (FIG. 15F), 385H06 (FIG. 15G), 386A03 (FIG. 15H), 386A05 (FIG. 15I), 386A07 (FIG. 15J), 386F01 (FIG. 15K), 386F10 (FIG. 15L), 386F11 (FIG. 15M), 386H05 (FIG. 15N), 387A03 (FIG. 15O), 387A09 (FIG. 15P), 387B01 (FIG. 15Q), and 387C02 (FIG. 15R).

Figure 30A:
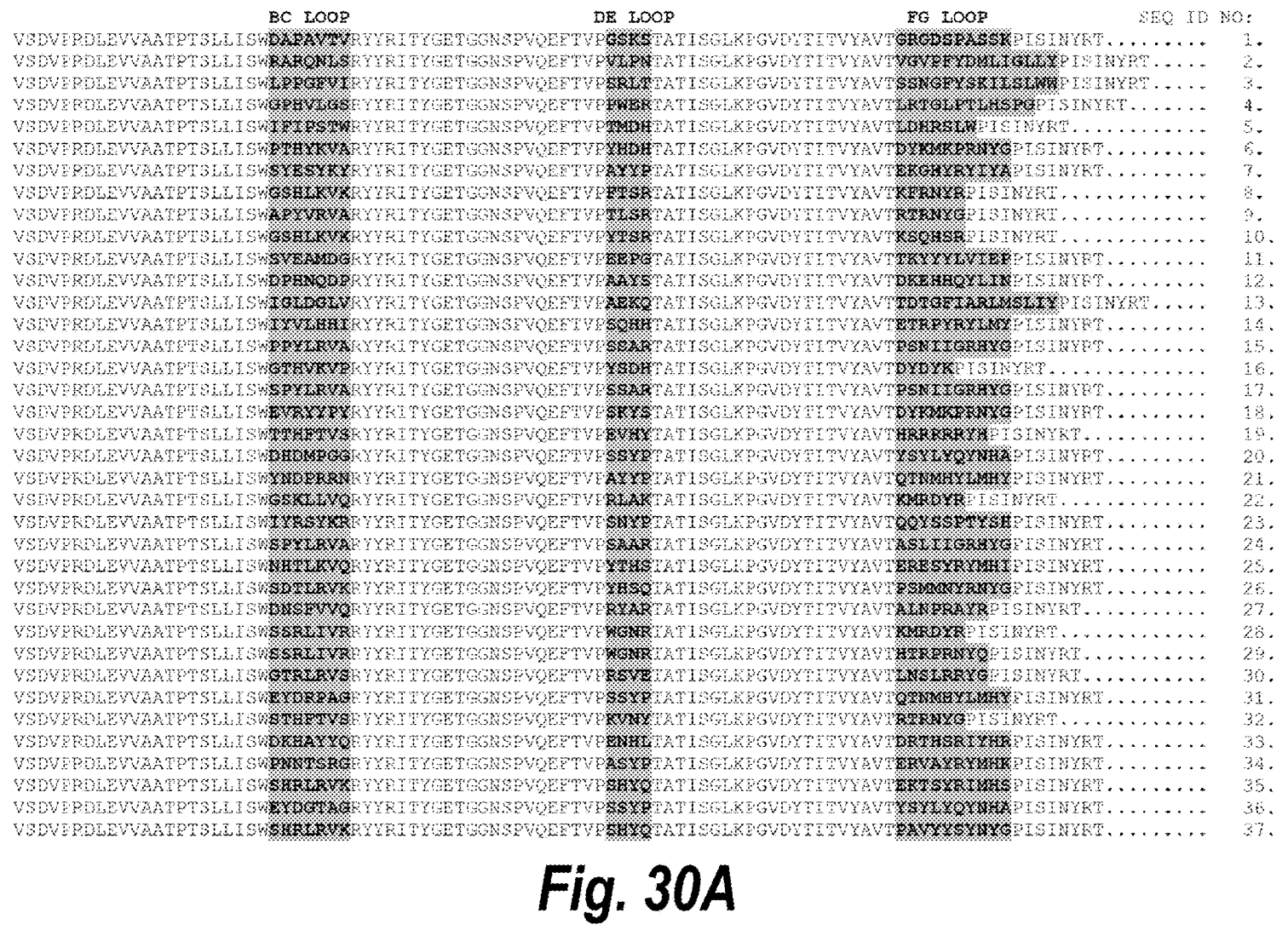
Figure 30B:
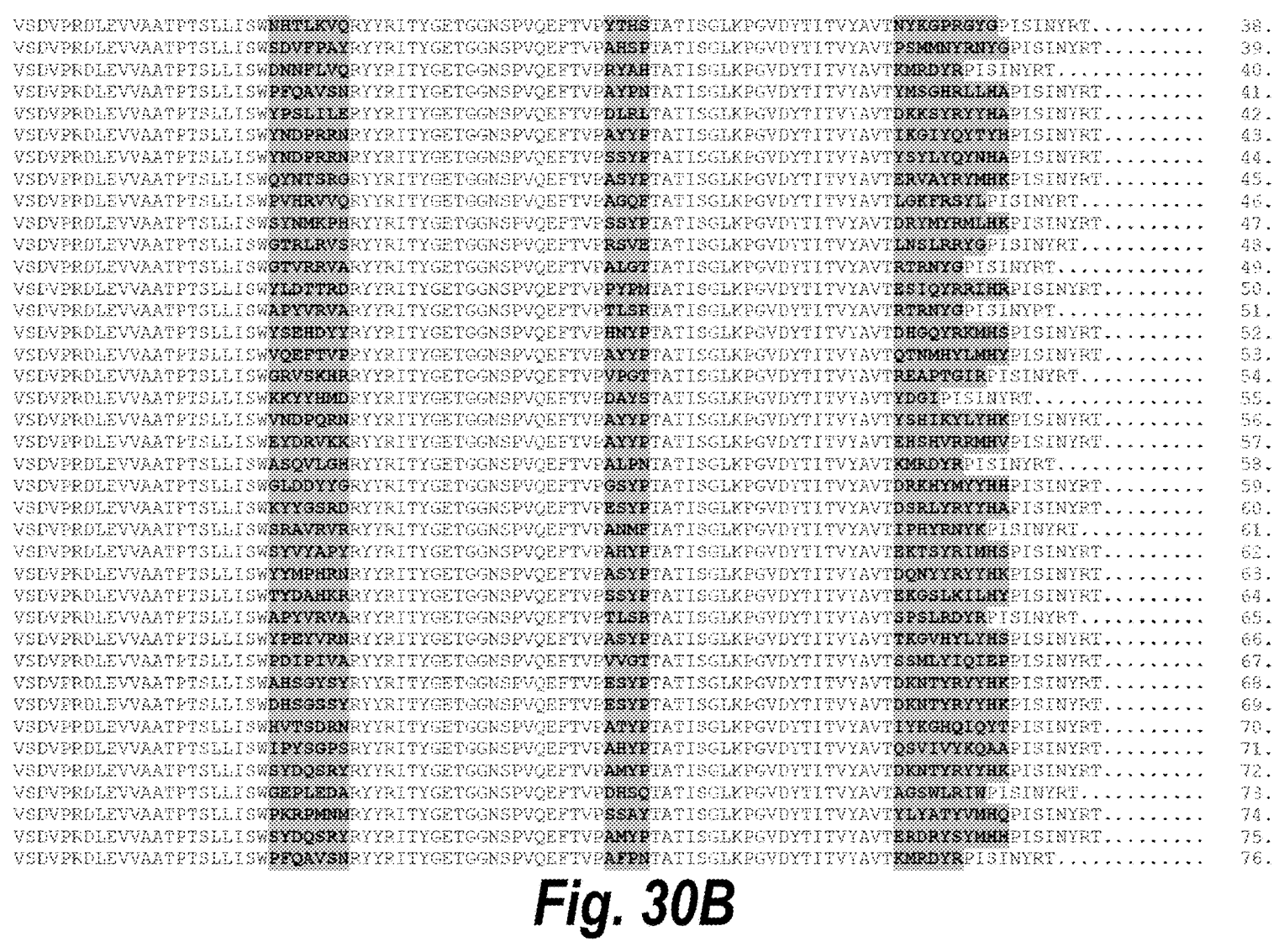
Figure 30C:
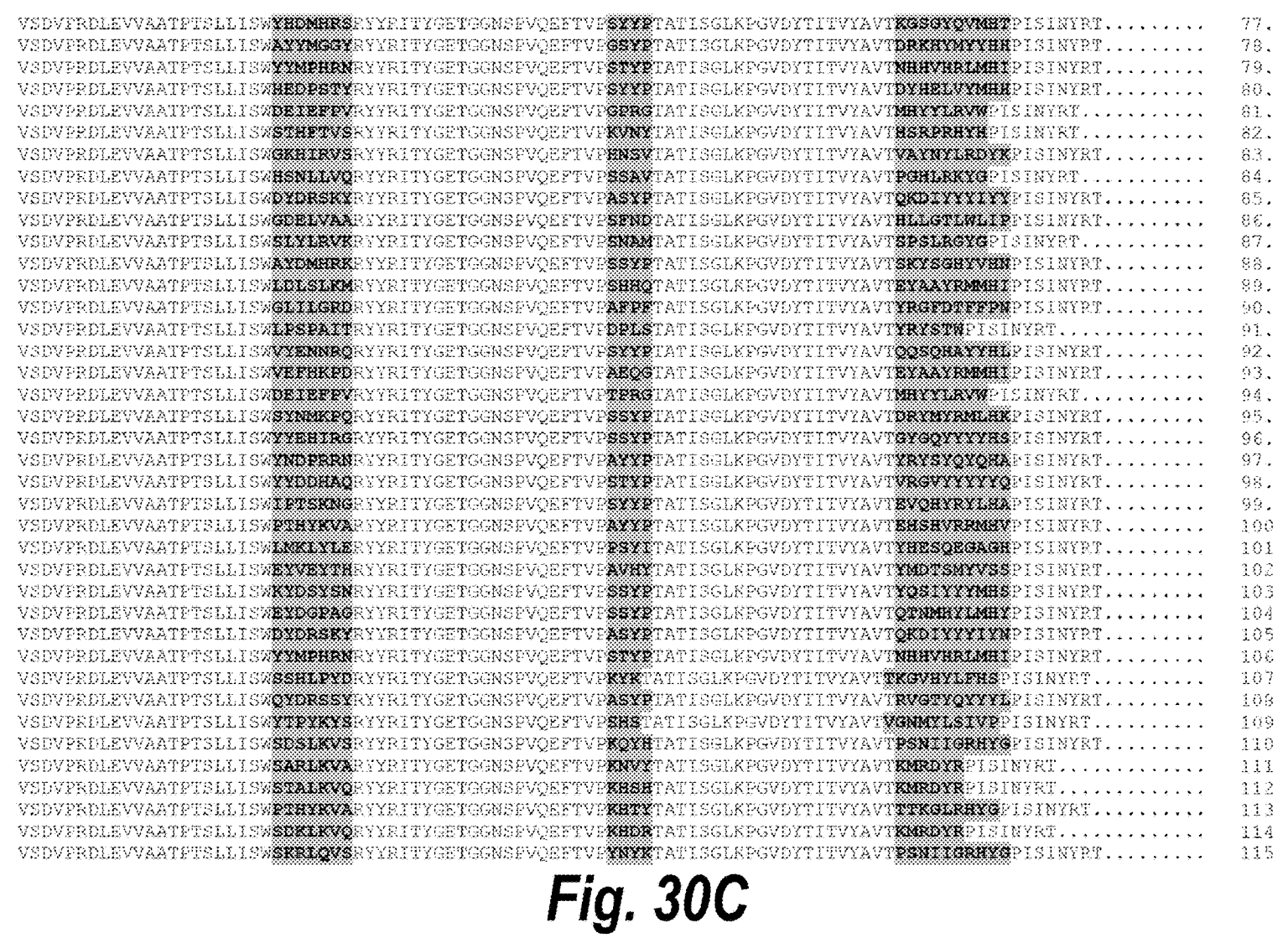
Figure 30D:
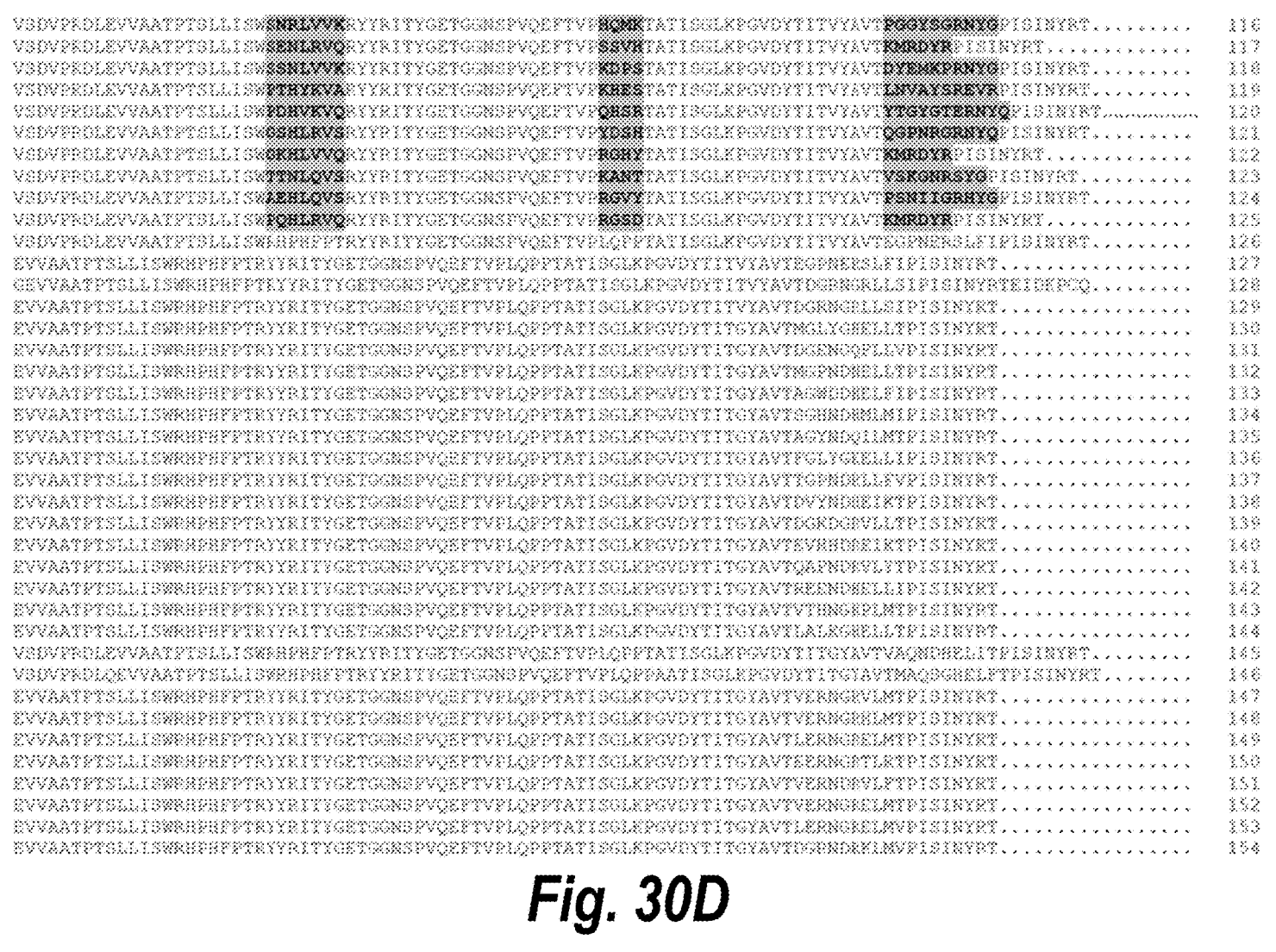
Figure 30E:
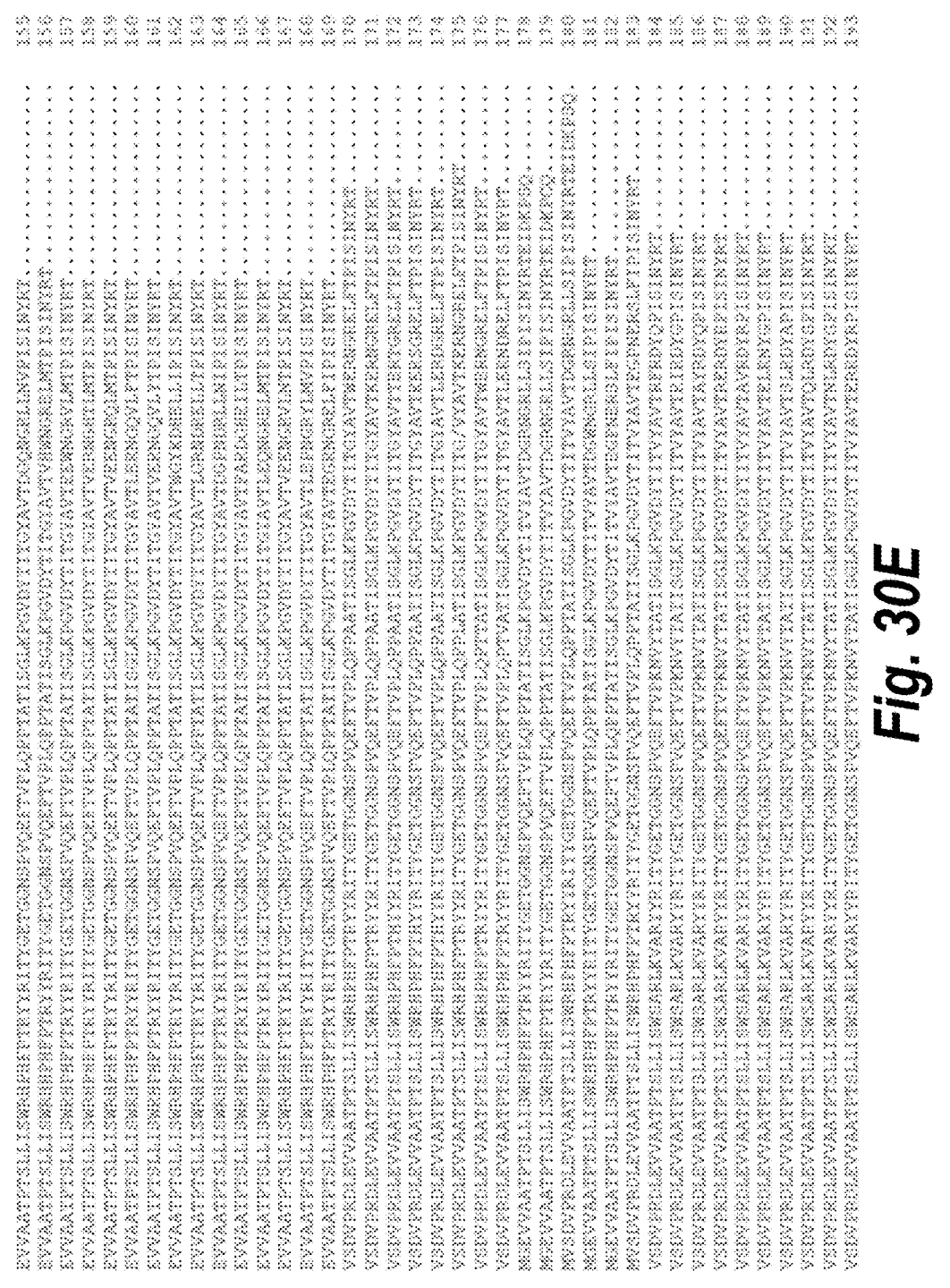
Figure 30F:
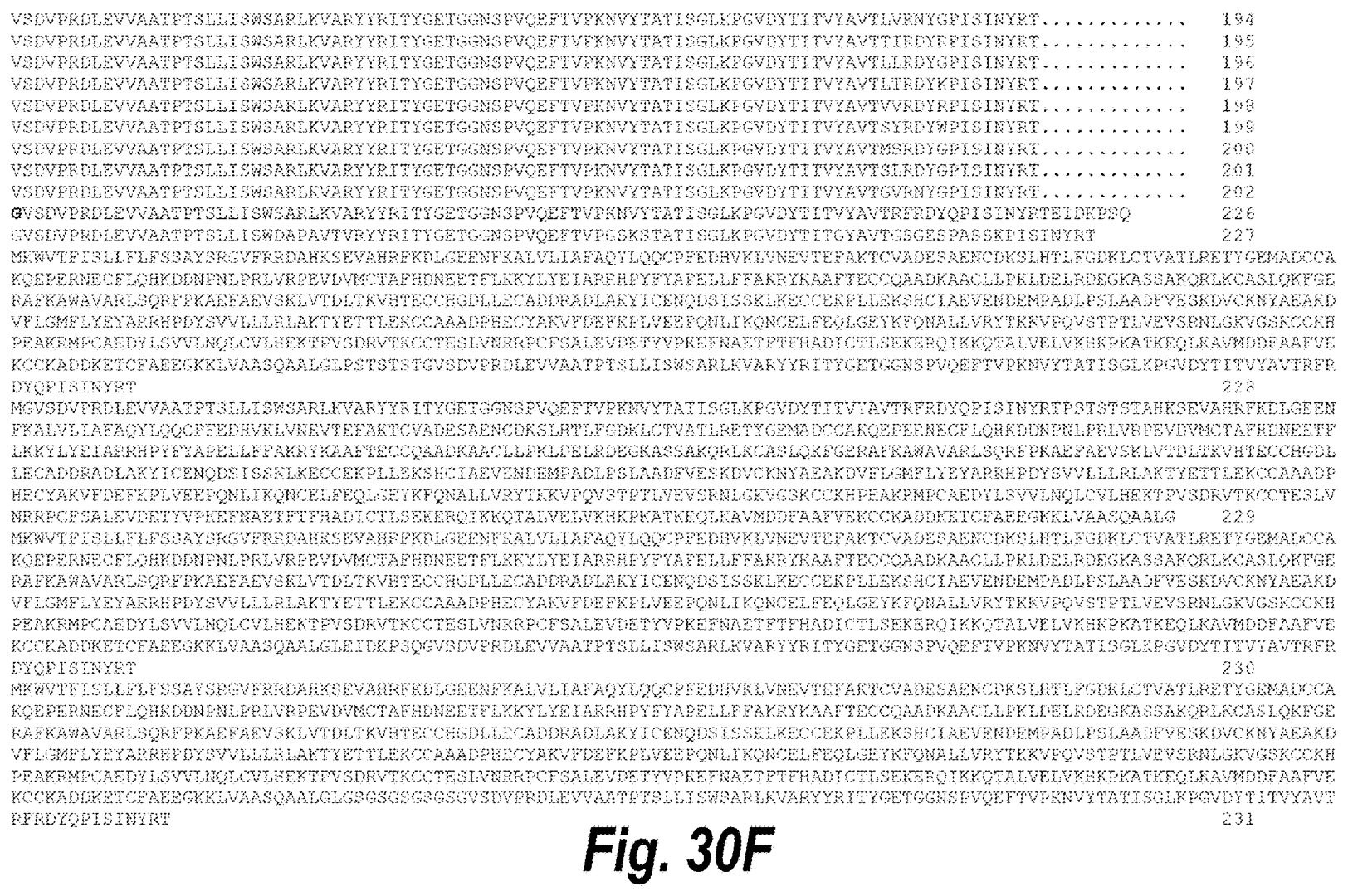
Figure 30H:
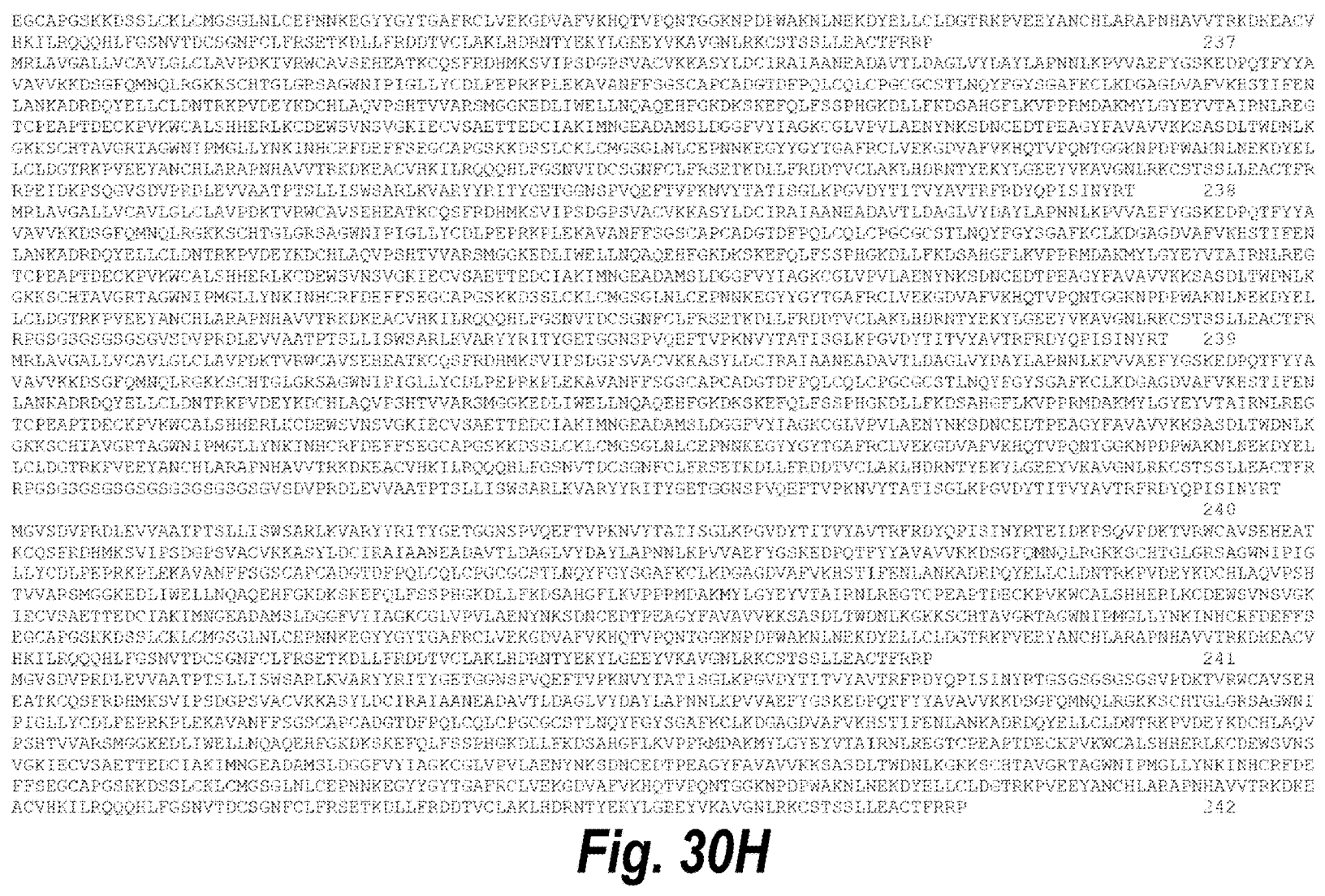
Figure 30I:
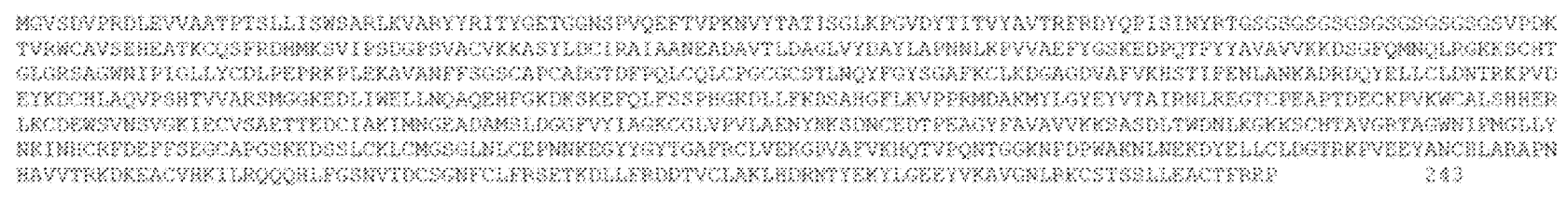

FIGS. 30A-30I depicts the amino acid sequences of the wild-type tenth module of the human fibronectin type III domain (SEQ ID NO: 1), the IGF-IR competitive clones identified in Example 2 (SEQ ID NOS: 2-109), the optimized 218C04 clones from Example 8 (SEQ ID NOS: 110-125), exemplary VEGFR-2 binding $^{10}$Fn3 polypeptides (SEQ ID NOS: 126-183), the optimized 338A06 clones from Example 18 (SEQ ID NOS: 184-202), the IGF-IR binding clone 385A08 control from FIG. 21 (SEQ ID NO: 226), the fibronectin scaffold protein control from FIG. 23 (SEQ ID NO: 227), exemplary HSA-IGF-IR fusion proteins (SEQ ID NOS: 228-235), and exemplary transferrin-IGF-IR fusion proteins (SEQ ID NOS: 236-243). The BC, DE, and FG loops are shaded in SEQ ID NOS: 1-125. FIG. 30A shows SEQ ID NOs: 1-37, FIG. 30B shows SEQ ID NOs: 38-76, FIG. 30C shows SEQ ID NOs: 77-115, FIG. 30D shows SEQ ID NOs: 116-154, FIG. 30E shows SEQ ID NOs: 155-193, FIG. 30F shows SEQ ID NOs: 194-231, FIG. 30G shows SEQ ID NOs: 232-236, FIG. 30H shows SEQ ID NOs: 237-242, and FIG. 30I shows SEQ ID NO: 243.

DETAILED DESCRIPTION OF THE INVENTION

Definitions

The methodology described herein has been successfully used to develop proteins of the invention, that include but are not limited to, single domain IGF-IR binding polypeptides derived from at least two related groups of protein structures: those proteins having an immunoglobulin fold and those proteins having an immunoglobulin-like fold.

By a "polypeptide" is meant any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D). The term "single domain polypeptide" is used to indicate that the target binding activity (e.g., IGF-IR binding activity) of the subject polypeptide is situated within a single structural domain, as differentiated from, for example, antibodies and single chain antibodies, where antigen binding activity is generally contributed by both a heavy chain variable domain and a light chain variable domain. It is contemplated that a plurality of single domain polypeptides of the sort disclosed herein could be connected to create a composite molecule with increased avidity. Likewise, a single domain polypeptide may be attached (e.g., as a fusion protein) to any number of other polypeptides, such as fluorescent polypeptides, targeting polypeptides and polypeptides having a distinct therapeutic effect.

The term "PK" is an acronym for "pharmokinetic" and encompasses properties of a compound including, by way of example, absorption, distribution, metabolism, and elimination by a subject. A "PK modulation protein" or "PK moiety" refers to any protein, peptide, or moiety that affects the pharmokinetic properties of a biologically active molecule when fused to or administered together with the biologically active molecule. Examples of a PK modulation protein or PK moiety include PEG, human serum albumin (HSA) binders (as disclosed in U.S. Publication Nos. 20050287153 and 20070003549), human serum albumin, Fc or Fc fragments, and sugars (e.g., sialic acid).

Figure 24:
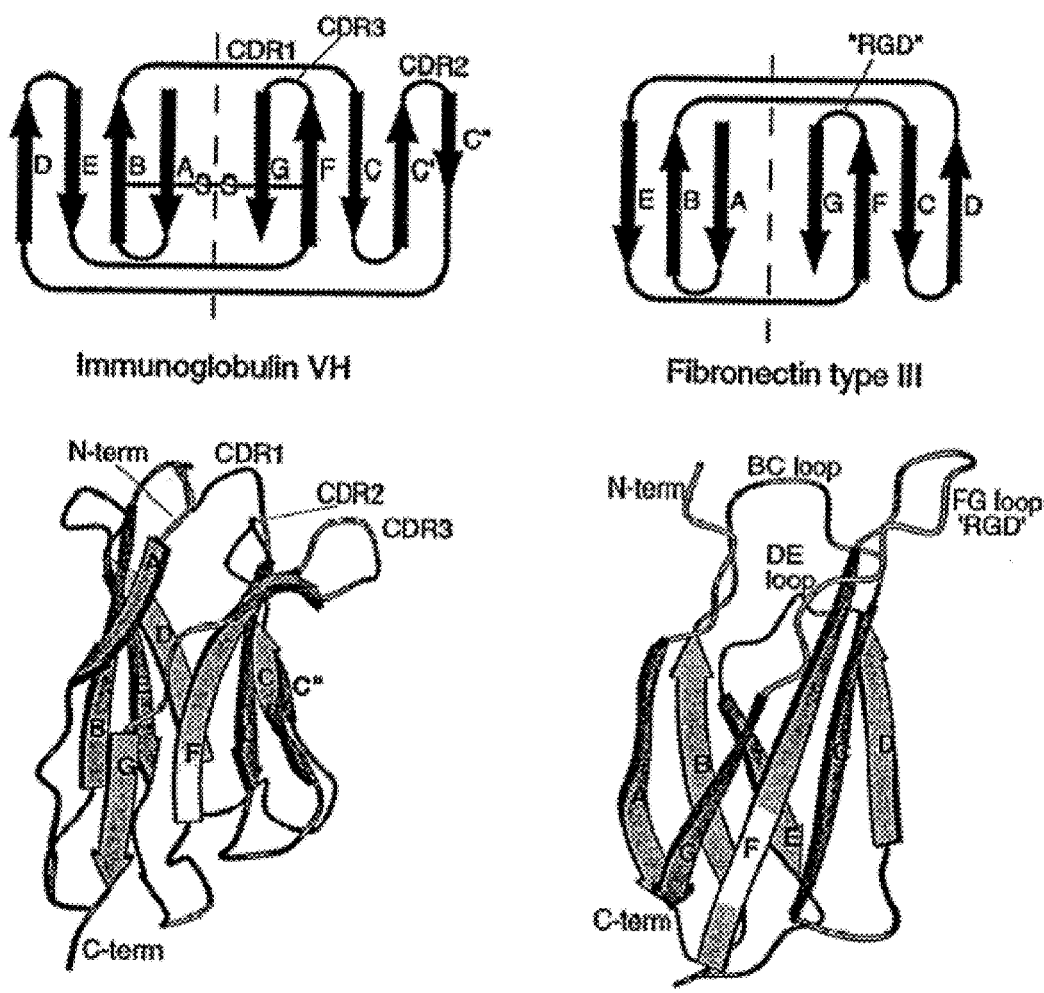
FIG. 24. $V_H$ and $^{10}Fn3$ domain structures. The structural organization is depicted for a single domain polypeptide having an immunoglobulin fold (a $V_H$ domain of an immunoglobulin, left side) and a single domain polypeptide having an immunoglobulin-like fold (a $^{10}Fn3$ domain, right side).

Single domain polypeptides of either the immunoglobulin or immunoglobulin-like scaffold will tend to share certain structural features. For example, the polypeptide may comprise between about 80 and about 150 amino acids, which amino acids are structurally organized into a set of beta or beta-like strands, forming beta sheets, where the beta or beta-like strands are connected by intervening loop portions. Examples of the structural organization for the heavy chain variable domain and the $^{10}$Fn3 domain are shown in FIG. 24. The beta sheets form the stable core of the single domain polypeptides, while creating two "faces" composed of the loops that connect the beta or beta-like strands. As described herein, these loops can be varied to create customized ligand binding sites, and, with proper control, such variations can be generated without disrupting the overall stability of the protein. In antibodies, three of these loops are the well-known Complementarity Determining Regions (or "CDRs").

Scaffolds for formation of a single domain polypeptides should be highly soluble and stable in physiological conditions. Examples of immunoglobulin scaffolds are the single domain $V_H$ or $V_L$ scaffold, as well as a single domain camelid $V_{HH}$ domain (a form of variable heavy domain found in camelids) or other immunoglobulin variable domains found in nature or engineered in the laboratory. In the single domain format disclosed herein, an immunoglobulin polypeptide need not form a dimer with a second polypeptide in order to achieve binding activity. Accordingly, any such polypeptides that naturally contain a cysteine which mediates disulfide cross-linking to a second protein can be altered to eliminate the cysteine. Alternatively, the cysteine may be retained for use in conjugating additional moieties, such as PEG, to the single domain polypeptide.

Other scaffolds may be non-antibody scaffold proteins. By "non-antibody scaffold protein or domain" is meant a non-antibody polypeptide having an immunoglobulin-like fold. By "immunoglobulin-like fold" is meant a protein domain of between about 80-150 amino acid residues that includes two layers of antiparallel beta-sheets, and in which the flat, hydrophobic faces of the two beta-sheets are packed against each other. An example of such a scaffold is the "fibronectin-based scaffold protein", by which is meant a polypeptide based on a fibronectin type III domain (Fn3). An example of fibronectin-based scaffold proteins are Adnectins™ (Adnexus Therapeutics, Inc.). Fibronectin is a large protein which plays essential roles in the formation of extracellular matrix and cell-cell interactions; it consists of many repeats of three types (types I, II, and III) of small domains (Baron et al., 1991). Fn3 itself is the paradigm of a large subfamily which includes portions of cell adhesion molecules, cell surface hormone and cytokine receptors, chaperoning, and carbohydrate-binding domains. For reviews see Bork & Doolittle, Proc Natl Acad Sci USA. 1992 Oct. 1; 89(19):8990-4; Bork et al., J Mol Biol. 1994 Sep. 30; 242(4):309-20; Campbell & Spitzfaden, Structure. 1994 May 15; 2(5):333-7; Harpez & Chothia, J Mol Biol. 1994 May 13; 238(4):528-39).

Preferably, the fibronectin-based scaffold protein is a "10Fn3" scaffold, by which is meant a polypeptide variant based on the tenth module of the human fibronectin type III protein in which one or more of the solvent accessible loops has been randomized or mutated, particularly one or more of the three loops identified as the BC loop (amino acids 23-30), DE loop (amino acids 52-56) and FG loop (amino acids 77-87) (the numbering scheme is based on the sequence on the wild-type tenth module of the human fibronectin type III domain: VSDVPRDLEVVAATPT-SLLISWDAPAVTVRYYRITYGETGGNSPVQEFTVPG-SKSTAT ISGLKPGVDYTITVYAVTGRGDSPASSKPIS-INYRT (SEQ ID NO:1). Preferably, fibronectin-based scaffold proteins are based on SEQ ID NO:1.

A variety of mutant 10Fn3 scaffolds have been reported. In one aspect, one or more of Asp 7, Glu 9, and Asp 23 is replaced by another amino acid, such as, for example, a non-negatively charged amino acid residue (e.g., Asn, Lys, etc.). These mutations have been reported to have the effect of promoting greater stability of the mutant 10Fn3 at neutral pH as compared to the wild-type form (See, PCT Publication No. WO02/04523). A variety of additional alterations in the 10Fn3 scaffold that are either beneficial or neutral have been disclosed. See, for example, Batori et al., Protein Eng. 2002 December; 15(12):1015-20; Koide et al., Biochemistry 2001 Aug. 28; 40(34):10326-33.

Both variant and wild-type $^{10}$Fn3 proteins are characterized by the same structure, namely seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO:1, the AB loop corresponds to residues 15-16, the BC loop corresponds to residues 22-30, the CD loop corresponds to residues 39-45, the DE loop corresponds to residues 51-55, the EF loop corresponds to residues 60-66, and the FG loop corresponds to residues 76-87. As shown in FIG. 24, the BC loop, DE loop, and FG loop are all located at the same end of the polypeptide. Similarly, immunoglobulin scaffolds tend to have at least seven beta or beta-like strands, and often nine beta or beta-like strands. Fibronectin-based scaffold proteins can include other Fn3 type fibronectin domains as long as they exhibit useful activities and properties similar to $^{10}$Fn3 type domains.

A single domain polypeptide disclosed herein may have at least five to seven beta or beta-like strands distributed between at least two beta sheets, and at least one loop portion connecting two beta or beta-like strands, which loop portion participates in binding to IGF-IR, with the binding characterized by a dissociation constant that is less than $1\times10^{-6}$M, and preferably less than $1\times10^{-8}$M. As described herein, polypeptides having a dissociation constant of less than $5\times10^{-9}$M are particularly desirable for therapeutic use in vivo to inhibit ligand signaling. Polypeptides having a dissociation constant of between $1\times10^{-6}$M and $5\times10^{-9}$M may be desirable for use in detecting or labeling, ex vivo or in vivo, IGF-IR proteins.

Optionally, the "IGF-IR binding protein" will bind specifically to IGF-IR relative to other related proteins from the same species. By "specifically binds" is meant a polypeptide that recognizes and interacts with a target protein (e.g., IGF-IR) but that does not substantially recognize and interact with other molecules in a sample, for example, a biological sample. In preferred embodiments a polypeptide of the invention will specifically bind a IGF-IR with a $K_D$ at least as tight as 500 nM. Preferably, the polypeptide will specifically bind a IGF-IR with a $K_D$ of 1 pM to 500 nM, more preferably 1 pM to 100 nM, more preferably 1 pM to 10 nM, and most preferably 1 pM to 1 nM or lower.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays known in the art for evaluating such antibody effector functions.

Figure 3:
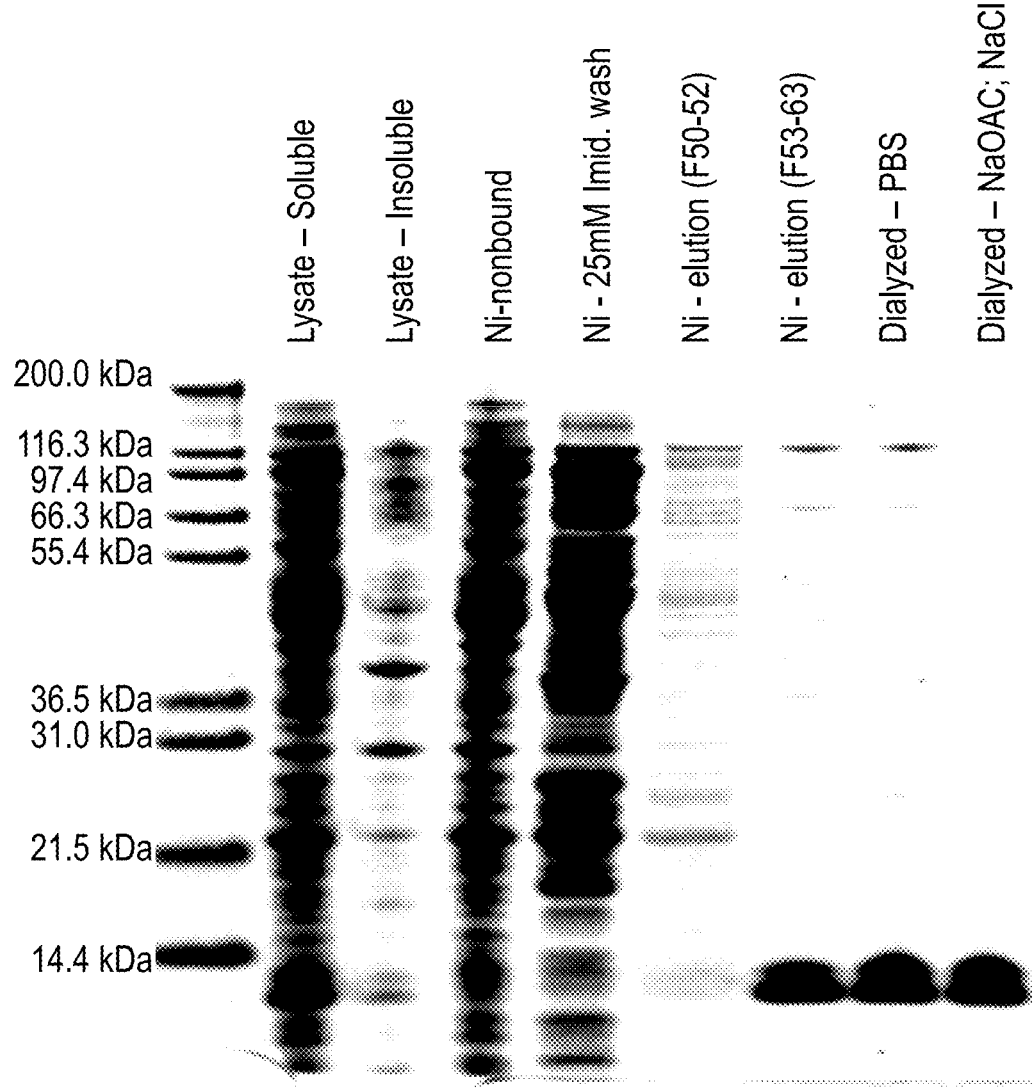
FIG. 3. SDS PAGE of Purification Steps of Human IGF-IR Competitive Clone 218C04. An SDS PAGE gel illustrating a typical mid-scale purification and quality of final product of a human IGF-IR competitive fibronectin scaffold domain protein, the lead clone 218C04 in this instance, as described in Example 35. Samples are loaded onto a 10% NuPAGE minigel and stained using Sypro-orange.

A "native sequence Fc region" comprises an amino acid sequence identical to the amino acid sequence of an Fc region found in nature. FIG. 3 provides amino acid sequences of native sequence human and murine IgG Fc regions.

A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

A "polypeptide chain" is a polypeptide wherein each of the domains thereof is joined to other domain(s) by peptide bond(s), as opposed to non-covalent interactions or disulfide bonds.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

Targets may also be fragments of said targets. Thus a target is also a fragment of said target, capable of eliciting an immune response. A target is also a fragment of said target, capable of binding to a single domain antibody raised against the full length target.

A fragment as used herein refers to less than 100% of the sequence (e.g., 99%, 90%, 80%, 70%, 60%, 50%, 40%, 30%, 20%, 10% etc.), but comprising 5, 6, 7, 8, 9, 10, 12, 13, 14, 15, 16, 17, 18, 19, 20, 21, 22, 23, 24, 25 or more amino acids. A fragment is of sufficient length such that the interaction of interest is maintained with affinity of $1 \times 10^{-6}$M or better.

A fragment as used herein also refers to optional insertions, deletions and substitutions of one or more amino acids which do not substantially alter the ability of the target to bind to a single domain antibody raised against the wild-type target. The number of amino acid insertions deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A protein of the invention that "induces cell death" is one which causes a viable cell to become nonviable. The cell is generally one which expresses the antigen to which the protein binds, especially where the cell overexpresses the antigen. Preferably, the cell is a cancer cell, e.g., a breast, ovarian, stomach, endometrial, salivary gland, lung, kidney, colon, thyroid, pancreatic or bladder cell. In vitro, the cell may be, for example, a SKBR3, BT474, Calu 3, MDA-MB453, MDA-MB-361 or SKOV3 cell. Cell death in vitro may be determined in the absence of complement and immune effector cells to distinguish cell death induced by antibody dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the protein of the invention is able to induce cell death, loss of membrane integrity as evaluated by uptake of propidium iodide (PI), trypan blue (see Moore et al. Cytotechnology 17:1-11 (1995)) or 7AAD can be assessed relative to untreated cells.

A protein of the invention that "induces apoptosis" is one that induces programmed cell death as determined by binding of apoptosis related molecules or events, such as annexin V, fragmentation of DNA, cell shrinkage, dilation of endoplasmic reticulum, cell fragmentation, and/or formation of membrane vesicles (called apoptotic bodies). The cell is one which expresses the antigen to which the protein binds and may be one which overexpresses the antigen. The cell may be a tumor cell, e.g. a breast, ovarian, stomach, endometrial, salivary gland, lung, kidney, colon, thyroid, pancreatic or bladder cell. In vitro, the cell may be, for example, SKBR3, BT474, Calu 3 cell, MDA-MB453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering as disclosed in the example herein; and nuclear/chromatin condensation along with DNA fragmentation can be evaluated by any increase in hypodiploid cells. Preferably, the protein that induces apoptosis is one which results in about 2 to 50 fold, preferably about 5 to 50 fold, and most preferably about 10 to 50 fold, induction of annexin binding relative to untreated cell in an annexin binding assay using cells expressing the antigen to which the protein of the invention binds.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the time to disease progression (TTP) and/or determining the response rates (RR).

Overview

The present inventors have invented novel proteins of the invention that bind IGF-IR with advantageous properties, including, but not limited to: monovalent or multivalent binding modes (e.g., one or more than one domains that bind a particular target (including IGF-IR and other tyrosine kinase receptors); high selectivity for the desired target over other receptors, particularly with respect to proteins binding IGF-IR selectively over the insulin receptor; tunable affinity, including a range from about 100 nM to less than about 10 pM (including femtomolar affinity); specific antagonist activity while having minimal or undetectable agonist activity; blocking of IGF-I or IGF-II binding or activation; monospecific or multispecific binding to desired targets; single or multiple epitope binding; prolonged serum half life in rat; sub-cutaneous (SC) or intravenous (IV) dosing; small size (e.g. ~5 kDa to ~40 kDa); Tm's over about 55° C. or over about 60° C.; and substantially monomeric nature (e.g. single peak on size exclusion chromatography (SEC), such as about 90% of the area, about 95% of the area or about 98% of the area).

Making and Testing of Novel Proteins by the Trillions

As one aspect of the invention, an estimated 1-5 trillion different protein variants were made, along with 1-5 trillion RNA and DNA variants corresponding to such proteins and encoding such proteins. The proteins that were made were tested for binding to human IGF-IR, and in some instances were further expressed and purified and subjected to a variety of biological, biochemical and biophysical assays and measurements to assist in identifying suitable useful proteins, particularly therapeutics.

In addition, over 5000 protein variants were expressed in E. coli, using examples of vectors and polynucleotides of the invention, and tested for expression levels and a variety of biological, biochemical and biophysical assays. Depending on the results of these measurements different, selected proteins were advanced to make further optimized variations with characteristics described herein. Many such proteins were also tested for selectivity with respect the insulin receptor.

The inventors were the first to apply this type of extensive assessment of protein and domain binding to IGF-IR. One way to rapidly make and test proteins of the invention for this type of assessment is the nucleic acid-protein fusion technology of Adnexus Therapeutics, Inc. This disclosure describes the use of such in vitro expression and tagging technology, termed PROfusion™, that exploits nucleic acid-protein fusions (RNA- and DNA-protein fusions) to identify novel single and multiple domain polypeptides and amino acid motifs that are important for binding to IGF-IR and other protein including tyrosine kinase receptors. Nucleic acid-protein fusion technology is a technology that covalently couples a protein to its encoding genetic information. PROfusion™ technology was used to screen collections of nucleic acids encoding single domain polypeptides constructed using a scaffold based on the human fibronectin type three domain ($^{10}$Fn3) or constructed from the variable domains of antibody light chains. The expressed polypeptides, termed a "library" of scaffold proteins, were screened for polypeptides that could bind a target with high affinity. We isolated from this library of scaffold proteins novel single domain polypeptides that bind to IGF-IR and that inhibit IGF-IR biological activities. Furthermore, it was discovered that many independently randomized loops situated in immunoglobulin or immunoglobulin-like scaffolds tended to converge to a related set of consensus sequences that participated in IGF-IR binding. Therefore, it is expected that polypeptides having these consensus sequences will be useful as IGF-IR binding agents even when separated from the protein context in which they were identified. See, for example, examples and tables herein. Such polypeptides may be used as independent, small peptide IGF-IR binding agents or may be situated in other proteins, particularly proteins that share an immunoglobulin or immunoglobulin-like fold. (For a detailed description of the RNA-protein fusion technology and fibronectin-based scaffold protein library screening methods see Szostak et al., U.S. Pat. Nos. 6,258,558; 6,261,804; 6,214,553; 6,281,344; 6,207,446; 6,518,018; PCT Publication Nos. WO00/34784; WO01/64942; WO02/032925; and Roberts and Szostak, Proc Natl. Acad. Sci. 94:12297-12302, 1997, herein incorporated by reference.)

As discussed above, the present disclosure demonstrates that single domain polypeptides having certain desirable properties, such as high affinity binding to IGF-IR, antagonist effects with respect to one or more of ligands of such receptor and improved pharmacokinetics, can be used as effective anti-cancer agents. While it is expected that the effectiveness of such polypeptides as anti-cancer agents is related to the role of IGF ligand and receptors in cancer, we do not wish to be bound to any particular mechanism.

To our knowledge, the present disclosure represents the first successful effort to use an Fn3-based polypeptide designed to achieve a therapeutic effect in vitro and in vivo for IGF-IR. Many of the improvements and discoveries made in achieving in vivo effectiveness will be broadly applicable to other Fn3-based polypeptides to this and other targets and other protein moieties and domains, generally proteins less than about 50 kDa or about 40 kDa. In other words, although ligand binding properties of an Fn3-based polypeptide will generally be determined by a relatively small number of amino acids situated in solvent accessible loop regions, other features, such as pharmacokinetic features, of Fn3-based polypeptides will tend to be determined by the majority of the protein that is not directly involved in ligand binding and that is conserved from protein to protein regardless of the target protein. This has been the case with antibodies, where a few loops, called CDR regions, mediate antigen binding, while other features of in vivo antibody behavior are largely dictated by the conserved framework regions and constant domains.

Additional Protein Embodiments

Proteins of the invention include a single domain polypeptide described herein which is generally a polypeptide that binds to a target, such as IGF-IR, and where target binding activity situated within a single structural domain, as differentiated from, for example, antibodies and single chain antibodies, where antigen binding activity is generally contributed by both a heavy chain variable domain and a light chain variable domain. The disclosure also provides larger proteins that may comprise single domain polypeptides that bind to target. For example, a plurality of single domain polypeptides may be connected to create a composite molecule with increased avidity or multivalency. Likewise, a single domain polypeptide may be attached (e.g., as a fusion protein) to any number of other polypeptides. In certain aspects a single domain polypeptide may comprise at least five to seven beta or beta-like strands distributed among at least two beta sheets, as exemplified by immunoglobulin and immunoglobulin-like domains. A beta-like strand is a string of amino acids that participates in the stabilization of a single domain polypeptide but does not necessarily adopt a beta strand conformation. Whether a beta-like strand participates in the stabilization of the protein may be assessed by deleting the string or altering the sequence of the string and analyzing whether protein stability is diminished. Stability may be assessed by, for example, thermal denaturation and renaturation studies. Preferably, a single domain polypeptide will include no more than two beta-like strands. A beta-like strand will not usually adopt an alpha-helical conformation but may adopt a random coil structure. In the context of an immunoglobulin domain or an immunoglobulin-like domain, a beta-like strand will most often occur at the position in the structure that would otherwise be occupied by the most N-terminal beta strand or the most C-terminal beta strand. An amino acid string which, if situated in the interior of a protein sequence would normally form a beta strand, may, when situated at a position closer to an N- or C-terminus, adopt a conformation that is not clearly a beta strand and is referred to herein as a beta-like strand.

In certain embodiments, the disclosure provides single domain polypeptides that bind to IGF-IR. Preferably the single domain polypeptides bind to human IGF-IR and a model species IGF-IR. A single domain polypeptide may comprise between about 80 and about 150 amino acids that have a structural organization comprising: at least seven beta strands or beta-like strands distributed between at least two beta sheets, and at least one loop portion connecting two beta strands or beta-like strands, which loop portion participates in binding to IGF-IR. In other words a loop portion may link two beta strands, two beta-like strands or one beta strand and one beta-like strand. Typically, one or more of the loop portions will participate in IGF-IR binding, although it is possible that one or more of the beta or beta-like strand portions will also participate in IGF-IR binding, particularly those beta or beta-like strand portions that are situated closest to the loop portions. A single domain polypeptide may comprise a structural unit that is an immunoglobulin domain or an immunoglobulin-like domain. A single domain polypeptide may bind to any part of IGF-IR, although polypeptides that bind to an extracellular domain of a IGF-IR are preferred. Binding may be assessed in terms of equilibrium constants (e.g., dissociation, $K_D$) and in terms of kinetic constants (e.g., on rate constant, $k_{on}$ and off rate constant, $k_{off}$). A single domain polypeptide will typically be selected to bind to IGF-IR with a $K_D$ of less than about $10^{-6}$M, or less than about $10^{-7}$M, about $5\times10^{-8}$M, about $10^{-8}$M or less than about $10^{-9}$M. IGF-IR binding polypeptides may compete for binding with one, or two or more members of the IGF family, particularly IGF-I and IGF-II, and may inhibit one or more IGF-IR-mediated biological events, such as proliferation of cancer cells and cancer metastasis. IGF-IR binding polypeptides may be used for therapeutic purposes as well as for any purpose involving the detection or binding of IGF-IR. Polypeptides for therapeutic use will generally have a $K_D$ of less than $5\times10^{-8}$M, less than $10^{-8}$M or less than $10^{-9}$M, although higher $K_D$ values may be tolerated where the $k_{off}$ is sufficiently low or the $k_{on}$ is sufficiently high. In certain embodiments, a single domain polypeptide that binds to IGF-IR will comprise a consensus or one or more sequences of the IGF-IR binding sequences selected from the IGF-IR binding clones described herein. Preferably, such sequence will be situated in a loop, particularly the BC, DE, and FG loops as described in PCT Publication No. WO2005/056764A2 by Chen et al.

In certain embodiments, the single domain polypeptide comprises an immunoglobulin (Ig) variable domain. The Ig variable domain may, for example, be selected from the group consisting of: a human $V_L$ domain, a human $V_H$ domain and a camelid $V_{HH}$ domain. One, two, three or more loops of the Ig variable domain may participate in binding to IGF-IR, and typically any of the loops known as CDR1, CDR2 or CDR3 will participate in IGF-IR binding.

In certain embodiments, the single domain polypeptide comprises an immunoglobulin-like domain. One, two, three or more loops of the immunoglobulin-like domain may participate in binding to IGF-IR. A preferred immunoglobulin-like domain is a fibronectin type III (Fn3) domain. Such domain may comprise, in order from N-terminus to C-terminus, a beta or beta-like strand, A; a loop, AB; a beta or beta-like strand, B; a loop, BC; a beta or beta-like strand C; a loop CD; a beta or beta-like strand D; a loop DE; a beta or beta-like strand, E; a loop, EF; a beta or beta-like strand F; a loop FG; and a beta or beta-like strand G. See FIG. 24 for an example of the structural organization. Optionally, any or all of loops AB, BC, CD, DE, EF and FG may participate in IGF-IR binding, although preferred loops are BC, DE and FG and in particular loops BC and FG. A preferred Fn3 domain is an Fn3 domain derived from human fibronectin, particularly the $10^{th}$ Fn3 domain of fibronectin, referred to as $^{10}$Fn3. It should be noted that none of IGF-IR binding polypeptides disclosed herein have an amino acid sequence that is identical to native $^{10}$Fn3; the sequence has been modified to obtain IGF-IR binding proteins, but proteins having the basic structural features of $^{10}$Fn3, and particularly those retaining recognizable sequence homology to the native $^{10}$Fn3 are nonetheless referred to herein as "$^{10}$Fn3 polypeptides". This nomenclature is similar to that found in the antibody field where, for example, a recombinant antibody $V_L$ domain generated against a particular target protein may not be identical to any naturally occurring $V_L$ domain but nonetheless the protein is recognizably a $V_L$ protein. A $^{10}$Fn3 polypeptide may be at least 60%, 65%, 70%, 75%, 80%, 85%, or 90% identical to the human $^{10}$Fn3 domain, shown in SEQ ID NO:1. Much of the variability will generally occur in one or more of the loops. Each of the beta or beta-like strands of a $^{10}$Fn3 polypeptide may consist essentially of an amino acid sequence that is at least 80%, 85%, 90%, 95% or 100% identical to the sequence of a corresponding beta or beta-like strand of SEQ ID NO: 1, provided that such variation does not disrupt the stability of the polypeptide in physiological conditions. A $^{10}$Fn3 polypeptide may have a sequence in each of the loops AB, CD, and EF that consists essentially of an amino acid sequence that is at least 80%, 85%, 90%, 95% or 100% identical to the sequence of a corresponding loop of SEQ ID NO:1. In many instances, any or all of loops BC, DE, and FG will be poorly conserved relative to SEQ ID NO:1. For example, all of loops BC, DE, and FG may be less than 20%, 10%, or 0% identical to their corresponding loops in SEQ ID NO: 1. In some embodiments, only the BC and FG loops will be poorly conserved relative to SEQ ID NO:1.

In certain embodiments, the disclosure provides polypeptides comprising a tenth fibronectin type III ($^{10}$Fn3) domain, wherein the $^{10}$Fn3 domain comprises a loop, AB; a loop, BC; a loop, CD; a loop, DE; a loop EF; and a loop FG; and has at least one loop selected from loop BC, DE, and FG with an altered amino acid sequence relative to the sequence of the corresponding loop of the human $^{10}$Fn3 domain. By "I" is meant one or more amino acid sequence alterations relative to a template sequence (corresponding human fibronectin domain) and includes amino acid additions, deletions, and substitutions. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In some embodiments, one or more loops selected from BC, DE, and FG may be extended or shortened in length relative to the corresponding human fibronectin loop. In some embodiments, the length of the loop may be extended by from 2-25 amino acids. In some embodiments, the length of the loop may be decreased by from 1-11 amino acids. In particular, the FG loop of $^{10}$Fn3 is 12 residues long, whereas the corresponding loop in antibody heavy chains ranges from 4-28 residues. To optimize antigen binding, therefore, the length of the FG loop of $^{10}$Fn3 is preferably randomized in length as well as in sequence to cover the CDR3 range of 4-28 residues to obtain the greatest possible flexibility and affinity in antigen binding. In some embodiments, the integrin-binding motif may be replaced by an amino acid sequence in which a polar amino acid-neutral amino acid-acidic amino acid sequence (in the N-terminal to C-terminal direction).

In some embodiments, the polypeptide comprising a $^{10}$Fn3 domain comprises the amino acid sequence of any one of SEQ ID NOS: 2-125 or 184-202. Additional sequences may be added to the N- or C-terminus. For example, an additional MG sequence may be placed at the N-terminus. The M will usually be cleaved off, leaving a GVS . . . sequence at the N-terminus. In some embodiments, linker sequences may be placed at the C-terminus of the $^{10}$Fn3 domain, e.g., SEQ ID NOS: 203 and 226.

In certain embodiments, the disclosure provides a non-antibody polypeptide comprising a domain having an immunoglobulin-like fold that binds to IGF-IR. The non-antibody polypeptide may have a molecular weight of less than 20 kDa, or less than 15 kDa and will generally be derived (by, for example, alteration of the amino acid sequence) from a reference, or "scaffold", protein, such as an Fn3 scaffold. The non-antibody polypeptide may bind IGF-IR with a $K_D$ less than $10^{-6}$M, or less than $10^{-7}$M, less than $5 \times 10^{-8}$M, less than $10^{-8}$M or less than $10^{-9}$M. The unaltered reference protein either will not meaningfully bind to IGF-IR or will bind with a $K_D$ of greater than $10^{-6}$M. The non-antibody polypeptide may inhibit IGF-IR signaling, particularly where the non-antibody polypeptide has a $K_D$ of less than $5 \times 10^{-8}$M, less than $10^{-8}$M or less than $10^{-9}$M, although higher $K_D$ values may be tolerated where the $k_{off}$ is sufficiently low (e.g., less than $5 \times 10^{-4}$ s$^{-1}$). The immunoglobulin-like fold may be a $^{10}$Fn3 polypeptide.

In certain embodiments, the disclosure provides a polypeptide comprising a single domain having an immunoglobulin fold that binds to IGF-IR. The polypeptide may have a molecular weight of less than 20 kDa, or less than 15 kDa and will generally be derived (by, for example, alteration of the amino acid sequence) from a variable domain of an immunoglobulin. The polypeptide may bind IGF-IR with a $K_D$ less than $10^{-6}$M, or less than $10^{-7}$M, less than $5 \times 10^{-8}$M, less than $10^{-8}$M or less than $10^{-9}$M. The polypeptide may inhibit IGF-IR signaling, particularly where the polypeptide has a $K_D$ of less than $5 \times 10^{-8}$M, less than $10^{-8}$M or less than $10^{-9}$M, although higher $K_D$ values may be tolerated where the $k_{off}$ is sufficiently low or where the $k_{on}$ is sufficiently high. In certain preferred embodiments, a single domain polypeptide having an immunoglobulin fold derived from an immunoglobulin light chain variable domain and capable of binding to IGF-IR may comprise an amino acid sequence selected from the IGF-IR binding clones described herein.

In certain preferred embodiments, the disclosure provides IGF-IR binding polypeptides comprising the amino acid sequence of any of the IGF-IR binding clones described herein with the most desirable biochemical features. In the case of a polypeptide comprising such amino acid sequences, a PEG moiety or other moiety of interest may be covalently bound to the cysteine at position from about 85 to 100 depending on the protein. The PEG moiety may also be covalently bonded to an amine moiety in the polypeptide. The amine moiety may be, for example, a primary amine found at the N-terminus of a polypeptide or an amine group present in an amino acid, such as lysine or arginine. In certain embodiments, the PEG moiety is attached at a position on the polypeptide selected from the group consisting of: a) the N-terminus; b) between the N-terminus and the most N-terminal beta strand or beta-like strand; c) a loop positioned on a face of the polypeptide opposite the target-binding site; d) between the C-terminus and the most C-terminal beta strand or beta-like strand; and e) at the C-terminus.

In certain aspects, the disclosure provides short peptide sequences that mediate IGF-IR binding. Such sequences may mediate IGF-IR binding in an isolated form or when inserted into a particular protein structure, such as an immunoglobulin or immunoglobulin-like domain. Examples of such sequences include those disclosed as in the tables and other sequences that are at least 85%, 90%, or 95% identical to SEQ ID 1 or any other sequence listed herein and retain IGF-IR binding activity. Accordingly, the disclosure provides substantially pure or isolated polypeptides comprising an amino acid sequence that is at least 85% identical to the sequence of any of such sequences, wherein said polypeptide binds to a IGF-IR and competes with an IGF species for binding to IGF-IR. Examples of such polypeptides include a polypeptide comprising an amino acid sequence that is at least 80%, 85%, 90%, 95% or 100% identical to an amino acid sequence at least 85% identical to the sequence of any in the tables. Preferably such polypeptides will inhibit a biological activity of an IGF and may bind to IGF-IR with a $K_D$ less than $10^{-6}$M, or less than $10^{-7}$M, less than $5 \times 10^{-8}$M, less than $10^{-8}$M or less than $10^{-9}$M.

In certain embodiments, any of the IGF-IR binding polypeptides described herein may be bound to one or more additional moieties, including, for example, a moiety that also binds to IGF-IR (e.g., a second identical or different IGF-IR binding polypeptide), a moiety that binds to a different target (e.g., to create a dual-specificity binding agent), a labeling moiety, a moiety that facilitates protein purification or a moiety that provides improved pharmacokinetics. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). Moieties that tend to slow clearance of a protein from the blood, herein referred to as "PK moieties", include polyoxyalkylene moieties, e.g., polyethylene glycol, sugars (e.g., sialic acid), and well-tolerated protein moieties (e.g., Fc, Fc fragments or serum albumin). The polypeptides of the invention may be fused to albumin or a fragment (portion) or variant of albumin as described in U.S. Publication No. 20070048282. The single domain polypeptide may be attached to a moiety that reduces the clearance rate of the polypeptide in a mammal (e.g., mouse, rat, or human) by greater than three-fold relative to the unmodified polypeptide. Other measures of improved pharmacokinetics may include serum half-life, which is often divided into an alpha phase and a beta phase. Either or both phases may be improved significantly by addition of an appropriate moiety. Where polyethylene glycol is employed, one or more PEG molecules may be attached at different positions in the protein, and such attachment may be achieved by reaction with amines, thiols or other suitable reactive groups. Pegylation may be achieved by site-directed pegylation, wherein a suitable reactive group is introduced into the protein to create a site where pegylation preferentially occurs. In a preferred embodiment, the protein is modified so as to have a cysteine residue at a desired position, permitting site directed pegylation on the cysteine. PEG may vary widely in molecular weight and may be branched or linear. Notably, the present disclosure establishes that pegylation is compatible with target binding activity of $^{10}$Fn3 polypeptides and, further, that pegylation improves the pharmacokinetics of such polypeptides. Accordingly, in one embodiment, the disclosure provides pegylated forms of $^{10}$Fn3 polypeptides, regardless of the target that can be bound by such polypeptides.

In some embodiments, the polypeptide of the invention comprises a conjugate of a fibronectin-based scaffold protein and a PK moiety. The fibronectin-based scaffold protein may bind any human protein and is preferably derived from an $^{10}$Fn3 domain. The PK moiety may be any moiety that improves the pharmacokinetics of the fibronectin-based scaffold protein. In some embodiments, the PK moiety at least doubles the serum half-life of the scaffold protein. In some embodiments, the PK moiety is linked to the scaffold protein via a polypeptide linker. Exemplary polypeptide linkers include PSTSTST (SEQ ID NO: 244), EIDKPSQ (SEQ ID NO: 245), and GS linkers, such as GSGSGSGSGS (SEQ ID NO: 246) and multimers thereof. In some embodiments the PK moiety is human serum albumin. In some embodiments, the PK moiety is transferrin.

In certain aspects, the disclosure provides methods for using an IGF-IR binding protein to inhibit IGF biological activity in a cell or to inhibit a biological activity mediated by IGF-IR. The cell may be situated in vivo or ex vivo, and may be, for example, a cell of a living organism, a cultured cell or a cell in a tissue sample. The method may comprise contacting said cell with any of the IGF-IR-inhibiting polypeptides disclosed herein, in an amount and for a time sufficient to inhibit such biological activity.

In certain aspects, the disclosure provides methods for treating a subject having a condition which responds to the inhibition of IGF or IGF-IR. Such a method may comprise administering to said subject an effective amount of any of the IGF-IR inhibiting polypeptides described herein. A condition may be one that is characterized by inappropriate IGF-IR biology. Any of the IGF-IR inhibiting polypeptides described herein may be used for the preparation of a medicament for the treatment of a disorder, particularly a disorder selected from the group consisting of: an autoimmune disorder, a restenosis, and a cancer.

In certain aspects, the disclosure provides methods for detecting IGF-IR in a sample. A method may comprise contacting the sample with a IGF-IR binding polypeptide described herein, wherein said contacting is carried out under conditions that allow polypeptide-IGF-IR complex formation; and detecting said complex, thereby detecting said IGF-IR in said sample. Detection may be carried out using any technique known in the art, such as, for example, radiography, immunological assay, fluorescence detection, mass spectroscopy, or surface plasmon resonance. The sample will often by a biological sample, such as a biopsy, and particularly a biopsy of a tumor, a suspected tumor. The sample may be from a human or other mammal. The IGF-IR binding polypeptide may be labeled with a labeling moiety, such as a radioactive moiety, a fluorescent moiety, a chromogenic moiety, a chemiluminescent moiety, or a hapten moiety. The IGF-IR binding polypeptide may be immobilized on a solid support.

Another aspect of the disclosure relates to a nucleic acid comprising a nucleic acid sequence encoding a polypeptide disclosed herein. In certain embodiments, a nucleic acid may comprise a nucleic acid sequence encoding a polypeptide selected from the group consisting of any of the protein sequences in the tables disclosed herein.

A further aspect of the disclosure relates to an expression vector comprising a nucleic acid operably linked with a promoter, wherein the nucleic acid encodes a polypeptide disclosed herein. Another aspect of the disclosure relates to a cell comprising a nucleic acid disclosed herein. Also provided is a method of producing the polypeptide that binds IGF-IR comprising: expressing a nucleic acid encoding a polypeptide of the disclosure. In certain embodiments, the nucleic acid may comprise a sequence that encodes a polypeptide selected from the group consisting of any of the sequences in the tables disclosed herein and their corresponding proteins. In certain embodiments, the nucleic acid is expressed in a cell. Alternatively, the nucleic acid is expressed in a cell-free system.

In certain aspects, the disclosure provides discoveries that may be applicable to any $^{10}$Fn3 polypeptide, regardless of which target the polypeptide is engineered to bind. As noted above, the disclosure demonstrates that PEG can be used successfully to improve the pharmacokinetics of a $^{10}$Fn3 polypeptide, while not interfering meaningfully with target binding. Accordingly, the disclosure provides pegylated $^{10}$Fn3 polypeptides that bind to target and have improved pharmacokinetics relative to the non-pegylated polypeptide. In a further embodiment, the disclosure demonstrates that a deletion of the first eight amino acids of a $^{10}$Fn3 polypeptide can increase target binding affinity. Accordingly, the disclosure provides $^{10}$Fn3 polypeptides lacking the initial eight amino acids (amino acids numbered in reference to the sequence of SEQ ID NO:1). It is understood that one or two amino acids may be added back to the deleted form of the polypeptide so as to facilitate translation and proper processing. The disclosure demonstrates that subcutaneous administration of a $^{10}$Fn3 polypeptide results in a delayed release of polypeptide into the bloodstream and a decreased maximum serum concentration of the $^{10}$Fn3 polypeptide. Accordingly, the disclosure provides methods for administering a $^{10}$Fn3 polypeptide to a patient by a subcutaneous administration. This route of administration may be useful to achieve a delayed release relative to intravenous administration, and/or to decrease the maximum serum concentration of the $^{10}$Fn3 polypeptide by at least 25% or at least 50% relative to the maximum serum concentration achieved by intravenous administration of an equal dosage. The administered $^{10}$Fn3 polypeptide may be attached to a moiety that increases the serum half-life (or decreases clearance rate, or similarly affects another pharmacokinetic parameter) of the $^{10}$Fn3 polypeptide, such as a polyethylene glycol moiety. Preferably, the administered $^{10}$Fn3 polypeptide comprises an amino acid sequence that is at least 60%, 65%, 70%, 75%, 80%, 85%, 90% identical to SEQ ID NO:1.

In certain aspects, the disclosure provides single domain polypeptides that bind to a preselected target protein from a first mammal and to a homolog thereof from a second mammal. Such single domain polypeptides are particularly useful where the first mammal is a human and the second mammal is a desirable mammal in which to conduct preclinical testing, such as a mouse, rat, guinea pig, dog, or non-human primate. The disclosure demonstrates that single domain polypeptides can be engineered to have such dual specificity, and that the dual specificity simplifies drug development by allowing testing of the same polypeptide in human cells, human subjects and animal models. Preferably, the preselected target protein of the first mammal and the homolog thereof from the second mammal are sufficiently similar in amino acid sequence to allow generation of dual specificity polypeptides. For example, the preselected target protein and the homolog from the second mammal may share at least 80%, 90%, or 95% identity across a region of at least 50 amino acids, and optionally may share at least 80%, 90%, or 95% identity across the entire protein sequence or across the sequence of the extracellular domain, in the case of a membrane protein. A single domain polypeptide with this type of dual specificity binding characteristic may comprise an immunoglobulin or immunoglobulin-like domain, and will preferably bind to both the preselected human target protein and to the homolog thereof with a dissociation constant of less than $1 \times 10^{-6}$M, $1 \times 10^{-7}$M, $5 \times 10^{-8}$M, $1 \times 10^{-8}$M or $1 \times 10^{-9}$M.

Additional Assays
Inhibition of IGF-IR Via Tyrosine Phosphorylation IGF-IR Levels or Tumor Cell Growth In Vivo by IGF-IR Binding Proteins of the Invention In a further embodiment, proteins of the invention provide for an IGF-IR binder that inhibits IGF-IR tyrosine phosphorylation or receptor levels in vivo or both. In one embodiment, administration of IGF-IR binder to an animal causes a reduction in IGF-IR phosphotyrosine signal in IGF-IR-expressing tumors. In a preferred embodiment, the IGF-IR binder causes a reduction in phosphotyrosine signal by at least 20%. In a more preferred embodiment, the IGF-IR binder causes a decrease in phosphotyrosine signal by at least 50%, more preferably 60%. In an even more preferred embodiment, the binder causes a decrease in phosphotyrosine signal of at least 70%, more preferably 80%, even more preferably 90%.

In another embodiment, administration of IGF-IR binder to an animal causes a reduction in IGF-IR levels in IGF-IR-expressing tumors. In a preferred embodiment, the IGF-IR binder causes a reduction in receptor levels by at least 20% compared to an untreated animal. In a more preferred embodiment, the IGF-IR binder causes a decrease in receptor levels to at least 50%, more preferably 60% of the receptor levels in an untreated animal. In an even more preferred embodiment, the binder causes a decrease in receptor levels by at least 70%, more preferably 80%.

In Vivo Modulation

In another embodiment of a protein of the invention, an IGF-IR binder inhibits tumor cell growth in vivo. The tumor cell may be derived from any cell type including, without limitation, epidermal, epithelial, endothelial, leukemia, sarcoma, multiple myeloma, or mesodermal cells. Examples of common tumor cell lines for use in xenograft tumor studies include A549 (non-small cell lung carcinoma) cells, DU-145 (prostate) cells, MCF-7 (breast) cells, Colo 205 (colon) cells, 3T3/]GF-IR (mouse fibroblast) cells, NCI H441 cells, HEP G2 (hepatoma) cells, MDA MB 231 (breast) cells, HT-29 (colon) cells, MDA-MB-435s (breast) cells, U266 cells, SH-SYSY cells, Sk-Mel-2 cells, NCI-H929, RPM18226, and A431 cells. In a preferred embodiment, the binder inhibits tumor cell growth as compared to the growth of the tumor in an untreated animal. In a more preferred embodiment, the binder inhibits tumor cell growth by 50%. In an even more preferred embodiment, the binder inhibits tumor cell growth by 60%, 65%, 70%, or 75%. In one embodiment, the inhibition of tumor cell growth is measured at least 7 days after the animals have started treatment with the binder. In a more preferred embodiment, the inhibition of tumor cell growth is measured at least 14 days after the animals have started treatment with the binder. In another preferred embodiment, another antineoplastic agent is administered to the animal with the IGF-IR binder. In a preferred embodiment, the antineoplastic agent is able to further inhibit tumor cell growth. In an even more preferred embodiment, the antineoplastic agent is adriamycin, taxol, tamoxifen, 5-fluorodeoxyuridine (5-FU) or CP-358,774.

Additional Bispecific and Multi-Specific Embodiments

In many embodiments it will be desirable to make multi-specific compositions, e.g. compositions that bind more that more than one target or other protein of interest. In one aspect, proteins of the invention comprise a first protein with a binding affinity of about 10 nM (other appropriate affinity described herein) to first desired target (e.g., IGF-IR) or less and binds an undesired, related target (e.g., human insulin receptor) with a binding affinity of about 1 uM (other appropriate affinity described herein) or greater and binding with respect to the desired target (e.g., human IGF-IR) and is preferably a single domain or substantially monovalent and is linked to attached to a second protein with a binding affinity of about 10 nM (other appropriate affinity described herein) to a second desired target (e.g., EGFR, c-Met, c-kit, Her2, FGFR1, VEGFR2, VEGF-A, VEGF-B, VEGF-C, VEGF-D, folate receptor) or less and binds an undesired, related target (e.g., human insulin receptor) with a binding affinity of about 1 uM (other appropriate affinity described herein) or greater and is preferably a single domain or substantially monovalent. Such molecules with bispecific affinity can be further attached to other molecules, including other proteins described herein.

In one aspect, proteins of the invention comprise a first $^{10}$Fn3 domain that binds to IGF-IR and a second $^{10}$Fn3 domain that binds VEGFR2. VEGFR-2 binding polypeptides were generated as described in PCT Publication No. WO2005/056764, which is hereby incorporated by reference. Sequences of the preferred VEGFR-2 binding $^{10}$Fn3 polypeptides useful for the invention are shown in FIG. 30

SEQ ID NOS: 126-183. Proteins of the invention include the disclosed amino acid sequences with deletions of the first 8 amino acids and may include additional amino acids at the N- or C-termini. For example, an additional MG sequence may be placed at the N-terminus. The M will usually be cleaved off, leaving a GEV . . . sequence at the N-terminus. The re-addition of the normal 8 amino acids at the N-terminus also produces a VEGFR2 binding protein with desirable properties. In some embodiments, the N-terminal methionine is cleaved off. For use in vivo, a form suitable for pegylation may be generated. In one embodiment, a C-terminal tail comprising a cysteine can be added (for example, EIDKPCQ (SEQ ID NO: 225) is added at the C-terminus)

In one aspect, proteins of the invention comprise a first protein with a binding affinity of about 10 nM (other appropriate affinity described herein) to first desired target (e.g., EGFR) or less and binds an undesired, related target (e.g., human insulin receptor) with a binding affinity of about 1 uM (other appropriate affinity described herein) or greater and is preferably a single domain or substantially monovalent and is linked to attached to a second protein with a binding affinity of about 10 nM (other appropriate affinity described herein) to a second desired target (e.g., Her2, folate receptor) or less and binds an undesired, related target (e.g., human insulin receptor) with a binding affinity of about 1 uM (other appropriate affinity described herein) or greater and is preferably a single domain or substantially monovalent. Such molecules with bispecific affinity can be further attached to other molecules, including other proteins described herein.

In one aspect, proteins of the invention comprise a first protein with a binding affinity of about 10 nM (other appropriate affinity described herein) to first desired target (e.g., EGFR) or less and binds an undesired, related target (e.g. human insulin receptor) with a binding affinity of about 1 uM (other appropriate affinity described herein) or greater and is preferably a single domain or substantially monovalent and is linked to attached to a second protein with a binding affinity of about 10 nM (other appropriate affinity described herein) to a second desired target (e.g., VEGFR2) or less and binds an undesired, related target (e.g., VEGFR1) with a binding affinity of about 1 uM (other appropriate affinity described herein) or greater and is preferably a single domain or substantially monovalent. Such molecules with bispecific affinity can be further attached to other molecules, including other proteins described herein.

In one aspect, proteins of the invention comprise a first protein with a binding affinity of about 10 nM (other appropriate affinity described herein) to first desired target (e.g., Her2) or less and binds an undesired, related target (e.g., Her4) with a binding affinity of about 1 uM (other appropriate affinity described herein) or greater and is preferably a single domain or substantially monovalent and is linked to attached to a second protein with a binding affinity of about 10 nM (other appropriate affinity described herein) to a second desired target (e.g., VEGFR2) or less and binds an undesired, related target (e.g., VEGFR1) with a binding affinity of about 1 uM (other appropriate affinity described herein) or greater and is preferably a single domain or substantially monovalent. Such molecules with bispecific affinity can be further attached to other molecules, including other proteins described herein.

In one aspect, proteins of the invention comprise a first protein with a binding affinity of about 10 nM (other appropriate affinity described herein) to first desired target (e.g., FGFR1, c-Met, c-kit) or less and binds an undesired, related target (e.g. human insulin receptor) with a binding affinity of about 1 uM (other appropriate affinity described herein) or greater and is preferably a single domain or substantially monovalent and is linked to attached to a second protein with a binding affinity of about 10 nM (other appropriate affinity described herein) to a second desired target (e.g., VEGFR2) or less and binds an undesired, related target (e.g., VEGFR1) with a binding affinity of about 1 uM (other appropriate affinity described herein) or greater and is preferably a single domain or substantially monovalent. Such molecules with bispecific affinity can be further attached to other molecules, including other proteins described herein.

In one aspect, proteins of the invention comprise a first protein with a binding affinity of about 10 nM (other appropriate affinity described herein) to first desired target (e.g., Her2) or less and binds an undesired, related target (e.g. human insulin receptor) with a binding affinity of about 1 uM (other appropriate affinity described herein) or greater and is preferably a single domain or substantially monovalent and is linked to attached to a second protein with a binding affinity of about 10 nM (other appropriate affinity described herein) to a second desired target (e.g., Her3) or less and binds an undesired, related target (e.g., Her4) with a binding affinity of about 1 uM (other appropriate affinity described herein) or greater and is preferably a single domain or substantially monovalent. Such molecules with bispecific affinity can be further attached to other molecules, including other proteins described herein.

Additional PEG Embodiments

This is, to our knowledge, the first time that PEG (or functionally similar molecule) can be used to connect two proteins that are non-antibody moieties that bind a single target, particularly proteins wherein each binding protein is comprised of a single domain or multiple domains, usually wherein each domain is about 50 or about 60 or about 75 amino acids or more (as opposed to small peptides of 5 to 20 amino acids). Preferably fibronectin scaffold proteins can be used advantageously in such embodiments and more preferably with the proper engineering of Cys or Lys amino acids.

This is, to our knowledge, the first time that PEG (or functionally similar molecule) can be used to connect two proteins that are non-antibody moieties that bind a two or more different targets or protein of interest (e.g., a PK modulating protein), particularly proteins wherein each binding protein is comprised of a single domain or multiple domains, usually wherein each domain is about 50 or about 60 or about 75 amino acids or more (as opposed to small peptides of 5 to 20 amino acids). Preferably fibronectin scaffold proteins can be used advantageously in such embodiments and more preferably with the proper engineering of Cys or Lys amino acids.

In addition, nonPEG and PEG aspects of the invention include antibody moieties (e.g., camel antibodies and their derivatives, as well as single chain and domain antibodies; and particularly those expressed from microbes) and antibody-like moieties (e.g., derivatives of lipocalins, ankyrins, multiple Cys-Cys domains, and tetranectins; and particularly those expressed from microbes), particularly those less than about 40 kDa that are connect by PEG, and more particularly those that have a limited number of cys amino acids.

There are many properties and advantages of PEG linked proteins of the invention not previously recognized or discovered. When such proteins are expressed in microbes it may be preferable to isolate domains and then link them via PEG or other polymeric linker. PEG, or other functionally operably polymeric linkers, can be used to optimally vary the distance between each protein moiety to create a protein with one or more of the following characteristics: 1) reduced or increased steric hindrance of binding of one or more protein domain when binding to a protein of interest (e.g., a target), 2) connect two or more domains that bind different targets, 3) increase protein stability or solubility without searching for additional amino acid substitutions to increase stability or solubility (e.g., solubility at least about 20 mg/ml, or at least about 50 mg/ml), 4) decrease protein aggregation without searching for additional amino acid substitutions to decrease stability (e.g., as measured by SEC), 4) increase the overall avidity or affinity of the protein for the protein of interest by adding additional binding domains. Additional advantages of PEG linked proteins include rapidly making monospecific, multi-valent binding modes, as well as multi-specific, monovalent or multivalent binding modes depending on the number of protein targeting moieties that are included in the PEG linked protein.

$^{10}$Fn3 polypeptides of the invention can be pegylated and retain ligand binding activity. In a preferred embodiment, the pegylated $^{10}$Fn3 polypeptide is produced by site-directed pegylation, particularly by conjugation of PEG to a cysteine moiety at the N- or C-terminus. Accordingly, the present disclosure provides a target-binding $^{10}$Fn3 polypeptide with improved pharmacokinetic properties, the polypeptide comprising: a $^{10}$Fn3 domain having from about 80 to about 150 amino acids, wherein at least one of the loops of said $^{10}$Fn3 domain participate in target binding; and a covalently bound PEG moiety, wherein said $^{10}$Fn3 polypeptide binds to the target with a $K_D$ of less than 100 nM and has a clearance rate of less than 30 mL/hr/kg in a mammal. The PEG moiety may be attached to the $^{10}$Fn3 polypeptide by site directed pegylation, such as by attachment to a Cys residue, where the Cys residue may be positioned at the N-terminus of the $^{10}$Fn3 polypeptide or between the N-terminus and the most N-terminal beta or beta-like strand or at the C-terminus of the $^{10}$Fn3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines. In addition, the invention includes this type of N or C terminal PEG conjugation to antibody moieties (e.g., camel antibodies and their derivatives, as well as single chain and domain antibodies; and particularly those expressed from microbes) and antibody-like moieties (e.g., derivatives of lipocalins, ankyrins, multiple Cys-Cys domains, and tetranectins; and particularly those expressed from microbes), particularly those less than 40 kDa that are connect by PEG, and more particularly those that have a limited number of cys amino acids.

In one specific embodiment of the present invention, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. Examples of the modified polypeptide of the invention include PEGylated proteins further described herein.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_{n-1}$CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, European Published Application No. 473084A and U.S. Pat. No. 5,932,462. One form of PEGs includes two PEG side-chains (PEG2) linked via the primary amino groups of a lysine (Monfardini, C., et al., Bioconjugate Chem. 6 (1995) 62-69).

Although PEG is well-known, this is, to our knowledge, the first demonstration that a two separate $^{10}$Fn3 polypeptides can be pegylated and retain ligand binding activity. In a preferred embodiment, the pegylated $^{10}$Fn3 polypeptide is produced by site-directed pegylation, particularly by conjugation of PEG to a cysteine moiety at the N- or C-terminus. Accordingly, the present disclosure provides a target-binding $^{10}$Fn3 polypeptide with improved pharmacokinetic properties, the polypeptide comprising: a $^{10}$Fn3 domain having from about 80 to about 150 amino acids, wherein at least one of the loops of said $^{10}$Fn3 domain participate in target binding; and a covalently bound PEG moiety, wherein said $^{10}$Fn3 polypeptide binds to the target with a $K_D$ of less than 100 nM and has a clearance rate of less than 30 mL/hr/kg in a mammal. The PEG moiety may be attached to the $^{10}$Fn3 polypeptide by site directed pegylation, such as by attachment to a Cys residue, where the Cys residue may be positioned at the N-terminus of the $^{10}$Fn3 polypeptide or between the N-terminus and the most N-terminal beta or beta-like strand or at the C-terminus of the $^{10}$Fn3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski, A. et al, J. Biol. Chem., 252, 3571 (1977) and J. Biol. Chem., 252, 3582 (1977), Zalipsky, et al., and Harris et. al., in: Poly(ethylene glycol) Chemistry: Biotechnical and Biomedical Applications; (J. M. Harris ed.) Plenum Press: New York, 1992; Chap. 21 and 22). It is noted that a binding polypeptide containing a PEG molecule is also known as a conjugated protein, whereas the protein lacking an attached PEG molecule can be referred to as unconjugated.

A variety of molecular mass forms of PEG can be selected, e.g., from about 1,000 Daltons (Da) to 100,000 Da (n is 20 to 2300), for conjugating to binding polypeptides of the invention. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

In a specific embodiment of the invention, a IGF-IR or other receptor binding polypeptide is covalently linked to one poly(ethylene glycol) group of the formula: —CO—$(CH_2)_x$—$(OCH_2CH_2)_m$—OR, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's ε-amino group of a lysine is the available (free) amino group.

The above conjugates may be more specifically presented by formula (II): P—NHCO—$(CH_2)_x$—$(OCH_2CH_2)_m$—OR (II), wherein P is the group of a binding polypeptide as described herein, (i.e. without the amino group or amino groups which form an amide linkage with the carbonyl shown in formula (II); and wherein R is lower alkyl; x is 2 or 3; m is from about 450 to about 950 and is chosen so that the molecular weight of the conjugate minus the binding polypeptide is from about 10 to about 40 kDa. As used herein, the given ranges of "m" have an orientational meaning. The ranges of "m" are determined in any case, and exactly, by the molecular weight of the PEG group.

One skilled in the art can select a suitable molecular mass for PEG, e.g., based on how the pegylated binding polypeptide will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 10: 91-114 (1993).

In one embodiment of the invention, PEG molecules may be activated to react with amino groups on a binding polypeptide, such as with lysines (Bencham C. O. et al., Anal. Biochem., 131, 25 (1983); Veronese, F. M. et al., Appl. Biochem., 11, 141 (1985).; Zalipsky, S. et al., Polymeric Drugs and Drug Delivery Systems, adrs 9-110 ACS Symposium Series 469 (1999); Zalipsky, S. et al., Europ. Polym. J., 19, 1177-1183 (1983); Delgado, C. et al., Biotechnology and Applied Biochemistry, 12, 119-128 (1990)).

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (see U.S. Pat. No. 5,281,698 and U.S. Pat. No. 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively.

Pegylation of a $^{10}Fn3$ polypeptide can be performed according to the methods of the state of the art, for example by reaction of the binding polypeptide with electrophilically active PEGs (supplier: Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C., et al., Bioconjugate Chem. 6 (1995) 62-69). Such methods may used to pegylated at an ε-amino group of a binding polypeptide lysine or the N-terminal amino group of the binding polypeptide.

In another embodiment, PEG molecules may be coupled to sulfhydryl groups on a binding polypeptide (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments where PEG molecules are conjugated to cysteine residues on a binding polypeptide, the cysteine residues are native to the binding polypeptide, whereas in other embodiments, one or more cysteine residues are engineered into the binding polypeptide. Mutations may be introduced into an binding polypeptide coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework based on which binding polypeptides are designed and evolved has been solved (see Himanen et al., Nature. (2001) 20-27; 414 (6866):933-8) and thus the surface-exposed residues identified. In one embodiment, cysteine residues are introduced into binding polypeptides at or near the N- and/or C-terminus, or within loop regions.

In some embodiments, the pegylated binding polypeptide comprises a PEG molecule covalently attached to the alpha amino group of the N-terminal amino acid. Site specific N-terminal reductive amination is described in Pepinsky et al., (2001) JPET, 297,1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) J. Biol. Chem. 254,12579, and in Chamow et al., (1994) Bioconjugate Chem. 5, 133.

In another embodiment, pegylated binding polypeptide comprises one or more PEG molecules covalently attached to a linker, which in turn is attached to the alpha amino group of the amino acid residue at the N-terminus of the binding polypeptide. Such an approach is disclosed in U.S. Publication No. 2002/0044921 and PCT Publication No. WO94/01451.

In one embodiment, a binding polypeptide is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, *Bioconjug Chem.* 2004; 15(5):1005-1009.

Monopegylation of a binding polypeptide can also be produced according to the general methods described in PCT Publication No. WO94/01451. WO94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of a binding polypeptide to activated PEG in the conjugation reaction can be from about 1:0.5 to 1:50, between from about 1:1 to 1:30, or from about 1:5 to 1:15. Various aqueous buffers can be used in the present method to catalyze the covalent addition of PEG to the binding polypeptide. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer. Other ratios will be used when making multi-specific PEG linked proteins, such as about 1:4 to 1:8, or about 1:3 to 1:5

Conventional separation and purification techniques known in the art can be used to purify PEGylated binding polypeptide, such as size exclusion (e.g., gel filtration) and ion exchange chromatography. Products may also be separated using SDS-PAGE. Products that may be separated include mono-, di-, tri-poly- and un-pegylated binding polypeptide, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment, PEGylated binding polypeptide of the invention contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in PEG-binding polypeptide is from about 3,000 Da to 60,000 Da, optionally from about 10,000 Da to 36,000 Da. In a one embodiment, the PEG in pegylated binding polypeptide is a substantially linear, straight-chain PEG.

In one embodiment of the invention, the PEG in pegylated binding polypeptide is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-binding polypeptide, more preferably at least 90%, and most preferably at least 95%.

In another embodiment, the pegylated binding polypeptides of the invention will preferably retain at least about 25%, 50%, 60%, 70%, 80%, 85%, 90%, 95% or 100% of the biological activity associated with the unmodified protein. In one embodiment, biological activity refers to its ability to bind to VEGFR-2 or IGF-IR, as assessed by $K_D$, $k_{on}$ or $k_{off}$. In one specific embodiment, the pegylated binding polypeptide protein shows an increase in binding to VEGFR or IGF-IR relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Additional Vector & Polynucleotide Embodiments

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc Natl Acad Sci USA. 2003 Jan. 21; 100(2):438-42; Sinclair et al. Protein Expr Purif. 2002 October; 26(1):96-105; Connell N D. Curr Opin Biotechnol. 2001 October; 12(5):446-9; Makrides et al. Microbiol Rev. 1996 September; 60(3):512-38; and Sharp et al. Yeast. 1991 October; 7(7):657-78.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated.

The proteins of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* .alpha.-factor leaders), or acid phosphatase leader, the *C. albicans* glucoamylase leader, or the signal described in PCT Publication No. WO90/13646. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2.mu. plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian or eukaryotic cells are those that enable the identification of cells competent to take up the multivalent antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding multivalent antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6.mu.m circular plasmid pKD1 can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., Bio/Technology, 9:968-975 (1991).

Expression and cloning vectors usually contain a promoter that is recognized by the host organism and is operably linked to the nucleic acid encoding the protein of the invention, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the protein of the invention.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP Patent Publication No. 73,657. Yeast enhancers also are advantageously used with yeast promoters.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human .beta.-interferon cDNA in mouse cells under the control of a thymidine kinase promoter from herpes simplex virus. Alternatively, the rous sarcoma virus long terminal repeat can be used as the promoter.

Transcription of a DNA encoding proteins of the invention by higher eukaryotes is often increased by inserting an enhancer sequence into the vector. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the multivalent antibody-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the multivalent antibody. One useful transcription termination component is the bovine growth hormone polyadenylation region. See WO94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York, 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Additional Expression & Cell Embodiments

Preferred proteins for production and cell embodiments are fibronectin based scaffolds and related proteins. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41 P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for protein-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP Patent Publication No. 402,226); *Pichia pastoris* (EP Patent Publication No. 183,070); *Candida*; *Trichoderma reesia* (EP Patent Publication No. 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated proteins of the invention are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

In some instance it will be desired to produce proteins in vertebrate cells, such as glycosylation, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59. (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; a human hepatoma line (Hep G2); and myeloma or lymphoma cells (e.g., Y0, J558L, P3 and NS0 cells) (see U.S. Pat. No. 5,807,715). Plant cell cultures of cotton, corn, potato, soybean, *petunia*, tomato, and tobacco can also be utilized as hosts.

Host cells are transformed with the herein-described expression or cloning vectors for protein production and cultured in conventional nutrient media modified as appropriate for inducing promoters, selecting transformants, or amplifying the genes encoding the desired sequences.

Culturing Cells

The host cells used to produce the proteins of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO90/03430; WO87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

Proteins of the invention can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The proteins of the present invention can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Additional Glycosylation Embodiments

In some embodiments it may be preferable to glycosylate proteins of the invention. Preferably, such proteins are fibronectin based scaffolds. Fibronectin based scaffolds do not normally contain glycosylation sites, however, such glycosylation may be engineered into the protein.

Glycosylation of proteins is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. These can be engineered into the proteins of the invention, in particular fibronectin-based scaffold proteins and their corresponding polynucleotides. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the proteins of the invention are conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding such amino acid sequence variants of the proteins of the invention are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the protein (e.g., fibronectin-based scaffold protein).

It may be desirable to modify proteins of the invention with respect to effector function, e.g., so as to enhance antigen-dependent cell-mediated cytotoxicity (ADCC) and/or complement dependent cytotoxicity (CDC) of the antibody. This may be achieved by introducing an active portion of an Fc region, as well as one or more amino acid modifications in an Fc region of the protein (e.g., fibronectin-based scaffold protein), thereby generating a variant Fc region. The Fc region variant may comprise a human Fc region sequence (e.g., a human IgG1, IgG2, IgG3 or IgG4 Fc region) comprising an amino acid modification (e.g., a substitution) at one or more amino acid positions.

In one embodiment, the variant Fc region may mediate antibody-dependent cell-mediated cytotoxicity (ADCC) in the presence of human effector cells more effectively, or bind an Fc gamma receptor (FcγR) with better affinity, than a native sequence Fc region. Such Fc region variants may comprise an amino acid modification at any one or more of positions 256, 290, 298, 312, 326, 330, 333, 334, 360, 378 or 430 of the Fc region, wherein the numbering of the residues in the Fc region is that of the EU index as in Kabat.

Additional Antibody Based Proteins, Including Moieties and Derivatives

Additional embodiments of the invention, include single domain antibodies are antibodies whose complementary determining regions are part of a single domain polypeptide. Preferably, directed to IGF-IR, as well as included in the PEG linked proteins of invention. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. According to one aspect of the invention, a single domain antibodies as used herein is a naturally occurring single domain antibody known as heavy chain antibody devoid of light chains. Such single domain antibodies are disclosed in WO94/04678 for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, dromedary, llama, vicuna, alpaca and guanaco. Other species besides Camelidae may produce heavy chain antibodies naturally devoid of light chain; such VHHs are within the scope of the invention.

VHHs, according to the present invention, and as known to the skilled in the art are heavy chain variable domains derived from immunoglobulins naturally devoid of light chains such as those derived from Camelidae as described in WO94/04678 (and referred to hereinafter as VHH domains or nanobodies). VHH molecules are about 10.times. smaller than IgG molecules. They are single polypeptides and very stable, resisting extreme pH and temperature conditions. Moreover, they are resistant to the action of proteases which is not the case for conventional antibodies. Furthermore, in vitro expression of VHHs produces high yield, properly folded functional VHHs. In addition, antibodies generated in Camelids will recognize epitopes other than those recognized by antibodies generated in vitro through the use of antibody libraries or via immunization of mammals other than Camelids (WO9749805). As such, anti EGFR VHH's may interact more efficiently with EGFR than conventional antibodies, thereby blocking its interaction with the EGFR ligand(s) more efficiently. Since VHH's are known to bind into 'unusual' epitopes such as cavities or grooves (WO97/49805), the affinity of such VHH's may be more suitable for therapeutic treatment.

Another embodiment of the present invention is an anti-Epidermal Growth Factor Receptor consisting of a sequence corresponding to that of a Camelidae VHH directed towards EGFR or a closely related family member. The invention also relates to a homologous sequence, a function portion or a functional portion of a homologous sequence of said polypeptide. The invention also relates to nucleic acids capable of encoding said polypeptides. A single domain antibody of the present invention may be directed against EGFR or a closely related family member.

According to the invention, as and discussed herein, a polypeptide construct may further comprise single domain antibodies directed against other targets such as, for example, serum albumin. A single domain antibody directed against a target means a single domain antibody that is capable of binding to said target with an affinity of better than $10^{-6}$M.

The present invention further relates to single domain antibodies is a VHH belonging to a class having human-like sequences. One such class is characterized in that the VHHs carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. As such, polypeptides belonging to this class show a high amino acid sequence homology to human VH framework regions and said polypeptides might be administered to a human directly without expectation of an unwanted immune response therefrom, and without the burden of further humanization.

Another human-like class of Camelidae single domain antibodies has been described in PCT Publication No. WO03/035694 and contain the hydrophobic FR2 residues typically found in conventional antibodies of human origin or from other species, but compensating this loss in hydrophilicity by the charged arginine residue on position 103 that substitutes the conserved tryptophan residue present in VH from double-chain antibodies. As such, peptides belonging to these two classes show a high amino acid sequence homology to human VH framework regions and said peptides might be administered to a human directly without expectation of an unwanted immune response therefrom, and without the burden of further humanization. The invention also relates to nucleic acids capable of encoding said polypeptides. Polypeptides may include the full length Camelidae antibodies, namely Fc and VHH domains.

Anti-albumin VHH's may interact in a more efficient way with serum albumin which is known to be a carrier protein. As a carrier protein some of the epitopes of serum albumin may be inaccessible by bound proteins, peptides and small chemical compounds. Since VHH's are known to bind into 'unusual' or non-conventional epitopes such as cavities (WO97/49805), the affinity of such VHH's to circulating albumin may be more suitable for therapeutic treatment. The serum protein may be any suitable protein found in the serum of subject, or fragment thereof. In one aspect of the invention, the serum protein is serum albumin, serum immunoglobulins, thyroxine-binding protein, transferrin, or fibrinogen. Depending on the intended use such as the required half-life for effective treatment and/or compartmentalization of the target antigen, the VHH-partner can be directed to one of the above serum proteins.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VH domain; (vii) isolated CDR regions; (viii) F(ab').sub.2 fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP Patent Publication No. 404,097; WO93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10): 1057-1062 (1995); and U.S. Pat. No. 5,641,870).

Various techniques have been developed for the production of antibody fragments that may be used to make antibody fragments used in the invention. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab').sub.2 fragments (Carter et al., Bio/Technology 10:163-167 (1992)). According to another approach, F(ab').sub.2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

Alternative Targeted Protein Therapeutics

In certain embodiments, the proteins of the invention described herein may comprise one or more avimer sequences. Avimers are a type of binding proteins that have affinities and specificities for various target molecules, including those described herein. These proteins can be included in the PEG linked embodiments of the invention. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains, that may exhibit improved affinity (in some cases sub-nanomolar) and specificity compared with single-epitope binding proteins. In various embodiments, avimers may be attached to, for example, with PEG or polypeptide linkers. Additional details concerning methods of construction and use of avimers are disclosed, for example, in U.S. Patent Publication Nos. 20040175756, 20050048512, 20050053973, 20050089932 and 20050221384, the Examples section of each of which is incorporated herein by reference, as well as the entire document.

In certain embodiments, the proteins of the invention described herein may comprise one or more lipocalin related sequences, e.g., anticalins or lipocalin derivatives. Anticalins or lipocalin derivatives are a type of binding proteins that have affinities and specificities for various target molecules, including those described herein. Such proteins are described in US Patent Publication No. 20060058510—Anticalins, US Patent Publication No. 20060088908—"Muteins of human neutrophil gelatinase-associated lipocalin and related proteins", US Patent Publication No. 20050106660—"Muteins of apolipoprotein d" and PCT Publication No. WO2006/056464. These proteins can be included in the PEG linked embodiments of the invention.

In certain embodiments, the proteins of the invention described herein may comprise one or more tetranectin C-type lectin related sequences or trinectins, e.g., tetranectin C-type lectin or tetranectin C-type lectin derivatives. Tetranectin C-type lectins or tetranectin C-type lectin derivatives are a type of binding proteins that have affinities and specificities for various target molecules including those described herein. Different tetranectin C-type lectin and related proteins are described in PCT Publication Nos. WO2006/053568, WO2005/080418, WO2004/094478, WO2004/039841, WO2004/005335, WO2002/048189, WO98/056906, and U.S. Patent Publication No. 20050202043. These proteins can be included in the PEG linked embodiments of the invention.

In certain embodiments, the proteins of the invention described herein may comprise one or more natural ankyrin repeat proteins, e.g., DARPins (Molecular Partners).

In certain embodiments, the proteins of the invention described herein may comprise one or more Affibodies™. Affibodies™ are derived from the IgG binding domain of Staphyloccal Protein A. Novel binding properties can be achieved by altering residues located near the binding surface of the Protein A domain.

In certain embodiments, the proteins of the invention described herein may comprise one or more cystein knot based protein scaffolds, i.e., microbodies (Selecore/Nascacell). In certain embodiments, the proteins of the invention described herein may comprise one or more Trans-Bodies™. Trans-Bodies™ are based on transferrin scaffolds (BioResis/Pfizer).

In certain embodiments, the proteins of the invention described herein may comprise binding proteins based on gamma-crystallin or ubiquitin. These so-called Affilin™. (Scil Proteins) molecules are characterized by the de novo design of a binding region in beta sheet structures of the proteins. Affilin™ molecules have been described in U.S. Publication No. 20070248536.

Toxins and Other Molecules Linked to Proteins of the Invention

The proteins of the invention as disclosed herein, may be linked to a cytotoxic agent. Such embodiments can be prepared by in vitro or in vivo methods as appropriate. In vitro methods, include conjugation chemistry well know in the art including chemistry compatible with proteins, such as chemistry for specific amino acids, such as Cys and Lys. In order to link a cytotoxic agent to protein of the invention, a linking group or reactive group is used. Suitable linking groups are well known in the art and include disulfide groups, thioether groups, acid labile groups, photolabile groups, peptidase labile groups and esterase labile groups. Preferred linking groups are disulfide groups and thioether groups. For example, conjugates can be constructed using a disulfide exchange reaction or by forming a thioether bond between the antibody and the cytotoxic agent. Preferred cytotoxic agents are maytansinoids, taxanes and analogs of CC-1065.

In vivo methods include linking toxic, tagging or labeling proteins to proteins of the invention as fusion proteins. A single polypeptide is produced using an encoding polynucleotide for the desired polypeptide. Toxic proteins can be controlled by expressing in toxin resistant or insensitive cells or with inducible promoters in cells that are sensitive.

Although not limiting, in various embodiments, proteins of the invention may be linked to proteins, such as a bacterial toxin, a plant toxin, ricin, abrin, a ribonuclease (RNase), DNase I, a protease, Staphylococcal enterotoxin-A, pokeweed antiviral protein, gelonin, diphtherin toxin, *Pseudomonas* exotoxin, *Pseudomonas* endotoxin, Ranpimase (Rap), Rap (N69Q), an enzyme, or a fluorescent protein.

Maytansinoids and maytansinoid analogs are among the preferred cytotoxic agents. Examples of suitable maytansinoids include maytansinol and maytansinol analogs. Suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Taxanes are also preferred cytotoxic agents. Taxanes suitable for use in the present invention are disclosed in U.S. Pat. Nos. 6,372,738 and 6,340,701.

CC-1065 and its analogs are also preferred cytotoxic drugs for use in the present invention. CC-1065 and its analogs are disclosed in U.S. Pat. Nos. 6,372,738; 6,340,701; 5,846,545 and 5,585,499.

An attractive candidate for the preparation of such cytotoxic conjugates is CC-1065, which is a potent anti-tumor antibiotic isolated from the culture broth of *Streptomyces zelensis*. CC-1065 is about 1000-fold more potent in vitro than are commonly used anti-cancer drugs, such as doxorubicin, methotrexate and vincristine (B. K. Bhuyan et al., Cancer Res., 42, 3532-3537 (1982)).

Cytotoxic drugs such as methotrexate, daunorubicin, doxorubicin, vincristine, vinblastine, melphalan, mitomycin C, chlorambucil, and calicheamicin are also suitable for the preparation of conjugates of the present invention, and the drug molecules can also be linked to the antibody molecules through an intermediary carrier molecule such as serum albumin.

For diagnostic applications, the antibodies of the present invention typically will be labeled with a detectable moiety. The detectable moiety can be any one which is capable of producing, either directly or indirectly, a detectable signal. For example, the detectable moiety may be a radioisotope, such as H3, C14 or 13, P32, S35, or I131; a fluorescent or chemiluminescent compound, such as fluorescein isothiocyanate, rhodamine, or luciferin; or an enzyme, such as alkaline phosphatase, beta-galactosidase or horseradish peroxidase.

Conjugation

Any method known in the art for conjugating the a protein to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982). In vitro methods, include conjugation chemistry well know in the art including chemistry compatible with proteins, such as chemistry for specific amino acids, such as Cys and Lys. In order to link a moiety (such as PEG) to a protein of the invention, a linking group or reactive group is used. Suitable linking groups are well known in the art and include disulfide groups, thioether groups, acid labile groups, photolabile groups, peptidase labile groups and esterase labile groups. Preferred linking groups are disulfide groups and thioether groups depending on the application. For fibronectin based scaffolds or other proteins with out a cys amino acid, a cys can be engineered in a location to allow for activity of the protein to exist while creating a location for conjugation.

Imaging and Other Applications

The proteins of the invention also are useful for in vivo imaging, wherein an protein labeled with a detectable moiety such as a radio-opaque agent or radioisotope is administered to a subject, preferably into the bloodstream, and the presence and location of the labeled protein in the host is assayed. This imaging technique is useful in the staging and treatment of malignancies. The protein may be labeled with any moiety that is detectable in a host, whether by nuclear magnetic resonance, radiology, or other detection means known in the art.

The proteins of the invention also are useful as affinity purification agents. In this process, the antibodies are immobilized on a suitable support, such a Sephadex resin or filter paper, using methods well known in the art.

The proteins of the invention also are useful as reagents in biological research, based on their inhibition of the function of IGF-IR in cells.

The proteins of the invention can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

Additional Agents that May be Used with Appropriate Embodiments of the Invention In other therapeutic treatments or compositions, the proteins of the invention are co-administered, or administered sequentially, with one or more additional therapeutic agents. Suitable therapeutic agents include, but are not limited to, targeted therapeutics, other targeted biologics, and cytotoxic or cytostatic agents. In some instances in will be preferred to administer agents from the same or separate therapeutically acceptable vial, syringe or other administration device that holds a liquid formulation.

Cancer therapeutic agents are those agents that seek to kill or limit the growth of cancer cells while having minimal effects on the patient. Thus, such agents may exploit any difference in cancer cell properties (e.g., metabolism, vascularization or cell-surface antigen presentation) from healthy host cells. Differences in tumor morphology are potential sites for intervention: for example, the second therapeutic can be an antibody such as an anti-VEGF antibody that is useful in retarding the vascularization of the interior of a solid tumor, thereby slowing its growth rate. Other therapeutic agents include, but are not limited to, adjuncts such as granisetron HCl, androgen inhibitors such as leuprolide acetate, antibiotics such as doxorubicin, antiestrogens such as tamoxifen, antimetabolites such as interferon alpha-2a, cytotoxic agents such as taxol, enzyme inhibitors such as ras farnesyl-transferase inhibitor, immunomodulators such as aldesleukin, and nitrogen mustard derivatives such as melphalan HCl, and the like.

The therapeutic agents that can be combined with proteins of the invention for improved anti-cancer efficacy include diverse agents used in oncology practice (Reference: Cancer, Principles & Practice of Oncology, DeVita, V. T., Hellman, S., Rosenberg, S. A., 6th edition, Lippincott-Raven, Philadelphia, 2001), such as docetaxel, paclitaxel, doxorubicin, epirubicin, cyclophosphamide, trastuzumab, capecitabine, tamoxifen, toremifene, letrozole, anastrozole, fulvestrant, exemestane, goserelin, oxaliplatin, carboplatin, cisplatin, dexamethasone, antide, bevacizumab, 5-fluorouracil, leucovorin, levamisole, irinotecan, etoposide, topotecan, gemcitabine, vinorelbine, estramustine, mitoxantrone, abarelix, zoledronate, streptozocin, rituximab, idarubicin, busulfan, chlorambucil, fludarabine, imatinib, cytarabine, ibritumomab, tositumomab, interferon alpha-2b, melphalam, bortezomib, altretamine, asparaginase, gefitinib, erlonitib, anti-EGF receptor antibody (e.g., cetuximab or panitumab), ixabepilone, epothilones or derivatives thereof, and conjugates of cytotoxic drugs and antibodies against cell-surface receptors. Preferred therapeutic agents are platinum agents (such as carboplatin, oxaliplatin, cisplatin), taxanes (such as paclitaxel, docetaxel), gemcitabine, and camptothecin.

The one or more additional therapeutic agents can be administered before, concurrently, or after the antibody, antibody fragment or conjugate of the invention. The skilled artisan will understand that for each therapeutic agent there may be advantages to a particular order of administration. Similarly, the skilled artisan will understand that for each therapeutic agent, the length of time between which the agent, and an antibody, antibody fragment or conjugate of the invention is administered, will vary.

Formulation and Administration

Therapeutic formulations of the invention are prepared for storage by mixing the described proteins having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations herein may also contain more than one active compound as necessary for the particular indication being treated, preferably those with complementary activities that do not adversely affect each other. Examples of combinations of active compounds are provided in herein. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the proteins of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated proteins of the invention may remain in the body for a long time, they may denature or aggregate as a result of exposure to moisture at 37 C, resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

While the skilled artisan will understand that the dosage of each therapeutic agent will be dependent on the identity of the agent, the preferred dosages can range from about 10 mg/square meter to about 2000 mg/square meter, more preferably from about 50 mg/square meter to about 1000 mg/square meter. For preferred agents such as platinum agents (carboplatin, oxaliplatin, cisplatin), the preferred dosage is about 10 mg/square meter to about 400 mg/square meter, for taxanes (paclitaxel, docetaxel) the preferred dosage is about 20 mg/square meter to about 150 mg/square meter, for gemcitabine the preferred dosage is about 100 mg/square meter to about 2000 mg/square meter, and for camptothecin the preferred dosage is about 50 mg/square meter to about 350 mg/square meter. The dosage of this and other therapeutic agents may depend on whether the antibody, antibody fragment or conjugate of the invention is administered concurrently or sequentially with a therapeutic agent.

For therapeutic applications, the proteins or conjugates of the invention are administered to a subject, in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. The protein may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. The method of the present invention can be practiced in vitro, in vivo, or ex vivo.

Administration of a protein of the invention, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being co-administered.

When present in an aqueous dosage form, rather than being lyophilized, the protein typically will be formulated at a concentration of about 0.1 mg/ml to 100 mg/ml, although wide variation outside of these ranges is permitted. For the treatment of disease, the appropriate dosage of antibody or conjugate will depend on the type of disease to be treated, as defined above, the severity and course of the disease, whether the antibodies are administered for preventive or therapeutic purposes, the course of previous therapy, the patient's clinical history and response to the antibody, and the discretion of the attending physician. The protein is suitably administered to the patient at one time or over a series of treatments.

Depending on the type and severity of the disease, preferably from about 1 mg/square meter to about 2000 mg/square meter of protein is an initial candidate dosage for administration to the patient, more preferably from about 10 mg/square meter to about 1000 mg/square meter of antibody whether, for example, by one or more separate administrations, or by continuous infusion. For repeated administrations over several days or longer, depending on the condition, the treatment is repeated until a desired suppression of disease symptoms occurs. However, other dosage regimens may be useful and are not excluded.

The present invention also includes kits comprising one or more of the elements described herein, and instructions for the use of those elements. In a preferred embodiment, a kit of the present invention includes antibody, antibody fragment or conjugate of the invention, and a therapeutic agent. The instructions for this preferred embodiment include instructions for inhibiting the growth of a cancer cell using the protein of the invention, and the therapeutic agent, and/or instructions for a method of treating a patient having a cancer using the antibody, antibody fragment or conjugate of the invention, and the therapeutic agent.

Preferably, the therapeutic agent used in the kit is selected from the group consisting of docetaxel, paclitaxel, doxorubicin, epirubicin, cyclophosphamide, trastuzumab, capecitabine, tamoxifen, toremifene, letrozole, anastrozole, fulvestrant, exemestane, goserelin, oxaliplatin, carboplatin, cisplatin, dexamethasone, antide, bevacizumab, 5-fluorouracil, leucovorin, levamisole, irinotecan, etoposide, topotecan, gemcitabine, vinorelbine, estramustine, mitoxantrone, abarelix, zoledronate, streptozocin, rituximab, idarubicin, busulfan, chlorambucil, fludarabine, imatinib, cytarabine, ibritumomab, tositumomab, interferon alpha-2b, melphalam, bortezomib, altretamine, asparaginase, gefitinib, erlonitib, anti-EGF receptor antibody (e.g., cetuximab or panitumumab), ixabepilone, and an epothilone or derivative thereof. More preferably, the therapeutic agent is a platinum agent (such as carboplatin, oxaliplatin, cisplatin), a taxane (such as paclitaxel, docetaxel), gemcitabine, or camptothecin.

The elements of the kits of the present invention are in a suitable form for a kit, such as a solution or lyophilized powder. The concentration or amount of the elements of the kits will be understood by the skilled artisan to varying depending on the identity and intended use of each element of the kit.

The cancers and cells there from referred to in the instructions of the kits include breast cancer, colon cancer, ovarian carcinoma, osteosarcoma, cervical cancer, prostate cancer, lung cancer, synovial carcinoma, pancreatic cancer, melanoma, multiple myeloma, neuroblastoma, and rhabdomyosarcoma.

ADDITIONAL PATENT REFERENCES

Methods and compositions described in the following additional Patent Applications and Patents are also included in this disclosure:
U.S. Patent Publication Nos. 20050186203; 20050084906; 20050008642; 20040202655; 20040132028; 20030211078; 20060083683; 20060099205; 20060228355; 20040081648; 20040081647; 20050074865; 20040259155; 20050038229; 20050255548; 20060246059; and U.S. Pat. Nos. 5,707,632; 6,818,418; and 7,115,396; and PCT Publication Nos. WO2005/085430; WO2004/019878; WO2004/029224; WO2005/056764; WO2001/064942; and WO2002/032925. This application claims priority to U.S. Provisional Application Nos. 60/860,605 and 60/879,666 filed Nov. 22, 2006 and Jan. 9, 2007, respectively, the contents of which are incorporated by reference in their entirety.

INCORPORATION BY REFERENCE

All documents and references, including patent documents and websites, described herein are individually incorporated by reference to into this document to the same extent as if there were written in this document in full or in part.

EXAMPLES

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

Example 1. Initial Identification of IGF-IR Binding Molecules

Figure 1:
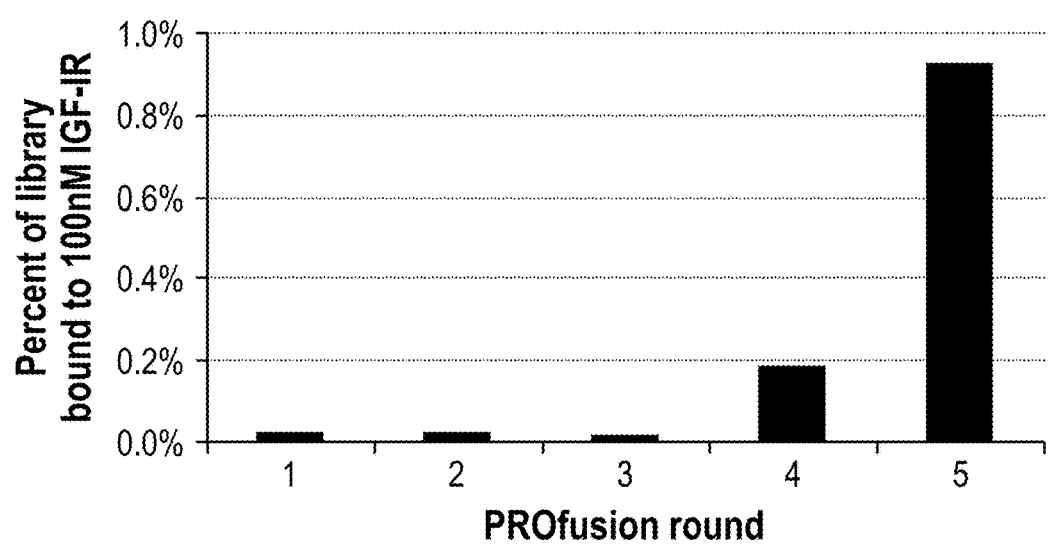
FIG. 1. Selection Profile for Isolation of Human IGF-IR Binding Clones. Shown is a graph illustrating an increase in the percent IGF-IR binding during the course of a PROfusion experiment with a library of random fibronectin scaffold domain proteins. A library of a trillion mRNA/cDNA-protein fusions was bound to 100 nM biotinylated IGF-IR in solution, and captured on streptavidin-coated magnetic beads. The cDNA was eluted, amplified by PCR, and used to generate a new library of mRNA/cDNA-protein fusions. 5 rounds of PROfusion were carried out in this manner and the percentage of library binding to IGF-IR was monitored by quantitative PCR.

A library of approximately $10^{13}$ RNA-protein fusion variants was constructed based on the scaffold of the tenth type 3 domain of human fibronectin with three randomized regions at positions 23-29, 52-55 and 77-86 (amino acid nos. are referenced to SEQ ID NO:1) (three loop library; Xu et al, Chemistry & Biology 9:933-942, 2002). After conversion to mRNA/cDNA heteroduplexes, the library of a trillion mRNA/cDNA-protein fusions was bound to 100 nM biotinylated IGF-IR in solution, and captured on streptavidin-coated magnetic beads. The cDNA was eluted, amplified by PCR, and used to generate a new library of mRNA/cDNA-protein fusions. Five rounds of selection were carried out in this manner and the percentage of library binding to IGF-IR was monitored by quantitative PCR after every round to identify target binding enrichment (FIG. 1).

Example 2: Identification of Competitive IGF-IR Clones

Proteins encoded by independent clones were analyzed for inhibition of target binding in the presence of IGF-IR using a competitive binding assay. Over one hundred clones were identified that inhibited the binding of IGF-I to IGF-IR, suggesting that these clones bound IGF-IR at or near the natural ligand (IGF-I) binding site. The SEQ ID NOs (see FIG. 30) of these one hundred clones and their percent inhibition in the competitive binding assay are presented in Table 1.

TABLE 1

SEQ ID NOs of IGF-IR Competitive Clones and % Inhibition

| Clone | SEQ ID NO: | % inhibition |
|---|---|---|
| 223B02 | 2 | 89.1% |
| 223A04 | 3 | 87.0% |
| 223F03 | 4 | 86.8% |
| 214D04 | 5 | 86.5% |
| 225E09 | 6 | 84.6% |
| 224A02 | 7 | 84.6% |
| 223A07 | 8 | 83.8% |
| 223E11 | 9 | 82.2% |
| 223H04 | 10 | 82.2% |
| 215G06 | 11 | 80.5% |
| 219F08 | 12 | 80.0% |
| 223B01 | 13 | 79.7% |
| 225B01 | 14 | 79.4% |
| 214C11 | 15 | 78.9% |
| 219C07 | 16 | 78.8% |
| 218C04 | 17 | 77.0% |
| 215A07 | 18 | 76.1% |
| 223D01 | 19 | 76.0% |
| 225D03 | 20 | 74.8% |
| 225A02 | 21 | 74.6% |
| 223A10 | 22 | 73.7% |
| 225B03 | 23 | 73.7% |
| 218C05 | 24 | 73.6% |
| 225A05 | 25 | 72.1% |
| 224A01 | 26 | 72.0% |
| 214F03 | 27 | 72.0% |
| 214A08 | 28 | 70.6% |
| 223H11 | 29 | 70.5% |
| 218B03 | 30 | 70.4% |
| 215E09 | 31 | 70.3% |
| 223A11 | 32 | 70.2% |
| 215H07 | 33 | 70.0% |
| 219G02 | 34 | 69.8% |
| 224F02 | 35 | 69.6% |
| 225A07 | 36 | 68.9% |
| 225B08 | 37 | 68.9% |
| 215E10 | 38 | 68.8% |
| 225B11 | 39 | 68.6% |
| 214C04 | 40 | 68.5% |
| 218F01 | 41 | 68.3% |
| 225H01 | 42 | 67.1% |
| 215D11 | 43 | 67.1% |
| 219H07 | 44 | 66.3% |
| 225A06 | 45 | 65.9% |
| 218A10 | 46 | 65.7% |
| 225H08 | 47 | 65.7% |
| 214B04 | 48 | 65.6% |
| 218F04 | 49 | 65.2% |
| 225A09 | 50 | 65.0% |
| 223G04 | 51 | 64.2% |
| 224H03 | 52 | 63.7% |

TABLE 1-continued

SEQ ID NOs of IGF-IR Competitive Clones and % Inhibition

| Clone | SEQ ID NO: | % inhibition |
|---|---|---|
| 215G08 | 53 | 63.6% |
| 218B06 | 54 | 62.7% |
| 224D05 | 55 | 62.5% |
| 224D01 | 56 | 62.3% |
| 225D09 | 57 | 61.8% |
| 218H08 | 58 | 61.6% |
| 225C05 | 59 | 61.1% |
| 224B02 | 60 | 60.2% |
| 214F04 | 61 | 59.6% |
| 225H10 | 62 | 58.4% |
| 215G10 | 63 | 58.2% |
| 225G09 | 64 | 58.1% |
| 223A09 | 65 | 58.0% |
| 225A10 | 66 | 58.0% |
| 215G07 | 67 | 58.0% |
| 215H06 | 68 | 57.6% |
| 215G01 | 69 | 57.4% |
| 225D11 | 70 | 57.3% |
| 225H09 | 71 | 56.8% |
| 215H03 | 72 | 56.4% |
| 218F11 | 73 | 56.4% |
| 225G07 | 74 | 56.1% |
| 225E05 | 75 | 55.7% |
| 218G01 | 76 | 54.3% |
| 224F01 | 77 | 53.6% |
| 225F05 | 78 | 53.0% |
| 219C04 | 79 | 52.5% |
| 215F02 | 80 | 50.7% |
| 223B05 | 81 | 50.6% |
| 214G08 | 82 | 50.5% |
| 219F03 | 83 | 50.3% |
| 214H01 | 84 | 50.0% |
| 215A03 | 85 | 49.7% |
| 214C08 | 86 | 49.6% |
| 214E04 | 87 | 49.2% |
| 219F07 | 88 | 49.1% |
| 215A05 | 89 | 49.0% |
| 214B07 | 90 | 48.7% |
| 214B10 | 91 | 48.5% |
| 215F10 | 92 | 48.1% |
| 215D01 | 93 | 47.9% |
| 223C04 | 94 | 46.8% |
| 219A09 | 95 | 46.7% |
| 219C11 | 96 | 46.6% |
| 215C05 | 97 | 46.6% |
| 215E11 | 98 | 46.3% |
| 225C03 | 99 | 45.9% |
| 219A06 | 100 | 45.9% |
| 215B03 | 101 | 45.7% |
| 215H09 | 102 | 45.7% |
| 219G08 | 103 | 45.4% |
| 225C06 | 104 | 45.3% |
| 215E01 | 105 | 45.3% |
| 219G10 | 106 | 44.9% |
| 219A11 | 107 | 44.7% |
| 215F05 | 108 | 44.7% |
| 219F04 | 109 | 44.3% |

Figure 2:
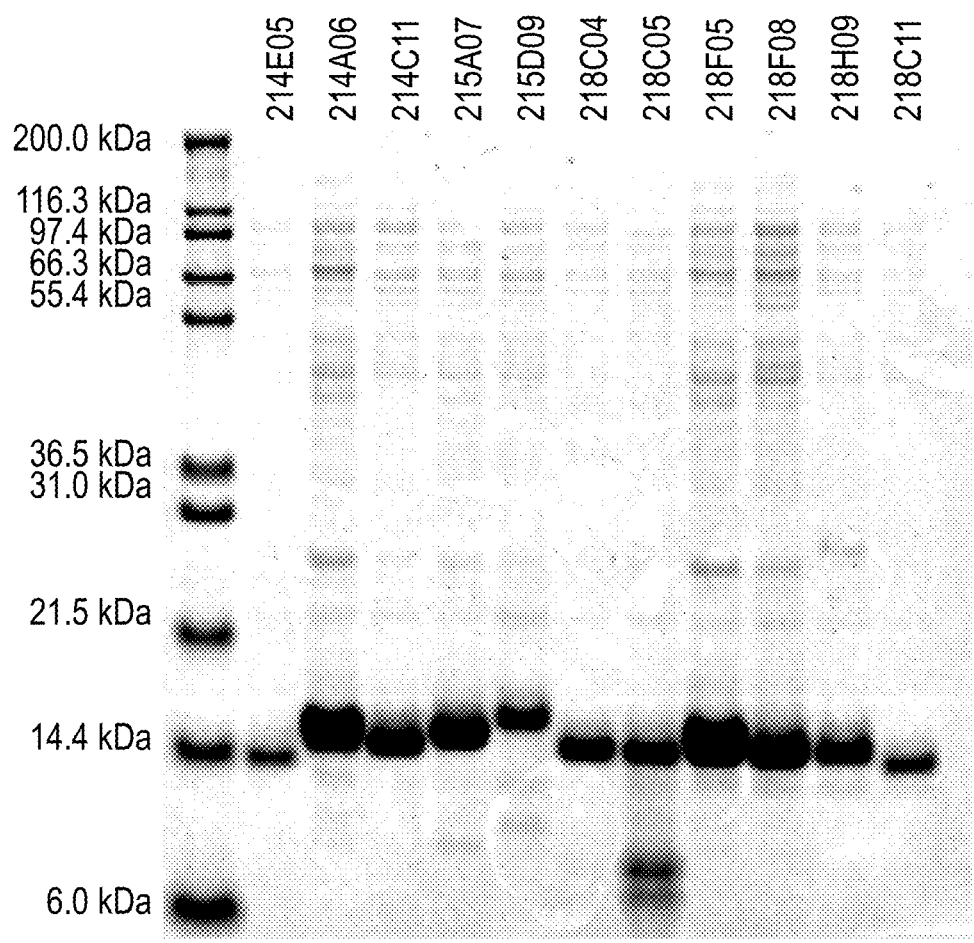
FIG. 2. SDS PAGE of Human IGF-IR Competitive Clones. Shown is a SDS PAGE gel showing human IGF-IR competitive Adnectins purified by HTPP as described in Example 35. Samples are loaded onto a 10% NuPAGE minigel and stained using Sypro-orange.

Example 3: Examination of the Electrophoretic Properties of IGF-IR Competitive Clones The purity and electrophoretic properties of selected clones were examined by SDS-PAGE (FIG. 2). These were found to be reasonably pure considering their single-column purification and had apparent molecular weights consistent with their theoretical masses (taking into account the additional mass associated with C-terminal tags).

Example 4: Identification of Sequence Families that Bind IGF-IR

Clones that were able to compete with IGF-I were sequenced and aligned using Vector NTI (Invitrogen). Most of the clones fell into three distinct families. One family was recognized by a conserved valine at position 6 of the BC loop and variable length FG loops containing a conserved arginine and tyrosine (Clones 218C04, 215D09, 214C04, 214F03, 214C03, 214E01, and 218F09). A second family was recognized by a conserved tyrosine and proline in the DE loop and was usually associated with an FG loop of exactly 10 amino acids (Clones 225D03, 215E09, 215B07, 215D11, 218E09, 309B01, 310A01, and 310A03). A third family of clones had an FG loop of 14 amino acids with conserved hydrophobic amino acids (Clones 223B01, 223B02, and 218F08). The remaining clones showed no similarity to the other families, could not be grouped into distinct families, and are not shown.

Example 5. Identification of a Candidate Clone Suitable for Optimization

The clones resulting from the above selection process are likely not to meet the stringent affinity, specificity, and biophysical requirements of a biotherapeutic and therefore require further mutagenesis wherein the binding loops are refined, or "optimized." In order to identify the clones farthest along this trajectory, a selected number of candidates were subjected to in-depth characterization. In this example, the characterization of one IGF-IR-competitive clone, 218C04, is described.

Figure 4:
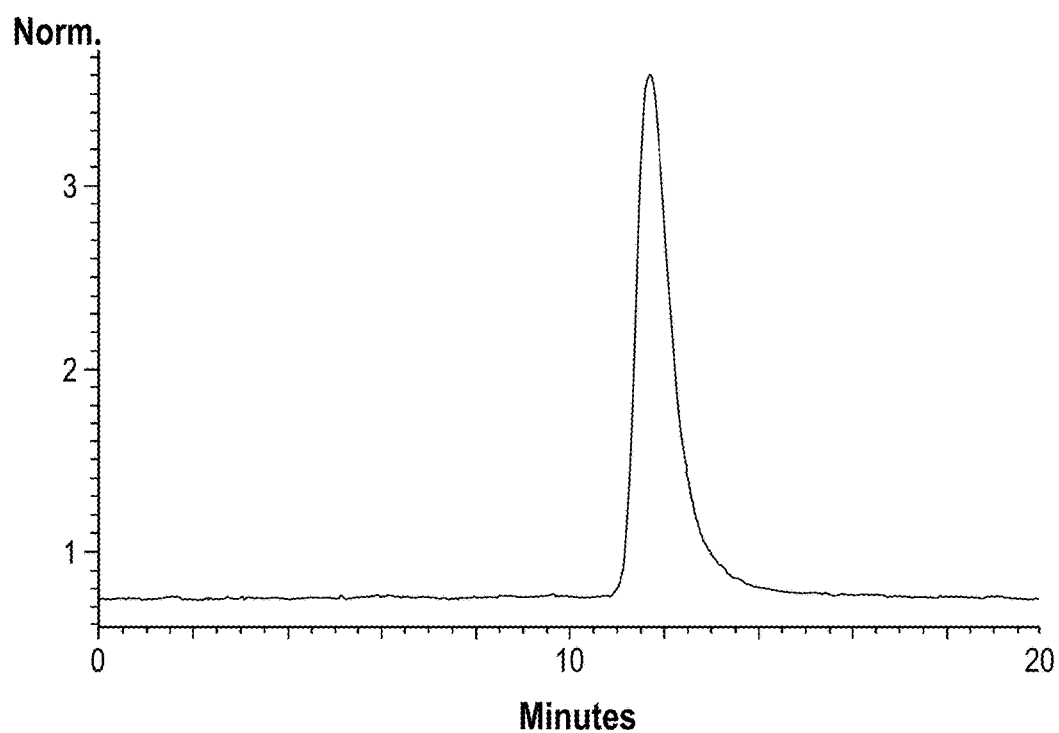
FIG. 4. Size-exclusion Chromatography of Human IGF-IR Competitive Clone 218C04. A size-exclusion chromatogram of a representative human IGF-IR competitive fibronectin scaffold domain protein lead, specifically clone 218C04. Details of the chromatography are described in Example 35. Fluorescence detection was employed.

A one liter *E. coli* growth was prepared and clone 218C04 was purified as indicated by SDS PAGE (FIG. 3). In an examination of biophysical properties, 218C04 was virtually all monomeric as reflected by SEC (FIG. 4) suggesting that this clone did not have a propensity to produce stable aggregates at higher protein concentrations. Surface plasmon resonance (BIAcore) analysis of the purified product revealed that the clone injected in the solution phase bound to immobilized IGF-IR with a KD of 1.8 nM. Collectively, these properties indicated that this clone was suitable for optimization.

Example 6. Optimization of an IGF-IR-Specific Clone

In the following example, the optimization of one IGF-IR-specific clone, 218C04, is described.

The sequence of clone 218C04 with the BC, DE, and FG loops, respectively, underlined is shown:

```
                                            (SEQ ID NO: 17)
VSDVPRDLEVVAATPTSLLISWSPYLRVARYYRITYGETGGNSPVQE
FTVPSSARTATISGLKPGVDYTITVYAVTPSNIIGRHYGPISINYRT
```

Three libraries were constructed in which one loop at a time was replaced with random sequence. The libraries were constructed at the DNA level as described below, except that random sequences in two out of three loops were replaced with fixed sequence corresponding to clone 218C04.

Figure 5A:
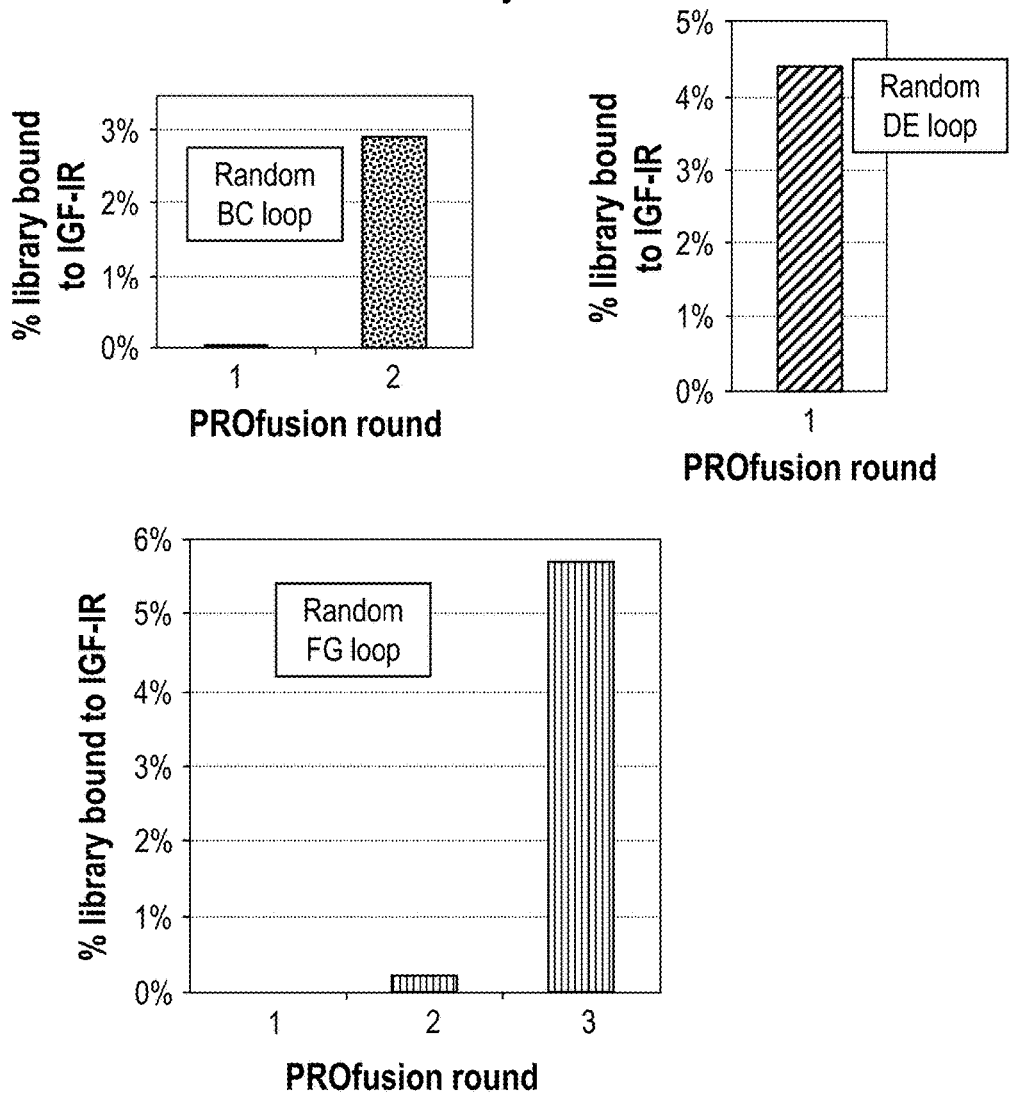
FIGS. 5A-5C. Optimization of Human IGF-IR Competitive Clone 218C04. Schematic illustrating typical optimization steps for human IGF-IR fibronectin scaffold domain protein leads, clone 218C04 in this example.
Figure 5B:

Amplification, synthesis of mRNA-protein fusions, and affinity selection were carried out with these three libraries. Binding percentages were monitored each round (FIG. 5a) and PROfusion was continued until each library showed binding above 1%. At this point, the random loops were amplified from each library and reassembled to make a master library in which all 3 loops had been optimized (FIG. 5b).

Figure 5C:
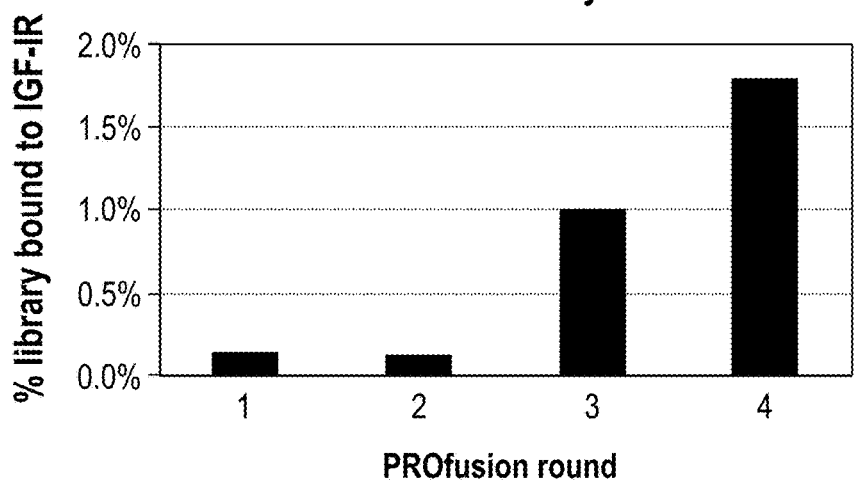

The master library containing all 3 optimized loops was taken through cycles of amplification, synthesis of mRNA-protein fusions, and affinity selections. IGF-IR was used at decreasing concentrations to select for the highest affinity binders (FIG. 5c).

Example 7. Competitive IGF-IR Assay to Assess Optimized Derivative Clones

Figure 6:
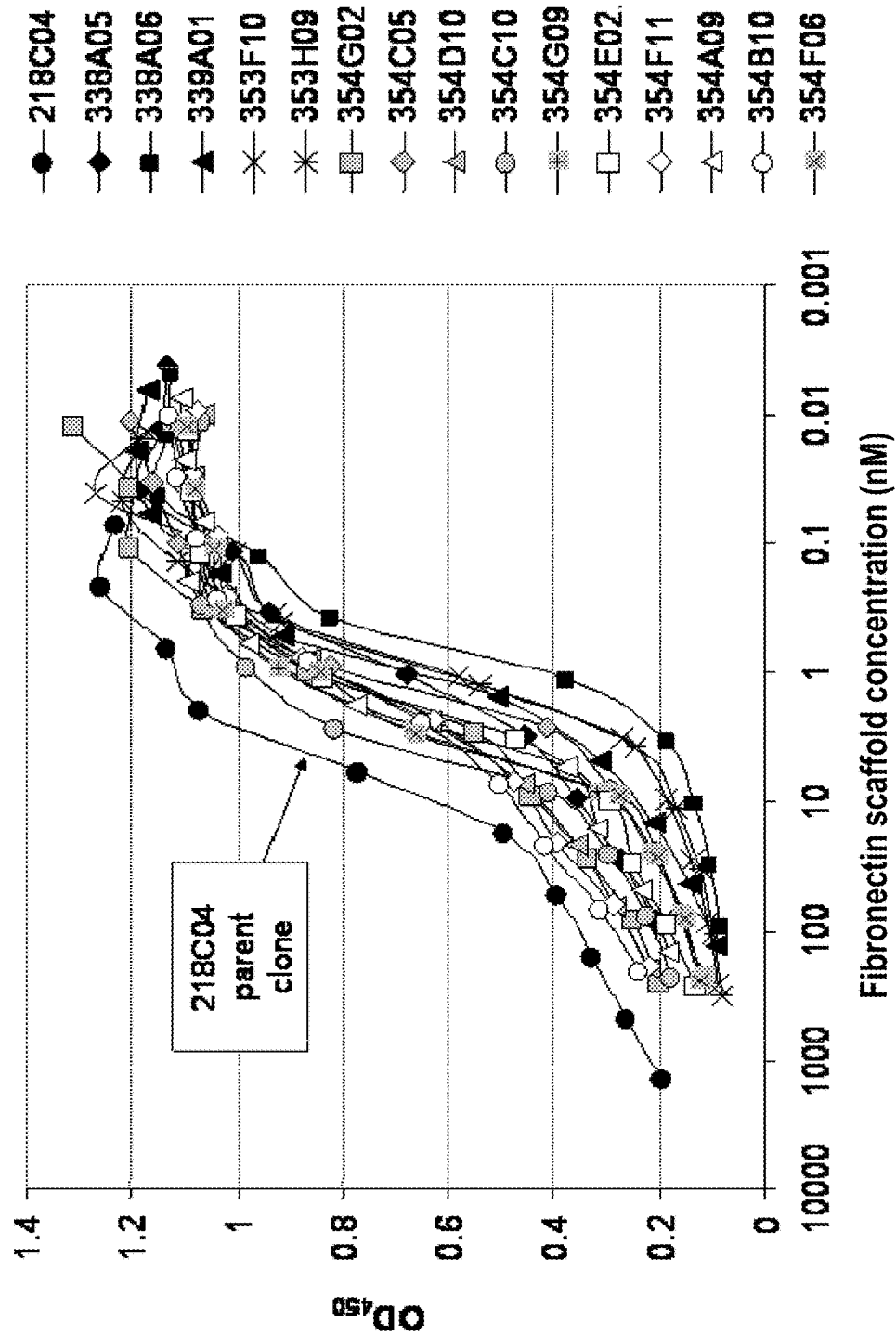
FIG. 6. IGF-I/IGF-IR Competitive Assay of Clone 218C04 Optimized Clones. A graph showing examples of optimized fibronectin scaffold domain proteins with improved ability to inhibit the interaction between IGF-I and IGF-IR in a competitive ELISA as described in Example 35.

Selected optimized fibronectin-based scaffold proteins were compared to a pre-optimized clone, clone 218C04 in this example, for their ability to inhibit the interaction between IGF-I and IGF-IR, in a competitive assay. Following HTPP and quantitation, many clones exhibit superior inhibition to the staring clone with IC50s in the low nM range (FIG. 6). One clone in particular, 338A06, appeared to have an IC50 at or below 1 nM in this assay (FIG. 6).

Example 8. Sequences of Optimized IGF-IR Competitive Clones

Following optimization of selected clones and assessment of derivatives for inhibition of the IGF-IGF-IR interaction in a competitive assay, clones were sequenced. See SEQ ID NOS: 110-125 in FIG. 30 and Table 2. Similar to the parental clone 218C04 in this example, all inhibitory derivatives clones contained a conserved valine residue in the BC loop. In addition, a conserved hydrophobic residue, typically leucine, was also frequently observed at a conserved position in the BC loop.

The FG loops of optimized clones also shared conserved residues with the parental clone 218C04 in specific positions in spite of variations in loop length. For this particular family of clones, the arginine-X-tyrosine motif appears to be an important motif required for functionality. This is found in all but one derivative clone and in this clone (354C10, arginine-X-valine) appears to be a tolerated, conservative substitution. Therefore, for the 218C04 family of clones, there appear to be four dominant positions, two in the BC loop and two in the FG loop, that appear to play the largest role in defining IGF-IR binding and inhibitory activity.

TABLE 2

| Clone | SEQ ID NO: |
| --- | --- |
| 338A05 | 110 |
| 338A06 | 111 |
| 339A01 | 112 |
| 353F10 | 113 |
| 353H09 | 114 |
| 354A09 | 115 |
| 354A10 | 116 |
| 354B10 | 117 |
| 354C05 | 118 |
| 354C10 | 119 |
| 354D10 | 120 |
| 354E02 | 121 |
| 354F11 | 122 |
| 354F06 | 123 |
| 354G02 | 124 |
| 354G09 | 125 |

Figure 7:
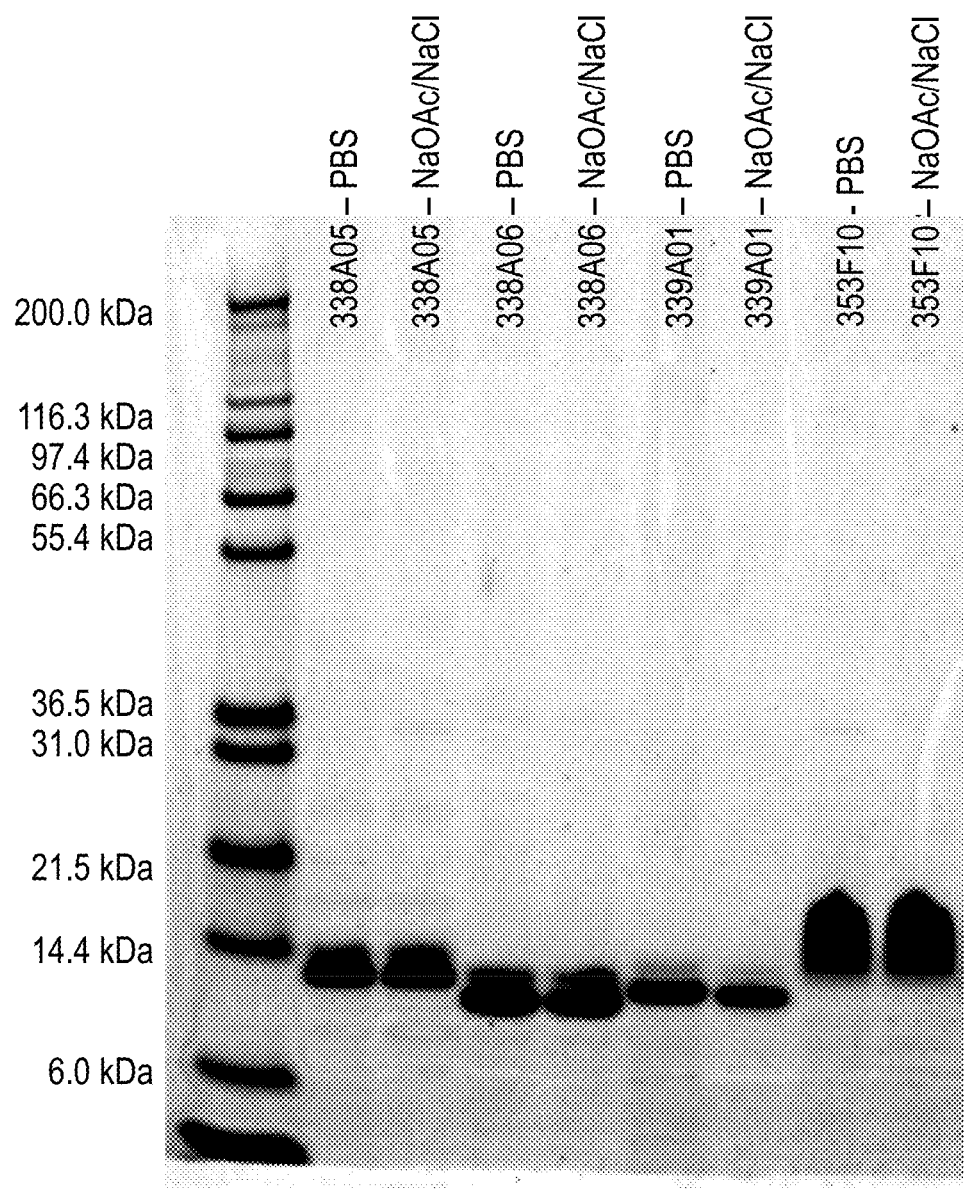
FIG. 7. SDS PAGE of Selected Clone 218C04 Optimized, Purified IGF-IR Clones. Shown is a SDS PAGE gel showing improved human IGF-IR competitive Adnectins derived from the optimization of leads and purified by HTPP as described in Example 35. Samples are loaded onto a 10% NuPAGE minigel and stained using Sypro-orange.

Example 9. Examination of the Electrophoretic Properties of Optimized IGF-IR Competitive Clones One liter *E. coli* growths of selected optimized clones were prepared and the proteins were purified. SDS PAGE (FIG. 7) revealed good purity in spite of single column purifications and apparent molecular weights for the clones consistent with their theoretical molecular weights (allowing for tags).

Figure 8:
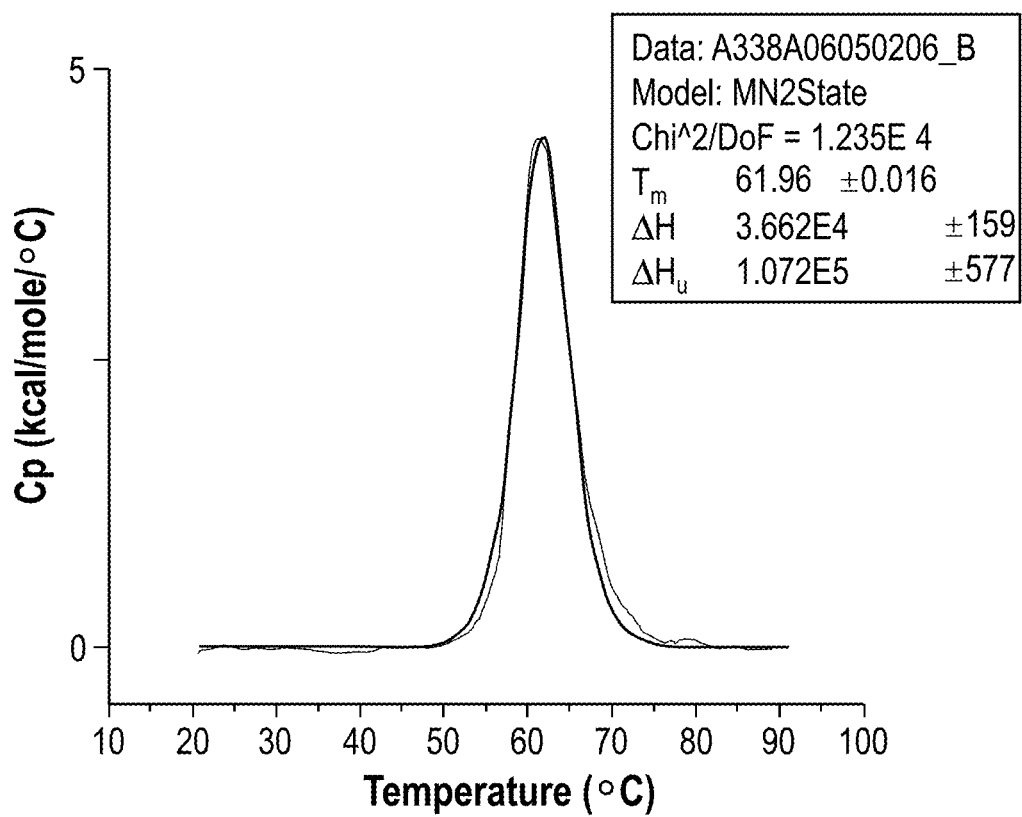
FIG. 8. Differential Scanning calorimetry of Optimized Competitive IGF-IR Clone 338A06. Differential scanning calorimetry (DSC) of a representative IGF-IR optimized clone, clone 338A06 in this instance. The black trace is the raw data, the red trace is the fit. DSC was conducted as described in Example 35.

Example 10. Examination of the Thermal Stability of Optimized IGF-IR Competitive Clones One liter E. coli growths of selected IGF-IR optimized clones were prepared and the proteins were purified. Differential Scanning calorimetry (DSC) was performed to characterize the energetics of unfolding, or melting temperature, $T_m$, of individual clones. Clone 338A06 exhibited an unfolding temperature of 62° C. (FIG. 8) indicating a highly stable structure. The melting temperatures of additional optimized clones are found in Table 3.

Example 11. Examination of the Solution Properties of Optimized IGF-IR Competitive Clones

TABLE 3

Melting temperatures of IGF-IR clones determined by differential scanning calorimetry

| Clone | ($T_m$, ° C.) |
|---|---|
| 338A05 | 68 |
| 353F10 | 59 |
| 353H09 | 55 |
| 354A10 | 46 |
| 368G05 | 56 |
| 375G10 | 59 |

Figure 9:
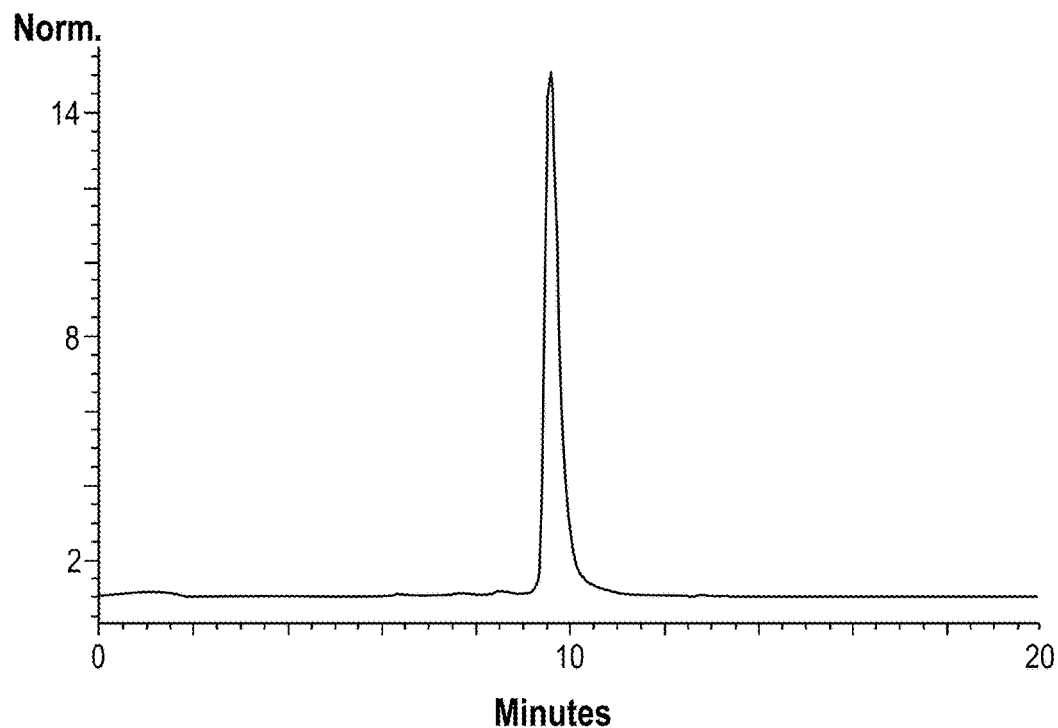
FIG. 9. SEC of Optimized IGF-IR Competitive Clone 338A06. A size-exclusion chromatogram of a representative human IGF-IR competitive fibronectin scaffold domain protein derived from the optimization process, specifically clone 338A06. Details of the chromatography are described in Example 35. Fluorescence detection was employed.
Figure 10:
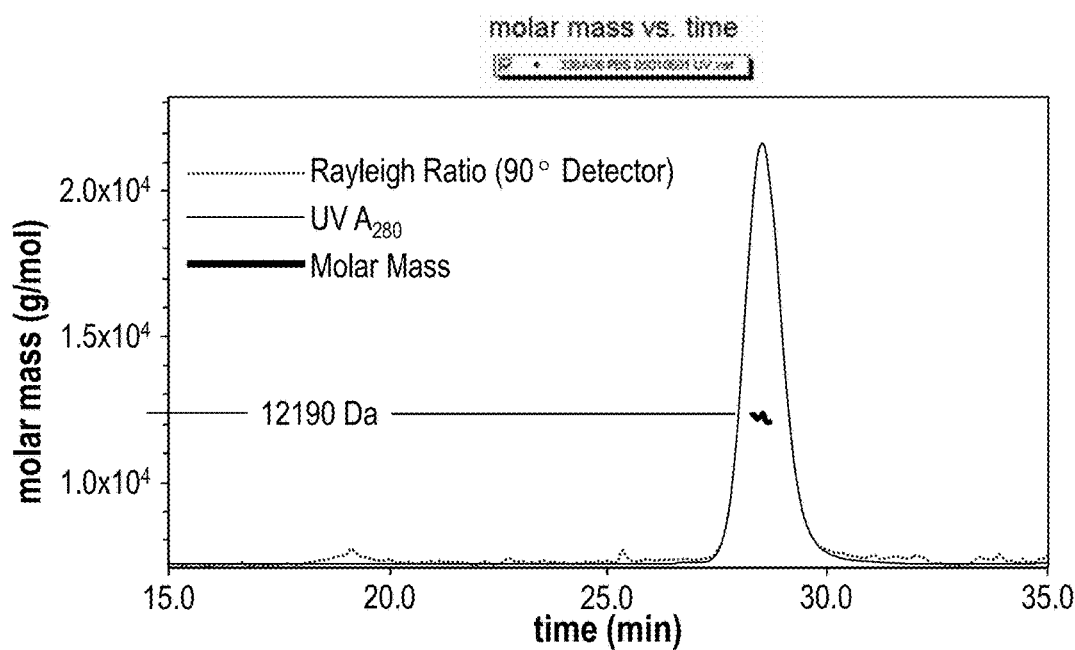
FIG. 10. SEC MALLS of Optimized IGF-IR Competitive Clone 338A06. SEC-MALLS analysis of fibronectin scaffold domain protein clone 338A06. Plot of elution time versus molar mass for the eluting peak. Rayleigh Ratio is the excess light scattered above that scattered by solvent alone (90° detector shown only).

One liter E. coli growths of selected optimized clones were prepared and the proteins were purified. Size-exclusion chromatography (SEC) revealed monomeric behavior, in this example for clone 338A06 (FIG. 9), indicating that at higher protein concentration, optimized clones did not have a tendency to aggregate. Monomericity was confirmed using SEC combined with Multi-Angle Laser Light Scattering (MALLS). "Classical" light scattering (also known as "static" or "Rayleigh" scattering or MALLS) provides a direct measure of molecular mass. It is therefore very useful for determining whether the native state of a protein is a monomer or a higher oligomer, and for measuring the masses of aggregates or other non-native species. In the present example, the analysis of clone 338A06 is presented. As shown in FIG. 10, SEC MALLS determined a mass of 12,190 Da for clone 338A06 that is well within experimental error for the predicted mass of 11,740 for the His-tagged monomer. This provides additional evidence that the clones are well-behaved monomers in solution.

Example 12. Determination of Binding Affinity and Kinetics of Optimized IGF-IR Competitive Clones One liter E. coli growths of selected optimized clones were prepared and the proteins were purified. Surface plasmon resonance (BIAcore) analysis was performed using recombinant, immobilized IGF-IR and solution-phase clones in order to determine binding kinetics and binding affinities. As shown in Table 4, binding affinities ranged from double-digit pM to single digit nM $K_D$s for the clones shown in the present example. Off-rates were in the $10^{-4}$ (1/s) range and on-rates were very fast, typically ~$10^6$ (1/M·s).

TABLE 4

Determination of $k_a$, $k_d$ and $K_D$ by BIAcore

| Clone | $k_a$ (1/M*s) × $10^{+6}$ | $k_d$(1/s) × $10^{-4}$ | $K_D$ (nM) |
|---|---|---|---|
| 353F10 | 3.7 | 2.1 | 0.056 |
| 353H09 | 3.8 | 2.2 | 0.057 |
| 338A06 | 2.2 | 4.3 | 0.069 |
| 354A10 | 1.1 | 1.8 | 0.158 |
| 338A05 | 1.3 | 3.3 | 0.261 |
| 375G10 | 1.3 | 7.0 | 0.538 |
| 339A01 | 1.2 | 6.7 | 0.565 |
| 368G05 | 0.0036 | 9.8 | 2.740 |

Example 13. Determination of Binding of Optimized IGF-IR Competitive Clones to the Insulin Receptor One liter E. coli growths of selected optimized clones were prepared and the proteins were purified. The homology of human IGF-IR to the human insulin receptor is approximately 56%. To ensure that the IGF-IR competitive clones are indeed specific for IGF-IR, they were evaluated at high concentration against the human insulin receptor using BIAcore methodology. The human insulin receptor was immobilized onto a BIAcore chip as was an irrelevant protein to control for non-specific binding. Clones were passed over the chip at 100 µM, a concentration which is more than 10,000-fold greater than the $K_D$ of binding IGF-IR for the majority of clones. The percentage of signal for insulin binding at similar concentration was recorded and is presented in Table 5. The majority of clones exhibited no or barely detectable binding to the insulin receptor at this high concentration illustrating that they indeed are specific to IGF-IR. The clones exhibiting some degree of binding to the insulin receptor appear to be selective binders.

TABLE 5

Insulin receptor (IR) binding by IGF-IR clones

| Clone | % IR Binding at 10 µM |
|---|---|
| 338A06 | 2 |
| 354A10 | 1 |
| 353F10 | 1 |
| 353H09 | 0 |
| 375G10 | 0 |
| 368G05 | 21 |
| 338A05 | 45 |
| 339A01 | >100 |
| Insulin | 100 |

Example 14. MALDI TOF Mass Spectrometry of IGF-IR Clone 338A06

Figure 11:
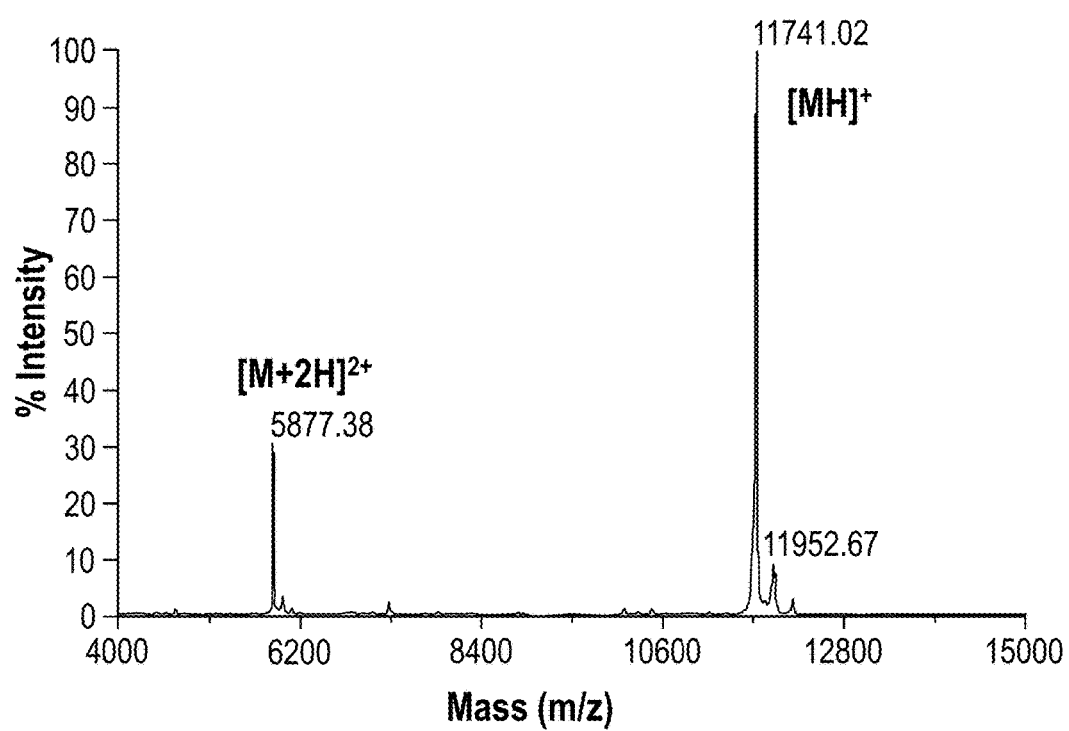
FIG. 11. Mass Spectrometry of IGF-IR Competitive Clone 338A06. MALDI MS of human IGF-IR competitive clone 338A06. Sample preparation and experimental conditions are as described in Example 35.

Mass spectrometry of the purified, optimized IGF-IR clones was performed to ensure identity. In the present example, clone 338A06 was examined. The predicted mass of clone 338A06 is 11741 atomic mass units (amu). MALDI TOF mass spectrometry of clone 338A06 revealed a mass of 11741 m/z after calibration with standards (FIG. 11). Additional minor species as higher m/z are observed however these are consistent with matrix adducts (FIG. 11). Therefore 338A06, and indeed all IGF-IR clones examined, gave masses consistent with their predicted masses.

Example 15. Activity of IGF-IR Competitive Clone 338A06 in Cell-Based Assays

Figure 12:
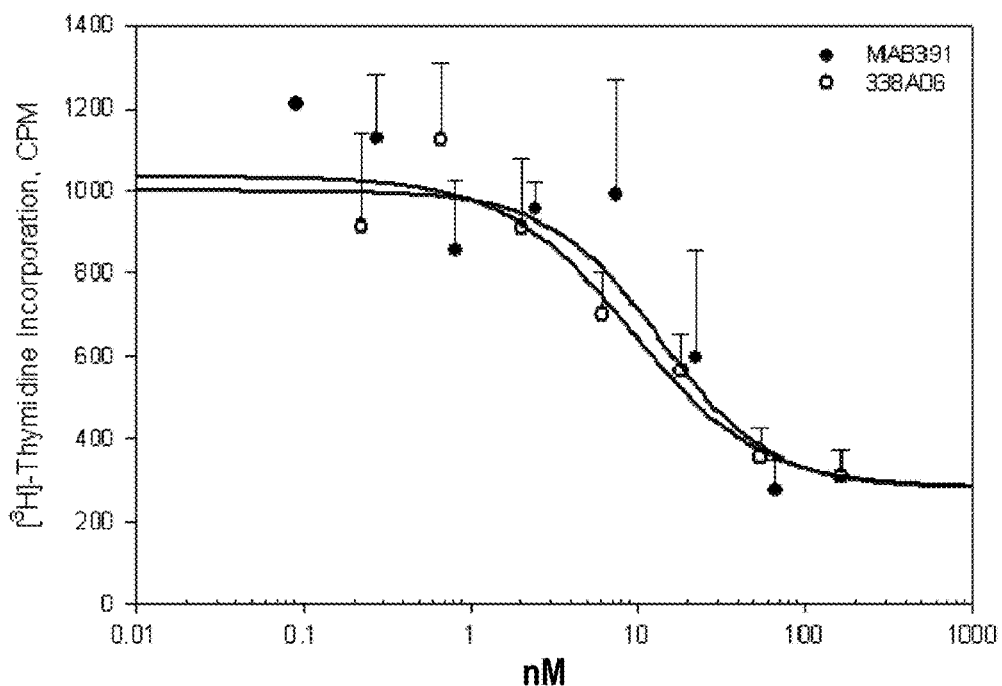
FIG. 12. IGF-I Proliferation assay of Clone 338A06. A graph representing the inhibition of IGF-I mediated mitogenesis by a selected human competitive IGF-IR binding clone, clone 338A06 in this instance. A comparison to a commercially available neutralizing anti-IGF-IR Mab (MAB391) was included. The human pancreatic adenocarcinoma cell line BxPC-3 was used as described in Example 35.

The purified, optimized IGF-IR clones were evaluated in cell-based assays in order to confirm activity. In one example, the inhibition of IGF-I-mediated mitogenesis by a selected clone 338A06 is demonstrated as shown in FIG. 12. The human pancreatic adenocarcinoma cell line BxPC-3 in IGF-I free medium was treated with a dilution series of clone 338A06 or a commonly used anti-IGF-IR monoclonal antibody (MAB391). After a 24 hour stimulatory exposure to IGF-I the cells were treated with $^3$H-Thymidine to measure cellular proliferation. As shown in FIG. 12, clone 338A06 inhibited IGF-I-dependant proliferation comparable to the monoclonal antibody control with an IC50 approximately 10-20 nM.

Figure 13:
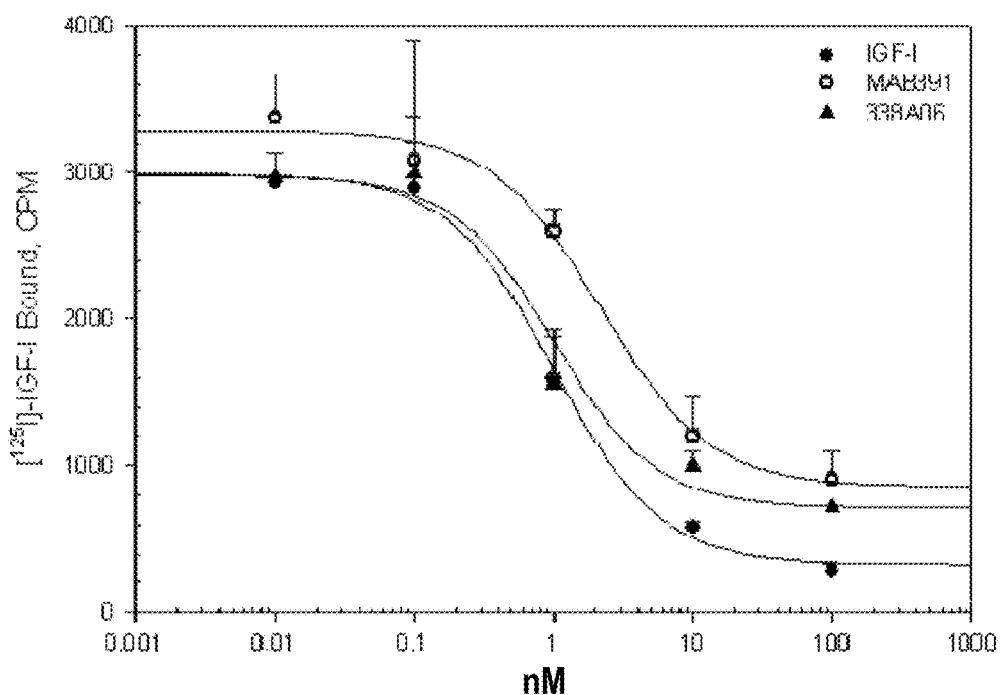
FIG. 13. IGF-IR Inhibition assay of IGF-IR Competitive Clone 338A06. A graph representing the disruption of the interaction between IGF-I and IGF-IR by a selected human competitive IGF-IR binding clone, clone 338A06 in this instance. A comparison to IGF-I and a commercially available neutralizing anti-IGF-IR Mab (MAB391) were included. The human breast adenocarcinoma MCF-7 was used as described in Example 35.

In a second cell-based assay, the inhibition of radiolabelled IGF-I binding to an IGF-IR-expressing cancer cell line by clone 338A06 is demonstrated. Human breast adenocarcinoma MCF-7 cells were pre-incubated for 30 minutes with clone 338A06, monoclonal antibody MAB391, or unlabeled IGF-1. After the incubation period, radiolabelled IGF-I was added. Cells were subsequently lysed and radioactivity was quantitated. As shown in FIG. 13, clone 338A06 and cold IGF-I had essentially comparable IC50s of approximately 1-2 nM whereas the monoclonal antibody appeared to be less potent with an IC50 of approximately 5 nM.

Example 16: Optimization of Clone 338A06

One of the commonly seen degradation processes seen for proteins during storage is the oxidation of methionine residues which may result in the potential loss of chemical and physical stability and biological activity. While the fibronectin-based scaffold protein clones do not contain methionine residues in their backbone, a selected number of IGF-IR competitive clones contain methionine in their loops. Optimization was performed in order to select for clones which retained the desirable properties of biological activity and biophysical properties of the starting clone but substituted the undesirable methionine residue(s) in the loops. In the present example, the optimization of clone 338A06, which contains a methionine residue in the FG loop, is shown.

Clone 338A06 was optimized using a single library with 6 random amino acids in the FG loop. The sequence of 338A06 (SEQ ID NO: 111) was incorporated into the BC and DE loops of the new library using the appropriate oligonucleotides.

The library was constructed as described below and double-stranded DNA was converted into mRNA-protein fusions to give about 1000 copies of each FG loop sequence. PROfusion cycles of amplification, mRNA-protein fusion formation and affinity selection were carried out. In the first round, the biotinylated IGF-IR concentration was 100 nM, but this was dropped in subsequent rounds to enrich for the highest affinity binders.

Example 17. Direct Binding Assay for Optimized Derivatives of 338A06

Figure 14:
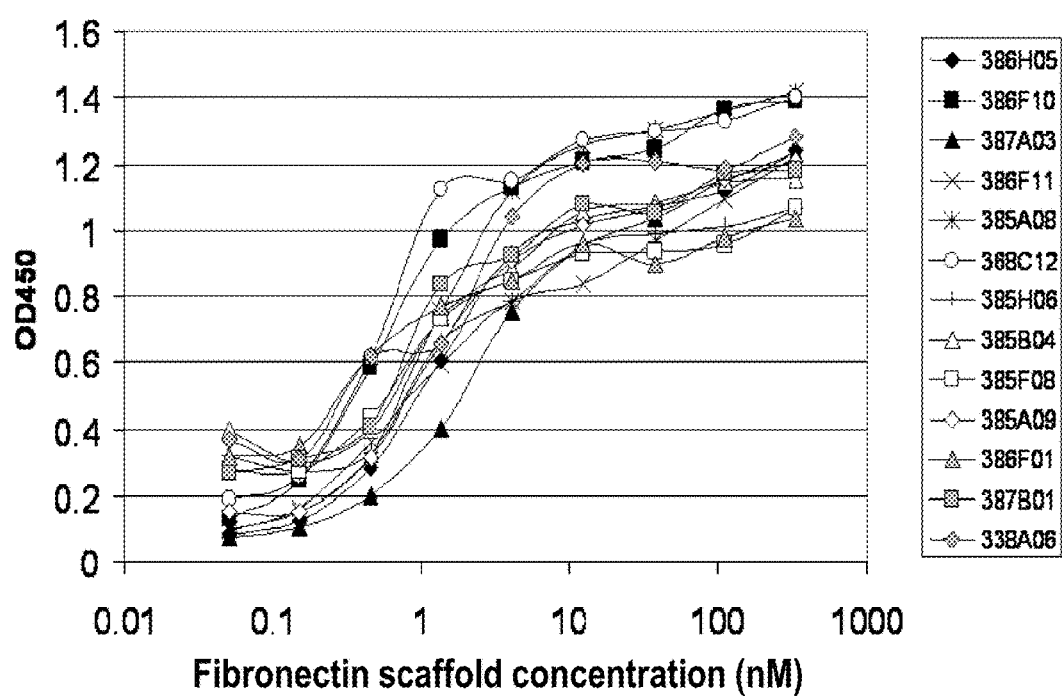
FIG. 14. IGF-IR Binding assay of Clone 338A06 FG Loop Optimized Clones. A graph showing the activity of clone 338A06 FG loop optimized clones in a direct binding ELISA as described in Example 35.

A direct binding assay was used to screen optimized derivatives of clone 338A06 for enhanced binding to IGF-IR. Clones that showed binding in a single-point assay were analyzed further using a gradient of clone concentrations. As shown in FIG. 14, a number of derivative clones bound IGF-IR with affinities comparable to the parent clone 338A06. Half-maximal binding was seen at a concentration of approximately 1 nM (FIG. 14).

Example 18. Sequences of Optimized 338A06 IGF-IR Competitive Clones

Following FG loop optimization of the 338A06 clone and assessment of derivatives for binding to IGF-IR in the direct binding assay, clones were sequenced. See SEQ ID NOS: 184-202 of FIG. 30 and Table 6. Of the clones presented in this example, only one clone contains methionine (clone 387A09) in the FG loop and this is in a position distinct from the parental 338A06 clone. Therefore, methionine in the FG loop of 338A06 clone does not appear to be important for functionality. The present invention affords a means of engineering out this destabilizing residue.

Consistent with the 218C04 derivation of these clones, the arginine-X-tyrosine motif is retained in all of the products of the 338A06 FG loop optimization effort. This provides yet additional evidence these two residues in this register appear to be dominant determinants in IGF-IR binding and inhibition in the context of the fibronectin-based scaffold protein fold for this particular family.

TABLE 6

| Clone | SEQ ID NO: |
|---|---|
| 385A08 | 184 |
| 385A09 | 185 |
| 385B04 | 186 |
| 385D05 | 187 |
| 385E01 | 188 |
| 385E04 | 189 |
| 385F08 | 190 |
| 385H06 | 191 |
| 386A03 | 192 |
| 386A05 | 193 |
| 386A07 | 194 |
| 386F01 | 195 |
| 386F10 | 196 |
| 386F11 | 197 |
| 386H05 | 198 |
| 387A03 | 199 |
| 387A09 | 200 |
| 387B01 | 201 |
| 387C02 | 202 |

Figures 15A, 15B, 15C, 15D, 15E, 15F:
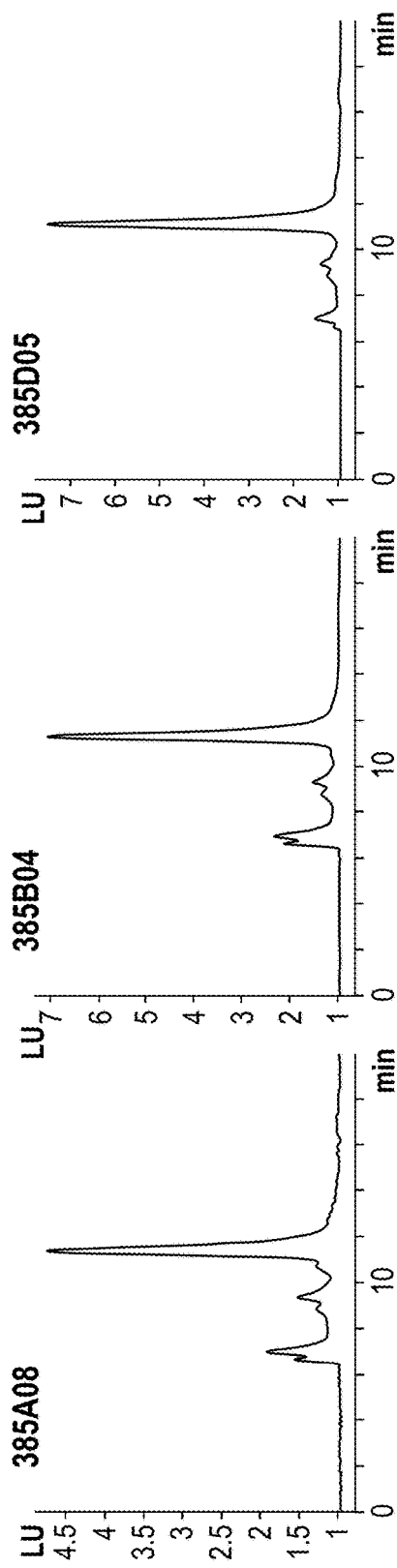
FIGS. 15A-15R. SECs of FG Loop Optimized 338A06 IGF-IR Competitive Clones. Size-exclusion chromatograms of eighteen selected FG Loop Optimized 338A06 IGF-IR Competitive clones. Chromatography conditions are described in Example 29. Fluorescence detection was employed.
Figures 15M, 15N, 15O, 15P, 15Q, 15R:
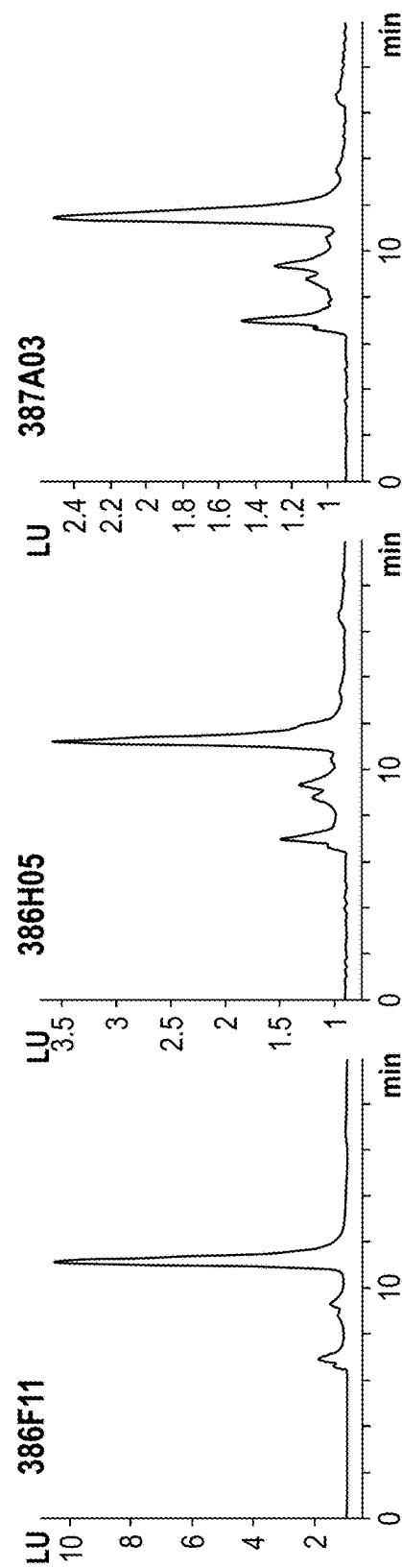

Example 19. Examination of the Solution Properties of FG Loop Optimized 338A06 IGF-IR Competitive Clones Size-exclusion chromatography (SEC) of HTPP material for FG loop optimized 338A06 IGF-IR competitive clones revealed monomeric behavior indicating that at higher protein concentration, optimized clones did not have a tendency to aggregate. Nine clones derived from the optimization and HTPP are presented in this example (FIG. 15).

Example 20. Determination of Binding Affinity and Kinetics of FG Loop Optimized 338A06 IGF-IR Competitive Clones One liter *E. coli* growths of selected FG loop optimized 338A06 IGF-IR competitive clones were prepared and the proteins were purified. BIAcore analysis was performed using recombinant, immobilized IGF-IR and solution-phase clones in order to determine binding kinetics and binding affinities. As shown in Table 7, binding affinities ranged from double-digit to triple digit pM for the clones shown in the present example. Off-rates were in the $10^{-4}$ (1/s) range and on-rates were very fast, typically ~$10^6$ (1/M·s).

TABLE 7

Determination of $k_a$, $k_d$ and $K_D$ by BIAcore

| Clone | $k_a$ (1/M*s) × 10$^{+6}$ | $k_d$(1/s) × 10$^{-4}$ | $K_D$ (pM) |
|---|---|---|---|
| 385A08 | 5.7 | 1.9 | 34 |
| 386A03 | 5.2 | 4.6 | 88 |
| 387B01 | 6.5 | 4.4 | 67 |
| 389A12 | 6.4 | 2.8 | 44 |
| 386F10 | 1.9 | 2.3 | 123 |

Example 21. Determination of Binding of FG Loop Optimized 338A06 IGF-IR Competitive Clones to the Insulin Receptor One liter E. coli growths of selected FG loop optimized 338A06 IGF-IR competitive clones were prepared and the proteins were purified. The homology of human IGF-IR to the human insulin receptor is approximately 56%. To ensure that the IGF-IR competitive clones are indeed specific for IGF-IR, they were evaluated at high concentration against the human insulin receptor using BIAcore methodology. The human insulin receptor was immobilized onto a BIAcore chip as was an irrelevant protein to control for non-specific binding. Clones were passed over the chip at 10 μM, a concentration which is more than 10,000-fold greater than the $K_D$ of binding IGF-IR for the majority of clones. The percentage of signal for insulin binding at similar concentration was recorded and is presented in Table 8. The majority of clones exhibited no detectable binding to the insulin receptor at this high concentration illustrating that these clones are indeed specific to IGF-IR.

TABLE 8

Insulin receptor binding by 338A06 FG Loop Optimized IGF-IR clones

| Clone | % IR Binding at 10 μM |
|---|---|
| 338A06 | 0 |
| 385A08 | 0 |
| 386A03 | 3 |
| 387B01 | 0 |
| 386F10 | 3 |
| 389A12 | 0 |
| Insulin | 100 |

Example 22. Examination of the Thermal Stability of FG Loop Optimized 338A06 Clones to IGF-IR One liter E. coli growths of selected FG loop optimized 338A06 IGF-IR competitive clones were prepared and the proteins were purified. Differential Scanning calorimetry (DSC) was performed to characterize the energetics of unfolding, or melting temperature, $T_m$, of individual clones. The clones tested exhibited unfolding temperatures of 58-63° C. indicating highly stable structures. The melting temperatures of the optimized clones are found in Table 9.

TABLE 9

Melting temperatures of IGF-IR clones determined by differential scanning calorimetry

| Clone | ($T_m$, ° C.) |
|---|---|
| 385A08 | 59 |
| 386A03 | 62 |
| 386F10 | 58 |
| 387B01 | 63 |
| 389A12 | 58 |

Figure 16:
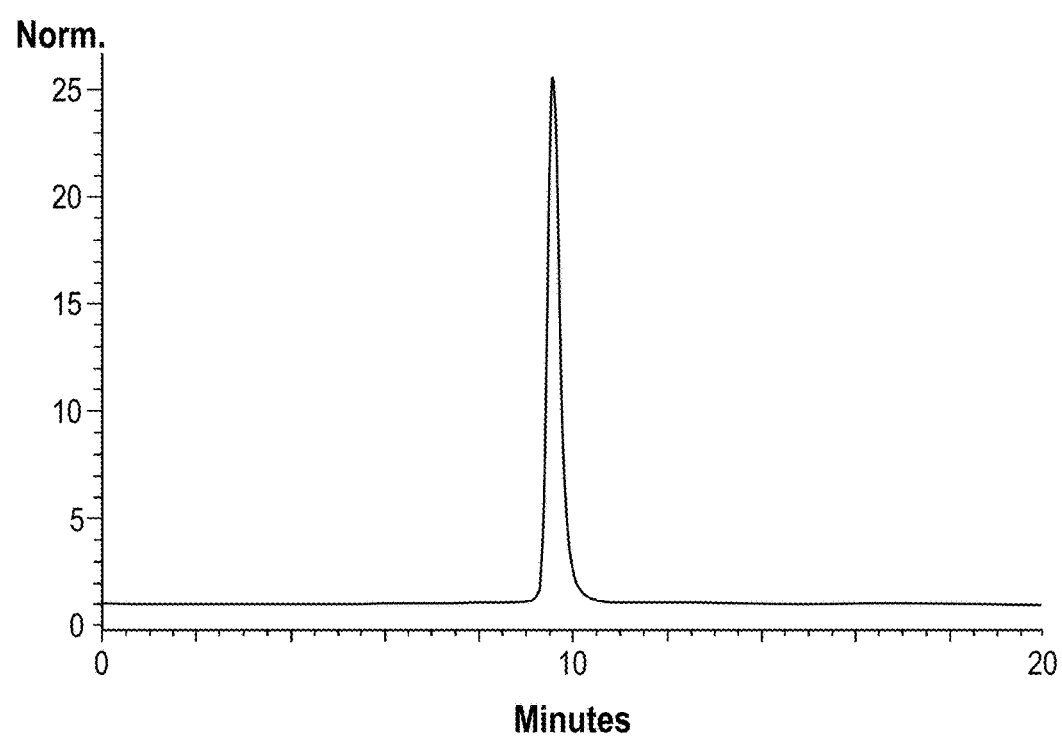
FIG. 16. SEC of IGF-IR FG Loop Optimized Clone 387B01. A size-exclusion chromatogram of a representative human FG loop optimized 338A06 IGF-IR competitive clone purified to the midscale level, specifically clone 387B01. Details of the chromatography are described in Example 35. Fluorescence detection was employed.

Example 23. Examination of the Solution Properties of FG Loop Optimized 338A06 IGF-IR Competitive Clones Following Purification One liter E. coli growths of selected FG loop optimized 338A06 IGF-IR competitive clones were prepared and the proteins were purified. Size-exclusion chromatography (SEC) of HTPP material for FG loop optimized 338A06 IGF-IR competitive clones revealed monomeric behavior indicating that at higher protein concentrations, optimized clones did not have a tendency to aggregate. In this example, the SEC profile of a representative clone 387B01 is presented (FIG. 16).

Figure 17:
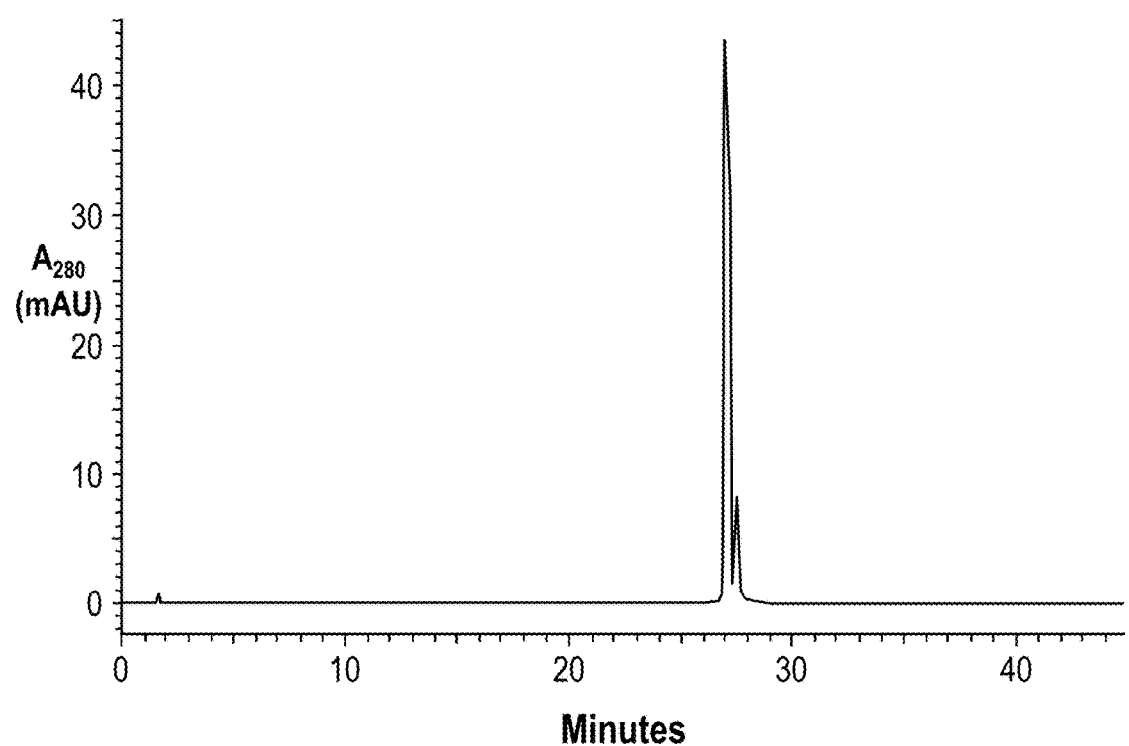
FIG. 17. RP-HPLC of IGF-IR FG Loop Optimized Clone 387B01. A RP-HPLC chromatogram of a representative human FG loop optimized 338A06 IGF-IR competitive clone purified to the midscale level, specifically clone 387B01. Details of the chromatography are described in Example 35. Detection at A280 nm was employed.

Example 24. Examination of the Purity and Homogeneity of FG Loop Optimized 338A06 Clones to IGF-IR by RP-HPLC Following Purification One liter E. coli growths of selected FG loop optimized 338A06 IGF-IR competitive clones were prepared and the proteins were purified. Reversed-Phase High Performance Liquid Chromatography (RP-HPLC) was performed to characterize the purity of clones as well as to establish clone homogeneity. All clones exhibited excellent purity and homogeneity following a single column purification that exploits the C-termini tag engineered into their C-termini as exemplified by the representative chromatogram shown in FIG. 17.

Figure 18:
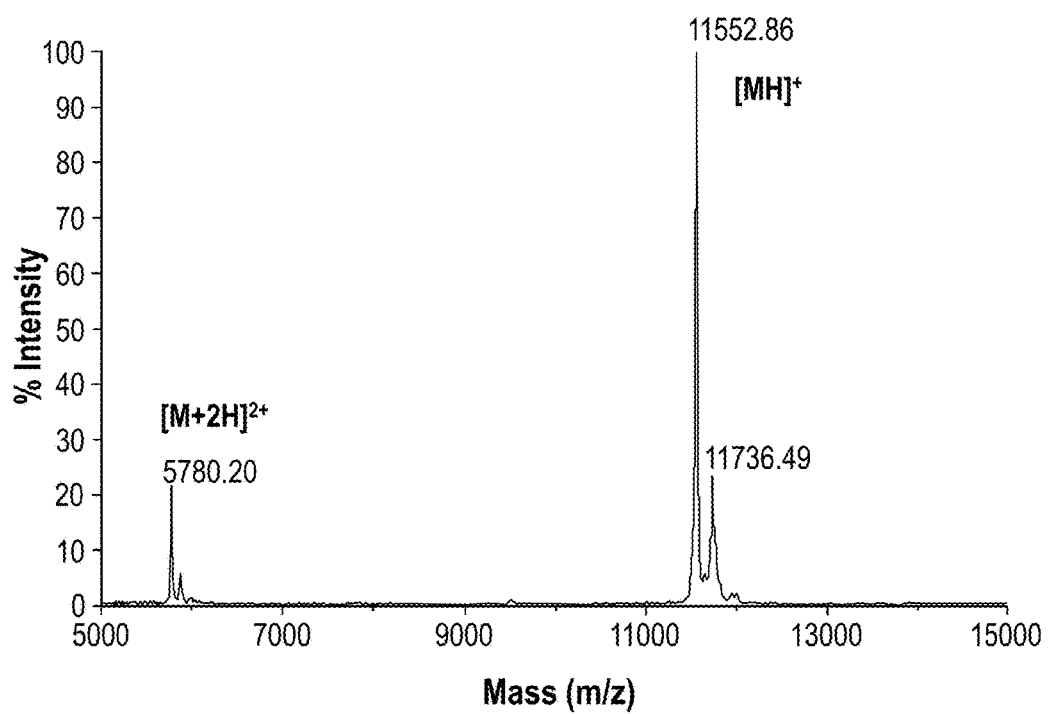
FIG. 18. MALDI TOF Mass Spectrometry of IGF-IR FG Loop Optimized Clone 387B01. MALDI MS of a representative human FG loop optimized 338A06 IGF-IR competitive clone purified to the midscale level, specifically clone 387B01. Sample preparation and experimental conditions are as described in Example 35.
Figure 19:
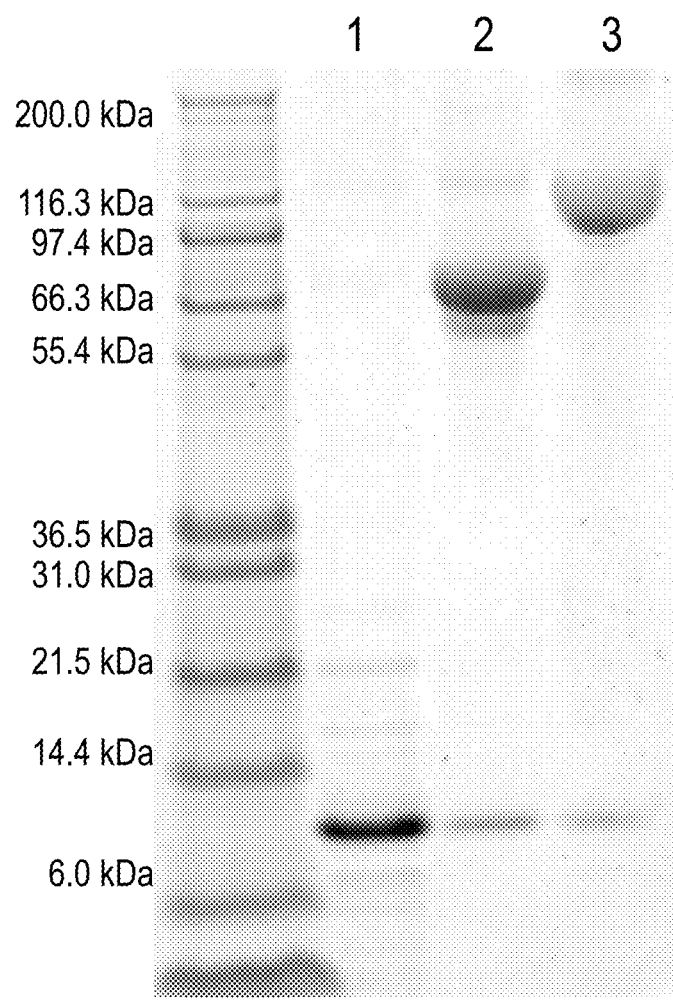
FIG. 19. SDS PAGE of PEGylated proteins. Shown is a SDS PAGE gel showing the PEGylation variants of 385A08. The PEGylation conditions are as described in Example 35. Samples are loaded onto a 10% NuPAGE minigel and stained using Sypro-orange.
Figure 20:
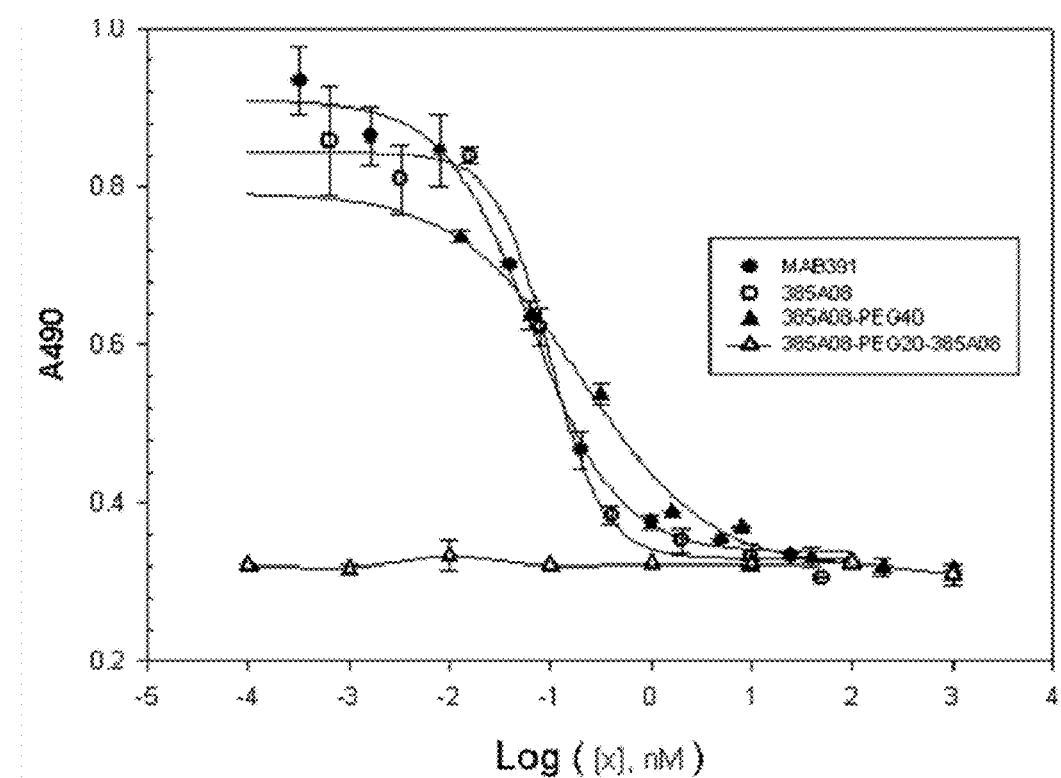
FIG. 20. Cell-based Assay of PEGylated Human IGF-IR Variants. A graph representing the inhibition of serum mediated proliferation by selected IGF-IR PEGylation variants of clone 385A08. The human plasmacytoma cell line NCI-H929 was used as described in Example 35.
Figure 21:
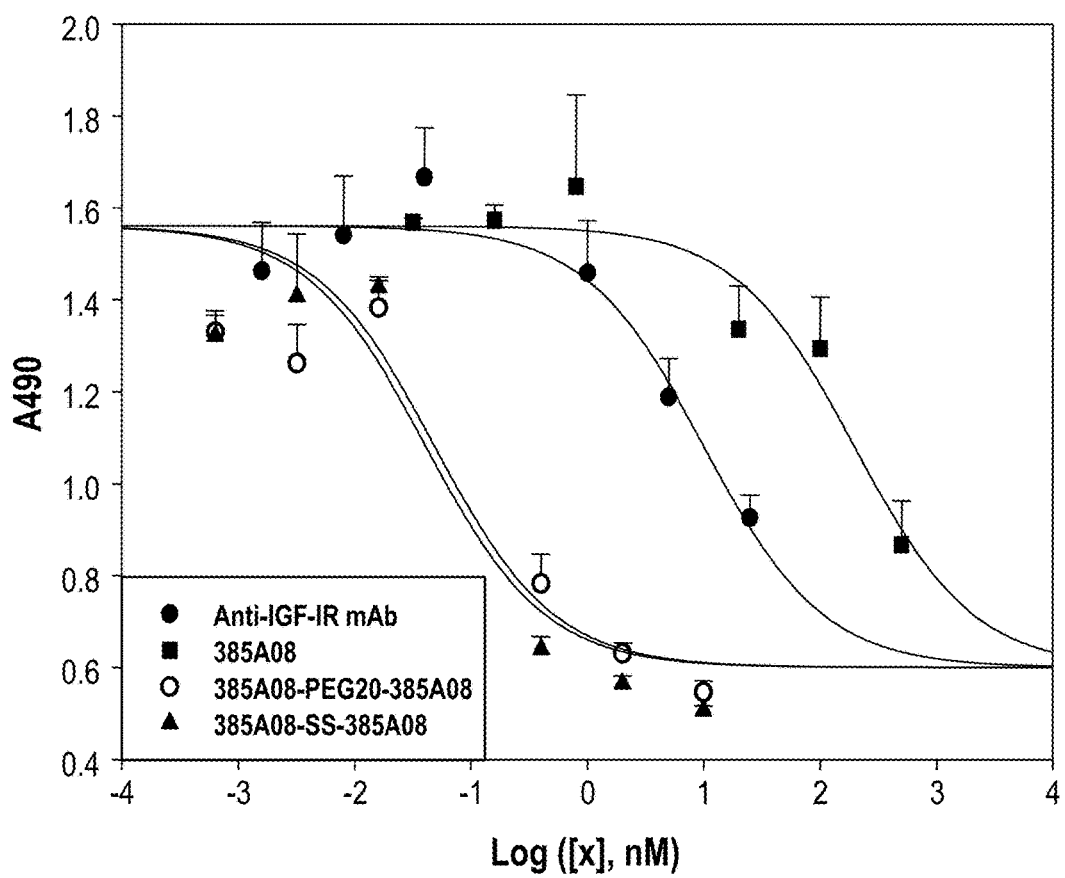
FIG. 21. Cell-based Assay of IGF-IR Multimers. A graph representing the inhibition of IGF mediated proliferation by selected IGF-IR binding fibronectin scaffold clones. The engineered lymphocyte cell line 32D:IGF-IR was plated in 96 well plates at a concentration of 10000 cells per well in RPMI (Invitrogen, Carlsbad, Calif.) containing 10% fetal bovine serum (Hyclone, Logan, Utah) in the presence of 100 ng/mL IGF and various concentrations of each IGF-IR antagonist (● IGF-IR monoclonal antibody MAB391; ■ IGF-IR binding clone 385A08 (SEQ ID NO: 226) ○ Two IGF-IR binding clones (SEQ ID NO: 203) linked by PEG: 385A08-PEG20-385A08; ▲ Two IGF-IR binding clones (SEQ ID NO: 203) linked by a disulfide bond: 385A08-SS-385A08).
Figure 22:
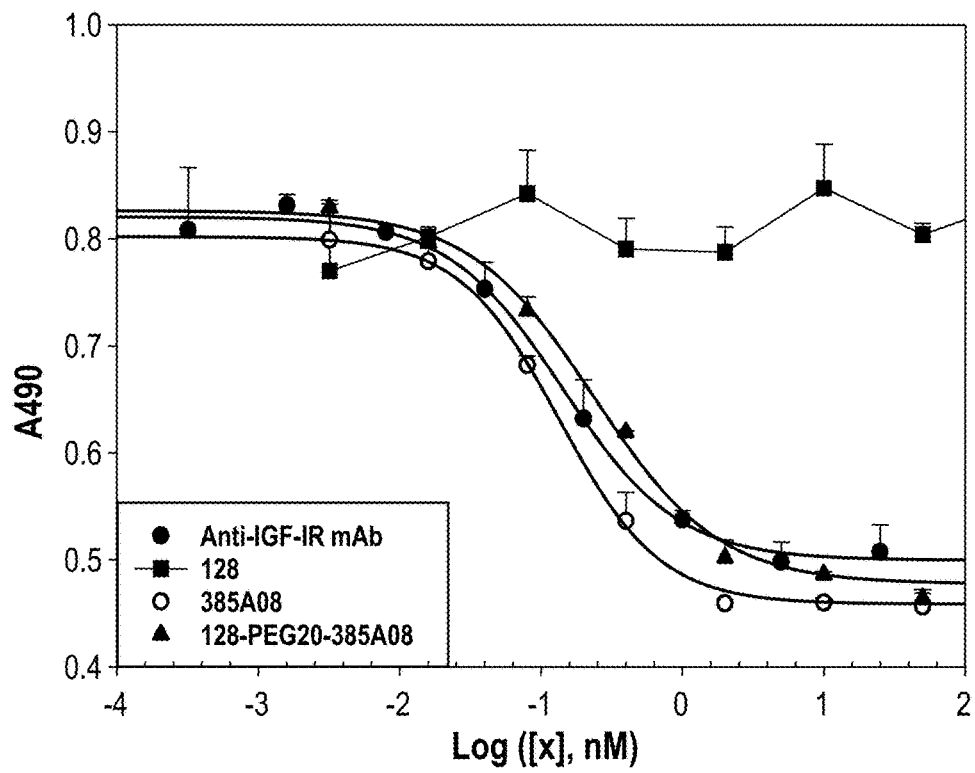
FIG. 22. Cell-based IGF-IR Assay of IGF-IR/VEGFR2 Multimers. A graph representing the inhibition of serum mediated proliferation by selected IGF-IR binding fibronectin scaffold clones. The human plasmacytoma cell line NCI-H929 (ATCC, Manassas, Va.) was plated in 96 well plates at a concentration of 25000 cells per well in DMEM (Invitrogen, Carlsbad, Calif.) containing 10% fetal bovine serum (Hyclone, Logan, Utah) in the presence of various concentrations of each IGF-IR antagonist (● anti-IGF-IR monoclonal antibody MAB391, R&D Systems, Minneapolis, Minn.; ○ IGF-IR binding clone 385A08 (SEQ ID NO: 203); ▲ VEGFR2/IGF-IR binding clones (SEQ ID NO: 203) linked by PEG: 385A08-PEG20-SEQ ID NO: 128; ■ VEGFR2 binding clone (SEQ ID NO: 128).
Figure 23:
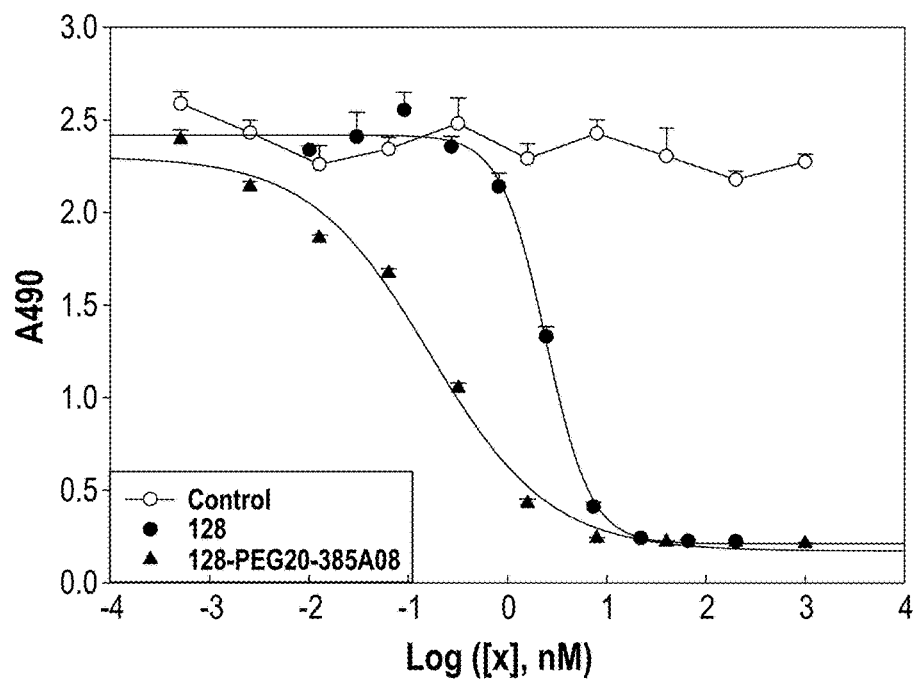
FIG. 23. Cell-based VEGFR2 Assay of IGF-IR/VEGFR2 Multimers. A graph representing the inhibition of VEGF mediated proliferation by selected IGF-IR binding fibronectin scaffold clones. The engineered pro-B cell line hKE8-3 (Ba/F3:VEGFR2) was plated in 96 well plates at a concentration of 25000 cells per well in RPMI (Invitrogen, Carlsbad, Calif.) containing 10% fetal bovine serum (Hyclone, Logan, Utah) in the presence of 5 ng/mL VEGF and various concentrations of each VEGFR2 antagonist (● VEGFR2 binding clone SEQ ID NO: 128; ○ Control SEQ ID NO: 227; ▲ VEGFR2/IGF-IR binding clones (SEQ ID NO: 203) linked by PEG: 385A08-PEG20-SEQ ID NO: 128).

Example 25. MALDI TOF Mass Spectrometry of FG Loop Optimized 338A06 Clones Following Purification One liter E. coli growths of selected FG loop optimized 338A06 IGF-IR competitive clones were prepared and the proteins were purified. Mass spectrometry of the purified, optimized IGF-IR clones was performed to ensure identity. In the present example, clone 387B01 was examined. The predicted mass of clone 387B01 is 11554 atomic mass units (amu). MALDI TOF mass spectrometry of clone 387B01 revealed a mass of approximately 11553 m/z after calibration with standards, well within experimental error of the instrumentation (FIG. 18). An additional minor species at higher m/z is observed. (FIG. 18). It is uncertain whether this is matrix adduct or a minor post-translationally modified species. Therefore 387B01, and indeed all IGF-IR clones examined, gave masses consistent with their predicted masses.

Example 26. PEGylation of Fibronectin-Based Scaffold Proteins

In order to perform in vivo studies, PEGylation of the fibronectin-based scaffold proteins was performed. In the present example, clone 385A08 was produced in an E. coli expression system with a C-terminal extension to yield the following protein sequence (C-terminal extension italicized in bold with Cys97 underlined):

(SEQ ID NO: 203)
GVSDVPRDLEVVAATPTSLLISWSARLKVARYYRITYGETGG

NSPVQEFTVPKNVYTATISGLKPGVDYTITVYAVTRFRDYQP

ISINYRTEIDKPCQ

The single sulfhydryl of the cysteine residue at position 97 was used to couple to PEG variants using standard maleimide chemistry to yield two different PEGylated forms of 385A08. Both a linear 20 kDa bifunctional PEG and a mono-functional branched 40 kDa PEG (NOF Corporation) were conjugated to clone 385A08 to produce 385A08-PEG20-385A08 and 385A08-PEG40, respectively. The PEGylated protein forms were purified from unreacted protein and PEG by anion exchange and size-exclusion chromatography. Covalent linkage of the two PEG forms of 385A08 was verified by SDS-PAGE (FIG. 11) and mass spectroscopy.

Example 27. Determination of Binding Affinity and Kinetics of PEGylated Fibronectin-Based Scaffold Clone Variants Surface plasmon resonance (BIAcore) analysis was performed using recombinant, immobilized IGF-IR and solution-phase analyte in order to determine binding kinetics and binding affinities of 385A08-PEG20-385A08 and 385A08-PEG40 variants. While the 385A08-PEG40 form was found to have an approximately 10-fold slower on-rate (ka) relative to unmodified 385A08, the 385A08-PEG20-385A08 form has an approximately two-fold faster on-rate (Table 10). The off-rates (kd; Table 10) of the variants relative to unmodified 385A08 were slightly increased for the 385A08-PEG40 form and slightly decreased for the 385A08-PEG20-385A08 variant.

TABLE 10

Determination of $k_a$, $k_d$ and $K_D$ by BIAcore

| Clone | $k_a$ (1/M*s) × $10^{+6}$ | $k_d$ (1/s) × $10^{-4}$ | $K_D$ (pM) |
|---|---|---|---|
| 385A08 | 6.9 | 1.6 | 23 |
| 385A08-PEG20-385A08 | 15 | 0.9 | 6 |
| 385A08-PEG40 | 0.6 | 2.1 | 355 |

Example 28. Evaluation of PEGylated Fibronectin-Based Scaffold Clone Variants in a IGF-IR Proliferation Assay The PEGylated fibronectin-based scaffold variants were assessed for inhibition of serum mediated proliferation using the human plasmacytoma cell line NCI-H929. In this cell line, the anti-IGF-IR MAB391 and the unmodified 385A08 demonstrated comparable degrees of inhibition of cell growth with an apparent IC50 of approximately 100 pM. The 385A08-PEG40 variant was slightly less inhibitory with an IC50 approaching 1 nM. On the other hand, the PEG20-385A08-PEG20 variant was extremely potent and essentially 100% inhibitory at all concentrations tested. Therefore an IC50 was less than 100 fM.

Example 29. Evaluation of Multimers of Fibronectin Scaffold IGF-IR Binders in an IGF-IR Proliferation Assay A murine lymphocyte cell line, 32D, expressing human IGF-IR was used to evaluate effects of IGF-IR antagonists. Antagonists comprising two fibronectin scaffold IGF-IR binding domains demonstrated a marked increase in inhibitory effects over a single fibronectin scaffold domain or an anti-IGF-IR antibody.

Example 30. Evaluation of Bispecific Fibronectin Scaffold Multimers in an IGF-IR Proliferation Assay Fibronectin scaffold proteins were assessed for inhibition of serum mediated proliferation using the human plasmacytoma cell line NCI-H929. In this cell line, the IGF-IR fibronectin scaffold and the IGF-IR/VEGFR2 bispecific fibronectin scaffold multimer demonstrated comparable degrees of inhibition of cell growth.

Example 31. Evaluation of Bispecific Fibronectin Scaffold Multimers in a VEGFR2 Proliferation Assay Fibronectin scaffold proteins were assessed for inhibition of a VEGF-dependent cell line. In this cell line, the VEGFR2 fibronectin scaffold and the IGF-IR/VEGFR2 bispecific fibronectin scaffold multimer demonstrated comparable degrees of inhibition of cell growth.

Example 32. Evaluation of Fibronectin Scaffold IGF-IR Binder HSA Conjugate

Figure 25:
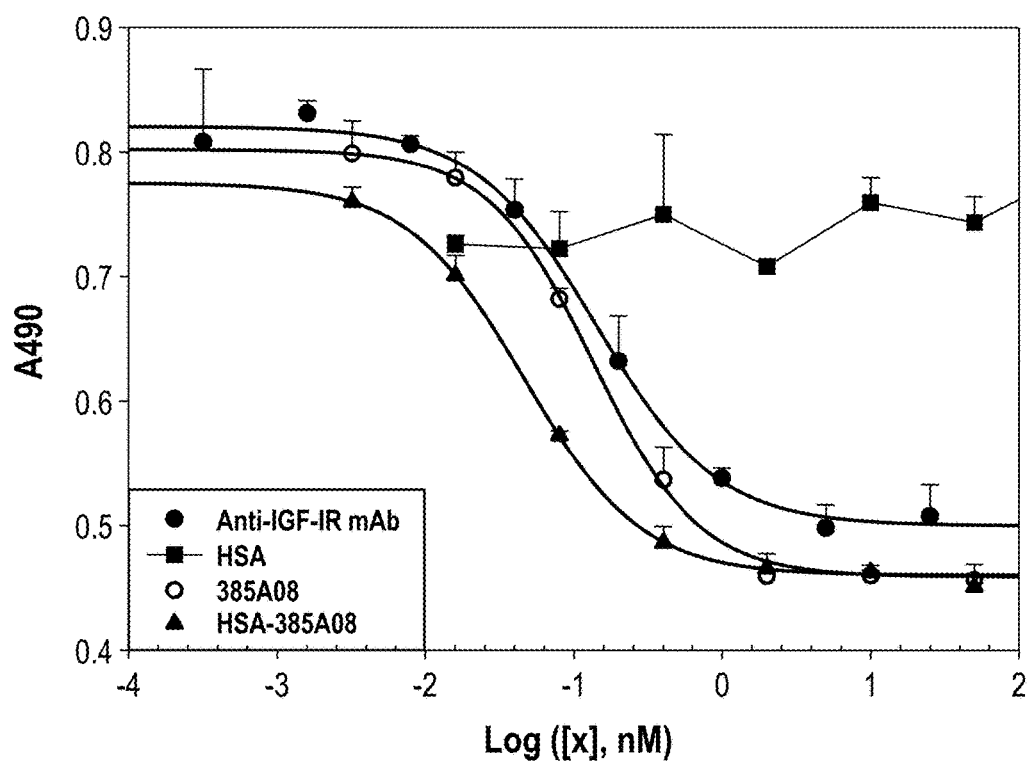
FIG. 25. Evaluation of Fibronectin Scaffold IGF-IR Binder linked to HSA. A graph representing the inhibition of serum mediated proliferation by selected IGF-IR binding fibronectin scaffold clones. The human plasmacytoma cell line NCI-H929 (ATCC, Manassas, Va.) was plated in 96 well plates at a concentration of 25000 cells per well in DMEM (Invitrogen, Carlsbad, Calif.) containing 10% fetal bovine serum (Hyclone, Logan, Utah) in the presence of various concentrations of each IGF-IR antagonist (● anti-IGF-IR monoclonal antibody MAB391, R&D Systems, Minneapolis, Minn.; ○ IGF-IR binding clone 385A08 (SEQ ID NO:203); ▲ HSA-385A08 (SEQ ID NO:203); ■ Human Serum Albumin (HSA, Invitrogen, Carlsbad, Calif.)). Cells were allowed to proliferate for 72 hours at 37° C., 5% $CO_2$. After the proliferation period, cells were exposed Cell Titer 96 Aqueous Proliferation Reagent (Promega, Madison, Wis.) and allowed to incubate for an additional four hours. Absorbance at 490 nm was measured on a Spectramax Plus 384 (Molecular Devices, Sunnyvale, Calif.), and the resulting data was analyzed using SigmaPlot (Systat Software, Point Richmond, Calif.).

Fibronectin scaffold proteins were assessed for inhibition of serum mediated proliferation using the human plasmacytoma cell line NCI-H929. IGF-IR and IGF-IR/HSA proteins demonstrated comparable degrees of inhibition of cell growth (see FIG. 25).

Figure 26:
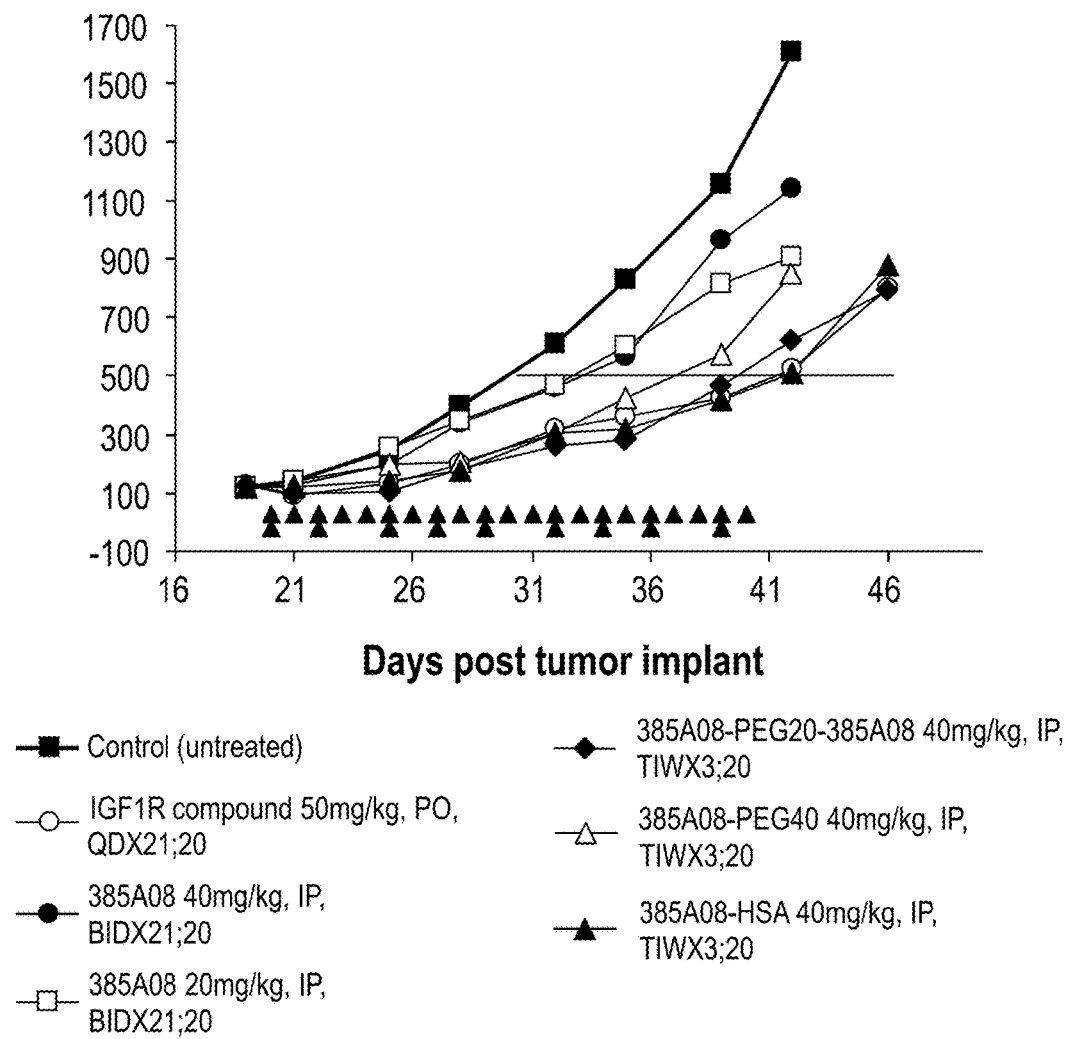
FIG. 26. In vivo tumor growth inhibition by IGF-IR constructs. The median tumor volume (mg) (y-axis) is plotted against days post tumor implant (x-axis). Triangles at the bottom of the X-axis indicate doses administered. IGFIR compound (an IGF-IR antagonist); 385A08 (SEQ ID NO: 226); 385A08-PEG20-385A08 (SEQ ID NO: 203-PEG20-SEQ ID NO: 203); 385A08-PEG40 (SEQ ID NO: 203); and 385A08-HSA (SEQ ID NO: 203) demonstrate varying degrees of tumor inhibition in an Rh41 xenograft model.
Figure 27:
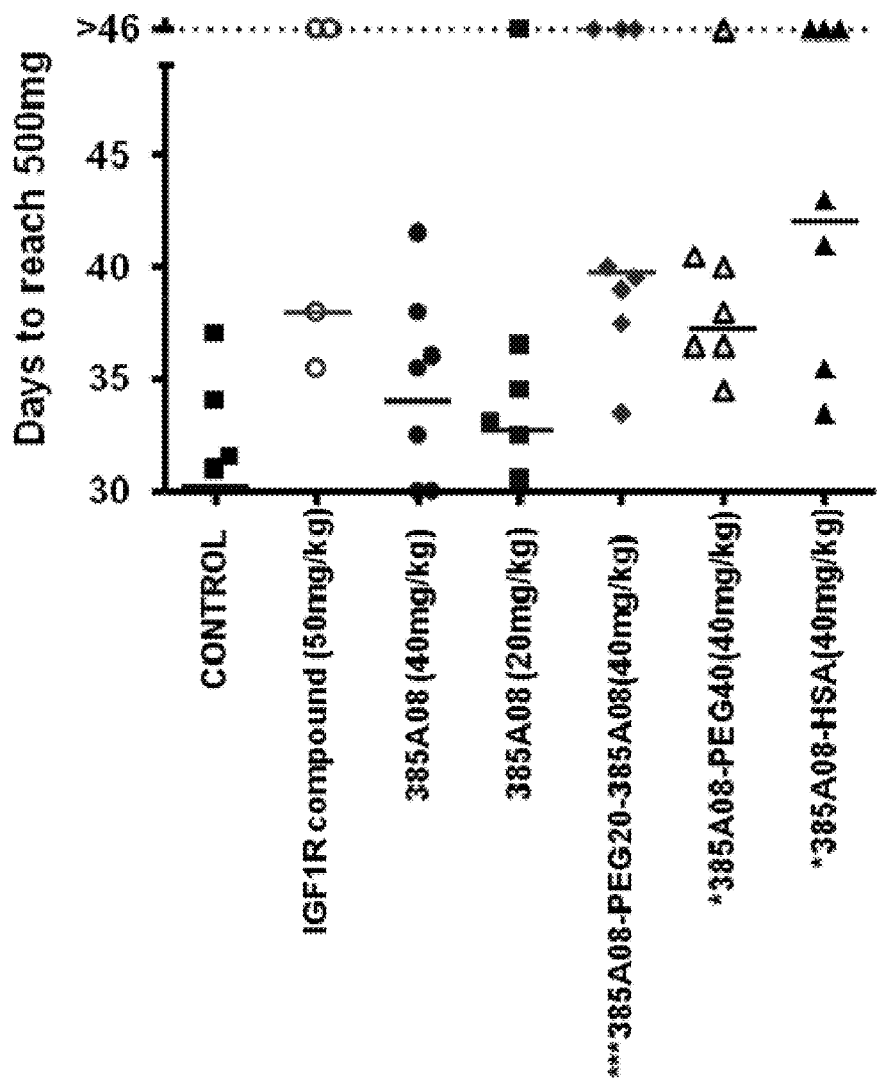
FIG. 27. In vivo tumor growth inhibition by IGF-IR constructs. The number of days to reach a median group tumor size of 500 mg (y-axis) is plotted against the different treatment groups as described in FIG. 26 (x-axis). The median time for group to reach target size is indicated by horizontal lines. *$p \leq 0.05$ or ***$p \leq 0.0005$ for time to reach 500 mg relative to control.

Various IGF-IR antagonists were tested for their in vivo antitumor activity in RH41 sarcoma xenografts (see FIGS. 26 and 27). Table 11 summarizes the results of the study.

TABLE 11

| | In vivo antitumor activity in the RH41 sarcoma study | | | | | | |
|---|---|---|---|---|---|---|---|
| Compound | Schedule, Route | Dose (mg/kg) | AVE weight change (g)$^c$ | LCK | % TGI* | p value for % TGI* | Outcome by LCK (% TGI) |
| IGF-IR Compound | qdx21; 20 po$^a$ | 50 | −0.9 | 0.5 | 70 | 0.004 | I(A) |

TABLE 11-continued

In vivo antitumor activity in the RH41 sarcoma study

| Compound | Schedule, Route | Dose (mg/kg) | AVE weight change (g)[c] | LCK | % TGI* | p value for % TGI* | Outcome by LCK (% TGI) |
|---|---|---|---|---|---|---|---|
| 385A08 | 2qdx20; 28 ip[b] | 40 | 1.0 | 0.2 | 19 | 0.301 | I(I) |
| 385A08 | 2qdx20; 28 ip[b] | 20 | 0.6 | 0.2 | 33 | 0.053 | I(I) |
| 385A08-PEG20-385A08 | TIWx3; 20 ip[b] | 40 | 0.1 | 0.6 | 66 | 0.001 | I(A) |
| 385A08-PEG40 | TIWx3; 20 ip[b] | 40 | 1.4 | 0.4 | 56 | 0.053 | I(A) |
| 385A08-HSA | TIWx3; 20 ip[b] | 40 | 0.8 | 0.7 | 71 | 0.013 | I(A) |
| Control (untreated) | — | — | 1.4 | — | — | 1.0 | — |

*Tumor growth inhibition and probability values calculated on day 39.
[a]Vehicle was 80% PEG400, 20% dH$_2$O.
[b]Vehicle was PBS.
[c]Average weight change for each group is the mean difference between weight at the start of treatment (Day 20) and after the end of treatment (Day 42).
TVDT was calculated for a size of 500 mg Abbreviations used are as follows: po, oral route; ip, intraperitoneal route; LCK, gross log cell kill calculated as LCK = T − C/(3.32 × TVDT) where T − C is the difference in time in days for the treated tumors (T) to reach a predetermined size (tumor target size) relative to the vehicle control group (C) divided by the tumor volume doubling time (TVDT) multiplied by 3.32.
TVDT was the median time in days for control tumors to reach the target size - median time in days for control tumors to reach half the target size; Outcome, a treatment regimen was considered active if it produced a statistically significant LCK of ≥1.0; % TGI, relative % tumor growth inhibition calculated as % TGI = [(C$_t$ − T$_t$)/(C$_t$ − C$_0$)] × 100 where C$_t$ = median tumor weight of control mice at time t in days after tumor implant, T$_t$ = median tumor weight of treated mice at time t, C$_0$ = median tumor weight of control mice at time 0.
% TGI value was calculated at various time points beginning after 1.5 tumor volume doubling times and sustained over a period of 3 tumor volume doubling times where possible. A % TGI value of >50% was considered active; q2dx5 (as an example of a schedule), compound was administered every other day for five doses.

Polypeptide fusion proteins of HSA-IGF-IR may also be generated. The following lists various N- and C-terminal HSA fusions to IGF-IR clone 385A08. The HSA leader and propeptide sequence is omitted in the C-terminal constructs. Fn linker1 is derived from the amino acid sequence linking the first and second fibronectin type III domains. Fn linker2 is derived from the amino acid sequence linking the tenth and eleventh fibronectin type III domains (see FIG. 30).
Human serum albumin (unprocessed)-Fn linker1-385A08; SEQ ID NO: 228
385A08-Fn linker1-Human serum albumin (processed); SEQ ID NO: 229
Human serum albumin (unprocessed)-Fn linker2-385A08; SEQ ID NO: 230
Human serum albumin (unprocessed)-(GS)$_5$ linker-385A08; SEQ ID NO: 231
Human serum albumin (unprocessed)-(GS)$_{10}$ linker-385A08; SEQ ID NO: 232
385A08-Fn linker2-Human serum albumin (processed); SEQ ID NO: 233
385A08-(GS)$_5$ linker-Human serum albumin (processed); SEQ ID NO: 234
385A08-(GS)$_{10}$ linker-Human serum albumin (processed); SEQ ID NO: 235

Example 33. Evaluation of Fibronectin Scaffold IGF-IR Binder Linked to Transferrin Fibronectin scaffold proteins fused to transferrin are assessed for inhibition of serum mediated proliferation using the human plasmacytoma cell line NCI-H929.
Polypeptide fusion proteins of transferrin-IGF-IR may be generated. The following lists various N- and C-terminal transferrin fusions to IGF-IR clone 385A08. The transferrin leader sequence is omitted in the C-terminal constructs (see FIG. 30).
Human transferrin (unprocessed)-Fn linker1-385A08; SEQ ID NO: 236
385A08-Fn linker1-Human transferrin (processed); SEQ ID NO: 237
Human transferrin (unprocessed)-Fn linker2-385A08; SEQ ID NO: 238
Human transferrin (unprocessed)-(GS)$_5$ linker-385A08; SEQ ID NO: 239
Human transferrin (unprocessed)-(GS)$_{10}$ linker-385A08; SEQ ID NO: 240
385A08-Fn linker2-Human transferrin (processed); SEQ ID NO: 241
385A08-(GS)$_5$ linker-Human transferrin (processed); SEQ ID NO: 242
385A08-(GS)$_{10}$ linker-Human transferrin (processed); SEQ ID NO: 243

Example 34. IGF-IR-Fc Fusion Proteins

Figure 29:
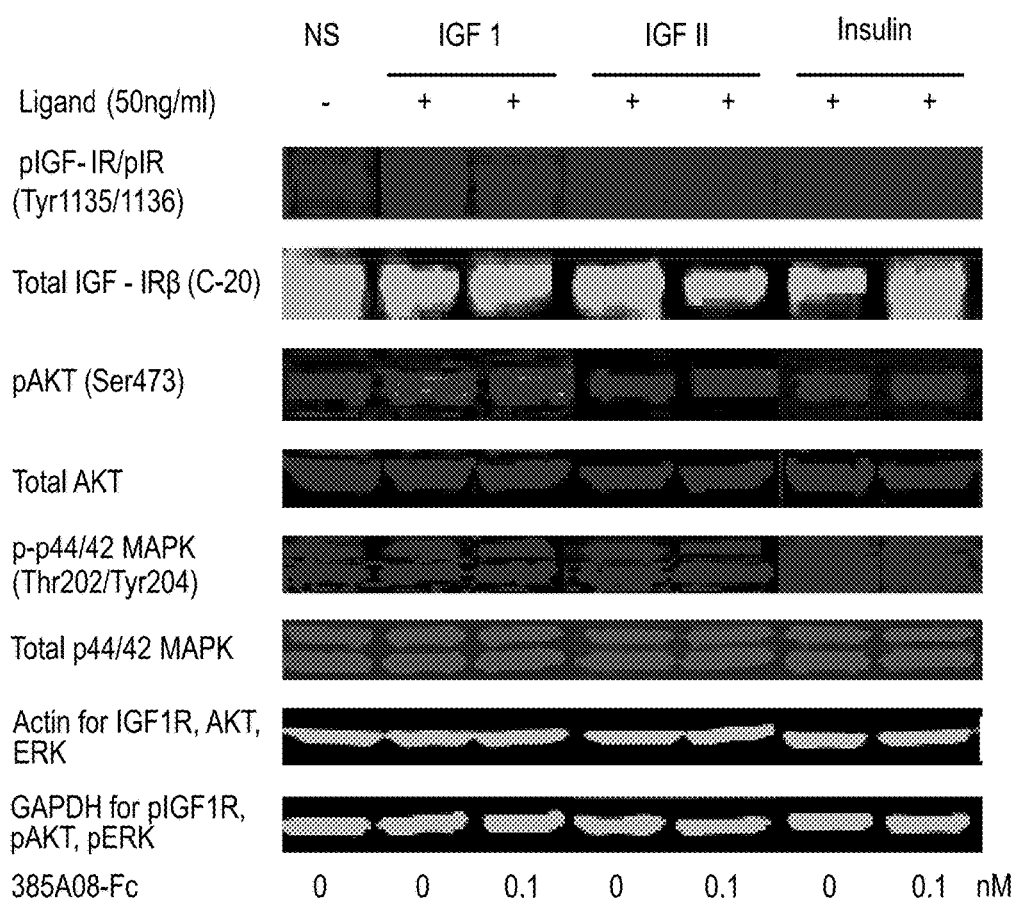
FIG. 29 depicts a Western Blot employed to assess the ability of 385A08-Fc to inhibit IGF-1R AKT and MAPK phosphorylation in Rh41 human rhabdomyosarcoma cells. Cells were stimulated with IGF-I, IGF-II, insulin ligands (50 ng/ml), or no stimulation (NS) and then treated with various concentrations of 385A08-Fc (SEQ ID NO: 226). Membranes were probed with antibodies as indicated, as well as phospho-specific antibodies.

Fibronectin-based scaffold proteins fused to Fc were evaluated for their ability to inhibit various cell lines. The IC50 values were determined for 385A08-Fc (amino acids 90-423 of SEQ ID NO: 247) in Rh41 cells (4.5 nM), DU4475 cells (>50 nM), H929 cells (0.15 nM), BXPC-3 (>500 nM), and HT-29 cells (>1000 nM). The IGF-IR-Fc fusion demonstrated a 91% maximum inhibition in the Rh41 cell line.
Fibronectin-based scaffold proteins fused to Fc were evaluated for their ability to inhibit IGF-1R, AKT and MAPK phosphorylation in Rh41 human rhabdomyosarcoma cells (see FIG. 29).
Fibronectin-based scaffold proteins fused to Fc were evaluated for their ability to inhibit proliferation in Rh41 and H929 cell lines (Table 12). Cells were treated with nM concentrations of 385A08-Fc as noted. The IC50 values are as follows: Rh41 Trial 1 (48.65 nM), Rh41 Trial 2 (39.43 nM), average of Rh1 trials (44 nM), and H929 trial (0.15 nM).

TABLE 12

Effect of 385A08-Fc on Cellular Proliferation in Rh41 and H929 cell lines

| | Rh41 Trial 1 | | Rh41 Trial 2 | | H929 Assay | |
|---|---|---|---|---|---|---|
| nM | [³H] incorporation | standard deviation | [³H] incorporation | standard deviation | [³H] incorporation | standard deviation |
| 50 | 54.9 | 2.67 | 52.1 | 3.27 | 20.2 | 1.52 |
| 10.0 | 61.9 | 1.56 | 59.3 | 1.14 | 18.4 | 0.89 |
| 2.0 | 77.9 | 2.86 | 78.6 | 1.9 | 20.6 | 0.62 |
| 0.4 | 97.1 | 2.26 | 94.6 | 1.08 | 32.0 | 1.97 |
| 0.08 | 102.9 | 1.14 | 98.4 | 0.52 | 57.1 | 3.87 |
| 0.016 | 101.2 | 1.26 | 102.5 | 0.95 | 80.1 | 3.09 |

Example 35. Examples of Methods Used Herein

The following materials and methods were used for the experiments described in the previous examples.

Recombinant Proteins:

Recombinant human, IGF-I, IGF-IR, insulin receptor (IR), anti-IGF-IR MAB391, and recombinant human VEGF-R2-Fc were obtained from R&D Systems (Minneapolis, Minn.). Biotinylation of IGF-IR was carried out in 1×PBS at 4° C. for 2 hours in the presence of EZ-Link™ Sulfo-NHS-LC-LC-Biotin (Pierce, Ill.). Excess of EZ-Link™ Sulfo-NHS-LC-LC-Biotin was removed by dialysis against 1×PBS. The level of biotinylation was determined by mass spectroscopy and protein concentrations were determined using Coomassie Protein Plus Assay (Pierce, Ill.).

Primers:

The following oligonucleotides were prepared by chemical synthesis for eventual use in library construction and mutagenesis of selected clones.

T7TMV:
(SEQ ID NO: 204)
5'-TAA TAC GAC TCA CTA TAG GGA CAA TTA CTA TTT ACA ATT ACA ATG-3'

FnAB:
(SEQ ID NO: 205)
5'-GGG ACA ATT ACT ATT TAC AAT TAC AAT GGT TTC TGA TGT GCC GCG CGA CCT GGA AGT GGT GCT GCA CAC CCC CAC CAG CCT GCT GAT CAG CTG G-3'

FnBC:
(SEQ ID NO: 206)
5'-AGC CTG CTG ATC AGC TGG NNS NNS NNS NNS NNS NNS NNS CGA TAT TAC CGC ATC ACT-3'

FnCD:
(SEQ ID NO: 207)
5'-AGG CAC AGT GAA CTC CTG GAC AGG GCT ATT GCC TCC TGT TTC GCC GTA AGT GAT GCG GTA ATA TCG-3'

FnDE:
(SEQ ID NO: 208)
5'-CAG GAG TTC ACT GTG CCT NNS NNS NNS NNS ACA GCT ACC ATC AGC GGC-3'

FnEF:
(SEQ ID NO: 209)
5'-AGT GAC AGC ATA CAC AGT GAT GGT ATA ATC AAC GCC AGG TTT AAG GCC GCT GAT GGT AGC TGT-3'

FnFG6:
(SEQ ID NO: 210)
5'-ACT GTG TAT GCT GTC ACT NNS NNS NNS NNS NNS NNS CCA ATT TCC ATT AAT TAC-3'
to give an FG loop with 6 random amino acids.

FnFG8: 5'-ACT GTG TAT GCT GTC ACT NNS NNS NNS NNS NNS NNS NNS NNS CCA ATT TCC ATT AAT TAC-3' (SEQ ID NO: 211) to give an FG loop with 8 random amino acids.

FnFG10: 5'-ACT GTG TAT GCT GTC ACT NNS NNS NNS NNS NNS NNS NNS NNS NNS NNS CCA ATT TCC ATT AAT TAC-3' (SEQ ID NO: 212) to give an FG loop with 10 random amino acids.

FnFG12: 5'-ACT GTG TAT GCT GTC ACT NNS NNS NNS NNS NNS NNS NNS NNS NNS NNS NNS NNS CCA ATT TCC ATT AAT TAC-3' (SEQ ID NO: 213) to give an FG loop with 12 random amino acids.

FnFG14: 5'-ACT GTG TAT GCT GTC ACT NNS NNS NNS NNS NNS NNS NNS NNS NNS NNS NNS NNS NNS NNS CCA ATT TCC ATT AAT TAC-3' (SEQ ID NO: 214) to give an FG loop with 14 random amino acids.

FnG:
(SEQ ID NO: 215)
5'-TTA AAT AGC GGA TGC CTT GTC GTC GTC GTC CTT GTA GTC TGT GCG GTA ATT AAT GGA AAT TGG-3'

FLAG:
(SEQ ID NO: 216)
5'-TTT TTT TTT TTT TTT TTT TTA AAT AGC GGA TGC CTT GTC GTC GTC GTC CTT GTA-3'

218C04BC:
(SEQ ID NO: 217)
5'-AGC CTG CTG ATC AGC TGG TCC CCG TAC CTG CGC GTC GCC CGA TAT TAC CGC ATC ACT-3'

218C04DE:
(SEQ ID NO: 218)
5'-CAG GAG TTC ACT GTG CCT TCC TCC GCC CGC ACA GCT ACC ATC AGC GGC-3'

218C04FG:
(SEQ ID NO: 219)
5'-ACT GTG TAT GCT GTC ACT CCG TCC AAC ATC ATC GGC CGT CAC TAT GGC CCA ATT TCC ATT AAT TAC-3'

FnB:
(SEQ ID NO: 220)
5'-AGC CTG CTG ATC AGC TGG-3'

FnD:
(SEQ ID NO: 221)
5'-CAG GAG TTC ACT GTG CCT-3'

FnF:
(SEQ ID NO: 222)
5'-ACT GTG TAT GCT GTC ACT-3'

338A06BC:
(SEQ ID NO: 223)
AGC CTG CTG ATC AGC TGG TCT GCG CGT CTG AAA GTT GCG CGA TAT TAC CGC ATC ACT

-continued

338A06DE:
(SEQ ID NO: 224)
CAG GAG TTC ACT GTG CCT AAA AAC GTT TAC ACA GCT
ACC ATC AGC GGC

Primary Library Construction:

A diverse library was constructed by extension of the overlapping synthetic oligonucleotides listed above, using KOD polymerase (EMD Biosciences, San Diego, Calif.). In these oligonucleotide designations, "N" indicates a mixture of A, C, G and T; and "S" indicates a mixture of C and G. Loop definitions are identical to those described previously (Xu et al, 2002). The BC loop was constructed by extension of 50 pmol FnBC with 100 pmol FnCD in a 1000 KOD reaction that was supplemented with 1M Betaine and 3% DMSO. The reaction was taken through 10 temperature cycles of 30 s at 94° C., 30 s at 52° C. and 1 min at 68° C. to ensure complete extension of the fragments. The DE and FG loops were constructed in a similar manner, using 200 pmol FnDE with 100 pmol FnEF for the DE loop and 100 pmol FnFG10 with 200 pmol FnG for the FG loop. Following extension of the 3 individual loops, the DE and FG loops were combined and extended together for an additional 10 temperature cycles of 30 s at 94° C., 30 s at 52° C. and 1 min at 68° C. The BC loop was extended with 100 pmol FnAB in the same manner. The DE/FG mixture and the BC loop were each diluted 10-fold with fresh KOD reagents and extended with FLAG and T7TMV respectively, for 10 temperature cycles 30 s at 94° C., 30 s at 52° C. and 1 min at 68° C. Finally the fragments were combined and extended together for 10 temperature cycles of 30 s at 94° C., 30 s at 52° C. and 1 min at 68° C. This produced a library with 7 random amino acids in the BC loop, 4 random amino acids in the DE loop, and 10 random amino acids in the FG loop. Additional libraries were constructed with different FG loop lengths by using oligonucleotides FnFG6, FnFG8, FnFG12 or FnFG14 instead of FnFG10. The libraries containing FG loop lengths between 6 and 14 amino acids were combined to give a variable-length FG library.

Construction of Single-Loop Randomized Libraries from Clone 218C04:

Three libraries were constructed in which single loops were replaced with random sequence. The libraries were constructed at the DNA level by overlap extension with KOD polymerase as described above, except that random sequences in two out of three loops were replaced with fixed sequence corresponding to clone 218C04. The fixed sequences were provided in the BC loop by oligonucleotide 218C04BC, and in the DE loop by oligonucleotide 218C04DE, and in the FG loop by oligonucleotide 218C04FG. These replaced the corresponding random oligonucleotides FnBC, FnDE, or FnFG10 during library construction.

The library in which the BC loop from clone 218C04 was replaced by random amino acids was made by assembling the oligonucleotides: T7TMV+FnAB+FnBC+FnCD+218C04DE+FnEF+218C04FG+FnG+FLAG as described above. The library in which the DE loop from clone 218C04 was replaced by random amino acids was made by assembling the oligonucleotides: T7TMV+FnAB+218C04BC+FnCD+FnDE+FnEF+218C04FG+FnG+FLAG. The library in which the FG loop from clone 218C04 was replaced by random amino acids was assembled from the oligonucleotides: T7TMV+FnAB+218C04BC+FnCD+218C04DE+FnEF+FnFG10+FnG+FLAG.

Construction of 3-Loop Randomized Libraries from Clone 218C04:

The three single-loop libraries derived from clone 218C04 were subjected to PROfusion selection as described above. The surviving clones in each library contained 2 loops from the parent clone and 1 loop from the random sequence that was compatible with binding of each fibronectin-based scaffold protein. The three random loops, one from each library, were amplified using oligonucleotide primers that bound the surrounding scaffold regions. The BC loop was amplified from the library containing the variable BC loop using oligonucleotide primers FnB and FnCD. The DE loop was amplified from the library containing the variable DE loop using oligonucleotide primers FnD and FnEF. The FG loop was amplified from the library containing the variable FG loop using oligonucleotide primers FnF and FnG. The three excised loops were purified by agarose gel electrophoresis, mixed in equal proportions and amplified by KOD polymerase with primers FnAB and FnG followed by T7TMV and FLAG.

Construction of a Single-Loop Random FG Library from Clone 338A06:

A library was constructed in which the FG loop of clone 338A06 was replaced by 6 random amino acids. KOD polymerase was used for overlap extension of the oligonucleotides T7TMV+FnAB+338A06BC+FnCD+338A06DE+FnEF+FnFG6+FnG+FLAG as described above. The loop sequences corresponding to clone 338A06 were introduced by oligonucleotides 338A06BC and 338A06DE, and the random 6-amino acid FG loop was introduced by oligonucleotide FnFG6.

RNA-Protein Fusion Production:

Double-stranded DNA libraries were converted into RNA-protein fusions (PROfusion) essentially as described (Xu et al, 2002, Kurz et al, Nuc. Acid Res. 28:83, 2000). Briefly, the DNA library was transcribed using an in vitro transcription kit (MEGAscript™, Ambion, Austin, Tex.) and the resulting RNA was desalted by size exclusion chromatography on a NAP-5 column (GE Healthcare). 2 nmol RNA was crosslinked by irradiation at 314 nM for 20 min in 200 µl of a solution containing 150 mM NaCl, 10 mM Tris-HCl (pH8) and a 1.5-fold excess of puromycin-containing linker (5'-Pso u agc gga ugc XXX XXX CC Pu-3' (Pu=puromycin, Pso=C6-psoralen, u, a, g, c=2'-OMe-RNA, X=9-atom PEG spacer.))

The mRNA-puromycin molecules were then translated in 3 ml rabbit reticulocyte lysate (Ambion, Austin, Tex.) in the presence of $^{35}$S-labeled methionine. The resulting mRNA-protein fusions were purified using oligo dT cellulose (GE Healthcare) and reverse-transcribed using superscript II reverse transcriptase (Invitrogen) and 2 nmol of the primer FLAG according to the manufacturers instructions.

The cDNA/mRNA-protein fusions were purified by M2 Flag agarose (Sigma, St Louis, Mo.) and quantitated by measuring the incorporated $^{35}$S methionine. This gave a purified library of approximately $10^{12}$ full length fibronectin-based scaffold proteins that were amplified by PCR using primers T7TMV and FLAG for use in subsequent PROfusion experiments.

Affinity Selection for Binding to IGF-IR:

Libraries of mRNA-protein fusions, prepared as described above, were incubated with Streptavidin-coated magnetic beads (M280 Streptavidin, Invitrogen) to remove fibronectin-based scaffold proteins that bind to Streptavidin. The beads were separated on a magnet and the unbound fraction was collected and added to 100 nM biotinylated IGF-IR in PBS with 0.05% Tween 20 and 1 mg/ml BSA (Ambion). After 30 min, the bound fibronectin-based scaffold proteins were captured on Streptavidin-coated magnetic beads and washed 6 times using a Kingfisher magnetic particle processor (Thermo Electron, Waltham, Mass.). The cDNA was eluted in 100 mM KOH, neutralized with 100 mM Tris-HCl, and amplified by PCR to generate a second-generation library enriched in molecules that bind IGF-IR. The consecutive processes of amplification, synthesis of mRNA-protein fusions, and affinity selection were carried out a total of 5 times and the number of bound molecules was monitored by quantitative PCR. The fibronectin-based scaffold protein populations obtained after rounds 4 and 5 were amplified and ligated by recombination (InFusion™, Clontech, Mountain View, Calif.) into an *E. coli* expression vector containing a promoter for T7 RNA polymerase and an in-frame $His_6$ tag. The ligated mixture was transformed into *E. coli* strain BL21 (DE3) pLysS (Invitrogen) that expresses T7 RNA polymerase upon induction with IPTG, thereby giving inducible protein expression.

Optimization of Clone 218C04 Containing 3 Random Loops:

The 3-loop randomized 218C04 library was taken through cycles of amplification, synthesis of mRNA-protein fusions, and affinity selections as described above. For the first round, IGF-IR was immobilized on epoxy-activated beads to avoid selection of streptavidin-binding peptides. Thereafter, biotinylated IGF-IR was used at decreasing concentrations to select for the highest affinity binders. From round 2 onwards, non-biotinylated insulin receptor (IR) was also included at a concentration of 1 µM to act as a negative selection for IR binding. After 4 rounds, the resulting fibronectin-based scaffold protein populations were cloned into *E. coli* for analysis as described above.

Optimization of Clone 338A06 Containing a 6 Amino Acid Random FG Loop:

The DNA library was converted into mRNA-protein fusions as described above to give about 1000 copies of each FG loop sequence. PROfusion cycles of amplification, mRNA-protein fusion formation and affinity selection were carried out as described above. In the first round, the biotinylated IGF-IR concentration was 100 nM, but this was dropped to 0.8 nM in round 2 and 0.4 nM in round 3. The target concentration was chosen such that the percentage of mRNA-protein fusions bound to IGF-IR was less than 0.1% in each case, as measured by quantitative PCR. By this method, fibronectin-based scaffold proteins with improved affinity would have an advantage compared to the population as a whole.

Competitive ELISA for IGF-IR:

MaxiSorp™ plates (Nunc International, Rochester, N.Y.) were coated with 30 nM IGF-IR in PBS at 4° C. overnight followed by blocking in OptEIA buffer (BD biosciences, San Diego, Calif.) for 3 hours at room temperature. Purified fibronectin-based scaffold proteins in OptEIA buffer were bound to each well for 1 hour at room temperature at concentrations ranging from 50 pM to 1 µM. After washing in PBST to remove unbound fibronectin-based scaffold proteins, 10 nM biotinylated IGF-I (Upstate, Temecula, Calif.) was added for 1 hour at room temperature to bind to unoccupied IGF-IR. The excess ligand was removed by washing with PBST and bound ligand was detected with streptavidin-HRP (Pierce, Rockford, Ill.) using TMB detection reagents (BD biosciences) according to the manufacturer's instructions Direct Binding ELISA for IGF-IR:

MaxiSorp™ plates (Nunc International, Rochester, N.Y.) were coated with 10 nM IGF-IR in PBS at 4° C. overnight followed by blocking in PBS-casein buffer (Pierce) for 3 hours at room temperature. Purified fibronectin-based scaffold proteins in casein buffer were bound to each well for 1 hour at room temperature at a concentration of 5 nM. The plate was washed with PBST and 100 µl of a 1:4000 dilution of His-HRP probe (Pierce) was added to each well with incubation for 15 min at room temperature. The wells were washed 5 times with PBST and the bound HRP was detected with TMB detection reagents (BD biosciences) according to the manufacturer's instructions. Clones that showed binding in this single-point assay were analyzed further using a gradient of fibronectin-based scaffold protein concentrations ranging from 30 pmol to 330 nM.

High Throughput Protein Production (HTPP):

Selected binders cloned into pDEST-14 vector and transformed into *E. coli* BL21 (DE3) pLysS cells were inoculated in 5 ml LB medium containing 50 µg/mL carbenicillin and 34 µg/mL chloromphenicol in a 24-well format and grown at 37° C. overnight. Fresh 5 ml LB medium (50 µg/mL carbenicillin and 34 µg/mL chloromphenicol) cultures were prepared for inducible expression by aspirating 200 µl from the overnight culture and dispensing it into the appropriate well. The cultures was grown at 37° C. until $A_{600}$ 0.6-1.0. After induction with 1 mM isopropyl-β-thiogalactoside (IPTG) the culture was grown for another 4 hours at 30° C. and harvested by centrifugation for 30 minutes at 3220 g at 4° C. Cell Pellets were frozen at −80° C.

Cell pellets (in 24-well format) were lysed by resuspension in 450 µl of Lysis buffer (50 mM $NaH_2PO_4$, 0.5 M NaCl, 1× Complete™ Protease Inhibitor Cocktail-EDTA free (Roche), 1 mM PMSF, 10 mM CHAPS, 40 mM Imidazole, 1 mg/ml lysozyme, 30 ug/ml DNAse, 2 ug/ml aprotonin, pH 8.0) and shaken at room temperature for 1 hour. Lysates were clarified and re-racked into a 96-well format by transfer into a 96-well Whatman GF/D Unifilter fitted with a 96-well, 650 µl catch plate and centrifuged for 5 minutes at 200 g. The clarified lysates were transferred to a 96-well Ni-Chelating Plate that had been equilibrated with equilibration buffer (50 mM $NaH_2PO_4$, 0.5 M NaCl, 10 mM CHAPS, 40 mM Imidazole, pH 8.0) and incubated for 5 min. Unbound material was removed by vacuum. The resin was washed 2×0.3 ml/well with Wash buffer #1 (50 mM $NaH_2PO_4$, 0.5 M NaCl, 5 mM CHAPS, 40 mM Imidazole, pH 8.0) with each wash removed by vacuum. Next the resin was washed with 3×0.3 ml/well with PBS with each wash step removed by vacuum. Prior to elution each well was washed with 50 µl Elution buffer (PBS+20 mM EDTA), incubated for 5 min and this wash discarded by vacuum. Protein was eluted by applying an additional 100 ul of Elution buffer to each well. After a 30 minute incubation at room temperature the plate(s) were centrifuged for 5 minutes at 200 g and eluted protein collected in 96-well catch plates containing 5 µl of 0.5M $MgCl_2$ affixed to the bottom of the Ni-plates. Eluted protein was quantified using a Bradford assay with BSA as the protein standard.

Mid-Scale Expression and Purification of Soluble Fibronectin-Based Scaffold Protein Binders:

For expression selected clone(s), followed by the $His_6$ tag, were cloned into a pDEST-14 vector and expressed in *E. coli* BL21 (DE3) pLysS cells. 20 ml of an inoculum culture (generated from a single plated colony) was used to inoculate 1 liter of LB medium containing 50 µg/mL carbenicillin and 34 µg/mL chloromphenicol. The culture was grown at 37° C. until $A_{600}$ 0.6-1.0. After induction with 1 mM isopropyl-β-thiogalactoside (IPTG) the culture was grown for another 4 hours at 30° C. and harvested by centrifugation for 30 minutes at ≥10,000 g at 4° C. Cell Pellets were frozen at −80° C. The cell pellet was resuspended in 25 mL of lysis buffer (20 mM $NaH_2PO_4$, 0.5 M NaCl, 1× Complete™ Protease Inhibitor Cocktail-EDTA free (Roche), 1 mM PMSF, pH 7.4) using an Ultra-turrax homgenizer (IKA works) on ice. Cell lysis was achieved by high pressure homogenization (≥18,000 psi) using a Model M-110S Microfluidizer (Microfluidics). The soluble fraction was separated by centrifugation for 30 minutes at 23,300 g at 4° C. The supernatant was clarified via 0.45 µm filter. The clarified lysate was loaded onto a HisTrap column (GE) pre-equilibrated with 20 mM $NaH_2PO_4$, 0.5 M NaCl, pH 7.4. The column was then washed with 25 column volumes of 20 mM $NaH_2PO_4$, 0.5 M NaCl, pH 7.4, followed by 20 column volumes of 20 mM $NaH_2PO_4$, 0.5 M NaCl, 25 mM imidazole pH 7.4, and then 35 column volumes of 20 mM $NaH_2PO_4$, 0.5 M NaCl, 40 mM imidazole pH 7.4. Protein was eluted with 15 column volumes of column volumes of 20 mM $NaH_2PO_4$, 0.5 M NaCl, 500 mM imidazole pH 7.4, fractions pooled based on absorbance at $A_{280}$ and dialyzed against 1×PBS or 50 mM NaOAc; 150 mM NaCl; pH4.5. Any precipitate was removed by filtering at 0.22 µm.

PEGylation of the Anti-IGF1R Fibronectin Scaffold

The fibronectin scaffold-PEG40 molecule was prepared by using a 2-fold excess of PEG-40-kDa (NOF Corporation) to the C-version of the fibronectin scaffold via maleimide chemistry. The reaction was allowed to proceed at room temperature for 2.5 hours. Free PEG-40 was separated from fibronectin scaffold-PEG-40 by Cation Exchange Chromatography (SP-HiTrap; GE). The reaction mixture was diluted 1:10 with 20 mM $NaH_2PO_4$, pH 6.7 and applied to an SP-HiTrap column pre-equilibrated with Equilibration buffer (20 mM $NaH_2PO_4$, 10 mM NaCl, pH 6.7), washed with Equilibration buffer and eluted using 20 mM $NaH_2PO_4$, 0.5M NaCl, pH 6.7. Eluted fractions were pooled based on SDS-PAGE analysis. The SP-pooled eluate was buffer exchanged via G25 Chromatography (GE) into PBS.

The PEG20-fibronectin scaffold-PEG20 was prepared by using a 2-fold excess of purified fibronectin scaffold-C to PEG-20-kDa (NOF Corporation) via maleimide chemistry. The reaction was carried out at room temperature for 1 hour. Unpegylated fibronectin scaffold was separated from the PEG20-fibronectin scaffold-PEG20 by SEC Chromatography (Superose 6; GE) in 20 mM $NaH_2PO_4$, 10 mM NaCl, pH 6.7 buffer. The fractions containing the PEG20-fibronectin scaffold-PEG20 were pooled and further purified to removed mono-pegylated fibronectin scaffold. This was achieved by cation exchange chromatography (SP; GE). A SP-HiTrap column was pre-equilibrated with Buffer A (20 mM $NaH_2PO_4$, 10 mM NaCl, pH 6.7), the SEC eluate was applied, the column was then washed with buffer A, and then a gradient from 0-10% buffer B (20 mM $NaH_2PO_4$, 1.0M NaCl, pH 6.7) over 5 column volumes and held for an additional 5 column volumes was run. PEG20-fibronectin scaffold-PEG20 was eluted from the SP-column by eluting with 50% Buffer B. Fractions were pooled by A280 and buffer exchanged into PBS by G25 Chromatography (GE).

Production of IGF-IR-PEG-VEGFR2 Binders

PEG 20 weighed on microbalance and dissolved to 100 mg/ml (5 mM) in 20 mM Sodium Phosphate/10 mM NaCl pH 6.7. PEG solution added to clone 385A08 (SEQ ID NO: 203) solution at a molar ratio of 5:1 (PEG:Protein). The reaction was incubated at room temperature for at least one hour with mixing.

To separate 385A08-PEG20 from uncoupled PEG, Bis-385A08, unPEGylated 385A08 monomer and 385A08 disulfide-linked dimer, the PEG-Protein reaction was loaded onto a HiTrap SP cation exchange column equilibrated with 20 mM Sodium Phosphate/10 mM NaCl pH 6.7 (Buffer A). Elution buffer (Buffer B) is 20 mM Sodium Phosphate/1.0M NaCl pH 6.7. Isocratic elution with 10% B (100 mM NaCl) isolates the 385A08-PEG20-species which is used to react with the VEGFR2 specific binder (SEQ ID NO: 128). Addition of the VEGFR2 specific binder to 385A08-PEG20- forms the 385A08-PEG20-VEGFR2 specific binder heterodimer.

Size exclusion chromatography was performed to separate uncoupled monomeric and dimeric the VEGFR2 specific binder from the 385A08-PEG20-VEGFR2 specific binder heterodimer. A Superdex 200 column was equilibrated with 20 mM Sodium Phosphate/10 mM NaCl pH 6.7. The 385A08-PEG20 plus the VEGFR2 specific binder reaction mixture was applied at a flow rate of 1.0 ml/min. Fractions corresponding the 385A08-PEG20-VEGFR2 specific binder were pooled as finished product.

BIAcore Analysis of the Soluble Fibronectin-Based Scaffold Proteins:

The binding kinetics of fibronectin-based scaffold proteins binding proteins to the target was measured using BIAcore 2000 or 3000 biosensors (Pharmacia Biosensor). A capture assay was developed utilizing an IGF-IR-Fc fusion. A similar reagent had been described by Forbes et al. (Forbes et al. 2002, European J. Biochemistry, 269, 961-968). The extracellular domain of human IGF-IR (aa 1-932) was cloned into a mammalian expression vector containing the hinge and constant regions of human IgG1. Transient transfection of the plasmid produced a fusion protein, IGF-IR-Fc which was subsequently purified by Protein A chromatography and captured on Protein A immobilized on Biasensor CM5 chips by amine coupling. The kinetic analysis involved the capture of IGF-IR-Fc on Protein A followed by injection of the fibronectin-based scaffold protein in solution and regeneration of the Protein A surface by glycine pH 2.0. Sensorgrams were obtained at each concentration and were evaluated using a program Biaevaluation, BIA Evaluation 2.0 (BIAcore), to determine the rate constants $k_a$ ($k_{on}$) and $k_d$ ($k_{off}$) The dissociation constant, $K_D$ was calculated from the ratio of rate constants $k_{off}/k_{on}$. Typically, a concentration series (2 uM to 0 uM) of purified fibronectin-based scaffold protein was evaluated for binding to protein A captured human IGF-IR-Fc fusion protein.

For experiments determining binding to human insulin receptor, recombinant human insulin receptor (IR) and recombinant human VEGF-R2-Fc were directly coupled to a CM5 Biasensor chip by amine group linkage following standard procedures recommended by Biacore (Uppsala, Sweden). In brief, 60 ug/mL of IR diluted in acetate 4.5 was coupled/immobilized to a level of 8300 RU and 11.9 ug/mL of VEGF-R2-Fc diluted in acetate 5.0 was immobilized to a level of 9700 RU on flow cells 2 and 3. A blank reference surface was prepared on FC1. Specific binding to either IR or VEGF-R2-Fc was calculated by subtracting the binding observed to the blank reference flow cell 1. Fibronectin-based scaffold proteins were diluted to 10 uM in HBS-EP (10 mM Hepes 150 mM NaCl 3 mM EDTA 0.05% Surfactant P20) and injected at 20 uL/min for 3 minutes over the flow cells at 25 C and dissociation was observed over 10 mins.

Differential Scanning Calorimetry:

Differential Scanning calorimetry (DSC) analysis of mid-scaled clones was performed to determine thermal stability. A 1 mg/ml solution of appropriate clone was scanned in a N-DSC II calorimeter (calorimetry Sciences Corp) by ramping the temperature from 5° C. to 95° C. at a rate of 1 degree per minute under 3 atm pressure. The data was analyzed vs. a control run of the appropriate buffer using a best fit using Orgin Software (OrginLab Corp).

Size-Exclusion Chromatography:

Size-exclusion chromatography (SEC) was performed using a TSKgel Super SW2000 column (TOSOH Biosciences, LLC), 4.6 mm×30 cm, on an Agilent 1100 HPLC system with UV detection at A214 nm and A280 nm and with fluorescence detection (excitation=280 nm, emission=350 nm). A buffer of 100 mM sodium sulfate, 100 mM sodium phosphate, 150 mM sodium chloride, pH 6.8 at a flow rate of 100 µL/min was employed. Samples (0.1 to 1 µg each) at a concentration of approximately 100 µg/mL were injected separately. Gel filtration standards (Bio-Rad Laboratories, Hercules, Calif.) were used for molecular weight calibration.

SEC MALLS Analysis of IGF-1R Fibronectin Scaffold Clones:

Size Exclusion Chromatography (SEC) was performed on a Waters Breeze HPLC system equipped with a Waters 2487 UV detector using a Superdex 200 column (GE Healthcare) with a mobile phase of 100 mM Sodium Sulfate, 100 mM Sodium Phosphate, 150 mM Sodium Chloride pH 6.8 applied at a flow rate of 0.6 ml/min. Samples were diluted to approximately 1.0 mg/ml with mobile phase and 50 µl was injected. Multi-Angle Laser Light Scattering (MALLS) analysis was performed using a miniDAWN Light Scattering detector (Wyatt Technology Corporation) and Optilab DSP Differential Refractometer (Wyatt Technology Corporation) plumbed in-line after the UV detector. Analysis of the light scattering data was performed using Astra V version 5.1.9.1 software (Wyatt Technologies Corporation). To calculate the concentration of the fibronectin-based scaffold protein by absorbance at 280 nm, a theoretical molar extinction coefficient based on amino acid sequence was used. For concentration determination by Refractive Index, an estimated specific refractive index increment (dn/dc) of 0.185 mL/g was used.

RP-HPLC Chromatography:

Reversed-phase HPLC (RP-HPLC) was performed using a C4 polymer column #259VHP5415 (Vydac), 4.6 mm×15 cm, heated to 60° C. on an Agilent 1100 HPLC system with UV detection at A214 nm and A280 nm and with fluorescence detection (excitation=280 nm, emission=350 nm). Solvent A consisted of MilliQ water containing 0.01% TFA, Solvent B was 100% HPLC-grade acetonitrile containing 0.01% TFA. A flow rate of 1 mL/min was employed. The elution scheme consisted of an equilibration condition of 10% B for 10 min followed by a linear gradient to 50% B over the course of 30 min. Under these conditions, fibronectin-based scaffold proteins eluted at approximately 25 to 30 minutes of total run time.

MALDI TOF Mass Spectrometry:

Fibronectin-based scaffold proteins were analyzed by Matrix Assisted Laser Desorption Ionization Time of Flight (MALDI-TOF) mass spectrometer (FIG. 14) using a Voyager DE PRO mass spectrometer (Applied Biosystems). Samples were diluted to approximately 1.0 mg/ml with 0.1% TFA. Approximately 12 µl of sample was loaded onto a C4 ZipTip (Millipore Corporation) and washed with 0.1% Trifluoroacetic Acid (TFA) to remove salts and contaminants. Sample was eluted directly from the ZipTip onto the target plate using 2 µl of Sinapinic Acid matrix (10 mg/ml in 70% Acetonitrile, 0.1% TFA). Standardization of the instrument was performed using two proteins of known mass: Cytochrome C (12361.96 Da) and Apomyoglobin (16952.27 Da) prepared to a final concentration of 5 µM in Sinapinic Acid and spotted onto the plate. Spectra were acquired with the following instrument settings: Accelerating Voltage 25000V, Grid Voltage 91%, Guide Wire 0.1%, Extraction Delay Time 400 nsec, Laser Intensity 3824. Raw spectra were processed in Data Explorer v. 4.5 (Applied Biosystems) by applying baseline correction and the Gaussian Smooth algorithm with a filter width value of 9.

Cell Mitogenesis Assay:

The human pancreatic adenocarcinoma cell line BxPC-3 (ATCC, Manassas, Va.) was plated in 96 well plates at a concentration of 2500 cells per well in RPMI 1640 (Invitrogen, Carlsbad, Calif.) containing 10% fetal bovine serum (Hyclone, Logan, Utah). The following day, cells were washed in starvation medium consisting of RPMI 1640 containing 0.1% BSA (Sigma, St. Louis, Mo.). Washed cells were pre-incubated for four hours in starvation medium containing various concentrations of each IGF-IR antagonist. Following the four hour pre-incubation, cells were exposed to IGF-I at 25 ng/mL and allowed to incubate for 24 hours at 37° C., 5% CO2. For the final four hours of incubation, cells were exposed to [$^3$H]-Thymidine (0.25 µCi/well; Perkin Elmer, Wellesley, Mass.). After the incubation period, cells were washed in PBS, lysed in 100 µL buffer consisting of 0.1% SDS+0.5 N NaOH, and counted on a TopCount NXT Scintillation Counter (Perkin Elmer, Wellesley, Mass.). The data were analyzed using SigmaPlot (Systat Software, Point Richmond, Calif.).

Cell-Based Receptor Blocking Assay:

The human breast adenocarcinoma MCF-7 (ATCC, Manassas, Va.) was plated in 24 well plates at a concentration of 50,000 cells per well in RPMI 1640 (Invitrogen, Carlsbad, Calif.) containing 10% fetal bovine serum (Hyclone, Logan, Utah). The following day, cells were washed in binding buffer consisting of RPMI 1640 containing 0.1% BSA (Sigma, St. Louis, Mo.), and then pre-incubated for 30 minutes on ice in 200 µL binding buffer containing IGF-IR competitor. After the pre-incubation period, 40 pM [125I] IGF-I (Perkin Elmer, Wellesley, Mass.), equivalent to approximately 60000 counts per minute, was added to each well and allowed to incubate for an additional three hours on ice with gentle agitation. The wells were then washed with ice cold PBS containing 0.1% BSA. Cells were lysed with 500 µL buffer consisting of 0.1% SDS+0.5 N NaOH. Radioactivity of the lysates was measured using a Wallac 1470 Gamma Counter (Perkin Elmer, Wellesley, Mass.), and the data were analyzed using SigmaPlot (Systat Software, Point Richmond, Calif.).

NCI-H929 Cell Proliferation Assay:

The human plasmacytoma cell line NCI-H929 (ATCC, Manassas, Va.) was plated in 96 well plates at a concentration of either 10000 or 25000 cells per well in DMEM (Invitrogen, Carlsbad, Calif.) containing 10% fetal bovine serum (Hyclone, Logan, Utah) containing various concentrations of IGF-IR antagonists. Cells were allowed to proliferate for 72 hours at 37° C., 5% CO2. After the proliferation period, cells were exposed to 20 µL of Cell Titer 96 Aqueous Proliferation Reagent (Promega, Madison, Wis.) and allowed to incubate for an additional four hours. Absorbance at 490 nm was measured on a Spectramax Plus 384 (Molecular Devices, Sunnyvale, Calif.), and the resulting data were analyzed using SigmaPlot (Systat Software, Point Richmond, Calif.).

32D:IGF-IR Cell Proliferation Assay

Cells ($10^4$) were seeded in 96 well plates in RPMI (Invitrogen, Carlsbad, Calif.) containing 10% fetal bovine serum (Hyclone, Logan, Utah) in the presence 100 ng/mL human IGF-I (R&D Systems, Minneapolis, Minn.) and IGF-IR antagonists. Cells were allowed to proliferate for 72 hours at 37° C., 5% $CO_2$. After the proliferation period, cells were exposed to Cell Titer 96 Aqueous Proliferation Reagent (Promega, Madison, Wis.) and allowed to incubate for an additional four hours. Absorbance at 490 nm was measured on a Spectramax Plus 384 (Molecular Devices, Sunnyvale, Calif.), and the resulting data was analyzed using SigmaPlot (Systat Software, Point Richmond, Calif.).

Ba/F3:VEGFR2 Cell Proliferation Assay

A murine IL-3-dependent pro-B cell line, Ba/F3, was engineered to overexpress a chimeric VEGR2 (extracellular domain)/EpoR(intracellular domain) thereby becoming a VEGF-dependent cell line. BaF3:VEGFR2 cells ($2.5 \times 10^4$) were seeded in 96 well plates in RPMI (Invitrogen, Carlsbad, Calif.) containing 10% fetal bovine serum (Hyclone, Logan, Utah) in the presence of VEGFR2 antagonists. Cells were allowed to proliferate for 72 hours at 37° C., 5% CO2. After the proliferation period, cells were exposed to Cell Titer 96 Aqueous Proliferation Reagent (Promega, Madison, Wis.) and allowed to incubate for an additional four hours. Absorbance at 490 nm was measured on a Spectramax Plus 384 (Molecular Devices, Sunnyvale, Calif.), and the resulting data was analyzed using SigmaPlot (Systat Software, Point Richmond, Calif.).

IGF-IR-HSA Conjugate Production

BM(PEO)2 was added in molar excess to clone 385A08 (SEQ ID NO: 203). The 385A08-BM(PEO)2 was isolated by cation exchange chromatography. Recombinant Human Serum albumin with free sulfhydryl group was added to 385A08-BM(PEO)2 to form HSA-385A08. The conjugate was further purified by anion and cation exchange chromatography.

IGF-IR-Fc Fusion Production

The carboxyl-terminus of 385A08 (SEQ ID NO: 226) (underlined) was joined to the amino-terminal region of an Fc fragment (Fc Hinge-CH2-CH3) (bold). A spacer (in lower case) was placed between the two in order to minimize the risk of steric hindrance. The expression vector was designed to allow the molecule to be expressed in *pichia* cells, which is faster than the traditional mammalian cell approach. The expression vector also includes an alpha factor signal peptide (in italics) to enable secretion during expression in *pichia* cells. This signal sequence is removed upon secretion and is not part of the final purified IGF-IR-Fc molecule. The sequence of the resulting expression construct is given below.

(SEQ ID NO: 247)
*MRFPSIFTAVLFAASSALAAPVNTTTEDETAQIPAEAVIGYSDLEGD*

*FDVAVLPFSNSTNNGLLFINTTIASIAAKEEGVSLEKR*EAEA<u>GVSDV</u>

<u>PRDLEVVAATPTSLLISWSARLKVARYYRITYGETGGNSPVQEFTVP</u>

<u>KNVYTATISGLKPGVDYTITVYAVTRFRDYQPISINYRTEIDKPSQ</u>d pgsEPKSCDKTHTCPPCPAPELLGGSSVFLFPPKPKDTLMISRTPEV

TCVVVDVSHEDPEVKFNWYVDGVEVHNAKTKPREEQYNSTYRVVSVL

TVLHQDWLNGKEYKCKVSNKALPAPIEKTISKAKGQPREPQVYTLPP

SRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

The expression construct was linearized and transformed into 3 *Pichia* host cells, X-33, GS115 and KM17H. Transformants were selected on zeocin plates and screened for IGF-IR-Fc expression in 2 ml cultures. Selected clones were grown in shake flasks at varied pH and purified by Protein A resin. Expression was observed at pH 6.5 to 7.0. A 1 L shake flask of one of the clones was used to express IGF-IR-DPGG-Ig at pH 6.7 and purify via Protein A and size exclusion.

Figure 28:
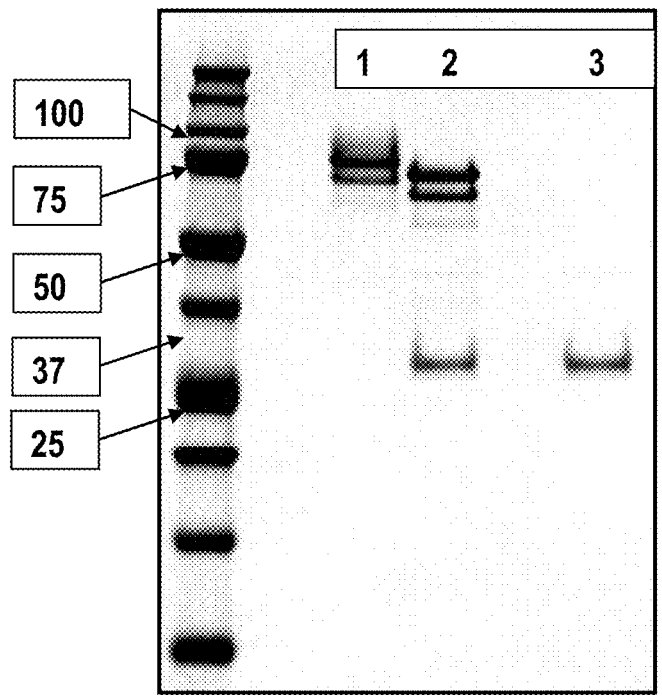
FIG. 28. Characterization of IGF-IR-Fc fusion construct. Top panel shows an SDS PAGE gel with molecular weight markers in the far left column, followed by nonreduced IGF-IR-Ig (lane 1), endo-H treated IGF-IR-Ig (lane 2), and Endo H (lane 3). The small shift to lower mass upon endo H treatment indicates the IGF-IR-Ig protein has a small amount of glycosylation. The lower panel shows an SDS PAGE gel, but in the presence of reducing agent, with molecular weight markers in the far left column, followed by untreated IGF-IR-Ig (lane 1), endo-H treated IGF-IR-Ig (lane 2), endo-H and SDS treated IGF-IR-Ig (lane 3) and Endo H (lane 4). As can be seen the observed mass is about half the size of the nonreduced samples, as is expected for a disulfide-linked intact IGF-IR-Ig.
Figure 28:
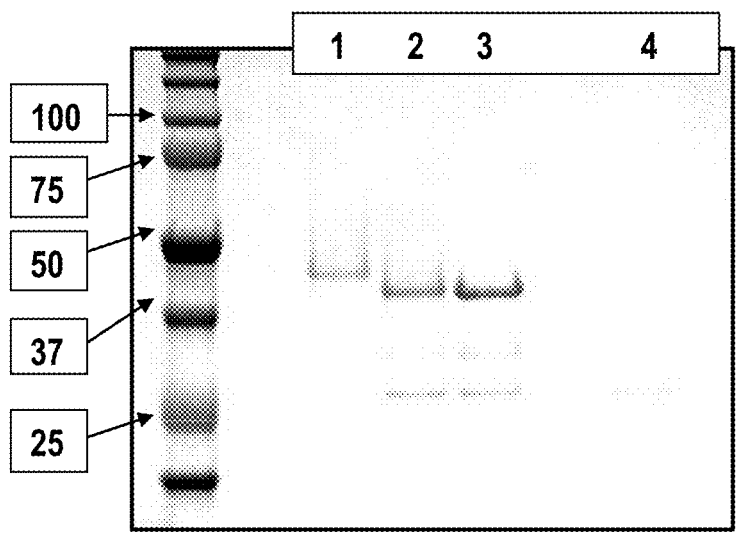

FIG. 28 depicts SDS PAGE analysis of the purified IGF-IR-Ig fusion protein. As can be seen the observed mass is about half the size of the nonreduced samples, as is expected for a disulfide-linked intact IGF-IR-Ig.

In Vivo Tumor Study of IGF-IR-HSA Conjugates

Tumors were propagated in nude mice. Tumor passages occurred every four weeks for human RH41 xenografts. With regard to efficacy testing human tumor xenografts were implanted in nude mice. All tumor passages were subcutaneous (sc).

Antitumor activity was evaluated in terms of: a) cures, and for the murine tumor models, increases in lifespan reflected by the relative median survival time (MST) of treated (T) versus control (C) groups (i.e. % T/C values); and b) primary tumor growth inhibition determined by calculating the relative median times for T and C mice to grow tumors of a predetermined "target" size (1 gm for all sc tumor models described) and expressed as T–C values, in days. The definition of a cured mouse was one whose tumor was undetectable, or <35 mg, when assessed more than 10 tumor volume doubling times (TVDTs) post-treatment. The activity criterion for tumor inhibition/reduction was a statistically significant delay in primary tumor growth consistent with ≥1 gross log cell kill (LCK). The following formula was employed to calculate LCK: LCK=T–C/(3.32×TVDT) Where, TVDT=median time (days) for control tumors to reach target size—median time (days) for control tumors to reach half the target size. The dose of a compound which yielded the maximum therapeutic effect, was termed the optimal dose (OD). Treatment groups (typically 8 mice) with more than one death attributable to drug toxicity were considered to have had excessively toxic treatments and their data were not used in the evaluation of antitumor activity. The maximum tolerated dose (MTD) is defined as the dose level immediately below which excessive toxicity (i.e. more than one death) occurred. Treated mice dying prior to having their tumors reach target size were considered to have died from drug toxicity. Statistical evaluations of data were performed using Gehan's generalized Wilcoxon test (Gehan, Biometrika 52:203-223, 1965).

The invention claimed is:

1. A method of treating a subject that has a cancer associated with increased insulin-like growth factor activity, the method comprising administering to a subject in need thereof a pharmaceutically effective amount of a polypeptide comprising an altered tenth fibronectin type III ($^{10}$Fn3) domain comprising an amino acid sequence that is at least 80% identical to any one of SEQ ID NOs: 184-203, and wherein the $^{10}$Fn3 domain binds human insulin-like growth factor-I receptor (IGF-IR) with a dissociation constant of about 1 μM or less.

2. The method of claim 1, wherein the altered $^{10}$Fn3 domain binds human IGF-IR with a disassociation constant of about 10 nM or less.

3. The method of claim 1, wherein the altered $^{10}$Fn3 domain comprises an amino acid sequence that is at least 85% identical to any one of SEQ ID NOs: 184-203.

4. The method of claim 1, wherein the altered $^{10}$Fn3 domain comprises an amino acid sequence that is at least 90% identical to any one of SEQ ID NOs: 184-203.

5. The method of claim 1, wherein the altered $^{10}$Fn3 domain comprises an amino acid sequence that is at least 95% identical to any one of SEQ ID NOs: 184-203.

6. The method of claim 1, wherein the altered $^{10}$Fn3 domain comprises an amino acid sequence that is identical to any one of SEQ ID NOs: 184-203.

7. The method of claim 1, wherein the altered $^{10}$Fn3 domain comprises an amino acid sequence of SEQ ID NO: 184.

8. The method of claim 1, wherein the polypeptide further comprises one or more pharmacokinetic (PK) moieties selected from: a polyoxyalkylene moiety, a human serum albumin binding protein, sialic acid, human serum albumin, transferrin, and an Fc fragment.

9. The method of claim 8, wherein the PK moiety is the polyoxyalkylene moiety and said polyoxyalkylene moiety is polyethylene glycol.

10. The method of claim 1, wherein the cancer is selected from the group consisting of breast cancer, colon cancer, ovarian carcinoma, osteosarcoma, cervical cancer, prostate cancer lung cancer, synovial carcinoma, pancreatic cancer, plasmacytoma, rhabdomyosarcoma and multiple myeloma.

* * * * *